(12) United States Patent
Rogers et al.

(10) Patent No.: US 11,883,165 B2
(45) Date of Patent: Jan. 30, 2024

(54) MICROFLUIDIC SYSTEMS FOR EPIDERMAL SAMPLING AND SENSING

(71) Applicants: NORTHWESTERN UNIVERSITY, Evanston, IL (US); THE BOARD OF TRUSTEES OF THE UNIVERSITY OF ILLINOIS, Urbana, IL (US)

(72) Inventors: John A. Rogers, Wilmette, IL (US); Jungil Choi, Chicago, IL (US); Tyler R. Ray, Evanston, IL (US); Johnathan T. Reeder, Plano, TX (US); Yurina Sekine, Evanston, IL (US); Amay J. Bandodkar, Evanston, IL (US); Yi Zhang, Evanston, IL (US); Hexia Guo, Evanston, IL (US); Sungbong Kim, Champaign, IL (US); Diana Ostojich, Evanston, IL (US)

(73) Assignees: NORTHWESTERN UNIVERSITY, Evanston, IL (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 452 days.

(21) Appl. No.: 17/027,887

(22) Filed: Sep. 22, 2020

(65) Prior Publication Data
US 2021/0000395 A1 Jan. 7, 2021

Related U.S. Application Data

(63) Continuation of application No. 16/616,770, filed as application No. PCT/US2018/035661 on Jun. 1, 2018, now Pat. No. 10,925,523.
(Continued)

(51) Int. Cl.
*A61B 5/145* (2006.01)
*A61B 5/00* (2006.01)
(Continued)

(52) U.S. Cl.
CPC ........ *A61B 5/14539* (2013.01); *A61B 5/0002* (2013.01); *A61B 5/053* (2013.01);
(Continued)

(58) Field of Classification Search
CPC ..... A61B 5/0002; A61B 5/145; A61B 5/1455; A61B 5/14551; A61B 5/14532;
(Continued)

(56) References Cited

U.S. PATENT DOCUMENTS

| 2002/0117315 A1* | 8/2002 | Gabower | ............. H05K 9/0073 174/377 |
|---|---|---|---|
| 2003/0073932 A1* | 4/2003 | Varey | ............... A61B 5/150343 600/573 |

(Continued)

FOREIGN PATENT DOCUMENTS

| CN | 101297189 A | 10/2008 |
|---|---|---|
| CN | 101351542 A | 1/2009 |

(Continued)

OTHER PUBLICATIONS

European Patent Office, "Supplementary Partial European Search Report for for EP Application No. 18809064.1", Munich, Germany, dated Jan. 28, 2021.
(Continued)

*Primary Examiner* — Chu Chuan Liu
(74) *Attorney, Agent, or Firm* — Locke Lord LLP; Tim Tingkang Xia, Esq.

(57) ABSTRACT

A microfluidic system includes a flexible substrate having a skin-facing surface and a back-facing surface; a microfluidic network at least partially embedded in or supported by the flexible substrate; a sensor fluidically connected to the microfluidic network, wherein the microfluidic network is configured to transport a biofluid from a skin surface to the sensor; and a capping layer, having a capping layer skin-
(Continued)

facing surface and a back-facing surface, wherein the back-facing surface of the capping layer is attached to the skin-facing surface of the substrate. The flexible substrate is at least partially formed of a thermoplastic elastomer or a polymer configured to provide a high barrier to vapor or liquid water transmission.

28 Claims, 67 Drawing Sheets

Related U.S. Application Data

(60) Provisional application No. 62/514,546, filed on Jun. 2, 2017, provisional application No. 62/514,374, filed on Jun. 2, 2017, provisional application No. 62/514,559, filed on Jun. 2, 2017, provisional application No. 62/514,455, filed on Jun. 2, 2017, provisional application No. 62/514,436, filed on Jun. 2, 2017, provisional application No. 62/514,489, filed on Jun. 2, 2017, provisional application No. 62/514,515, filed on Jun. 2, 2017, provisional application No. 62/514,520, filed on Jun. 2, 2017, provisional application No. 62/514,468, filed on Jun. 2, 2017.

(51) Int. Cl.
*A61B 5/053* (2021.01)
*A61B 5/103* (2006.01)
*A61B 5/1455* (2006.01)
*B01L 3/00* (2006.01)

(52) U.S. Cl.
CPC .......... *A61B 5/1032* (2013.01); *A61B 5/1455* (2013.01); *A61B 5/14517* (2013.01); *A61B 5/14546* (2013.01); *A61B 5/4842* (2013.01); *A61B 5/6806* (2013.01); *B01L 3/502715* (2013.01); *A61B 5/6833* (2013.01); *A61B 2562/028* (2013.01); *A61B 2562/164* (2013.01); *B01L 2300/025* (2013.01); *B01L 2300/0663* (2013.01); *B01L 2300/0803* (2013.01); *B01L 2300/0864* (2013.01); *B01L 2300/123* (2013.01); *B01L 2400/0406* (2013.01); *B01L 2400/0688* (2013.01)

(58) Field of Classification Search
CPC ... A61B 5/14539; A61B 5/053; A61B 5/1032; A61B 5/14517; A61B 5/14546; A61B 5/6806; A61B 5/6833; A61B 5/1486; A61B 2562/02; A61B 2562/0209; A61B 2562/0214; A61B 2562/0238; A61B 2562/028; A61B 2562/0295; A61B 2562/164
See application file for complete search history.

(56) References Cited

U.S. PATENT DOCUMENTS

| | | |
|---|---|---|
| 2003/0225362 A1 | 12/2003 | Currie et al. |
| 2007/0278097 A1 | 12/2007 | Bhullar |
| 2009/0076345 A1* | 3/2009 | Manicka ............... A61B 5/6833 600/509 |
| 2012/0150072 A1* | 6/2012 | Revol-Cavalier .... A61B 5/4266 600/573 |
| 2017/0100102 A1 | 4/2017 | Heikenfeld |
| 2017/0224257 A1 | 8/2017 | Rogers |
| 2017/0296114 A1* | 10/2017 | Ghaffari ............... A61B 5/4266 |
| 2018/0340903 A1* | 11/2018 | Heikenfeld ............... A61B 5/00 |

FOREIGN PATENT DOCUMENTS

| | | |
|---|---|---|
| CN | 101688864 A | 3/2010 |
| CN | 104838268 A | 8/2015 |
| CN | 106573201 A | 4/2017 |
| CN | 106793954 A | 5/2017 |
| CN | 2017218878 A | 12/2017 |
| CN | 108430308 A | 8/2018 |
| KR | 10-2017-0041291 A | 4/2017 |
| WO | 2016025430 A1 | 2/2016 |

OTHER PUBLICATIONS

KIPO, "Office Action for KR Application No. 10-2019-7038829", Korea, dated Apr. 28, 2021.
SIPO, "1st CN Office Action and Search Report for for CN Application No. 201880049165.4", China, dated Oct. 22, 2020.
SIPO, "1st CN Office Action and Search Report for CN Application No. 202010460709.5", China, dated Mar. 4, 2022.

* cited by examiner

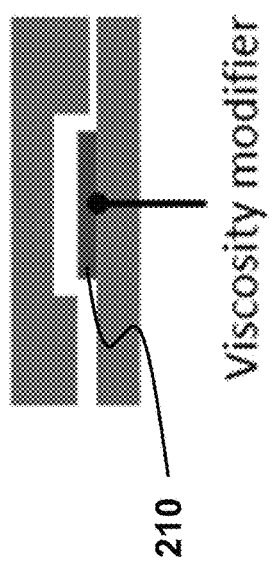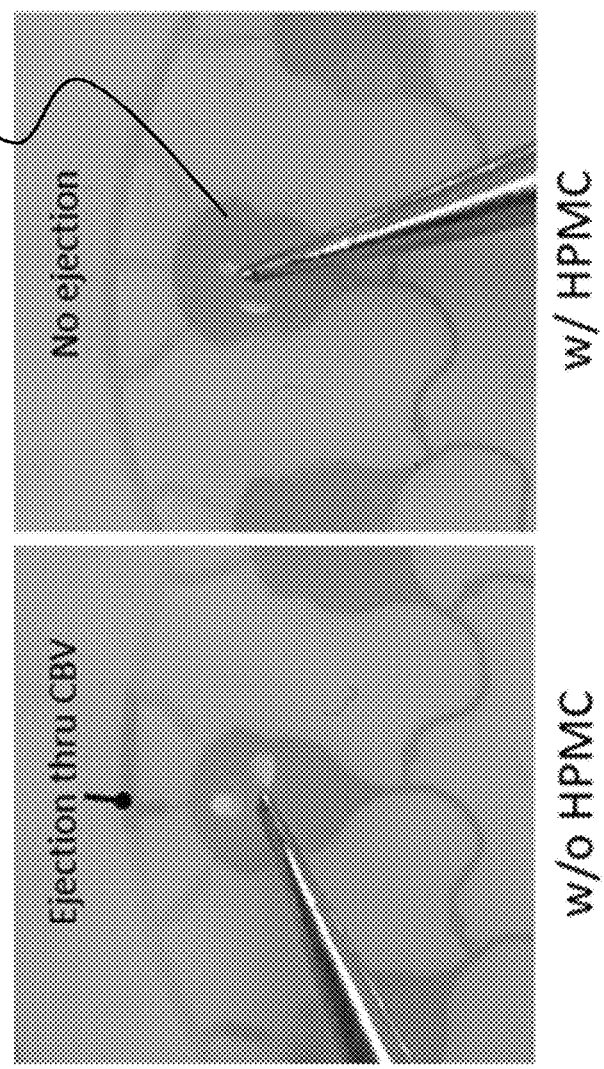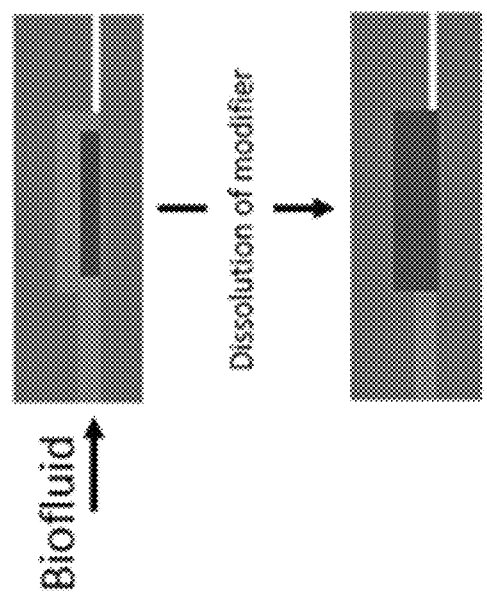
FIG. 17

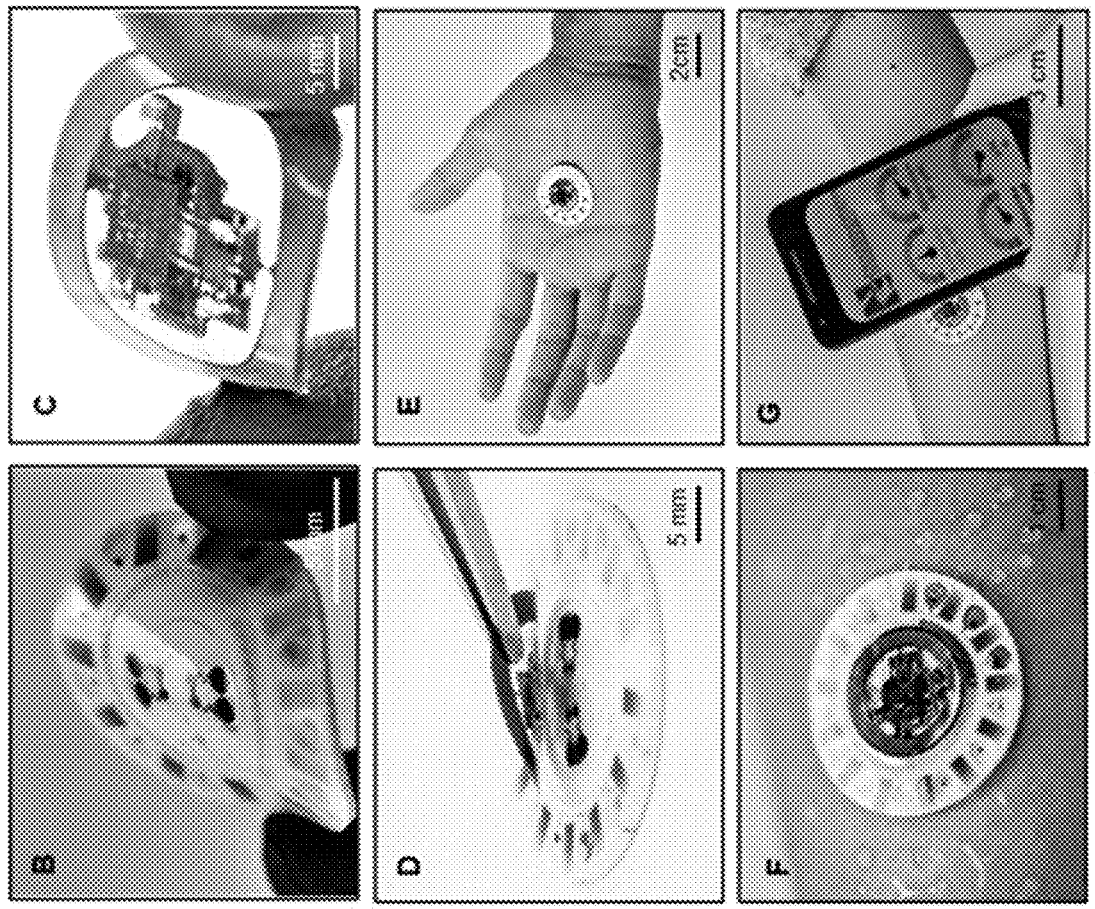
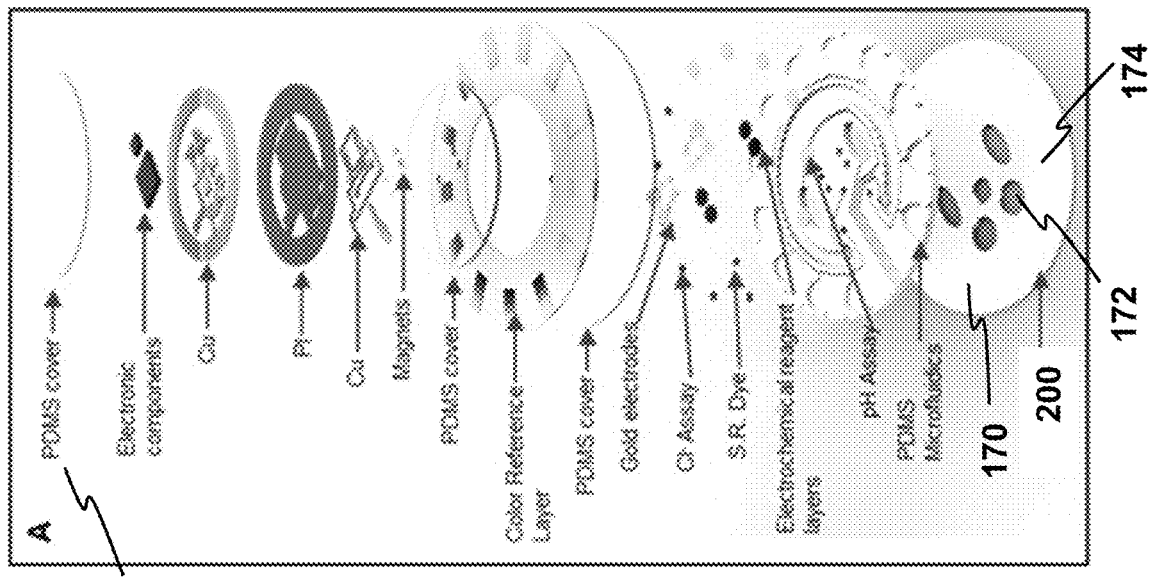
FIG. 20

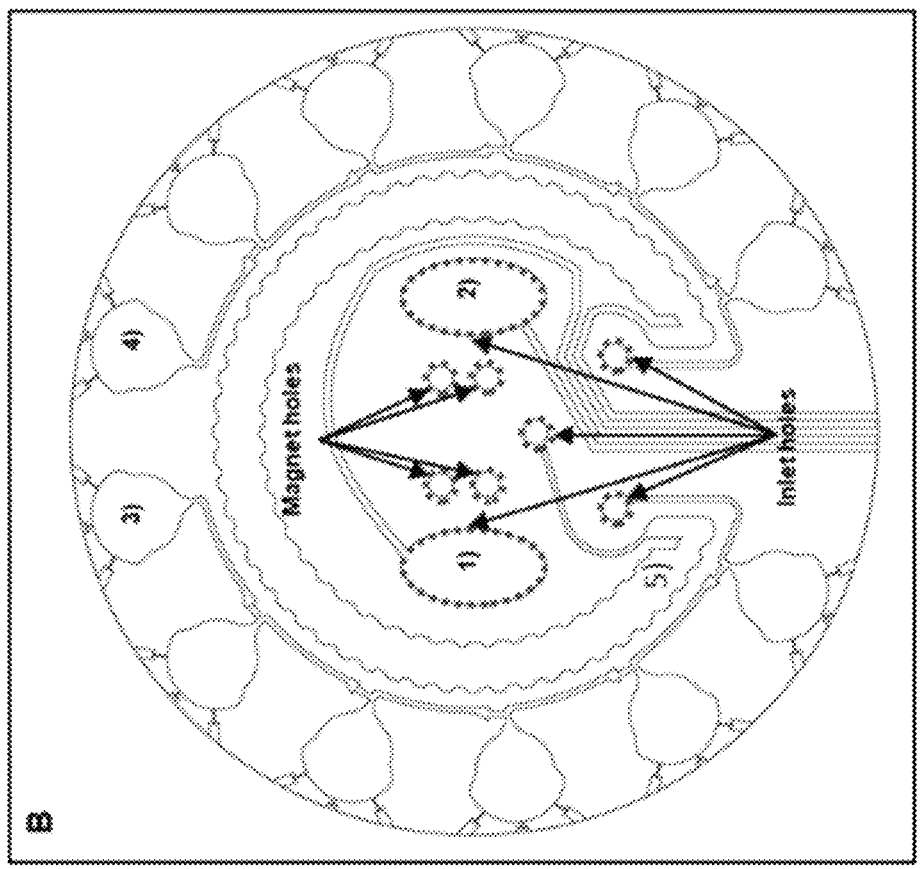
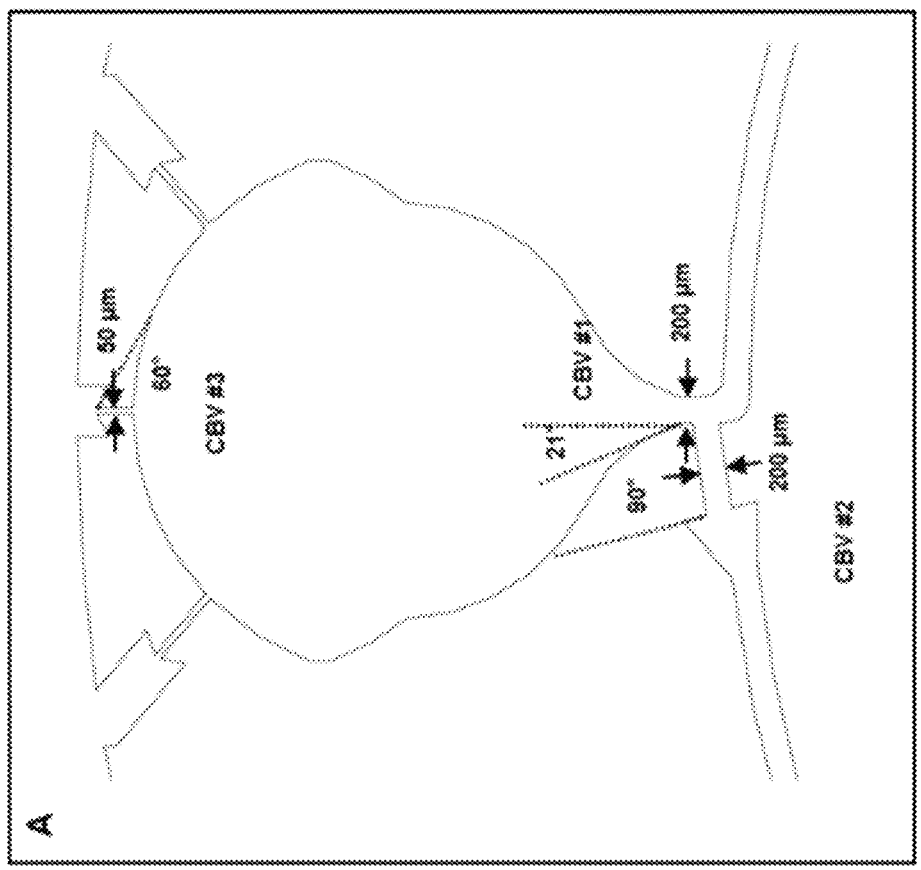
FIG. 28

Epifluidic Sensor

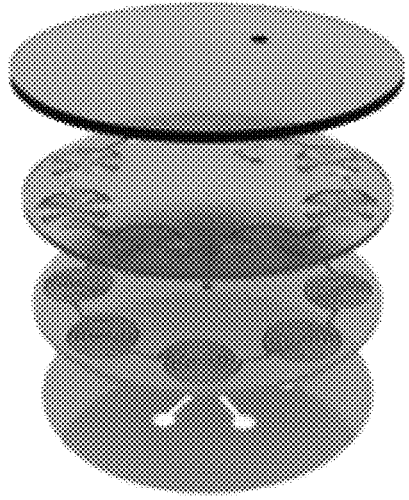

Medical-grade silicone and thin dimensions enables soft, flexible, intimate contact with skin.

→ *Capping layer:* Sweat removed through direct pipette extraction

→ *Analytics:* Collection and on-device analysis microfluidic channel network

→ *Adhesive:* Skin-safe adhesive for conformal, air & water-tight skin seal

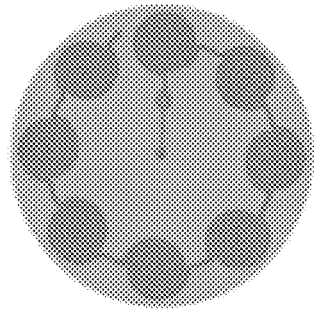

Each well stores 5 μL of sweat

Provides clear volume measurement in clinic

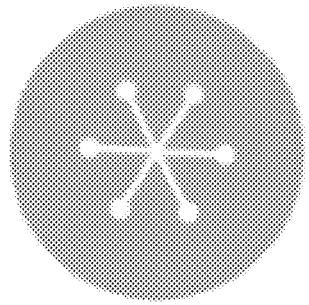

Patterned adhesive layer to structure flow of sweat into device

Flow results from sweat gland pressure

FIG. 36

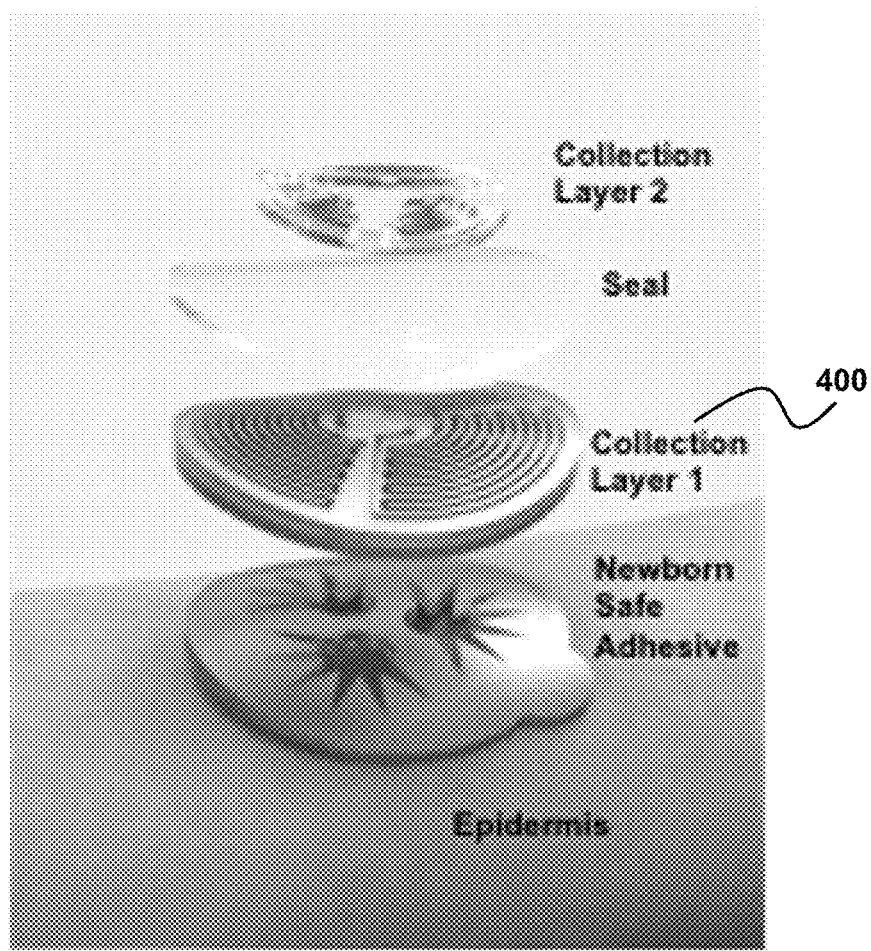
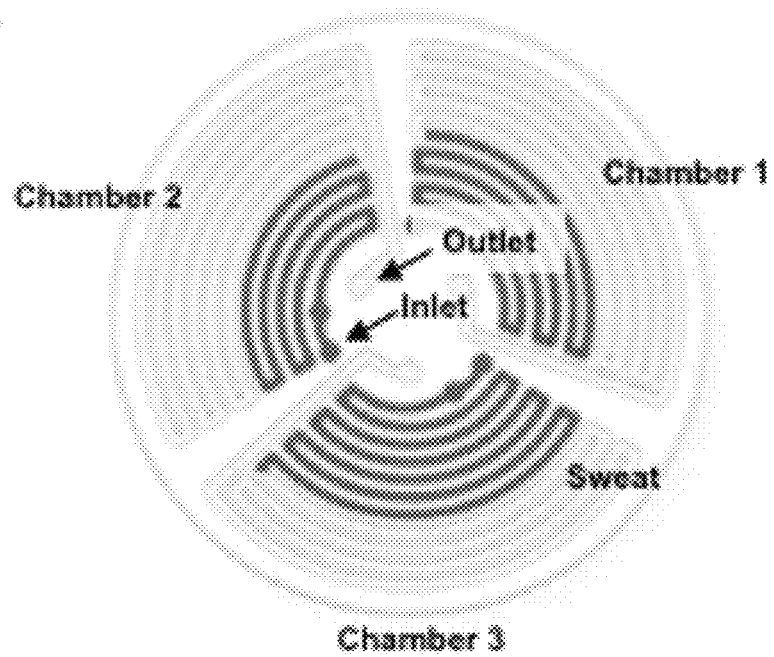
FIG. 37

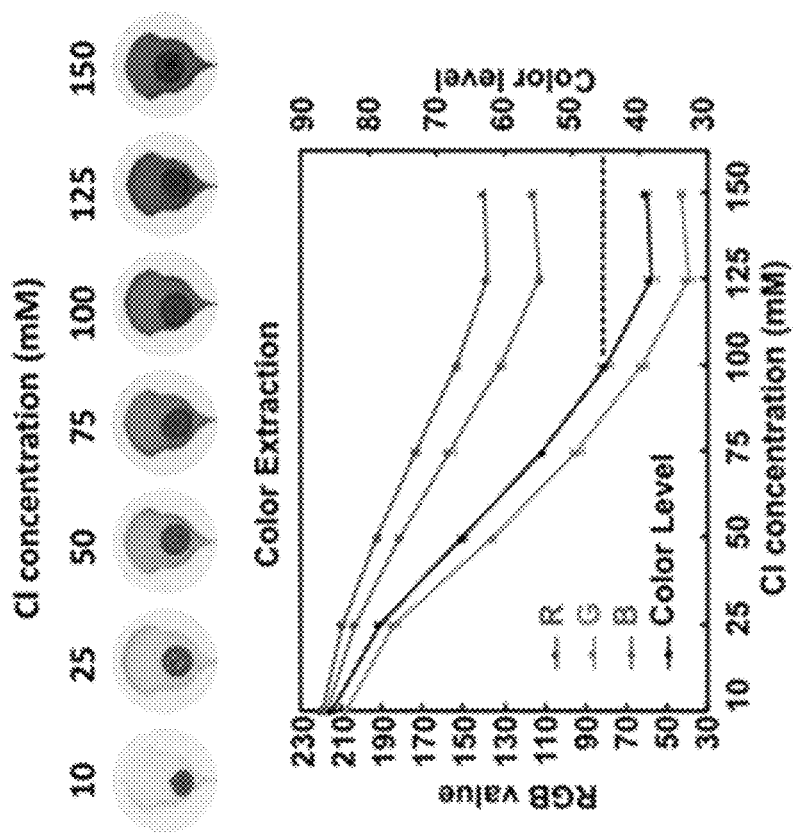
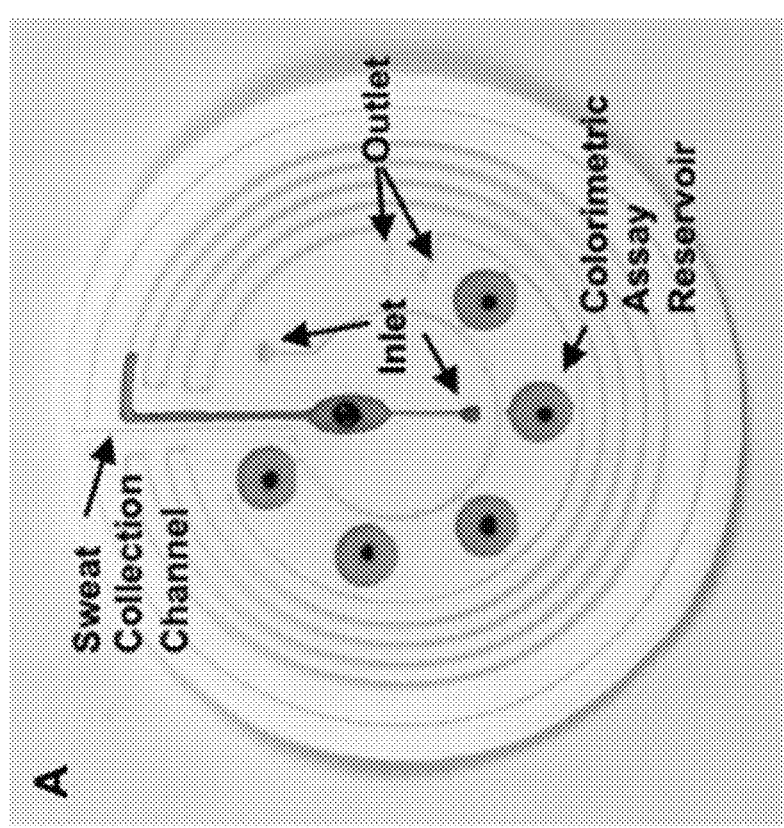
FIG. 65

MICROFLUIDIC SYSTEMS FOR EPIDERMAL SAMPLING AND SENSING

CROSS-REFERENCE TO RELATED PATENT APPLICATIONS

This application is a continuation application of U.S. patent application Ser. No. 16/616,770, filed Nov. 25, 2019, now allowed, which is a national stage entry of PCT Application Serial No. PCT/US2018/035661, filed Jun. 1, 2018, which itself claims priority to and he benefit of U.S. Provisional Patent Application Nos. 62/514,489, 62/514,515, 62/514,374, 62/514,455, 62/514,520, 62/514,468, 62/514,546, 62/514,559, and 62/514,436, all filed Jun. 2, 2017, each of which is incorporated herein in its entirety by reference.

FIELD OF THE INVENTION

The invention relates generally to biosensors, and more particularly to microfluidic systems for epidermal sampling and sensing.

BACKGROUND OF INVENTION

Microfluidics provides a versatile technology platform affecting a wide range of industries and commercial products. In the field of medical diagnostics, for example, microfluidics has been essential to the development of entirely new classes of sensors and assays with potential for revolutionizing medical diagnosis and the treatment of disease. Lab on a chip and microarray systems, for example, have been developed for clinical pathology taking advantage of microfluidic sample collection, preparation and handling to achieve highly sensitivity and rapid point of care analysis of biomarkers in minute quantities of biofluid. The advances in microfluidics have also been leveraged to support other biotechnology and medical applications including high throughput DNA sequencing, mass spectrometry-based proteomics, cellular expression and imaging.

Wearable systems are another technology for which advances in microfluidics has potential to enable new classes of products and advanced modes of functionality. Recent developments in epidermal electronics, for example, provide a class of skin-mounted sensors and actuators compatible with efficient microfluidic sampling at the interface of the skin. Such microfluidics-enabled epidermal systems have potential to support a broad range of clinical applications in healthcare including analysis of biomarkers, drug administration, and real time diagnosis and monitoring of medical conditions including diabetes, inflammation and hydration state. Examples include, US20060253011; 0520100179403; WO 2016/025468; WO 2016/025438; WO2010030609; US20070027383; US20070179371A1; U.S. Pat. Nos. 4,960,467; 6,198,953; and WO2009025698A1.

As will be understood from the forgoing, the development of wearable systems is needed in a manner that integrates microfluidic functionality with tissue mounted sensing and actuation. Wearable systems having physical formats and mechanical properties that provide a robust interface with the skin to achieve quantitatively reliable collection and handling of biofluids over clinically (and commercially) relevant time intervals are needed. In addition, microfluidic systems are needed that are capable of effective collection, pretreatment, storage and analysis of biofluids to support a range of applications for wearable systems, including for physical exertion applications, medical diagnostics and therapy, and general well-being.

There is a particular need for reliable biofluid collection, retention, and monitoring/analysis under a range of extreme environmental conditions, including in wet environments, dry environments, hot/cold temperatures, active/passive users, healthy/unwell users. Proved herein are systems that address these needs using specially configured microfluidic networks and associated components for desired fluidic collection and pathways depending on the application of interest.

SUMMARY OF THE INVENTION

Provided are microfluidic systems and methods for the measurement and characterization of biofluids in a manner that is versatile and that can be tailored to a wide range of applications. For example, the systems are compatible for monitoring a biofluid property in different flow regimes, including low flow and high flow regimes, where biofluids are correspondingly available in small quantities or in larger quantities. This can be achieved by providing a plurality of microfluidic networks, with each network tailored to a specific flow regime. One manner in which this can be achieved is by adjusting microfluidic geometry and size and fluid control elements within the microfluidic networks. For example, flow path can be further controlled with valves that open when a desired flow condition is satisfied, such as a plurality of capillary burst valves having specially selected and unique burst valve pressures so that controlled biofluid flow is achieved in the various microfluidic networks.

The microfluidic system may comprise: a flexible substrate; and at least two microfluidic networks, each microfluidic network configured to independently monitor a biofluid property; wherein each microfluidic network comprises: a microfluidic inlet conduit network at least partially embedded in or supported by the substrate; a biofluid inlet fluidically connected with the microfluidic inlet conduit network to introduce a biofluid from the skin surface to the microfluidic inlet conduit during use; a plurality of reservoir chambers, each reservoir chamber fluidically connected with the microfluidic inlet conduit network; a plurality of capillary burst valves fluidically connected with the microfluidic conduit network, each capillary burst valve positioned between fluidically adjacent reservoir chambers; and a plurality of colorimetric sensors, each positioned in a unique reservoir chamber to monitor the biofluid property.

The at least two microfluidic networks may differ from each other by (i) a biofluid inlet dimension, (ii) a reservoir chamber volume of each of the plurality of reservoir chambers, (iii) a burst pressure of each of the plurality of capillary burst valves, or (iv) any combination thereof.

The microfluidic system may comprise: a plurality of reservoir networks at least partially embedded in or supported by a flexible substrate, each reservoir network comprising: a reservoir chamber; a biofluid inlet fluidically connected to the reservoir chamber via a capillary burst valve, having a burst pressure, to introduce a biofluid from a skin surface to the reservoir chamber; an outlet fluidically connected to a reservoir chamber.

Also provided are methods for measuring a biofluid property for a biofluid released from skin using any of the microfluidic systems disclosed herein.

Any of the systems described herein may utilize a means for minimizing biofluid loss and/or increasing biofluid collection efficiency. For example, any of the systems described herein may utilize a capping layer to mitigate unwanted biofluid loss (or entry), to thereby provide improved device performance, reliability and accuracy. Any of the systems and methods described herein may contain a biofluid gelling agent in the microfluidic network, wherein conversion of a fluid into a gel within the microfluidic network decreases unwanted biofluid loss. Any of the systems and methods described herein may contain an absorbent in the microfluidic network, wherein the biofluid is at least partially absorbed by the absorbent, thereby minimizing biofluid loss. Any of the gelling agents and/or absorbents may be positioned in a reservoir chamber, or at specific locations in the network, depending on the application of interest and/or surrounding environmental conditions.

To facilitate reliable and efficient measurement, any of the systems and methods may utilize specially patterned elements, including patterned grating in a portion of the microfluidic network, to provide controlled change in an optical transmission property. In this manner, transmission of incident electromagnetic radiation through the patterned grating changes as a function of the amount of the biofluid in the microfluidic channel or reservoir chamber. An indicator may be provided in optical communication with the patterned grating, wherein changes in the transmission of incident electromagnetic radiation through the grating changes the appearance of the indicator.

The provided systems and methods utilize capillary force and/or heat sources to help drive biofluid generation and/or capture, which would otherwise be difficult to measure and/or characterize. The heat sources may be intrinsic to the system, such a heater. The heat sources may be extrinsic to the system, such as by hot water, generated by a shower or bath, for example, to generate biofluid release from a skin surface. An absorbent may be used in the microfluidic network to generate a biofluid collection force in a manner that draws out biofluid from the skin surface to the network for collection and analysis.

The systems and methods may be characterized as providing a platform for chrono-sampling, including for various fluid flow regimes and constituents therein, such as biomarkers. This may be achieved using multiple microfluidic networks. In this manner, the microfluidic system for monitoring a biofluid property may comprise: a flexible substrate; at least two microfluidic networks, each microfluidic network configured to independently monitor a biofluid property; wherein each microfluidic network comprises: a microfluidic inlet conduit network at least partially embedded in or supported by the substrate; a biofluid inlet fluidically connected with the microfluidic inlet conduit network to introduce a biofluid from a skin surface to the microfluidic inlet conduit during use; a plurality of reservoir chambers, each reservoir chamber fluidically connected with the microfluidic inlet conduit network; and a plurality of capillary burst valves fluidically connected with the microfluidic conduit network, each capillary burst valve positioned between fluidically adjacent reservoir chambers.

Any of the microfluidic systems may comprise a plurality of colorimetric sensors, wherein each colorimetric sensor is positioned in a unique reservoir chamber to monitor the biofluid property.

Any of the microfluidic systems may have at least two microfluidic networks that differ from each other by: (i) a biofluid inlet dimension, (ii) a reservoir chamber volume of each of the plurality of reservoir chambers, (iii) a burst pressure of each of the plurality of capillary burst valves, (iv) a chemical composition of a chemically-mediated reaction chamber, or (v) any combination thereof.

Any of the microfluidic systems may have a first microfluidic network configured to monitor a biofluid parameter associated with a low-flow biofluid regime and a second microfluidic network is configured to monitor a biofluid parameter associated with a high-flow biofluid regime, and the biofluid property is biofluid amount; biofluid analyte concentration; biomarker presence or absence; or a combination thereof. In this manner, a single system can accommodate large changes in biofluid generation, such as sweating in a hot, humid environment during strenuous exercise (corresponding to high sweat-rate) versus sedentary activity in a cool climate (very little sweat generated). As discussed herein below, additional components may be included to help drive biofluid collection, particularly in applications where no to little sweat is generated.

Sizing and geometry of inlets and microchannels can be selected to correspond to a desired flow range. In this aspect, various flow regimes are accommodated. For example, the microfluidic system may have a high biofluid loss regime that is at least 10 times greater than the low biofluid loss regime. By varying fluidic conduit sizes, flow resistance is effectively varied, thereby controlling flow-rate ($Q=\Delta P/R$). Similarly, use of capillary burst valves with selected burst-valve pressures may also be used to control biofluid introduction to different microfluidic networks.

Each microfluidic network may further comprise: at least one microfluidic outlet conduit, each microfluidic outlet conduit fluidically connected to at least one of the plurality of reservoir chambers and configured to relieve gas back pressure from the microfluidic inlet conduit network.

Any of the microfluidic systems may be described as having the plurality of reservoir chambers chemically decoupled from each other for independent biofluid property detection and/or time sequential biofluid property monitoring. This chemical decoupling may be achieved by selection of microchannel dimensions (e.g., length and width), particularly between fluidically adjacent reservoir chambers. For example, by ensuring Reynold's number is in the laminar range, including less than 100, or less than 10, or less than 1, mixing is minimized, and diffusion reduced for sufficiently long distances between adjacent reservoir chambers so that diffusion between the chambers is unlikely over the relevant time-scale.

Any of the microfluidic systems may further comprise a plurality of capillary burst valves, wherein at least one capillary burst valve is positioned between fluidically adjacent reservoir chambers. In this manner, pressure may be determined by visual observation of filling of reservoir chambers, with higher pressures associated with different reservoir filling.

Any of the systems may measure pressure of a biofluid, such as the pressure associated with one or more sweat glands. The microfluidic system for measuring a biofluid pressure may comprise: a flexible substrate; a plurality of reservoir networks at least partially embedded in or supported by the flexible substrate, wherein each reservoir network comprises: a reservoir chamber; a biofluid inlet fluidically connected to the reservoir chamber via a capillary burst valve to introduce a biofluid from a skin surface to the reservoir chamber, wherein the capillary burst valve has a burst pressure; and an outlet fluidically connected to the reservoir chamber; wherein the burst pressure of each capillary burst valve is selected to correspond to a pressure range of the biofluid from the skin surface.

At least one of the plurality of reservoir networks (e.g., reservoir chamber) may have a unique capillary burst valve pressure, thereby providing a unique pressure measure associated with the corresponding reservoir network. In this manner, any number of distinct pressures may be measured.

The biofluid inlet may be fluidically aligned with a biofluid source of the skin surface during use.

Any of the reservoir networks (chambers) may further comprise at least one colorimetric sensor to provide an optical readout.

At least a portion of the capillary burst valves may be fluidically aligned in a serial configuration and have a burst valve pressure that increases and spans a minimum to maximum pressure, such as a range that is greater than 0 kPa and less than 10 kPa, and any subranges thereof.

Any of the systems may have specific colorimetric sensor, such as a sensor comprising silver chloranilate. The microfluidic system to measure a biofluid property, may comprise: a flexible substrate; a microfluidic inlet conduit network at least partially embedded in or supported by the flexible substrate; a biofluid inlet fluidically connected to the microfluidic inlet conduit network to introduce a biofluid from the skin surface to the microfluidic inlet conduit during use; a plurality of reservoir chambers, each reservoir chamber fluidically connected with the microfluidic inlet conduit network; a plurality of capillary burst valves fluidically connected with the microfluidic conduit network, each capillary burst valve positioned between fluidically adjacent reservoir chambers; a microfluidic outlet conduit network fluidically connected with the plurality of reservoir chambers and configured to relieve gas back pressure from the microfluidic inlet conduit network; a plurality of colorimetric sensors, each positioned in a unique reservoir chamber to measure a biofluid property; and wherein: at least one of the colorimetric sensors has a color-responsive reagent to measure chloride in the biofluid. The color-responsive reagent may comprise silver chloranilate.

The microfluidic system may further comprise a color indicator strip positioned between any two fluidically adjacent reservoir chambers.

Any of the microfluidic systems may further comprise a capping layer connected to a skin-facing surface and/or a back-facing surface of the flexible substrate.

The microfluidic system may comprise: a flexible substrate having a skin-facing surface and a back-facing surface; a microfluidic network at least partially embedded in or supported by the flexible substrate; a sensor fluidically connected to the microfluidic network, wherein the microfluidic network is configured to transport a biofluid from a skin surface to the sensor; and a capping layer, having a capping layer skin-facing surface and a back-facing surface, wherein the back-facing surface of the capping layer is attached to the skin-facing surface of the substrate; wherein the flexible substrate is at least partially formed of a thermoplastic elastomer or a polymer configured to provide a high barrier to vapor or liquid water transmission.

The capping layer may be at least partially formed of a thermoplastic elastomer and an additive. The flexible substrate and the capping layer may be formed of a common thermoplastic elastomer composition. The flexible substrate and the capping layer may have a common additive.

Examples of thermoplastic elastomers include a styrene copolymer, such as selected from the group consisting of styrene-ethylene-butadiene-styrene (SEBS), styrene-isoprene-styrene (SIS), styrene-butadiene-styrene (SBS), and any combination thereof.

The thermoplastic elastomer may have a weight fraction of styrene copolymer selected from the range of 10% to 50%.

The additive may be a hydrocarbon compound characterized by a molecular weight less than a user-selected molecular weight, such as a molecular weight that is less than 1000 g/mol. The additive may be paraffin oil.

The thermoplastic elastomer may have a weight ratio of additive to styrene copolymer selected from the range of 1 to 3.

Any of the microfluidic systems may have a capping layer that comprises a spatially distributed pattern of relief, recess, or relief and recess features to achieve a desired mechanical property while maintaining high barrier to water vapor or liquid transmission. The pattern may comprise a symmetrical pattern. The pattern may be selected to achieve a desired mechanical property of flexibility and stretchability of the capping layer that is substantially matched to the flexible substrate. For example, the mechanical property may be a Young's modulus of less than 100 MPa, a net bending stiffness of less than 1 nN m, and/or a thickness of less than 5 mm.

The spatially distributed pattern may be spatially aligned with at least a portion of the microfluidic network. For example, recess features, including passages, may be aligned with inlets to facilitate biofluid flow to the microfluidic inlets.

An of the capping layers described herein may be at least partially formed of a rigid polymer selected from the group consisting of a polyolefin, a polyester, a fluorocarbon, a polyamide, a polyimide, and any combination thereof. The polyolefin may be selected from the group consisting of polyethylene, polypropylene and polyisobutylene; the polyester is selected from the group consisting of polyethylene terephthalate and polyethylene naphthalate; the fluorocarbon is selected from the group consisting of polyvinylidene chloride and polytetrafluoroethylene; the polyamide is a nylon; and/or the polyimide is a poly-oxydiphenylene-pyromellitimide.

Any of the microfluidic systems may further comprise an adhesive layer on the skin facing surface of the capping layer; wherein the adhesive layer comprises an adhesive compound capable of reversibly adhering the system to the skin surface. For systems that do not have a capping layer, the adhesive layer may be positioned on a skin-facing surface of the flexible substrate. The adhesive layer may comprise medical-grade acrylic.

The substrate, the capping layer, the adhesive compound, or any combination thereof may further comprise a tackifier additive. The substrate, the capping layer, or both the substrate and the capping layer may have a weight fraction of tackifier additive of between 30% to 80%. The tackifier additive may be rosin gum.

Any of the microfluidic systems may have a microfluidic network comprising a plurality of reservoirs and a microfluidic inlet conduit network having a biofluid inlet to introduce the biofluid to the microfluidic network; and wherein the microfluidic outlet conduit network is fluidically connected to the plurality of reservoirs. The microfluidic network may further comprise a microfluidic outlet conduit network fluidically connected to the plurality of reservoirs, the microfluidic inlet conduit network, and an outlet, and wherein the outlet is configured to (i) provide for release of gas back pressure from the microfluidic inlet conduit network, and (ii) prevent ingress of a liquid from a surrounding environment into the microfluidic outlet conduit network.

Any of the microfluidic systems may have a sensor that is a colorimetric sensor. Any of the microfluidic systems may have a sensor that is an electrochemical sensor. Any of the microfluidic systems may comprise two or more sensors, including at least one colorimetric sensor and one electrochemical sensor.

The colorimetric sensor may be positioned in one of the plurality of reservoirs. The electrochemical sensor may be positioned in one of the plurality of reservoirs.

Any of the microfluidic systems may further comprise a biofluid gelling additive or an absorbent contained within the microfluidic network.

Any of the microfluidic systems may have a biofluid gelling additive comprising two or more unique biofluid gelling additives.

The biofluid gelling agent may be configured to mix or react with the biofluid to increase a biofluid viscosity. The increase in biofluid viscosity may be by at least a factor of 2 of the biofluid viscosity before mixing or reacting with the biofluid gelling agent. In this manner, risk of leakage may be reduced, including through one or more of the CBV's. The biofluid gelling agent may comprise cellulose or a derivative thereof. The biofluid gelling agent may be methyl cellulose or hydroxypropyl methylcellulose.

The weight ratio of the biofluid gelling agent to biofluid, in at least one of the plurality of reservoirs, may be selected from the range of 0.1 to 1, or any subranges thereof.

An of the flexible substrates may be a functional substrate.

Also provided herein are microfluidic systems configured to minimize unwanted fluid loss from the system, such as to the surrounding environment or skin surface, including by a biofluid or an absorbent. Accordingly, the microfluidic system, may comprise: a flexible substrate; a microfluidic network at least partially embedded in or supported by the flexible substrate; a sensor fluidically connected to the microfluidic network, wherein the microfluidic network is configured transport a biofluid from a skin surface to the sensor; and a biofluid gelling additive or a biofluid absorbent contained in the microfluidic network to reduce biofluid loss from the microfluidic network.

The microfluidic network may comprise: a plurality of reservoirs; a biofluid inlet to introduce a biofluid to the microfluidic network; and a microfluidic inlet conduit network fluidically connected to the biofluid inlet and the plurality of reservoirs to introduce a biofluid to the reservoirs.

The microfluidic network may further comprise: a microfluidic outlet conduit network fluidically connected to the plurality of reservoirs; and an outlet fluidically connected to the microfluidic outlet conduit. The outlet is configured to: provide for release of gas back pressure from the microfluidic inlet conduit network, and prevent ingress of a liquid from an environment surrounding the system into the microfluidic outlet conduit network.

The sensor may be a colorimetric sensor or an electrochemical sensor. The sensor may be positioned in one of the plurality of reservoirs.

The microfluidic system may comprise two or more sensors, including for sensing different biofluid properties.

For microfluidic systems having a biofluid gelling additive, the biofluid gelling additive may be positioned in at least one of the plurality of reservoirs.

The microfluidic system may comprise two or more biofluid gelling additives.

The biofluid gelling agent may be configured to mix or react with the biofluid to increase a biofluid viscosity. The increase in biofluid viscosity may be by at least a factor of 2 of the biofluid viscosity before mixing or reacting with the biofluid gelling agent.

The biofluid gelling agent may be at least partially formed of cellulose or a derivative thereof, such as methyl cellulose or hydroxypropyl methylcellulose.

The weight ratio of the biofluid gelling agent to biofluid, in at least one of the plurality of reservoirs, may be selected from the range of 0.1 to 1.

Any of the microfluidic systems may further comprise a capping layer, having a capping layer skin facing surface and a back surface, wherein the back surface is affixed to a skin facing surface of the substrate.

The flexible substrate and/or capping layer may be at least partially formed of a thermoplastic elastomer having an additive. The substrate and the capping layer may have a common thermoplastic elastomer composition, or a different thermoplastic elastomer composition. The substrate and the capping layer may have a common additive.

The thermoplastic elastomer may be a styrene copolymer selected from the group consisting of styrene-ethylene-butadiene-styrene (SEBS), styrene-isoprene-styrene (SIS), styrene-butadiene-styrene (SBS), and any combination thereof. The thermoplastic elastomer may have a weight fraction of styrene copolymer selected from the range of 10% to 50%

The additive may be a hydrocarbon compound characterized by a molecular weight less than a user-selected molecular weight. The additive may be paraffin oil.

The thermoplastic elastomer may have a weight ratio of additive to styrene copolymer selected from the range of 1 to 3.

Any of the microfluidic systems may have a capping layer comprising a spatially distributed pattern of relief, recess, or relief and recess features to achieve a desired mechanical property while maintaining high barrier to water vapor or liquid transmission. The pattern may comprise a symmetrical pattern. The pattern may be selected to achieve a desired mechanical property of flexibility and stretchability of the capping layer that is substantially matched to the flexible substrate, wherein the mechanical property is one or more of a Young's modulus, a bending stiffness or an average thickness. In this aspect, substantially matched refers to a bulk property that is within 30% of the bulk property of the flexible substrate.

The pattern may be spatially aligned with at least a portion of the microfluidic network.

Any of the microfluidic systems may further comprise an expunge port fluidically connected with the reservoir chamber for the removal of biofluid from the reservoir chamber. In this manner, the microfluidic system, specifically the microfluidic network, may be reused.

Any of the microfluidic systems may further comprise optical components to facilitate detection of a biofluid property or characteristic. Examples of optical components include diffusors, lenses, diffraction grates and the like. An epidermally-mountable microfluidic system for measuring a characteristic of a biofluid from a skin surface may comprise: a flexible substrate; a biofluid inlet embedded on or supported by the substrate for receiving the biofluid from the skin surface; and a microfluidic channel fluidically connected to the biofluid inlet for receiving at least a portion of a biofluid from the biofluid inlet, the microfluidic channel having a patterned grating. In this manner, transmission of incident electromagnetic radiation through the patterned grating changes as a function of a biofluid amount in the microfluidic channel. The grating, of course, may be positioned in other components of the network, such as in a reservoir chamber.

The system may further comprise an indicator in optical communication the patterned grating; wherein changes in the transmission of incident electromagnetic radiation through the grating changes the appearance of the indicator.

The patterned grating may comprise a hydrophilic polymer; and wherein transmission of the incident electromagnetic radiation by the patterned grating increases when the chamber is filled with the biofluid.

The patterned grating may comprise a hydrophobic polymer; and wherein transmission of the incident electromagnetic radiation by the patterned grating decreases when the chamber is filled with the biofluid.

The system may further comprise an expunge port fluidically connected with the reservoir chamber for the removal of the biofluid from the reservoir chamber.

The system may further comprise an adhesive layer, such as an adhesive capable of reversibly adhering to the skin surface.

The adhesive layer may comprise medical grade acrylic or medical grade silicone.

The expunge port may comprise two outlets.

Any of the systems may further comprise a capillary burst valve fluidically connected to said expunge port and said reservoir chamber. The capillary burst valve may be positioned between said expunge port and said reservoir chamber.

The system may have a patterned grating that is nanopatterned or micropatterned.

The system may be configured to measure otherwise insensible sweat loss, including by the use of absorbents that assist in driving biofluid into the network. For example, the epidermal microfluidic system for measuring a characteristic of a biofluid; may comprise: a flexible substrate; a collection layer embedded in or supported by the flexible substrate, wherein the collection layer promotes transport of the biofluid from the skin surface; at least one reservoir chamber embedded in or supported by the flexible substrate and fluidically connected to the collection layer, the reservoir chamber having: an absorbent provided to receive at least a portion of the biofluid from the collection layer; and a sensor for measuring a characteristic of the biofluid received by the absorbent; wherein the absorbent provides a force for transporting the biofluid that is greater than a capillary force of the collection layer for transporting the biofluid.

The epidermal microfluidic system for measuring a characteristic of a biofluid, may comprise: a flexible substrate; a radiofrequency (RF) heater embedded in or supported by the flexible substrate; wherein the RF heater is capable of increasing a temperature of the skin surface, thereby increasing the release rate of the biofluid; and at least one sensor embedded in or supported by the flexible substrate to measure the characteristic of the biofluid.

The biofluid characteristic may be the amount of sweat loss or presence or absence of a biomarker contained in a biofluid released from a skin surface, such as a gland, a wound, or the like.

The sensor may be an electronic sensor. The electronic sensor may comprise one or more high sensitivity electrodes configured to measure a change in an electrical parameter caused by biofluid received by the absorbent. The electrical parameter may be capacitance or resistance.

The sensor may comprise one or more colorimetric assay reagents.

Any of the systems may further comprising a wireless communication device for transmitting wireless information corresponding to a characteristic of the biofluid from the skin surface.

Any of the systems may have a flexible substrate that comprises a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, chitosan, and any combination thereof.

Any of the systems may further comprise an adhesive layer configured to mount the system to a skin surface, including an adhesive layer that reversibly adheres the system to the skin surface. The adhesive layer may comprise medical grade acrylic or medical grade silicon.

Any of the systems may further comprise a protective layer embedded in or supported by the flexible substrate, such as a protective layer that prevents biofluid from escaping from the reservoir chamber or the sweat sensor. The protective layer may comprise polyethylene.

Any of the collection layers may have an average thickness selected from the range of 50 µm to 1 mm. The collection layer may be a mesh. The collection layer may have a plurality of pores having an average diameter selected from the range of 10 µm to 250 µm. The collection layer may comprise polyester.

Any of the systems may be incorporated into a glove.

Any of the systems by provide for a biofluid property that is visually observable.

Any of the systems may provide a signal corresponding to the biofluid property is transmitted from the system to an external receiving device.

The biofluid property may be one or more of sweat volume, sweat rate, or sweat loss. The biofluid property may be pH. The biofluid property may comprise the presence of, amount or concentration of an analyte in the biofluid or component thereof.

The analyte may be an electrolyte, a metabolite, or a biomarker in the biofluid or component thereof.

Any of the systems may provide a leading edge of biofluid in a sensor microfluidic channel or reservoir that is sensed as a function of time. The leading edge may be sensed visually or measured using a photodetector.

Any of the systems may further comprise an electronic sensor operably connected to the microfluidic network, wherein an amount of biofluid is proportional to an electrical resistivity or electrical conductivity parameter measured by the sensor.

Any of the systems may comprise a disposable portion comprising the microfluidics network and a reusable portion corresponding to an electronic device. wherein the disposable and reusable portions are connected to each other by one or more selectively releasable coupling elements. The selectively releasable coupling elements may comprise a magnet.

Any of the systems may comprise a plurality of distinct component layers arranged in a stacked configuration.

Also provided herein are associated methods of using any of the systems provided herein, such as a method of analyzing biofluid from a subject, the method comprising the steps of: contacting the flexible substrate of any systems provided herein with a skin surface of a subject; and analyzing the biofluid from the skin surface. The contacting the flexible substrate is intended to be broad, and to include indirect contact, such as by one or more intervening layers, such as adhesive layers, capping layer, collecting layer, microfluidic layer. Contacting may refer to conformal contact.

The biofluid may be sweat. The subject may be a human subject. The human subject may be undergoing a diagnostic procedure or a therapeutic procedure.

The subject may be a human subject monitoring the presence, onset or progression of a disease condition or undergoing a fitness activity.

The method may further comprise the step of increasing biofluid retention in the system by one or more of: increasing biofluid viscosity in the microfluidic network; and/or absorbing biofluid to an absorbent.

The analyzing step may comprise: observing biofluid volume in at least a portion of the microfluidic network; and/or observing a colorimetric change in a reservoir chamber.

The contacting step may comprise conformally contacting the flexible substrate with the skin surface, and any intervening layers between the flexible substrate and the skin surface.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

Representative Claims:

1. A microfluidic system for monitoring a biofluid property, the system comprising: a flexible substrate;
at least two microfluidic networks, each microfluidic network configured to independently monitor a biofluid property; wherein each microfluidic network comprises:
a microfluidic inlet conduit network at least partially embedded in or supported by the substrate;
a biofluid inlet fluidically connected with the microfluidic inlet conduit network to introduce a biofluid from a skin surface to the microfluidic inlet conduit during use;
a plurality of reservoir chambers, each reservoir chamber fluidically connected with the microfluidic inlet conduit network; and
a plurality of capillary burst valves fluidically connected with the microfluidic conduit network, each capillary burst valve positioned between fluidically adjacent reservoir chambers.

2. The microfluidic system of claim 1, further comprising a plurality of colorimetric sensors, wherein each colorimetric sensor is positioned in a unique reservoir chamber to monitor the biofluid property.

3. The microfluidic system of claim 1 or 2, wherein the at least two microfluidic networks differ from each other by: (i) a biofluid inlet dimension, (ii) a reservoir chamber volume of each of the plurality of reservoir chambers, (iii) a burst pressure of each of the plurality of capillary burst valves, (iv) a chemical composition of a chemically-mediated reaction chamber, or (v) any combination thereof.

4. The microfluidic system of any of claims 1-3, wherein a first microfluidic network is configured to monitor a biofluid parameter associated with a low-flow biofluid regime and a second microfluidic network is configured to monitor a biofluid parameter associated with a high-flow biofluid regime, and the biofluid property is biofluid amount; biofluid analyte concentration;
biomarker presence or absence; or a combination thereof.

5. The microfluidic system of claim 4, wherein the high biofluid loss regime is at least 10 times greater than the low biofluid loss regime.

6. The microfluidic system of any of claims 1-5, wherein each microfluidic network further comprises: at least one microfluidic outlet conduit, each microfluidic outlet conduit fluidically connected to at least one of the plurality of reservoir chambers and configured to relieve gas back pressure from the microfluidic inlet conduit network.

7. The microfluidic system of any of claims 1-6, wherein the plurality of reservoir chambers are chemically decoupled from each other for independent biofluid property detection and/or time sequential biofluid property monitoring.

8. The microfluidic system of any of claims 1-7, further comprising a plurality of capillary burst valves, wherein at least one capillary burst valve is positioned between fluidically adjacent reservoir chambers.

9. A microfluidic system for measuring a biofluid pressure, the system comprising: a flexible substrate;
a plurality of reservoir networks at least partially embedded in or supported by the flexible substrate, wherein each reservoir network comprises:
a reservoir chamber;
a biofluid inlet fluidically connected to the reservoir chamber via a capillary burst valve to introduce a biofluid from a skin surface to the reservoir chamber, wherein the capillary burst valve has a burst pressure; and
an outlet fluidically connected to the reservoir chamber;
wherein the burst pressure of each capillary burst valve is selected to correspond to a pressure range of the biofluid from the skin surface.

10. The system of claim 9, wherein at least one of the plurality of reservoir networks has a unique capillary burst valve pressure.

11. The system of any of claims 1-10, wherein the biofluid inlet is fluidically aligned with a biofluid source of the skin surface during use.

12. The system of any of claims 9-11, wherein each reservoir network further comprises at least one colorimetric sensor to provide an optical readout.

13. The system of any of claims 9-11, wherein at least a portion of the capillary burst valves are fluidically aligned in a serial configuration and have a burst valve pressure that increases and spans a range that is greater than 0 kPa and less than 10 kPa.

14. A microfluidic system to measure a biofluid property, the system comprising:
a flexible substrate;
a microfluidic inlet conduit network at least partially embedded in or supported by the flexible substrate;
a biofluid inlet fluidically connected to the microfluidic inlet conduit network to introduce a biofluid from the skin surface to the microfluidic inlet conduit during use;
a plurality of reservoir chambers, each reservoir chamber fluidically connected with the microfluidic inlet conduit network;
a plurality of capillary burst valves fluidically connected with the microfluidic conduit network, each capillary burst valve positioned between fluidically adjacent reservoir chambers;
a microfluidic outlet conduit network fluidically connected with the plurality of reservoir chambers and configured to relieve gas back pressure from the microfluidic inlet conduit network;
a plurality of colorimetric sensors, each positioned in a unique reservoir chamber to measure a biofluid property; and wherein: (i) at least one of the colorimetric sensors has a color-responsive reagent to measure chloride.

15. The microfluidic system of claim 14, further comprising a color indicator strip positioned between any two fluidically adjacent reservoir chambers 16. The microfluidic system of claim 14, wherein: (i) at least one of the colorimetric sensors has a color-responsive reagent comprising silver chloranilate.

17. The microfluidic system of any of claims 14-16, wherein the colorimetric sensors are configured to measure concentration of chloride in the biofluid.

18. The microfluidic system of any of claims 1-17, further comprising a capping layer connected to a skin-facing surface and/or a back-facing surface of the flexible substrate.

19. A microfluidic system, comprising:
a flexible substrate having a skin-facing surface and a back-facing surface;
a microfluidic network at least partially embedded in or supported by the flexible substrate;
a sensor fluidically connected to the microfluidic network, wherein the microfluidic network is configured to transport a biofluid from a skin surface to the sensor; and
a capping layer, having a capping layer skin-facing surface and a back-facing surface, wherein the back-facing surface of the capping layer is attached to the skin-facing surface of the substrate; wherein the flexible substrate is at least partially formed of a thermoplastic elastomer or a polymer configured to provide a high barrier to vapor or liquid water transmission.

20. The microfluidic system of claim 18 or 19, wherein the capping layer is at least partially formed of a thermoplastic elastomer and an additive.

21. The microfluidic system of claim 20, wherein the flexible substrate and the capping layer are formed of a common thermoplastic elastomer composition.

22. The microfluidic system of any of claims 18-21, wherein the flexible substrate and the capping layer have a common additive.

23. The microfluidic system of any of claims 19-22, wherein the thermoplastic elastomer is a styrene copolymer selected from the group consisting of styrene-ethylene-butadiene-styrene (SEBS), styrene-isoprene-styrene (SIS), styrene-butadiene-styrene (SBS), and any combination thereof.

24. The microfluidic system of any of claims 19-23, wherein the thermoplastic elastomer has a weight fraction of styrene copolymer selected from the range of 10% to 50%.

25. The microfluidic system of any of claims 19-24, wherein the additive is a hydrocarbon compound characterized by a molecular weight less than a user-selected molecular weight.

26. The microfluidic system of claim 25, wherein the additive is paraffin oil.

27. The microfluidic system of any of claims 19-26, wherein the thermoplastic elastomer has a weight ratio of additive to styrene copolymer selected from the range of 1 to 3.

28. The microfluidic system of any of claims 18-27, wherein the capping layer comprises a spatially distributed pattern of relief, recess, or relief and recess features to achieve a desired mechanical property while maintaining high barrier to water vapor or liquid transmission.

29. The microfluidic system of claim 28, wherein the pattern comprises a symmetrical pattern.

30. The microfluidic system of any of claim 28 or 29, wherein the pattern is selected to achieve a desired mechanical property of flexibility and stretchability of the capping layer that is substantially matched to the flexible substrate.

31. The microfluidic system of claim 30, wherein the mechanical property is Young's modulus of less than 100 MPa, a net bending stiffness of less than 1 nN m, and/or a thickness of less than 5 mm.

32. The microfluidic system of any of claims 28-31, wherein the pattern is spatially aligned with at least a portion of the microfluidic network.

33. The microfluidic system of any of claims 18-32, wherein the capping layer is at least partially formed of a rigid polymer selected from the group consisting of a polyolefin, a polyester, a fluorocarbon, a polyamide, a polyimide, and any combination thereof.

34. The microfluidic system of claim 33, wherein: the polyolefin is selected from the group consisting of polyethylene, polypropylene and polyisobutylene; the polyester is selected from the group consisting of polyethylene terephthalate and polyethylene naphthalate; the fluorocarbon is selected from the group consisting of polyvinylidene chloride and polytetrafluoroethylene; the polyamide is a nylon; and/or the polyimide is a poly-oxydiphenylene-pyromellitimide.

35. The microfluidic system of any of claims 18-34, further comprising an adhesive layer on the skin facing surface of the capping layer; wherein the adhesive layer comprises an adhesive compound capable of reversibly adhering the system to the skin surface.

36. The microfluidic system of claim 35, wherein the adhesive layer comprises medical-grade acrylic.

37. The microfluidic system of any of claims 35-36, wherein the substrate, the capping layer, the adhesive compound, or any combination thereof further comprise a tackifier additive.

38. The microfluidic system of claim 37, wherein the substrate, the capping layer, or both the functional substrate and the capping layer have a weight fraction of tackifier additive of between 30% to 80%.

39. The microfluidic system of any of claims 37-38, wherein the tackifier additive is rosin gum.

40. The microfluidic system of any of claims 19-39, wherein the microfluidic network comprises a plurality of reservoirs and a microfluidic inlet conduit network having a biofluid inlet to introduce the biofluid to the microfluidic network; and wherein the microfluidic outlet conduit network is fluidically connected to the plurality of reservoirs.

41. The microfluidic system of claim 40, wherein the microfluidic network further comprises a microfluidic outlet conduit network fluidically connected to the plurality of reservoirs, the microfluidic inlet conduit network, and an outlet, and wherein the outlet is configured to (i) provide for release of gas back pressure from the microfluidic inlet conduit network, and (ii) prevent ingress of a liquid from a surrounding environment into the microfluidic outlet conduit network.

42. The microfluidic system of any of claim 40 or 41, wherein the sensor is a colorimetric sensor.

43. The microfluidic system of any of claim 40 or 41, wherein the sensor is an electrochemical sensor.

44. The microfluidic system of any of claims 19-43 comprising two or more sensors, including at least one colorimetric sensor and one electrochemical sensor.

45. The microfluidic system of claim 44, wherein the colorimetric sensor is positioned in one of the plurality of reservoirs.

46. The microfluidic system of claim 44 or 45, wherein the electrochemical sensor is positioned in one of the plurality of reservoirs.

47. The microfluidic system of any of claims 1-46, further comprising a biofluid gelling additive or an absorbent contained within the microfluidic network.

48. The microfluidic system of claim 47, wherein the biofluid gelling additive comprises two or more unique biofluid gelling additives.

49. The microfluidic system of claim 47 or 48, wherein the biofluid gelling agent is configured to mix or react with the biofluid to increase a biofluid viscosity.

50. The microfluidic system of claim 49, wherein, the increase in biofluid viscosity is by at least a factor of 2 of the biofluid viscosity before mixing or reacting with the biofluid gelling agent.

51. The microfluidic system of any of claims 47-50, wherein the biofluid gelling agent comprises cellulose or a derivative thereof.

52. The microfluidic system of claim 51, wherein the biofluid gelling agent is methyl cellulose or hydroxypropyl methylcellulose.

53. The microfluidic system of any of claims 47-52, wherein the weight ratio of the biofluid gelling agent to biofluid, in at least one of the plurality of reservoirs, is selected from the range of 0.1 to 1.

54. The microfluidic system of any of claims 1-53, wherein the substrate is a functional substrate.

55. A microfluidic system, comprising:
a flexible substrate;
a microfluidic network at least partially embedded in or supported by the flexible substrate;
a sensor fluidically connected to the microfluidic network, wherein the microfluidic network is configured transport a biofluid from a skin surface to the sensor; and
a biofluid gelling additive or a biofluid absorbent contained in the microfluidic network to reduce biofluid loss from the microfluidic network.

56. The microfluidic system of claim 55, wherein the microfluidic network comprises: a plurality of reservoirs;
a biofluid inlet to introduce a biofluid to the microfluidic network; and
a microfluidic inlet conduit network fluidically connected to the biofluid inlet and the plurality of reservoirs to introduce a biofluid to the reservoirs.

57. The microfluidic system of claim 56, wherein the microfluidic network further comprises:
a microfluidic outlet conduit network fluidically connected to the plurality of reservoirs; and
an outlet fluidically connected to the microfluidic outlet conduit;
wherein the outlet is configured to:
provide for release of gas back pressure from the microfluidic inlet conduit network, and prevent ingress of a liquid from an environment surrounding the system into the microfluidic outlet conduit network.

58. The microfluidic system of any of claims 55-57, wherein the sensor is a colorimetric sensor.

59. The microfluidic system of any of claims 55-57, wherein the sensor is an electrochemical sensor.

60. The microfluidic system of any of claims 55-59, comprising two or more sensors.

61. The microfluidic system of claim 58, wherein the colorimetric sensor is positioned in one of the plurality of reservoirs.

62. The microfluidic system of claim 59, wherein the electrochemical sensor is positioned in one of the plurality of reservoirs.

63. The microfluidic system of any of claims 55-62, wherein the biofluid gelling additive is positioned in at least one of the plurality of reservoirs.

64. The microfluidic system of any of claims 55-63, comprising two or more biofluid gelling additives.

65. The microfluidic system of any of claims 55-64, wherein the biofluid gelling agent is configured to mix or react with the biofluid to increase a biofluid viscosity.

66. The microfluidic system of claim 65, wherein, the increase in biofluid viscosity is by at least a factor of 2 of the biofluid viscosity before mixing or reacting with the biofluid gelling agent.

67. The microfluidic system of any of claims 55-66, wherein the biofluid gelling agent is at least partially formed of cellulose or a derivative thereof.

68. The microfluidic system of claim 67, wherein the biofluid gelling agent is methyl cellulose or hydroxypropyl methylcellulose.

69. The microfluidic system of any of claims 55-68, wherein the weight ratio of the biofluid gelling agent to biofluid, in at least one of the plurality of reservoirs, is selected from the range of 0.1 to 1.

70. The microfluidic system of any of claims 55-69, further comprising a capping layer, having a capping layer skin facing surface and a back surface, wherein the back surface is affixed to a skin facing surface of the substrate.

71. The microfluidic system of any of claims 55-70, wherein the substrate is at least partially formed of a thermoplastic elastomer having an additive.

72. The microfluidic system of any of claims 70-71, wherein the capping layer is at least partially formed of a thermoplastic elastomer and an additive.

73. The microfluidic system of claim 72, wherein the substrate and the capping layer each comprise: a common thermoplastic elastomer composition, or a different thermoplastic elastomer composition.

74. The microfluidic system of any of claims 72-73, wherein the substrate and the capping layer have a common additive.

75. The microfluidic system of any of claims 71-74 wherein the thermoplastic elastomer is a styrene copolymer selected from the group consisting of styrene-ethylene-butadiene-styrene (SEBS), styrene-isoprene-styrene (SIS), styrene-butadiene-styrene (SBS), and any combination thereof.

76. The microfluidic system of claim 75, wherein the thermoplastic elastomer has a weight fraction of styrene copolymer selected from the range of 10% to 50%

77. The microfluidic system of any of claims 71-76, wherein the additive is a hydrocarbon compound characterized by a molecular weight less than a user-selected molecular weight.

78. The microfluidic system of claim 77, wherein the additive is paraffin oil.

79. The microfluidic system of any of claims 70-78, wherein the thermoplastic elastomer has a weight ratio of additive to styrene copolymer selected from the range of 1 to 3.

80. The microfluidic system of any of claims 70-79, wherein the capping layer comprises a spatially distributed pattern of relief, recess, or relief and recess features to achieve a desired mechanical property while maintaining high barrier to water vapor or liquid transmission.

81. The microfluidic system of claim 80, wherein the pattern comprises a symmetrical pattern.

82. The microfluidic system of any of claim 80 or 81, wherein the pattern is selected to achieve a desired mechanical property of flexibility and stretchability of the capping layer that is substantially matched to the flexible substrate, wherein the mechanical property is one or more of a Young's modulus, a bending stiffness or an average thickness.

83. The microfluidic system of any of claims 81-82, wherein the pattern is spatially aligned with at least a portion of the microfluidic network.

84. The microfluidic system of any of claims 55-83 wherein the capping layer is at least partially formed of a rigid polymer selected from the group of a polyolefin, a polyester, a fluorocarbon, a polyamide, a polyimide, and any combination thereof.

85. The microfluidic system of claim 84, wherein: the polyolefin is selected from the group consisting of polyethylene, polypropylene and polyisobutylene; the polyester is selected from the group consisting of polyethylene terephthalate and polyethylene naphthalate; the fluorocarbon is selected from the group consisting of polyvinylidene chloride and polytetrafluoroethylene; the polyamide is a nylon; and/or the polyimide is a poly-oxydiphenylene-pyromellitimide.

86. The microfluidic system of any of claims 55-85, further comprising an adhesive layer on the skin facing surface of the capping layer; wherein the adhesive layer comprises an adhesive compound capable of reversibly adhering the system to the skin surface.

87. The microfluidic system of claim 86, wherein the adhesive layer comprises medical-grade acrylic.

88. The microfluidic system of any of claims 86-87, wherein the substrate, the capping layer, the adhesive layer, or any combination thereof further comprise a tackifier additive.

89. The microfluidic system of claim 88, wherein the substrate, the capping layer, or both the substrate and the capping layer have a weight fraction of tackifier additive of between 30% to 80%.

90. The microfluidic system of any of claims 88-89, wherein the tackifier additive is rosin gum.

91. The microfluidic system of any of claims 1-80, further comprising an expunge port fluidically connected with the reservoir chamber for the removal of biofluid from the reservoir chamber.

92. An epidermally-mountable microfluidic system for measuring a characteristic of a biofluid from a skin surface; the system comprising:
a flexible substrate;
a biofluid inlet embedded on or supported by the substrate for receiving the biofluid from the skin surface; and
a microfluidic channel fluidically connected to the biofluid inlet for receiving at least a portion of a biofluid from the biofluid inlet, the microfluidic channel having a patterned grating;
wherein transmission of incident electromagnetic radiation through the patterned grating changes as a function of a biofluid amount in the microfluidic channel.

93. The system of claim 92, wherein the epidermal microfluidic system further comprises an indicator in optical communication the patterned grating; wherein changes in the transmission of incident electromagnetic radiation through the grating changes the appearance of the indicator.

94. The system of any of claims 92-93, wherein the patterned grating comprises a hydrophilic polymer; and wherein transmission of the incident electromagnetic radiation by the patterned grating increases when the chamber is filled with the biofluid.

95. The system of any of claims 92-93, wherein the patterned grating comprises a hydrophobic polymer; and wherein transmission of the incident electromagnetic radiation by the patterned grating decreases when the chamber is filled with the biofluid.

96. The system of any of claims 92-95, wherein the epidermal microfluidic system further comprises an expunge port fluidically connected with the reservoir chamber for the removal of the biofluid from the reservoir chamber.

97. The system of any of claims 92-96, further comprising an adhesive layer.

98. The system of claim 97, wherein the adhesive layer comprises an adhesive capable of reversibly adhering to the skin surface.

99. The system of claim 97, wherein the adhesive layer comprises medical grade acrylic or medical grade silicone.

100. The system of any of claims 96-99, wherein the expunge port comprises two outlets.

101. The system of any of claims 96-100, further comprising a capillary burst valve fluidically connected to said expunge port and said reservoir chamber.

102. The system of claim 101, wherein said capillary burst valve is positioned between said expunge port and said reservoir chamber.

103. The system of any of claims 92-102, wherein said patterned grating is nanopatterned or micropatterned.

104. An epidermal microfluidic system for measuring a characteristic of a biofluid; the system comprising:
a flexible substrate;
a collection layer embedded in or supported by the flexible substrate, wherein the collection layer promotes transport of the biofluid from the skin surface;
at least one reservoir chamber embedded in or supported by the flexible substrate and fluidically connected to the collection layer, the reservoir chamber having:
an absorbent provided to receive at least a portion of the biofluid from the collection layer; and
a sensor for measuring a characteristic of the biofluid received by the absorbent; wherein the absorbent provides a force for transporting the biofluid that is greater than a capillary force of the collection layer for transporting the biofluid.

105. An epidermal microfluidic system for measuring a characteristic of a biofluid, the system comprising:
a flexible substrate;
a radiofrequency (RF) heater embedded in or supported by the flexible substrate; wherein the RF heater is capable of increasing a temperature of the skin surface, thereby increasing the release rate of the biofluid;
at least one sensor embedded in or supported by the flexible substrate to measure the characteristic of the biofluid.

106. The microfluidic system of claims 104-105, wherein the biofluid characteristic is amount of sweat loss or presence or absence of a biomarker from a skin surface.

107. The system of any of claims 104-106, wherein the sensor is an electronic sensor.

108. The system of claim 107, wherein the electronic sensor comprises one or more high sensitivity electrodes configured to measure a change in an electrical parameter caused by biofluid received by the absorbent.

109. The system of claim 108, wherein the electrical parameter is capacitance.

110. The system of any of claims 104-109, wherein the sensor comprises one or more colorimetric assay reagents.

111. The system of any of claims 104-110, further comprising a wireless communication device for transmitting wireless information corresponding to a characteristic of the biofluid from the skin surface.

112. The system of any of claims 1-111, wherein said flexible substrate comprises a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, chitosan, and any combination thereof.

113. The system of any of claims 1-112, further comprising an adhesive layer configured to mount the system to a skin surface.

114. The system of claim 113, wherein the adhesive layer reversibly adheres the system to the skin surface.

115. The system or claim 114, wherein the adhesive layer comprises medical grade acrylic or medical grade silicon.

116. The system of any of claims 1-115, further comprising a protective layer embedded in or supported by the flexible substrate.

117. The system of claim 116, wherein the protective layer prevents biofluid from escaping from the reservoir chamber or the sweat sensor.

118. The system of claim 116, wherein said protective layer is polyethylene.

119. The system of claim 104, wherein the collection layer has an average thickness selected from the range of 50 μm to 1 mm.

120. The system of claim 104 or 119, wherein the collection layer is a mesh.

121. The system of claim 104 or 119, wherein the collection layer has a plurality of pores having an average diameter selected from the range of 10 μm to 250 μm.

122. The system of claim 104 or 119, wherein the collection layer is polyester.

123. The system any of claims 1-122 that is incorporated into a glove.

124. The system of any of claims 1-123, wherein the biofluid property is visually observable.

125. The system of any of claims 1-123, wherein a signal corresponding to the biofluid property is transmitted from said system to an external receiving device.

126. The system of any of claims 1-125, wherein the biofluid property is one or more of sweat volume, sweat rate, or sweat loss.

127. The system of any of claims 1-125, wherein the biofluid property is pH.

128. The system of any of claims 1-125, wherein the biofluid property comprises the presence of, amount or concentration of an analyte in said biofluid or component thereof.

129. The system of claim 128, wherein said analyte is an electrolyte, a metabolite, or a biomarker in said biofluid or component thereof.

130. The system of any of claims 1-129, wherein a leading edge of biofluid in a sensor microfluidic channel or reservoir is sensed as a function of time.

131. The system of claim 130, wherein the leading edge is sensed visually or measured using a photodetector.

132. The system of any of claims 1-131, wherein the flexible substrate is a functional substrate.

133. The system of any of claims 1-132, further comprising an electronic sensor operably connected to the microfluidic network, wherein an amount of biofluid is proportional to an electrical resistivity or electrical conductivity parameter measured by the sensor.

134. The system of any of claims 1-133, comprising a disposable portion comprising the microfluidics network and a reusable portion corresponding to an electronic device, wherein the disposable and reusable portions are connected to each other by one or more selectively releasable coupling elements.

135. The system of claim 134, wherein the selectively releasable coupling elements comprise a magnet.

136. The system of any of claims 1-135, comprising a plurality of distinct component layers arranged in a stacked configuration.

137. A method of analyzing biofluid from a subject, the method comprising the steps of: contacting the flexible substrate of any claims 1-136 with a skin surface of a subject; and analyzing the biofluid from the skin surface.

138. The method of claim 137, wherein said biofluid is sweat.

139. The method of any of claims 137-138, wherein said subject is a human subject.

140. The method of any of claims 137-138, wherein said subject is a human subject undergoing a diagnostic procedure.

141. The method of any of claims 137-138, wherein said subject is a human subject undergoing a therapeutic procedure.

142. The method of any of claims 137-138, wherein said subject is a human subject monitoring the presence, onset or progression of a disease condition.

143. The method of any of claims 137-138, wherein said subject is a human subject undergoing a fitness activity.

144. The method of any of claims 137-138, further comprising the step of increasing biofluid retention in the system by one or more of:
increasing biofluid viscosity in the microfluidic network; and/or absorbing biofluid to an absorbent.

145. The method of any of claims 137-144, wherein the analyzing comprises: observing biofluid volume in at least a portion of the microfluidic network; and/or observing a colorimetric change in a reservoir chamber.

146. The method of any of claims 137-145, wherein the contacting comprises conformally contacting the flexible substrate with the skin surface, and any intervening layers between the flexible substrate and the skin surface.

BRIEF DESCRIPTION OF THE DRAWINGS

FIG. 17 shows: Left, Cross section of a single microfluidic chamber containing a viscosity modifier (HPMC). Right, Comparison of a chamber filled with sweat with and without HPMC. Pressing the chamber without the modifier causes the CBV's to burst releasing the captured sweat. The chamber with HPMC does not burst in response to pressing, reflecting additional stability to the chamber and burst valve with a viscosity modifier.

FIG. 20 shows: (A) Schematic illustrating the exploded view of a hybrid battery-free system. Close-up image of (B) micro-fluidic patch with embedded sensors (C) battery-free NFC electronics. (D) Image illustrating the reversible magnetic attachment of the NFC electronics to the micro-fluidic patch. (E) Image of the complete system (F) Image illustrating device during sweating. (G) A phone interface that illustrates wireless communication and image acquisition.

FIG. 28 shows: (A) Schematic illustration of capillary bursting valves in a colorimetric detection chamber. (B) Schematic illustration of microfluidic channel: 1) Glucose detection chamber 2) lactate detection chamber 3) chloride chrono detection chambers 4) pH chrono detection chambers 5) sweat rate detection chamber. In this manner, any of the systems may be characterized as providing multiplexed detection, including with respect to time.

FIG. 36 shows an exemplary multilayer device having separate layer components in a stacked configuration. The layers can be individually patterned to facilitate any number of desired functionality, such as fluid transport through an adhesive layer, collection and analysis (analytics layer), fluid barrier layer (capping layer) with an outlet port for removal of biofluid.

FIG. 37 shows top panel (labeled as A) is a schematic of a collection device. (B) The device collection layer (1) comprises three independent chambers (e.g., three individual microfluidic networks), each with an inlet and outlet.

FIG. 65 shows: (A) Optical image of an epidermal collection device with integrated chloride colorimetric assay reservoirs. (B) The colorimetric assay increases in color intensity (violet) with increasing chloride concentration. When captured using a smartphone camera, the color provides a quantitative analysis of chloride levels.

(c) Correlation of sweat collection for a microfluidic device from the anterior forearm versus the normalized total body loss (based on initial weigh-in and final weigh-out with no fluid intake or restroom use during exercise). d) Correlation of sweat collection for a microfluidic device versus an absorbent patch. (e) Cumulative local sweat loss versus time measured from the forearm with a microfluidic device during exercise, while at rest, and during a subsequent exercise session.

Figure 68:
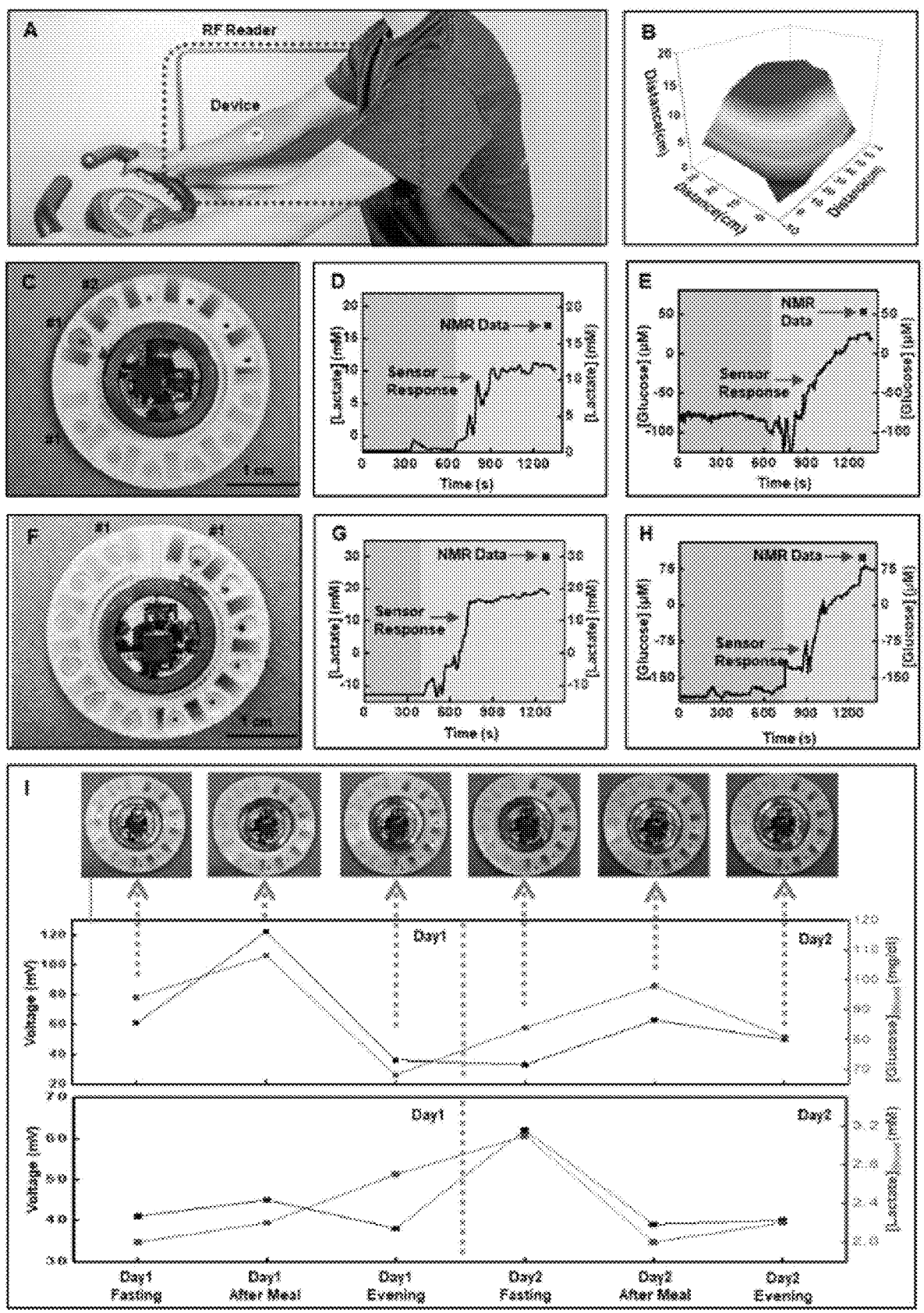

FIG. 68 shows human trials. (A) Photograph of a subject adorning the wireless battery-free hybrid sensor system. (B) Reading distance of device with large NFC antenna. (C) Image of complete system captured after a bout of cycling by a subject. Real-time wirelessly acquired sweat concentration levels for (D) lactate and (E) glucose. (F) Image of complete system captured after a bout of cycling by a subject. Real-time wirelessly acquired sweat concentration levels for (G) lactate and (H) glucose. (I) Correlation of data acquired from biofuel cell-based glucose and lactate sweat sensors with that acquired from blood glucose and lactate meter over a period of two days for subject #1. (D, E, G and H) Blue region represents no sweat while green indicates sweating of the human subjects.

Figure 69:
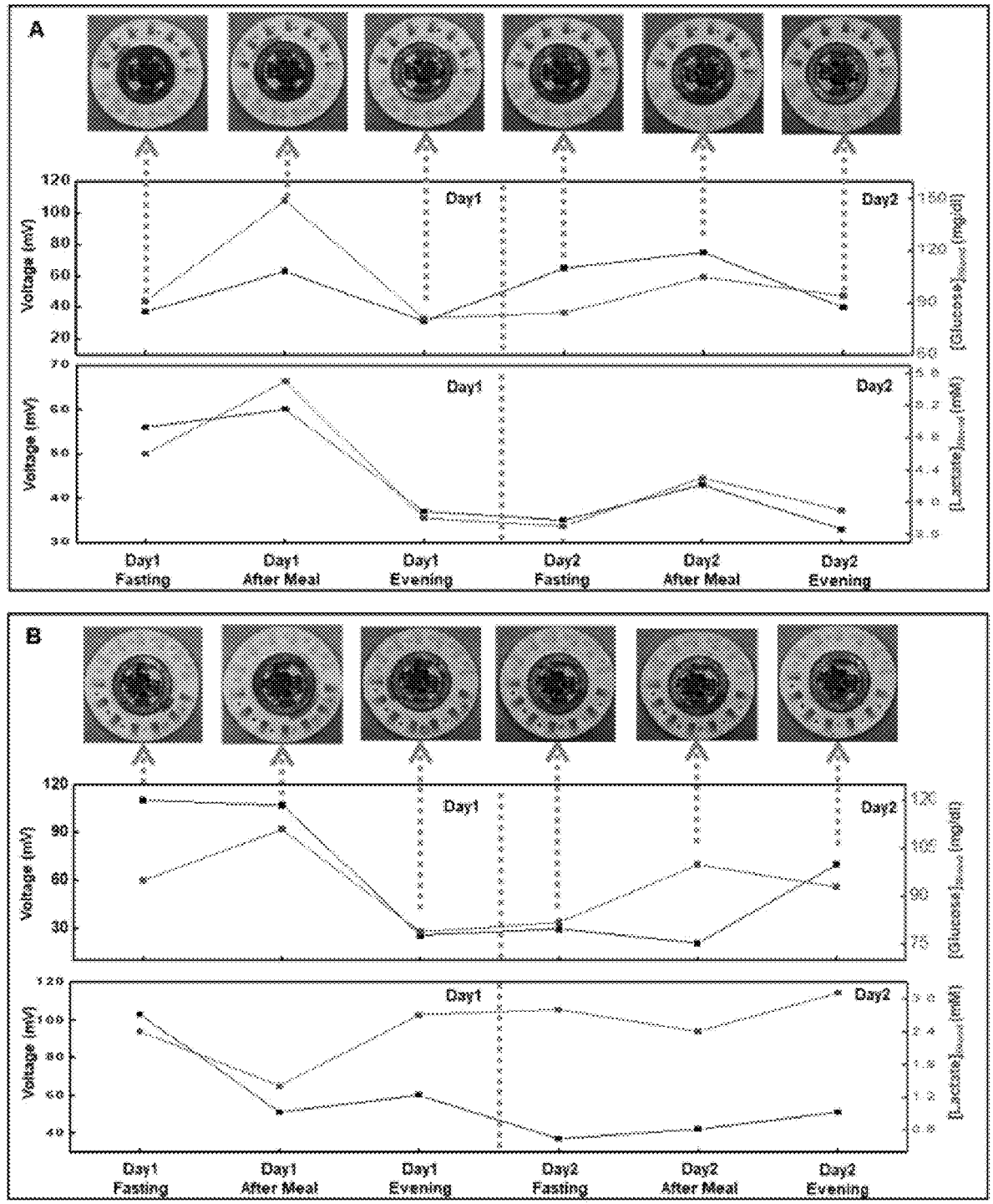

FIG. 69 shows correlation of data acquired from biofuel cell-based glucose and lactate sweat sensors with that acquired from blood glucose and lactate meter over a period of two days for (A) subject #2 and (B) subject #3.

Figure 70:
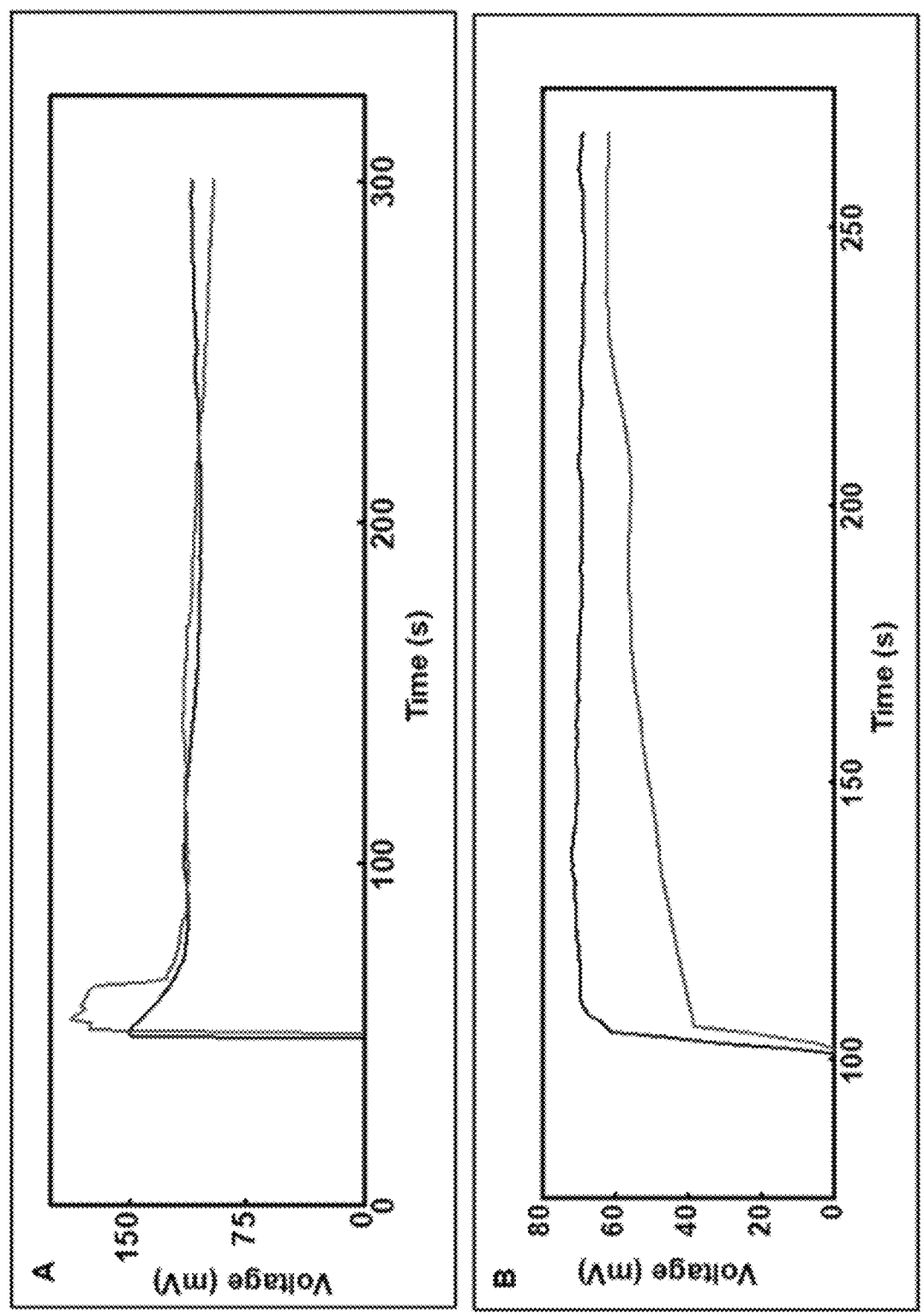

FIG. 70 shows: (A) Comparison of signal of fresh, unused glucose sensor (black) with that obtained from one after two-day human trial (red) when exposed to 300 μM glucose solution. (B) Comparison of signal of fresh, unused lactate sensor (black) with that obtained from one after two-day human trial (red) when exposed to 10 mM lactate solution.

Figure 71:
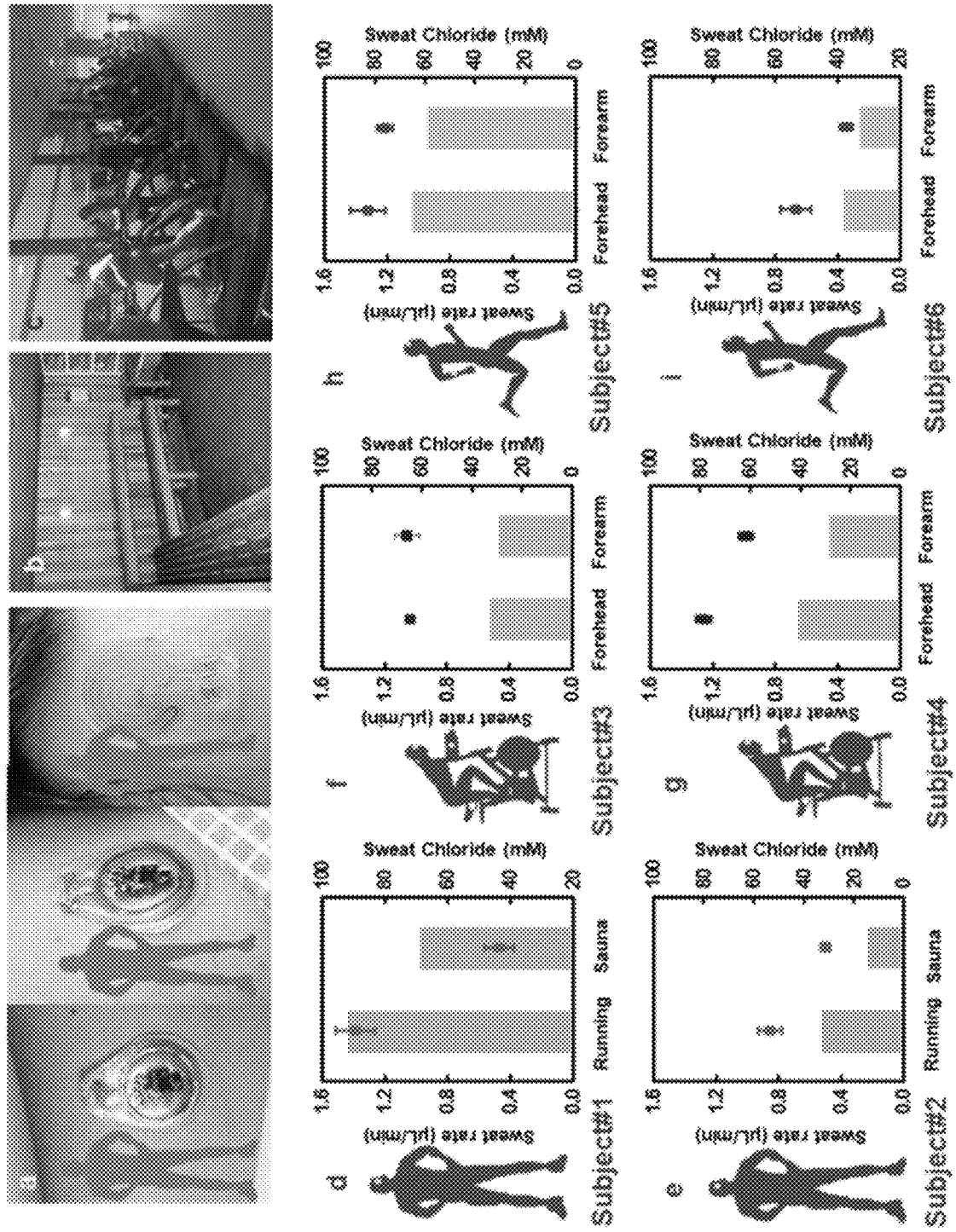

FIG. 71 shows human tests a: Various location on which the device is placed for the human tests, b: The sauna environment for thermal sweat test, c: The gym environment for exercise sweat test, d and e: The comparison of sweat excretion rate and sweat chloride concentration at running and sauna conditions with subject #1 and subject #2, and f-i: The comparison of sweat excretion rate and sweat chloride concentration at the device location, placed on forehead and forearm with subject #3, subject #4, subject #5, and subject #6.

Figure 72:
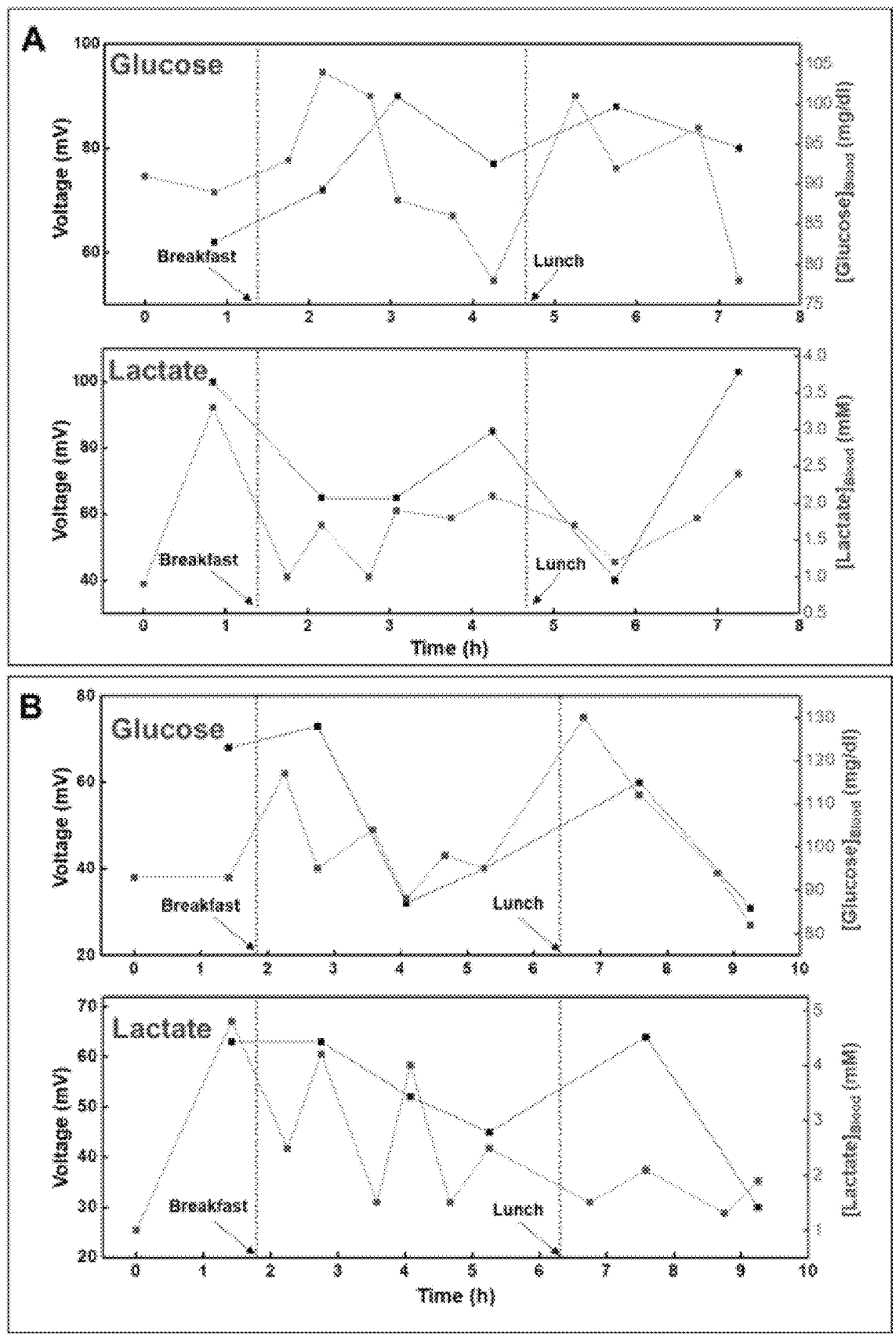

FIG. 72 shows correlation of data acquired from biofuel cell-based glucose and lactate sweat sensors with those acquired from blood glucose and lactate meters over a period of one day for (A) subject #1 and (B) subject #2.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Microfluidic device" refers to a system, device or device component containing liquid constrained in at least one physical dimension generally of the order of nanometers to millimeters, optionally nanometers to microns. Microfluidic devices may include structures for collecting, extracting, transporting, storing, analyzing and/or outputting fluids, including biofluids.

In some embodiments, the liquid is constrained to a lateral dimension selected over the range of 1 nm and 1 cm, such as a lateral dimension (e.g., depth) selected over the range of 1 nm to 5 mm, 100 nm to 1000 μm or 500 nm to 100 μm, and a lateral dimension (e.g., width) selected over the range of 1 nm to 1 cm, 10 μm to 2 mm or 1 μm to 10 mm. In embodiments, an axial (e.g., flow) direction in a microfluidic system, device or device component can be long, for example on the order of meters, but will more commonly be 0.1 cm to 100 cm or 1 cm to 50 cm. Microfluidics are distinguished herein from macrofluidics. In some embodiments, the invention provides tissue mounted, optionally skin mounted, microfluidic devices. Microfluidic devices of some embodiments are capable of determining the composition of a biofluid such as sweat, for example, the presence, absence, and/or amount of one or more biomarkers, optionally as a function of time. Microfluidic devices of some embodiments are capable of determining one or more physical parameters characteristics of a biofluid, such as amount, volume, release rate and/or absorption rate, optionally as a function of time.

"Tissue-mounted" refers to systems, devices or device components having at least one surface capable of being supported, directly or indirectly, by a tissue surface, for example in a configuration providing fluidic communication and/or conformal contact. Epidermal systems and devices are a subset of tissue-mounted systems wherein the system, device or device component has at least one surface capable of being supported, directly or indirectly, by a surface of the skin, for example in a configuration providing fluidic communication and/or conformal contact. The invention provides tissue-mounted devices, such as epidermal systems, capable of collection, storage, treatment, processing, handling and/or analysis of biofluids such as sweat.

The expression "at least partially embedded in" refers to a configuration wherein an element, such as a microfluidic network or component thereof, is at least partially, and optionally wholly, integrated on or within a layer and/or device component, such as a substrate. In an embodiment, for example, "at least partially embedded in" refers to a configuration wherein an embedded element, such as a microfluidic element such as an inlet, outlet, passage, channel, and/or reservoir, at least partially comprises one or more surfaces, recessed features, relief features or any combination thereof, within or on a layer or device component it is at least partially embedded in. In an embodiment, for example, "at least partially embedded in" refers to a configuration wherein an embedded element, such as an inlet, outlet, passage, channel, and/or reservoir, at least partially comprises features molded or embossed on or into a layer or device component it is at least partially embedded in. In an embodiment, for example, "at least partially embedded in" refers to a configuration wherein an embedded element, such as an inlet, outlet, passage, channel, and/or reservoir, at least partially comprises features at least partially comprising surfaces (e.g., top, bottom, walls, etc.) of a layer or device component it is at least partially embedded. In an embodiment, for example, "at least partially embedded in" refers to a configuration wherein an embedded element, such as an inlet, outlet, passage, channel, and/or reservoir, is at least partially covered or encapsulated by another device component, such as an top layer or barrier layer.

"Substrate" refers to a device component, such as a layer, having a surface that is capable of supporting, accommodating, embedding or otherwise integrating a structure, including a microfluidic structure, optical structure, electronic structure, thermal structure or any combination of these. Substrates in some embodiments are capable of supporting, accommodating, embedding or otherwise integrating a device component such as microfluidic device component, optical device component, electronic device component, structural device component or any combination of these. In some embodiments, a substrate is capable of at least partially forming an interface with the tissue of a subject, such as with the epidermis or other organ of a subject. In an embodiment, a substrate of the present devices, systems and methods is a biocompatible and/or bioinert material. In an embodiment, a substrate of the present devices, systems and methods is a polymer or elastomer material. Substrates of the invention include "functional substrates" which refers to a substrate component for a device having at least one function or purpose in addition to providing mechanical support for a component(s) disposed on or within the substrate such as a microfluidic functionality, a mechanical functionality, optical functionality or a thermal functionality. A functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another. Devices and systems of the invention may have more than one substrate, for example, such as embodiments having a bottom substrate capable of establishing an interface with skin and an upper substrate layer, such as a barrier layer providing an interface with an ambient environment. For example, the invention includes devices and systems having a multilayer geometry including a substrate and barrier layer.

In some embodiments, a substrate is mechanically matched to a tissue, such as mechanically matched to skin. In an embodiment, a mechanically matched substrate is optionally capable of providing an interface for establishing fluid communication and/or conformal contact with a surface of the tissue, such as skin. Devices and methods of certain embodiments incorporate substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a desired contour profile, for example a contour profile allowing for conformal contact with a surface characterized by a surface topography comprising recessed and/or relief features. In certain embodiments, a desired contour profile is that of tissue, such as skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In some embodiments, devices of the invention are capable of establishing conformal contact with tissue of a subject, such as a portion of the skin of a subject.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Sensing" refers to an action of detecting the presence, absence, amount, magnitude and/or intensity of one or more physical and/or chemical properties or characteristics. Sensor refers to a device or component thereof that is capable of sensing. Useful device components for sensing include, but are not limited to electrode elements, chemical or biological sensor elements, pH sensors, colorimetric sensors, electrochemical sensors, temperature sensors, strain sensors, mechanical sensors, position sensors, optical sensors and capacitive sensors.

"Actuating" refers to an action of acting on, stimulating, controlling, or otherwise affecting a structure, material or device component. Actuator refers to a device or component thereof that is capable of actuating. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 10000 microns, optionally less than 1000 microns and optionally less than 100 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, stretchable structures may also be flexible. Some stretchable structures (e.g., device components) are engineered to be able to undergo compression, elongation and/or twisting so as to be able to deform (and optionally operate) without fracturing. Stretchable structures include structures comprising stretchable materials, such as elastomers; and bent, coiled or serpentine structures capable of elongation, compression and/or twisting motion.

Devices of the present invention may optionally include one or more barrier layers. As used herein "barrier layer" refers to a device component spatially separating two or more other device components or spatially separating a device component from a structure, material, fluid or ambient environment external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid.

"Biofluid" refers to fluid generated by, extracted from or otherwise derived from the tissue of a subject, such as an organ of a subject. Biofluids include sweat, tears, saliva, gingival crevicular fluid, interstitial fluid, blood and combinations thereof.

As used herein, the term "fluidically connected" refers to the configuration of two or more components such that a fluid (e.g., a gas or a liquid) is capable of transport, flowing and/or diffusing from one component to another component, without adversely impacting the functionality of each of the components. Components may be in fluid communication via one or more elements such as channels, valves, tubes, containment structures, reservoirs, pumps or any combinations of these. Components may be in fluid communication are in a direct fluid communication manner wherein fluid is capable of transport directly from one component to another. Components may be in fluid communication in an indirect fluid communication manner wherein fluid is capable of transport indirectly from one component to another via one or more intermediate structures separating the components.

The term "operably connected" refers to a configuration of elements, wherein an action or reaction of one element affects another element, but in a manner that preserves each element's functionality. In an illustrative example, an electrochemical sensor operably connected to an electronic device providing for wireless power harvesting refers to the ability of the electrochemical sensor to be connected to the electronic device in such a way as to receive wireless power without adversely impacting the functionality of the electrochemical sensor and the electronic device. In another illustrative example, a sensor (e.g., capacitive sensor) operably connected to a microfluidic network refers to the sensor's ability to sense one or more parameters of a biofluid, or component thereof, which is being transported by the microfluidic network, without adversely impacting the functionality of the sensor or of the microfluidic network. The connection may be by a direct physical contact between elements. The connection may be indirect, with another element that indirectly connects the operably connected elements. For example, a capacitive sensor may be indirectly connected to the microfluidic network, with a dielectric layer physically separating the sensor and the microfluidic network.

The terms "electrical contact" and "electronic contact" refers to the ability of two or more materials and/or structures that are capable of transferring charge between them, such as in the form of the transfer of electrons or ions. The terms "electrical contact" and "electronic contact" may refer to a configuration of two or more components such that an electronic signal or charge carrier can be directly or indirectly transferred from one component to another. As used herein, the terms "electrical contact" and "electronic contact" include one way and two way electrical communication. In some embodiments, components in electrical contact or electronic contact are in indirect electrical communication wherein an electronic signal or charge carrier is indirectly transferred from one component to another via one or more intermediate structures, such as circuit elements, separating the components.

As used herein, the term "electrical load" may refer to voltage or current applied to electrodes, sensors or other device components. The term "electrical response" or "electrical parameter" may refer to a voltage, current, or impedance response of the electrodes or sensors to the electrical load. For example, applying a current between two electrodes (electrical load) may induce a voltage drop between the two electrodes (electrical response). The electrical load may be a DC or an AC load.

The term "BLE" refers to a Bluetooth low energy system.

The term "functionalized" may refer to modification of a material or layer surface to add chemical, physical, electrical, optical or electrochemical functionality. In an embodiment, biological molecules or reagents may be deposited onto an electrode in a process of forming an electrochemical sensor.

The term "wet environment" may refer to the system being in a high-humidity environment or being at least partially surrounded by a liquid. The term "high-humidity" refers to the relative humidity of the surroundings being >70%.

Provided herein are examples related to epidermal microfluidic systems and methods, including device architectures, components specifications, for temporally resolved epidermal sampling, collection and sensing of biofluids (e.g., sweat) and complementary methods of making and using the devices. Relevant device parameters and ranges for enabling well-defined temporal characterization of sweat including quantitative measurements of sweat rate, pressure and volume are described.

Other aspects include: Inlet, microfluidic network and CBV geometries, materials and dimensions for chrono-sampling; composite and multi-layer encapsulation and reinforcement strategies to mitigate fluid loss and address mechanical motion; microfluidic designs to address both high and low sweat regimes; integration of active and passive components to adjust sweat flow (e.g., absorbents, heaters, etc.); re-usable microfluidic systems; underwater microfluidic systems; Fluid purge and reset functionality.

Also provided herein are Epidermal Sensing Systems for Optical Readout, Visualization and Analysis of Biofluids. Provided are sensing systems and methods, including device architectures, components and specifications for optical readout, visualization and analysis of biofluids and components thereof (e.g., biomarkers), as well as complementary methods of making and using the devices.

Referring to the figures presented herein, a microfluidic system 10 may comprise a flexible substrate 20 and at least two microfluidic networks 30 40, with each network comprising a microfluidic inlet conduit network 40, a biofluid inlet 50 and a plurality of reservoir chambers 60. A plurality of capillary burst valves 70 may be in fluidic contact the microfluidic conduit network, with a valve positioned between fluidically adjacent reservoir chambers. To assist in fluid filling observation, colorimetric sensors 80 may be positioned in reservoir chambers. Microfluidic outlet conduit 90 may connect to the chamber 60, including to relieve gas back pressure to the chamber, thereby improving controlled and accurate filling of chambers.

Figure 7:
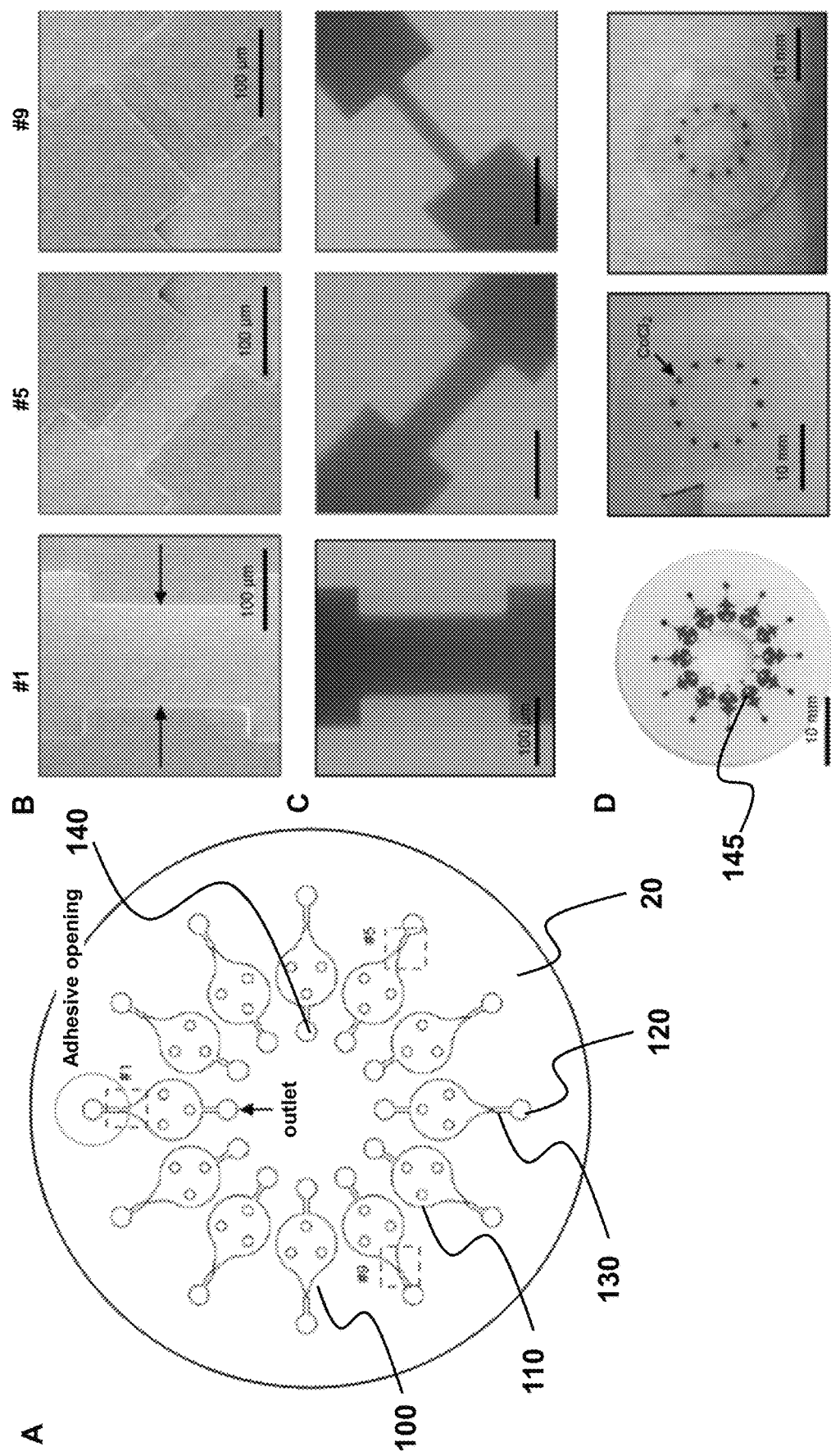
FIG. 7 shows: (A) schematic of the pressure measurement device with 12 different CBV; (B) The scanning electron micrograph (SEM) images of the CBVs, showing different sizes of different CBVs; (C) the optical microscopic images of blue dyed filled CBVs. (D) optical image of blue dyed filled device and $CoCl_2$ applied device on the skin.

Referring particularly to FIG. 7, a plurality of reservoir networks 100 may be embedded in flexible substrate 20. Each reservoir network 100 may comprise reservoir chambers 110, biofluid inlet 120, capillary burst valve 130, and outlet 140 fluidically connected to the reservoir chamber. A colorimetric sensor or fluid indicator 145 may assist with visualization of fluid filling in the network. In a similar manner, a color indicator strip 150 may be positioned between fluidically adjacent reservoir chambers 110 (see, e.g., FIG. 12).

Other examples of sensors beyond color-changing sensors, include sensors having electric or electronic components, including the sensors 160 illustrated in FIG. 20. As desired, a capping layer 170 may be provided on the top and/or skin-facing surface of the system. As desired, an adhesive layer 200 may help facilitate intimate and reliable skin surface contact. The capping layer may be patterned, such as with relief 172 and/or recess 174 features, including a recess feature that may be a passage to facilitate biofluid entry.

A biofluid gelling additive 210 may be provided in the microfluidic network, such as to increase viscosity (FIG. 17). An absorbent(s) 270 may be used in the microfluidic network.

Figure 29:
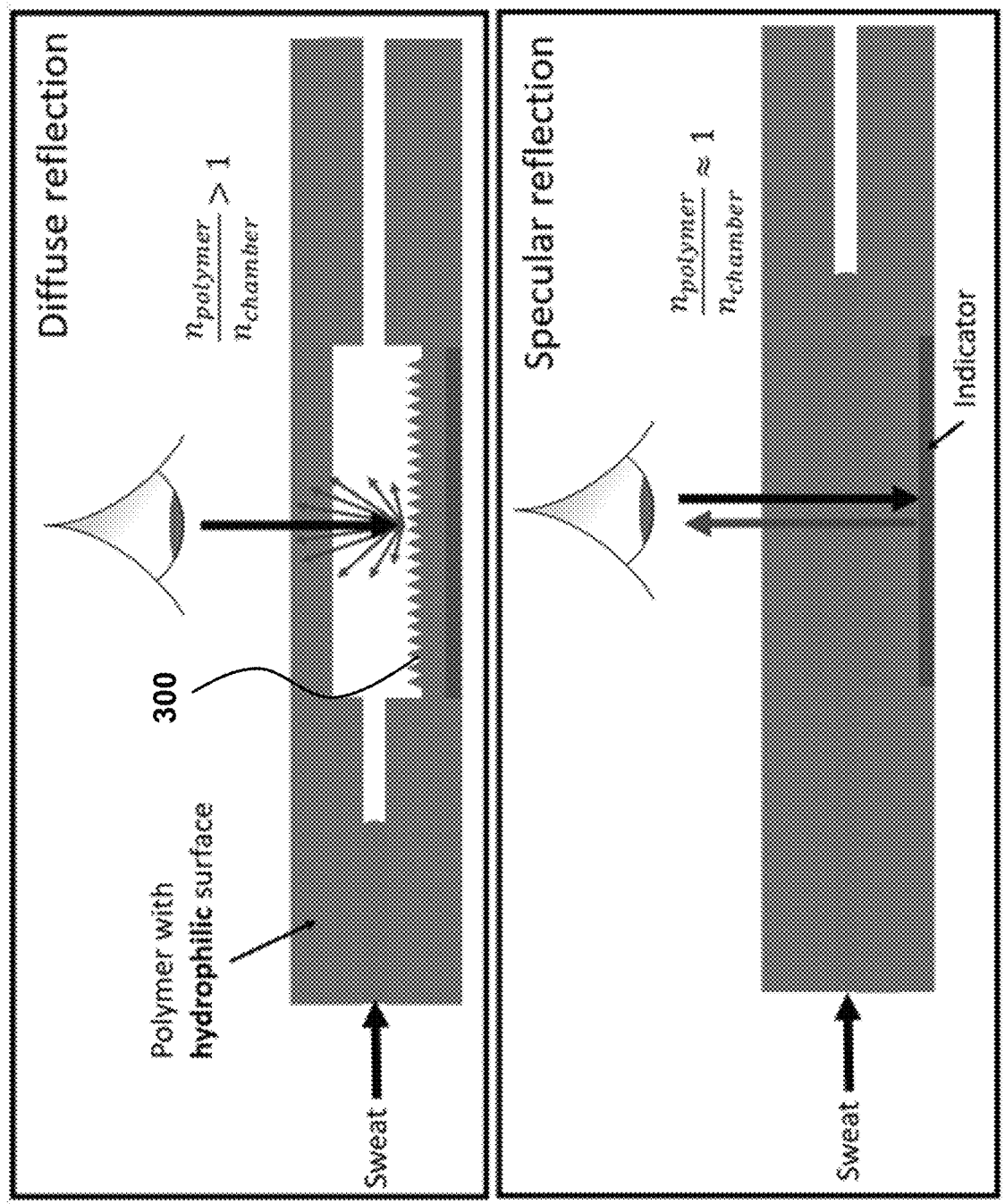
FIG. 29 illustrates a nano/micro patterned grating in a hydrophilic polymer which diffuses light when the chamber is empty, but transmits light when the chamber is full. A micropatterned grating in a hydrophilic surface scatters light when there is a refractive index mismatch and transmits light when the mismatch is negligible.
Figure 30:
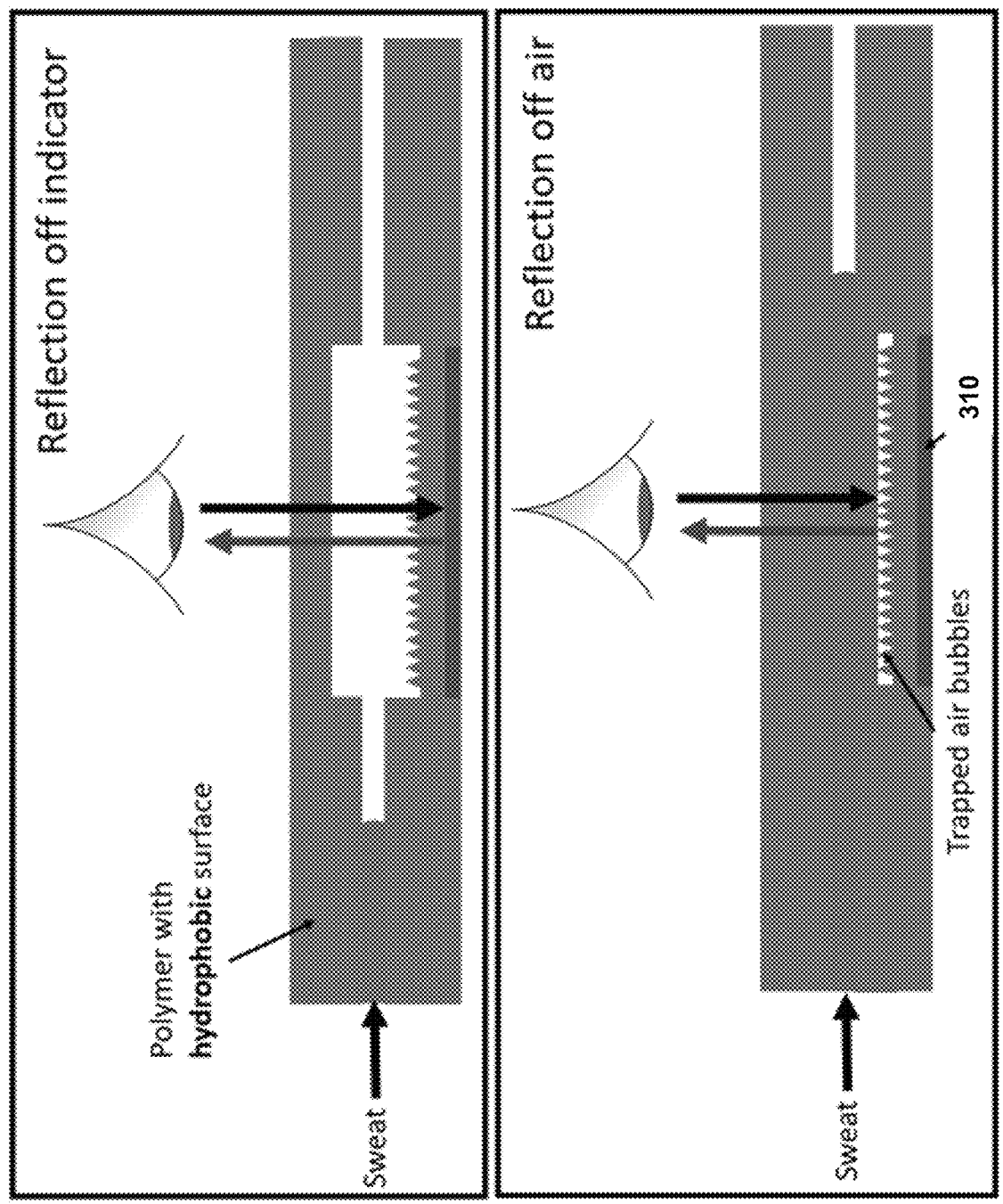
FIG. 30 illustrates a similar concept, but utilizes a hydrophobic polymer surface and a nano/micro patterned grating to trap air bubbles which reflect light when the chamber is full. Patterned features in a hydrophobic surface trap air bubbles when filled with sweat and reflect incident light, changing the appearance of the colored indicator.

FIGS. 29-30 illustrate use of patterned gratings 300 and indicators 310 to help facilitate observation of biofluid in the system.

Figure 31:
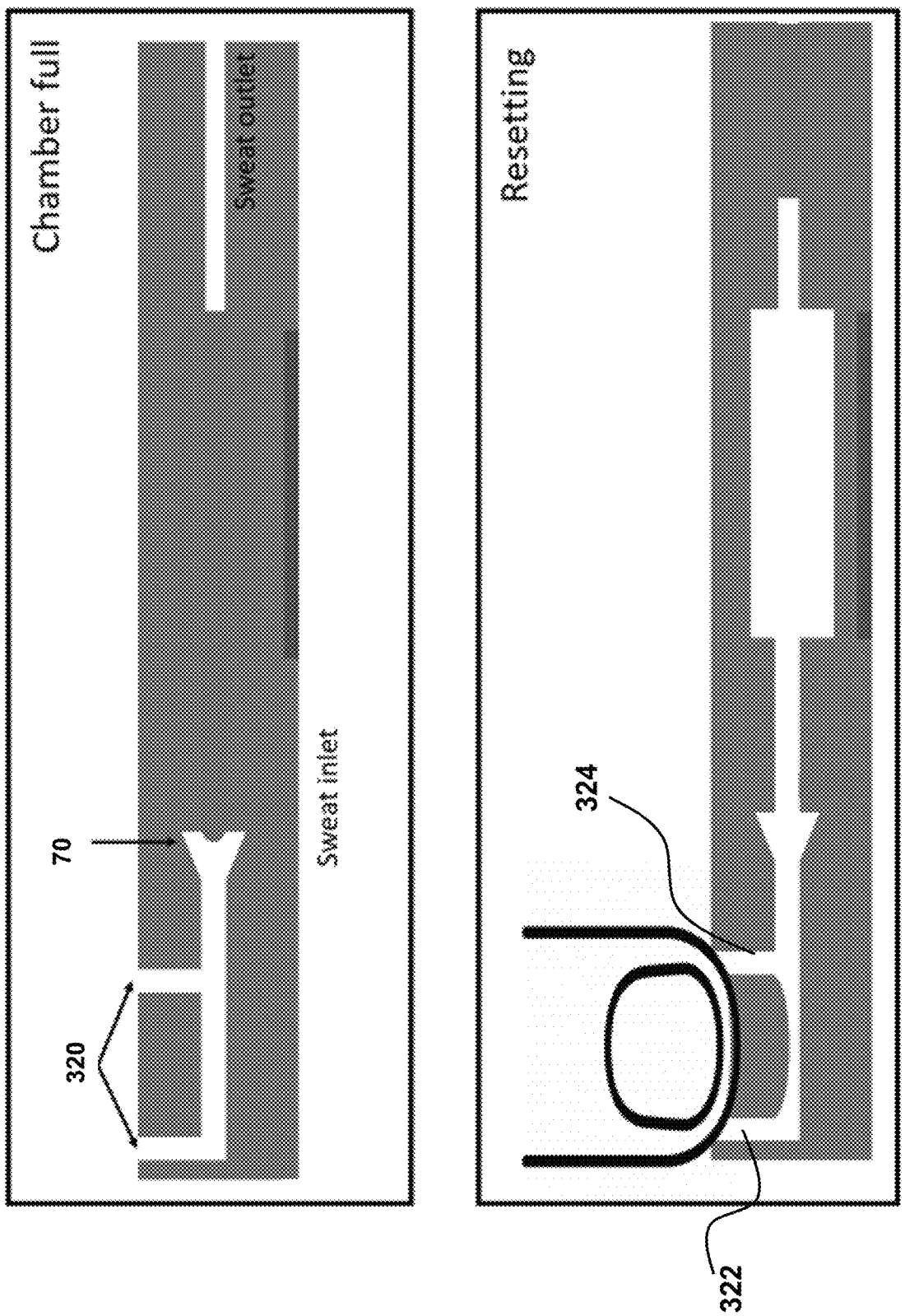
FIG. 31 illustrates a means of resetting the sensor to its initial state. Dual expunge ports reduce the likelihood of accidental sweat discharge, but when covered and pressed simultaneously empty the chamber and reset the device back to its initial state.
Figure 32:
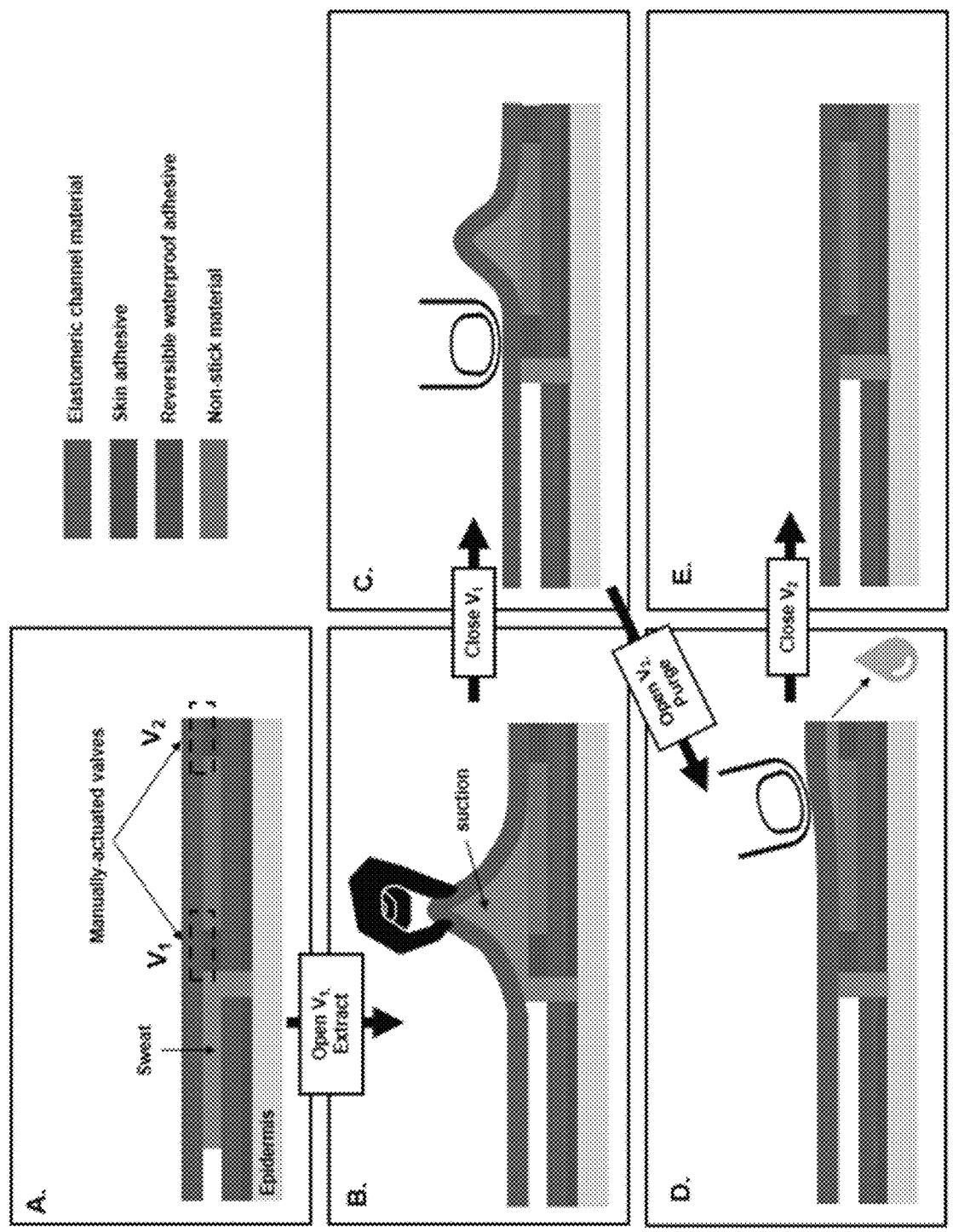
FIG. 32 shows purge system for resettable sweat device. (A) Cross section schematic showing the manually-actuated valves. (B) Step 1: Sweat is extracted from the channel via pinching and opening valve 1 by stretching the top elastomeric membrane. This creates suction which extracts sweat from the chamber. (C) Step 2: Seal valve 1 by pressing. (D) Open valve 2 and purge sweat. (E) The device is ready to be reused.

FIG. 31 illustrates expunge port that may be utilized to remove biofluid from the reservoir chamber. The expunge port may comprise two outlets 322 324.

Figure 15:
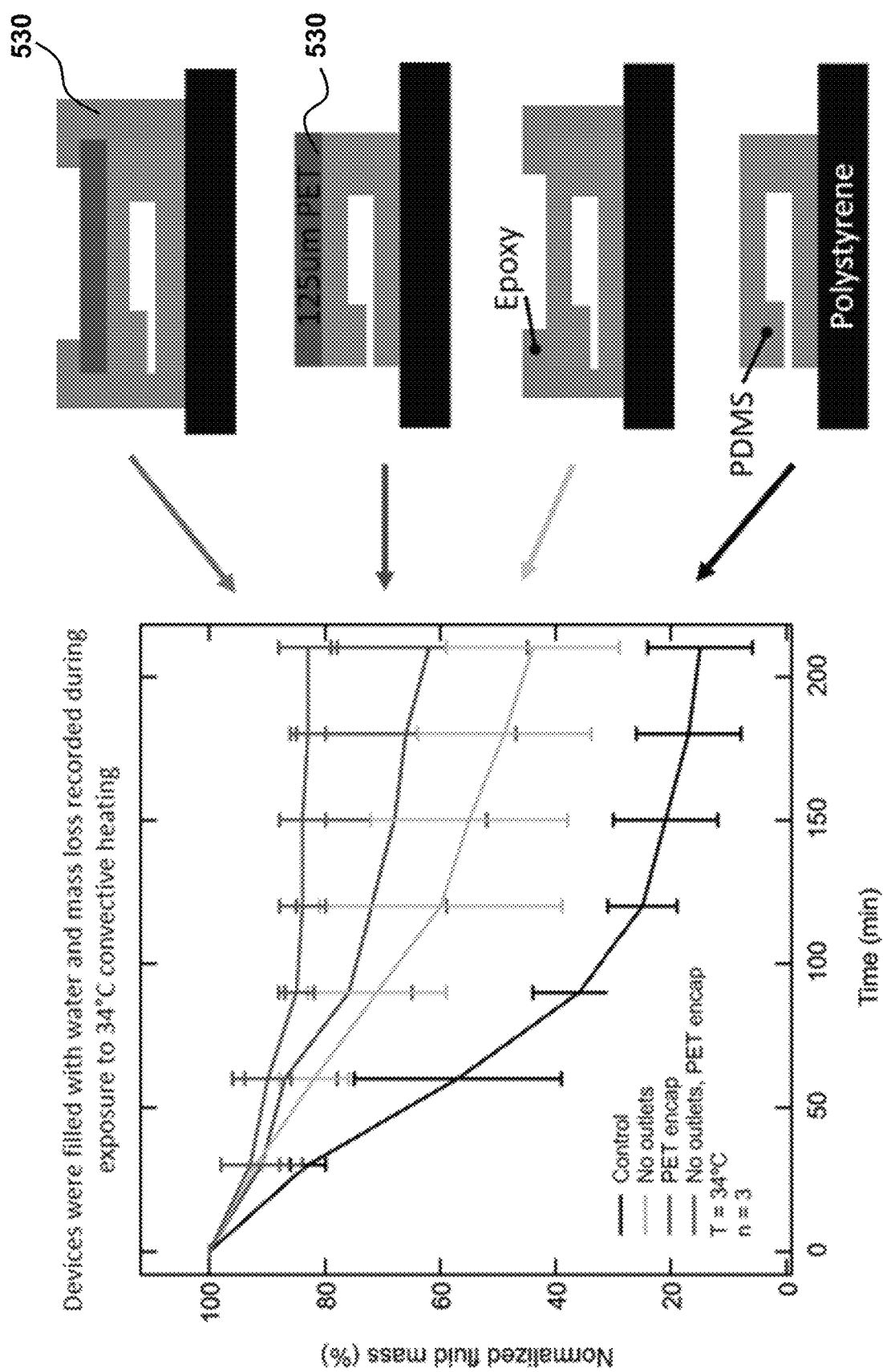
FIG. 15 illustrates cross sections of certain embodiments of the microfluidic systems disclosed herein. The data plot shows fluid loss due to evaporation from the microfluidic systems as a function of time. The data shows that water may evaporate through PDMS and that a capping layer, including a PET capping layer for example, reduces fluid loss.
Figure 21:
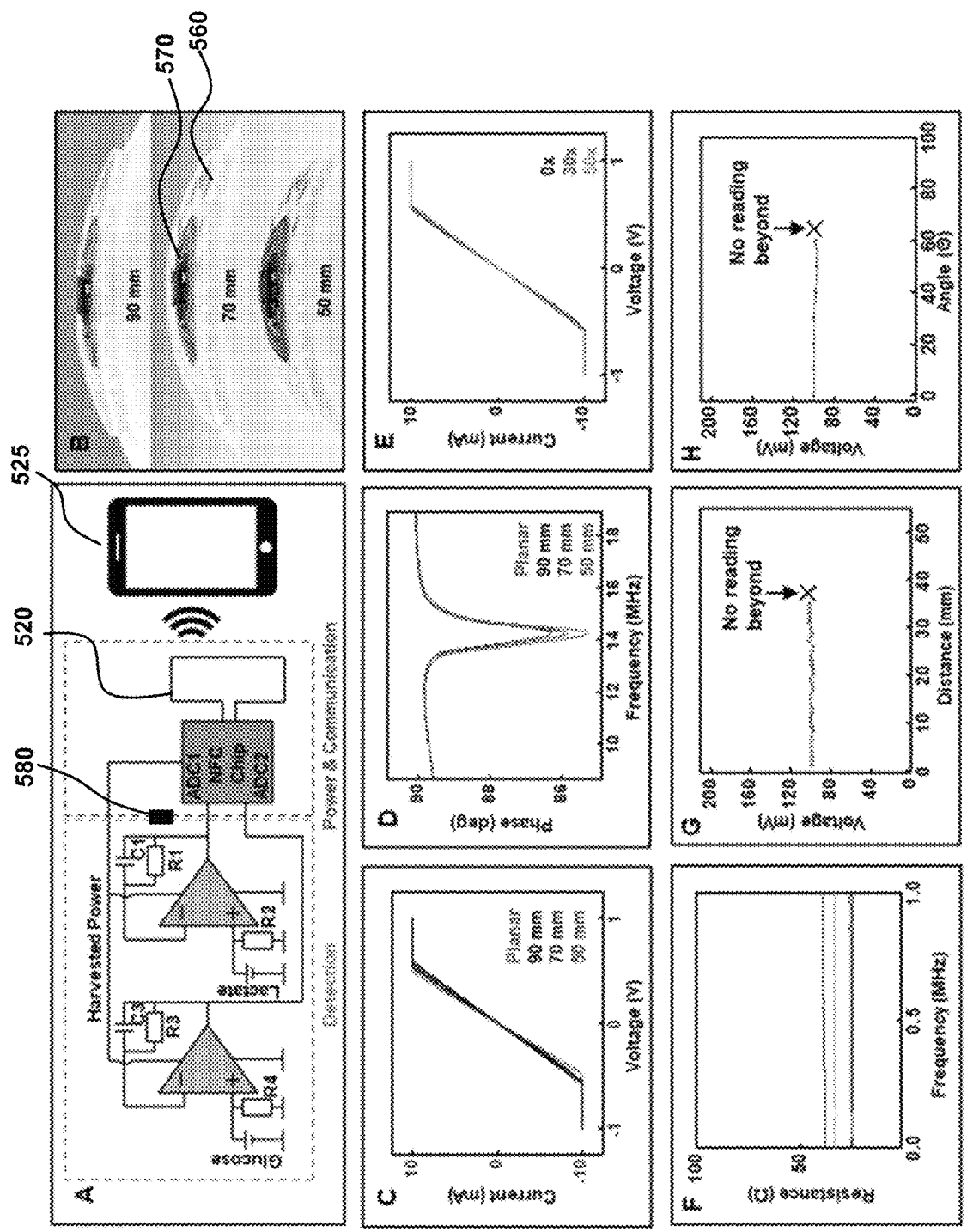
FIG. 21 shows electrical characterization of NFC electronics. (A) Simplified schematic of electrochemical sensor readout. (B) Image illustrating the device bent at decreasing radii. (C) I-V measurements of shorted sensors recoded with decreasing curvature radii (D) Phase response measurements of NFC electronics with decreasing radii. (E) I-V measurements of shorted sensors with repeated attachment and detachment of the electronics to the micro-fluidics. (F) Impedance of magnetic contacts over a wide range of frequencies. Effect of (G) distance and (H) angle between NFC reader and device on signal recording.

A collection layer 400 may promote or help facilitate biofluid transport from the skin (FIG. 37). Any of the systems may have a heater 500 to help regulate biofluid availability (FIG. 19) and/or may be incorporated into a glove 540. High sensitivity electrodes 510 may measure change in an electrical parameter, thereby measuring a biofluid parameter of interest. A wireless communication device 520 may facilitate transmission of information wirelessly, including to a receiver 525, such as a hand-held device (FIG. 21). A protective layer 530 may be embedded in or supported by the flexible substrate (FIG. 15). FIG. 21 illustrates that any of the systems may have a disposable portion 560 and a reusable portion 560, such as corresponding to the fluidics and electronics components, for example (FIG. 21), by releasable coupling element (580).

Example 1: Capillary Bursting Valves for Sequential Sampling (62/514,489 Atty Ref NU2017-059: 39-17P)

Figure 1:
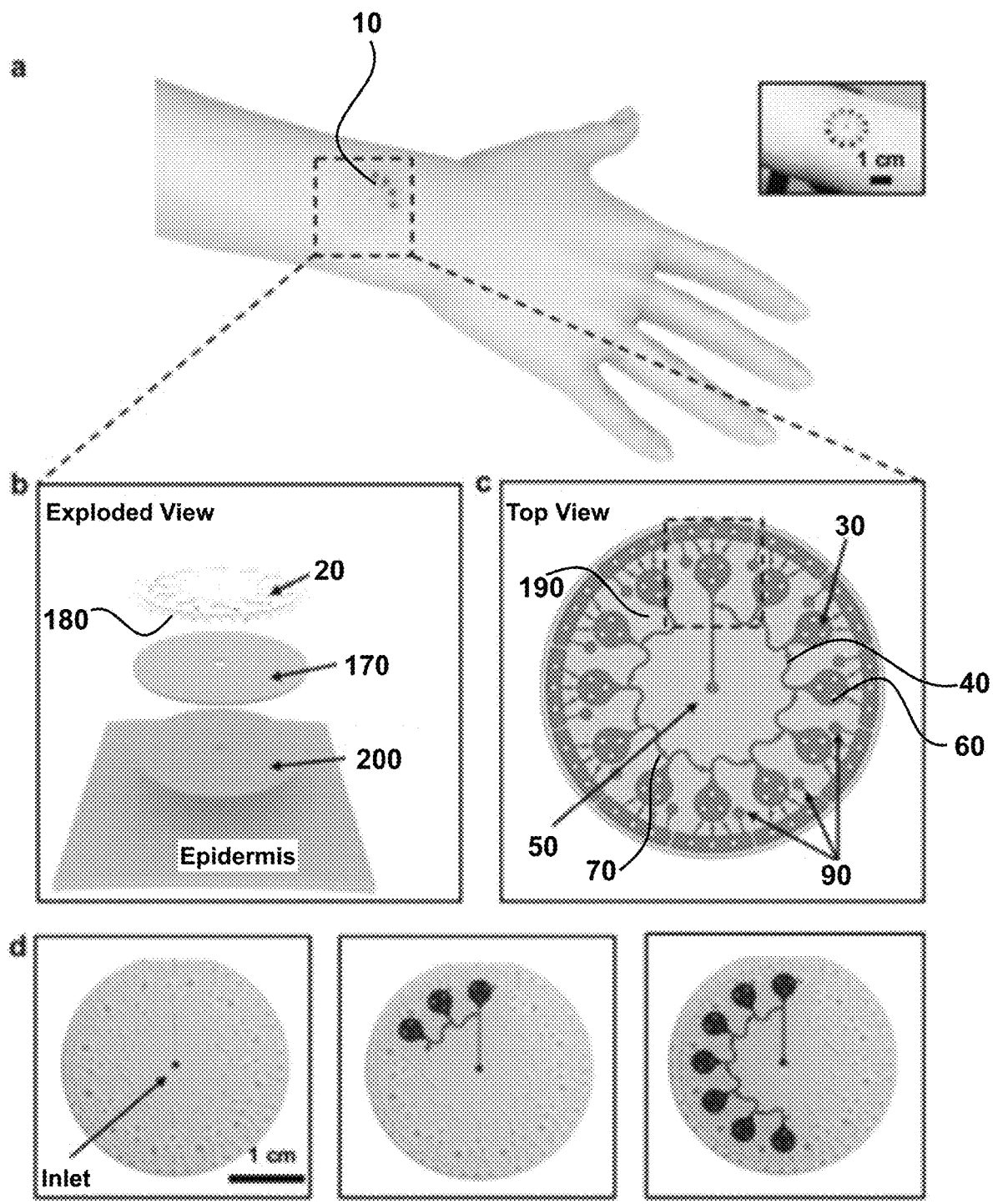
FIG. 1 shows: (a) Schematic illustrations and optical images (inset) of thin, soft microfluidic devices for chrono-sampling of sweat. (b) Exploded view illustration of a device and its interface with skin. (c) Top view illustration of microfluidic channels filled with blue-dyed water. (d) Optical images of in vitro testing of chrono-sampling of blue-dyed water in a working device.

Thin, Soft Microfluidic Devices for Chrono-Sampling of Sweat: The thin geometries and soft mechanics of these devices allows their intimate, comfortable bonding to the skin for the purpose of collecting, manipulating, analyzing, and storing sweat, captured in a sequential manner. An example device shown in FIG. 1 has a circular overall geometry with a diameter of 3 cm. The radial construction facilitates the use of centrifugation techniques for collection of sweat after removing the device from the skin, as described subsequently. The example design involves two layers of poly(dimethylsiloxane) (PDMS) supported on a medical-grade acrylic adhesive film for bonding to the skin. The first layer defines a network of microfluidic channels (e.g., 400 µm thickness; channel widths and heights are 200 and 300 respectively, for example) and the CBVs (designs described next). The second serves as a capping layer (e.g., 200 µm thickness; inlet), and the third (e.g., 50 µm thickness) establishes adhesion to the skin and defines openings (e.g., 2 mm diameter) from which sweat can enter the microfluidic system (e.g., 1 mm diameter, inlet; FIG. 1). The exemplary structure in FIG. 1 comprises a network of microfluidic channels that connects to 12 separate chambers in parallel by bridging channels (panel (c) of FIG. 1). Each chamber connects to an outlet opening (e.g., 0.5 mm diameter) designed to allow release of air that would otherwise be trapped in the chamber and serve as a source of backpressure to frustrate the filling of sweat into the chamber. In vitro tests using dyed water illustrate the clockwise flow through this network (panel (d) of FIG. 1). PDMS may be used due to its dimensional stability in water, materials biocompatibility, low modulus, elastic mechanical properties, and compatibility with simple molding and bonding processes for fabrication. Amino acids, glucose, and pyruvate may exhibit low absorption into PDMS. Certain chemistries, including certain vitamins and hormones, have comparatively high absorption, but their concentrations are generally not crucial to analysis of sweat. Testing indicates an absence of chemical contamination from the PDMS and the adhesive layer in analysis of biomarkers of interest in sweat. These same results suggest a minor (≈10%) decrease in glucose concentration, possibly due to slight absorption into the constituent materials of the device.

Principle and Design of the Capillary Bursting Valves for Sequential Sampling: The CBVs block flows at pressures lower than their characteristic bursting pressures (BPs). When liquid in a single connected channel encounters two separate CBVs with different BPs, at sufficient pressures, the flow will proceed first through the valve with lower BP. In this way, locating two CBVs with different BPs near the intersection between two channels allows control of the direction of flow. The Young-Laplace equation gives the BP in a rectangular channel as equation (1)

$$BP = -2\sigma\left(\frac{\cos\theta_I^*}{w} + \frac{\cos\theta_A}{h}\right), \quad (1)$$

where σ is the surface tension of liquid, θA is the contact angle of the channel, θI* is the min[θA+β; 180°], β is the diverging angle of the channel, w and h are the width and the height of the diverging section, respectively.

Figure 2:
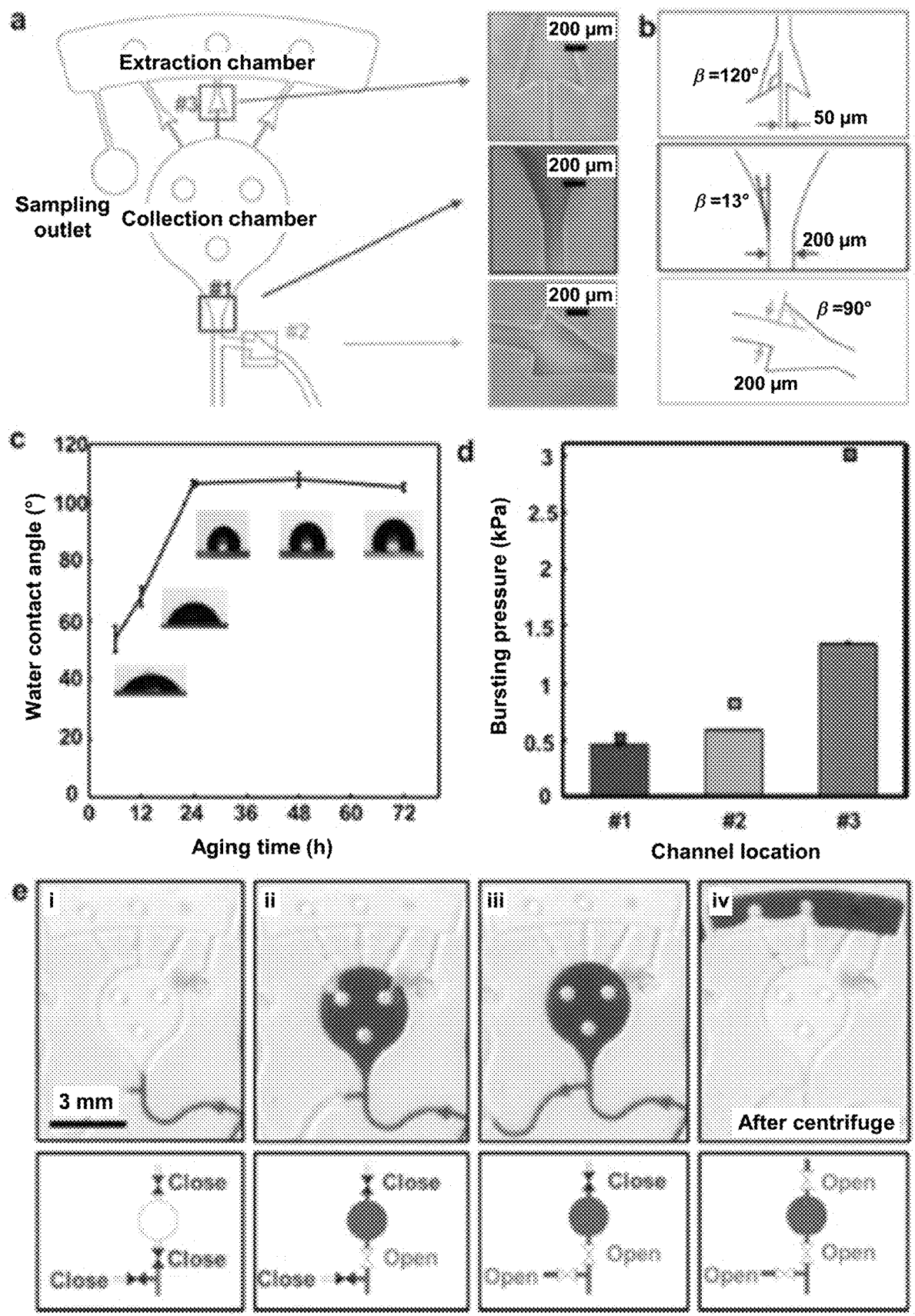
FIG. 2 shows: (a) Detailed schematic illustration of a unit cell in a device, including a collection chamber, extraction chamber, sampling outlet, and three capillary bursting valves (CBV) and SEM images of CBVs. (b) Sketch of capillary bursting valves with indicated channel width and diverging angle. (c) Measurement of contact angle of water on PDMS as a function of aging time after oxygen plasma treatment. (d) Experimental results (bars) and theoretical values (square box) of capillary bursting pressure of CBV #1, #2, and #3 of device after 1 day from oxygen plasma treatment. (e) Optical images and schematic illustrations of the working principle of the capillary bursting valves for chrono-sampling. (i) Before entering collection chamber (ii) filling the collection chamber (iii) flowing to next chamber (iv) after centrifugation.

For hydrophobic materials at high diverging angles, the BP increases with decreasing b and h. Each unit cell of the devices described here includes three CBVs, a collection chamber, an extraction chamber and a sampling outlet (FIG. 2(a)). In one embodiment, the first two CBVs, denoted #1 and #2, have diverging angles of 13° and 90°, respectively, and widths of 200 µm. The third CBV, i.e., #3, has a diverging angle of 120 Åã and a width of 50 µm (panel (b) of FIG. 2). The heights of these valves are 300 µm. According to Equation (1), the contact angle of the channel surfaces affects the BP. PDMS, which is naturally hydrophobic, becomes hydrophilic after exposure to oxygen plasma for the purpose of activating the surfaces to enable bonding. The hydrophobicity recovers after ≈24 h, to reach a constant, time-independent contact angle of 107°. Based on this parameter, the computed BPs for CBVs #1, #2, and #3 are 498.9 (BP #1), 881.7 (BP #2), and 3035.7 Pa (BP #3), respectively. Experimentally measured values are somewhat lower than these estimates, mainly due to imperfections in the fabrication and, in particular, diverging angles that are slightly smaller than the design values, as shown in the SEM images in panel (a) of FIG. 2. For example, in CBV #2 and #3, the sharp edges where the straight channel and the diverging section intersect are somewhat rounded, with radii of curvature of ≈35 and 27 µm, respectively. Liquid that initially arrives at CBVs #1 and #2 encounters them in their closed states (panel e(i) of FIG. 2). Upon reaching or exceeding BP #1, CBV #1 opens to allow flow into the chamber (panel e(ii) of FIG. 2). After filling this chamber, the liquid flow bursts CBV #2 at sufficient pressure (BP of CBV #2 is lower than that of CBV #3) (panel e(iii) of FIG. 2). By this process, all 12 chambers fill in a sequential manner, for flows that involve pressures larger than BP #2. Due to the pressure drop along the channel, the required pressure to fill the whole chambers is 1000 Pa and is higher than BP #2. For constant flow rate, this effect translates to time-sequenced sampling, or chrono-sampling. After use, the device can be removed from the skin and then inserted into a centrifuge (5000 rpm) to open CBV #3, thereby moving liquid from each of the storage chambers into corresponding extraction chambers to facilitate recovery for lab analysis (panel e(iv) of FIG. 2). The designs of the CBVs ensure that pressures generated by the sweat glands exceed BP #1 and BP #2, thereby allowing complete filling of the associated chambers, and that centrifugal pressures exceed BP #3. The pressure generated by the sweat glands exceeds BP #3, but it does not burst this valve until after filling the chamber.

Figure 3:
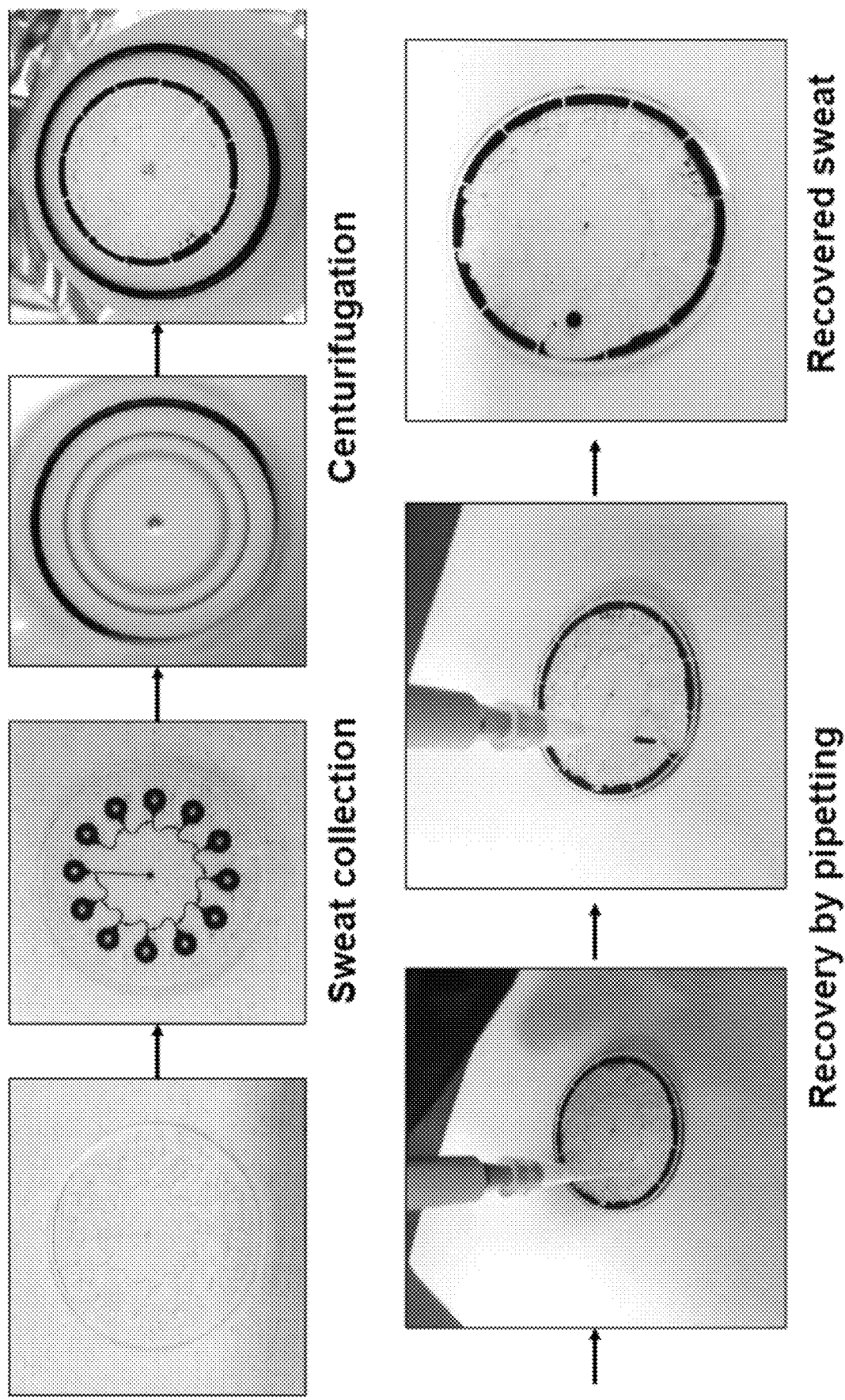
FIG. 3 shows a process of recovering liquid from chrono-sampling device.

Sweat Sample Extraction Process: After collecting sweat, a centrifuge is used to recover the sweat (FIG. 3). During the centrifuge, the sweat in the chamber is moved to extraction chamber and each sweat from different time is separated. We can extract the sweat by simple pipetting. This device contains about 3 µL from each chamber, for example.

Figure 4:
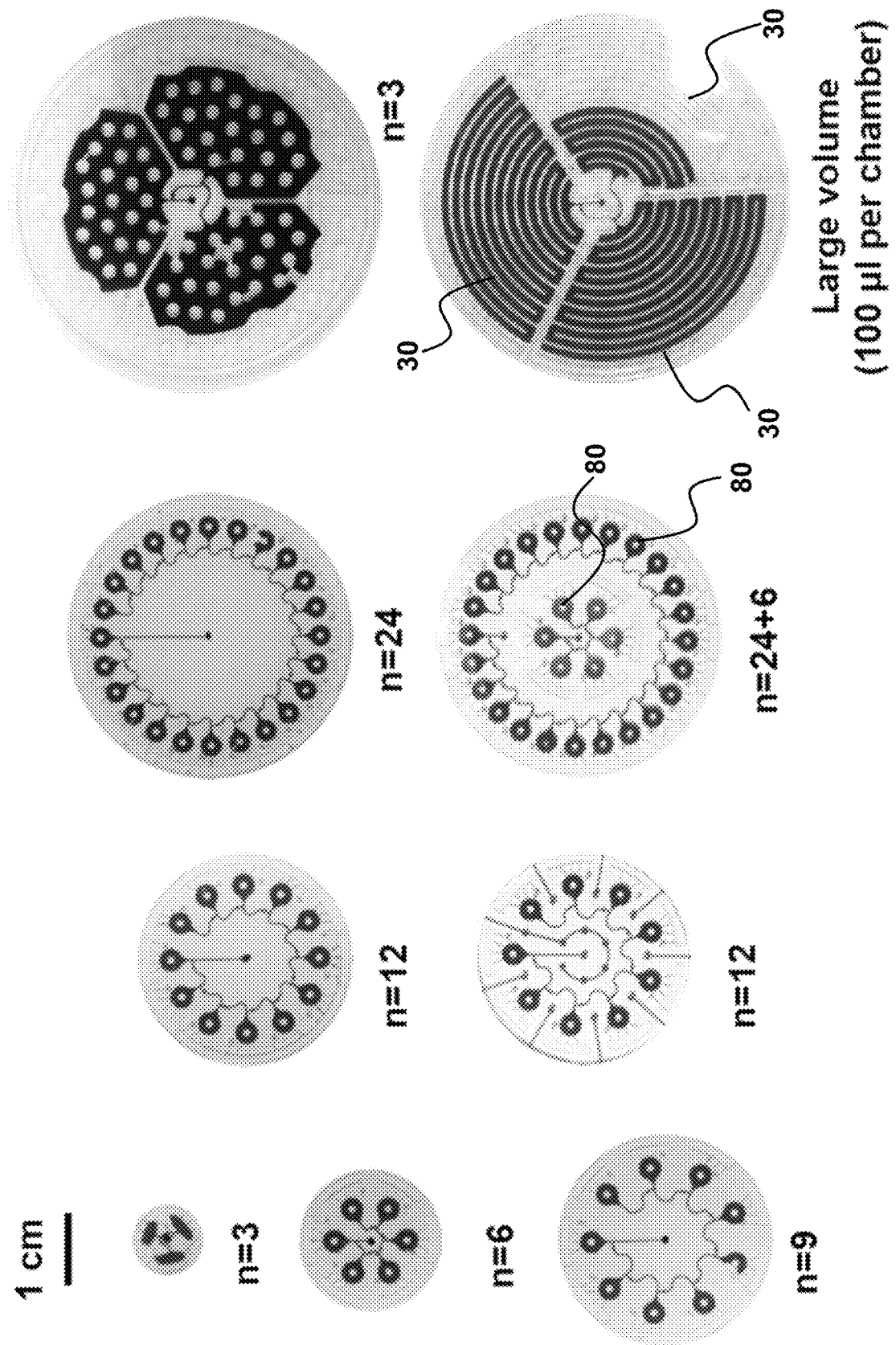
FIG. 4 shows microfluidic systems illustrating a variety of example designs of the systems disclosed herein, including, for example, different amounts and shapes of the reservoir chambers.

Various Size and Chamber Number of chrono-sampling device: Microfluidic systems may have various dimensions (e.g., 1cm-5 cm in diameter) with different numbers (e.g., 1-24) of chambers, sizes of chambers, and shapes of chambers for chrono-sampling devices (FIG. 4). Microfluidic system design may be tuned to the application. The small devices may be used for short-term sweating and the large device may be used for long-term exercise. The volume of chamber may be expanded to 100 uL for complex in vitro analysis. Two microfluidic networks may be incorporated in one microfluidic system.

Figure 5:
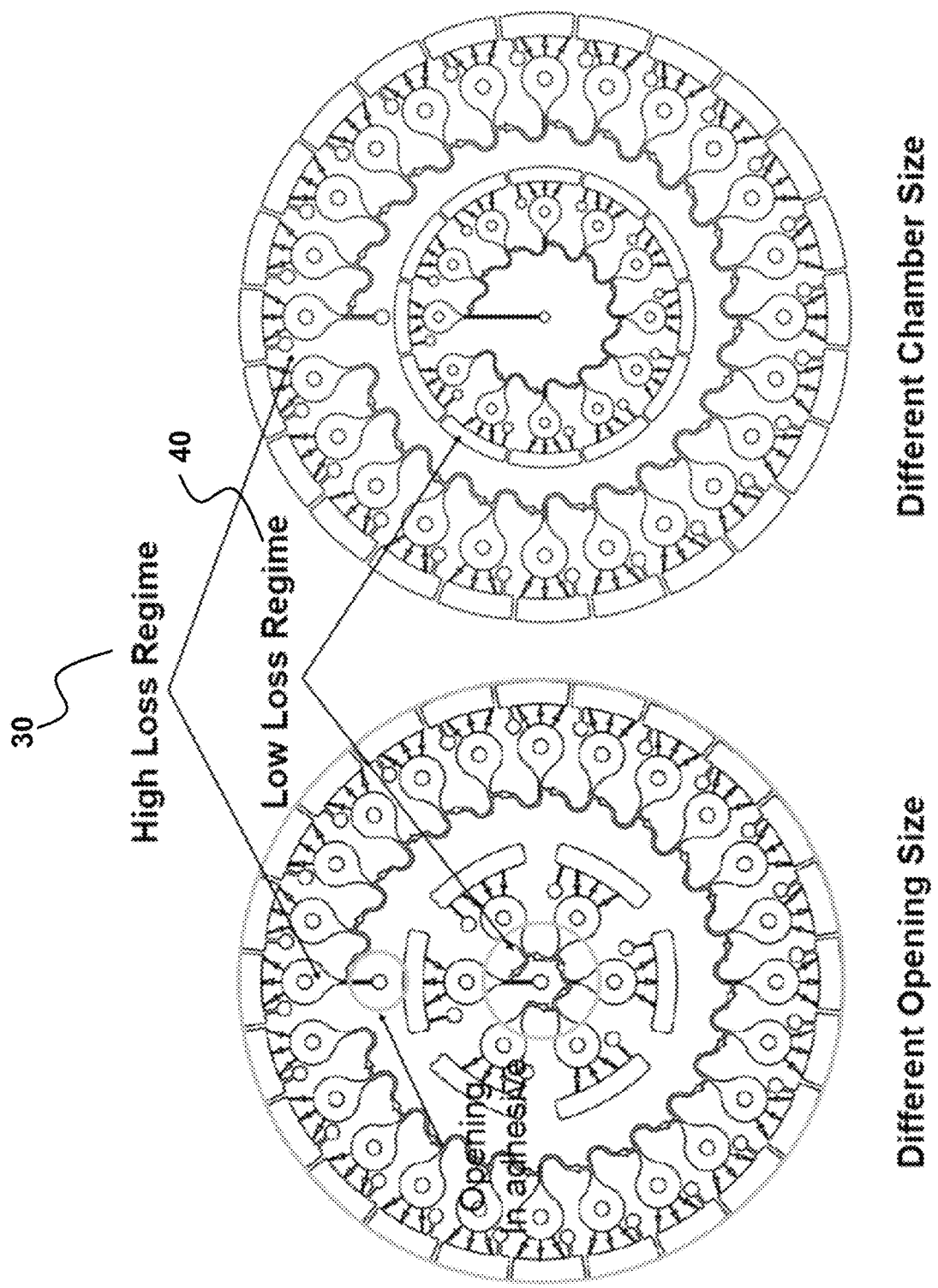
FIG. 5 shows two example microfluidic system having two microfluidic networks. Differences between two microfluidic networks in a single microfluidic system may include capillary burst valve burst pressure (e.g., size), reservoir chamber size and shape, and inlet size, thereby providing a high and low loss biofluid regime in a single system.

Designs for Accurate Measurement of Sweat Loss: As a detail, a single microfluidic system may be used for high biofluid loss regime and the other is used for low loss regime (FIG. 5). Each of two different microfluidic networks is used for a different measuring regime. In the left device, by changing the collecting area, the outer unit collects sweat rapidly. The area of opening in adhesive is 4 times bigger in outside. Therefore, the sweat fills four times faster in outside device. Therefore, the outside device can be used as minute hand of a watch. Using both units we can calculate sweat rate more accurately. See also Addendum A.

Figure 6:
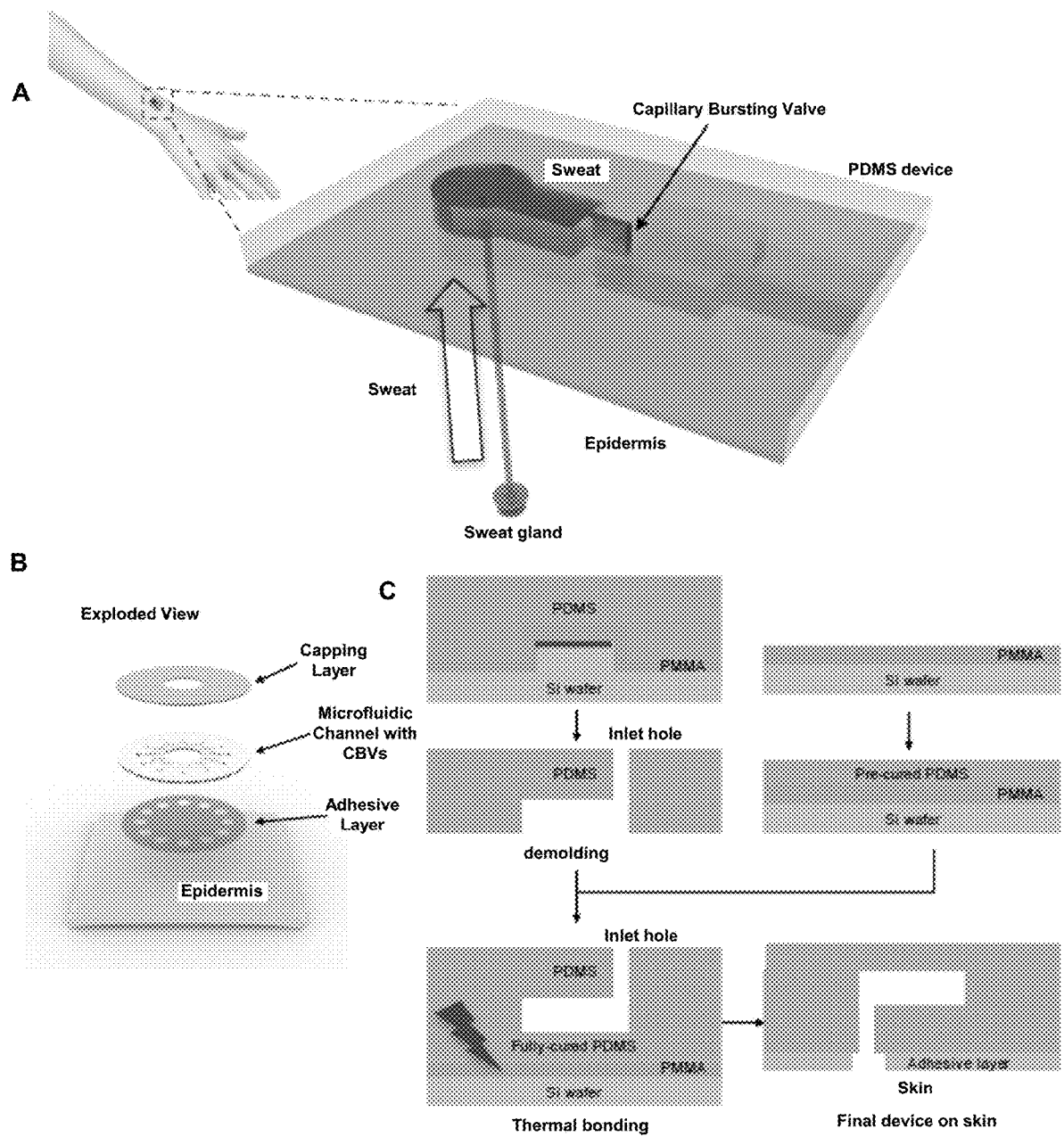
FIG. 6 shows: (A) Schematic to measure pressure of sweat from sweat gland using capillary bursting valve; (B) The exploded view of the device having a capping layer, microfluidic channel with CBVs and adhesive layer; (C) Fabrication steps for the device.

Thin, Soft Microfluidic Devices for Measuring Pressure from Sweat Gland: Sweat is coming from sweat gland by the pressure generated from osmotic pressure. The pressure can be derived from following equation.

$$P = \sigma RT \Delta C$$

where $\sigma$ is the osmotic reflection coefficient, R is the gas constant, T is the temperature of the body, and $\Delta C$ is the difference in concentration between plasma and sweat often represented in terms of osmolality. For example, the device is attached to the skin and sweat gland is connected to the microfluidic channel with capillary bursting valve (FIG. 6). When sweat is coming from the sweat gland, if the pressure from sweat gland is higher than the bursting pressure of valve, it will burst in the chamber. The example device is composed of three layers; capping layer, microfluidic channel layer and adhesive layer with opening of sweat. For the fabrication of the device, photo-lithographic process is performed.

Serial CBVs with Different Bursting Pressure:

In FIG. 7, a microfluidic system has 12 values with different bursting pressure accomplished by changing the valve size from 120 µm to 10 µm (FIG. 7). The bursting pressure increases. If the sweat has pressure higher than such valves it will burst and stop at certain valve. To visualize the bursting of valve, cobalt chloride is used in the chamber. When there is bursting the color is changed to red. The device may detect from 1.2 kPa to 6.5 kPa, for example. In vitro tests measure the bursting pressure of the device and numerical analysis yielded well matched values.

Figure 8:
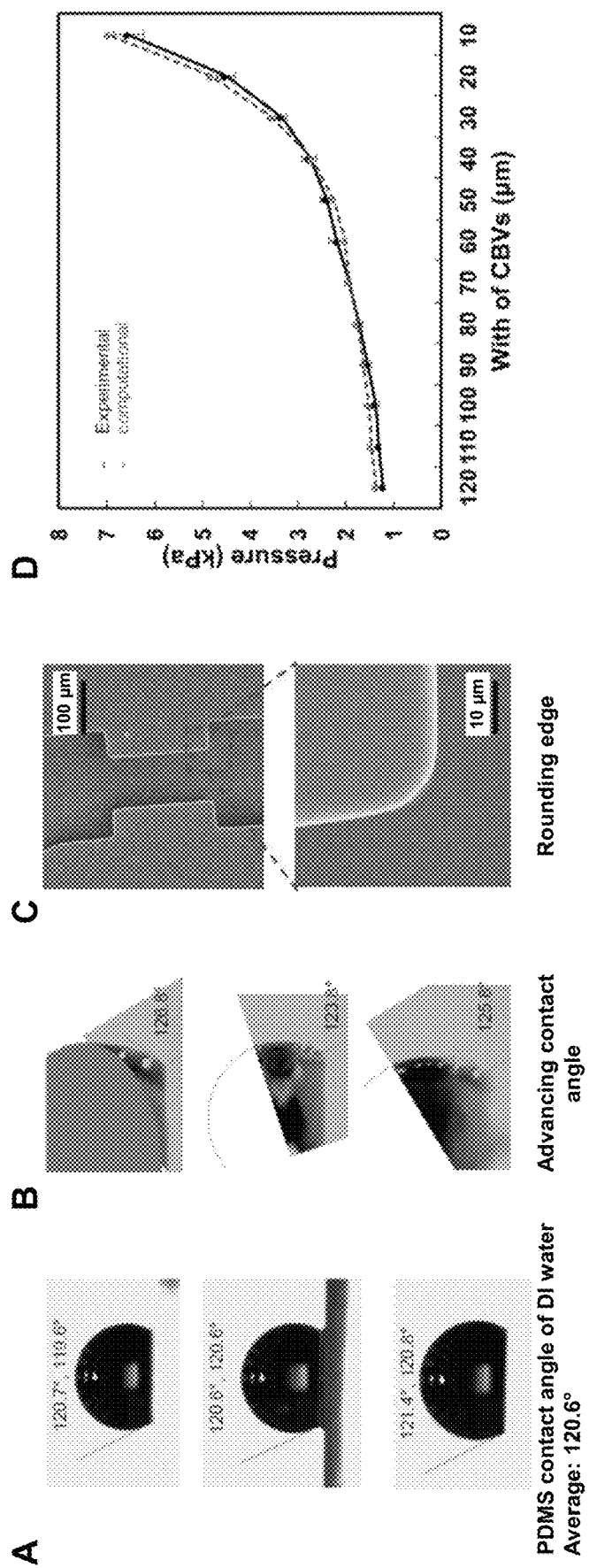
FIG. 8 shows: (a) the water contact angle on the PDMS; (b) The critical advancing contact angle of water on the PDMS; (c) the SEM images of rounding edge of the CBVs; (d) the bursting pressure of the CBVs from in vitro test and numerical calculation.

Calculation of bursting pressure in vitro and in computing: For the calculation of bursting pressure of CBVs (equation 1), we have to know the static and advancing contact angle of the surface of the device. We measure the values by using contact angle goniometer (FIG. 8). Also, the rounding edge of the CBVs affects to the bursting pressure. We measured the rounding edge using SEM image. Finally, we measure the bursting pressure using pressure generator and numerical calculation, as described above for Eq. (1).

Figure 9:
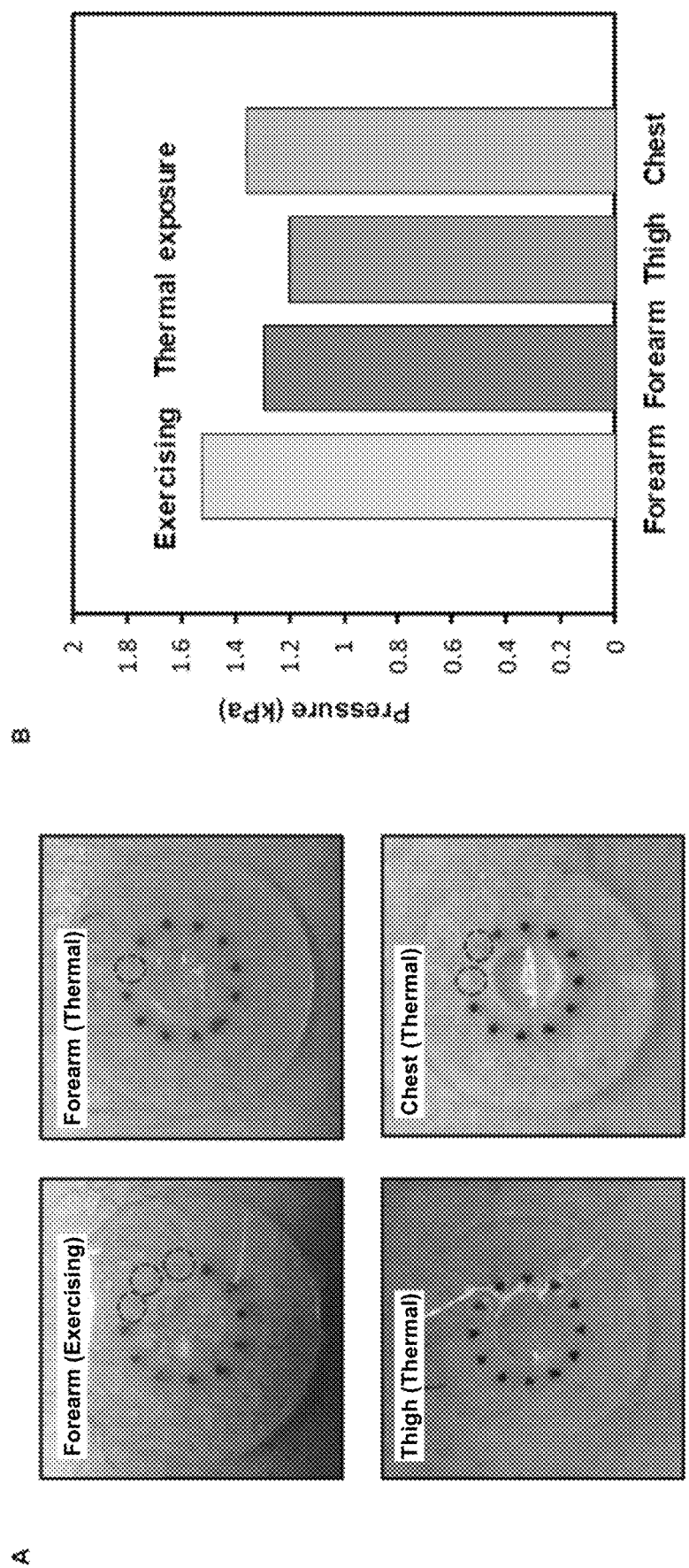
FIG. 9 shows: (a) the optical images of measurement of pressure of sweat gland from exercising and thermal exposure in sauna; (b) the graph of the measured pressure of the sweat gland with different condition and region of the body.

In situ Sweat Pressure Measurement: FIG. 9 shows the pressure measured in exercising and thermal exposure conditions using the microfluidic system. The overall pressure value is measured as 1-2 kPa, in this example, which is smaller than the test using sweat inducer and micropipette. This may be the first time sweat pressure at normal sweating condition has been measured. The pressure at exercising is higher than thermal exposure. The pressure is proportional to skin temperature and concentration difference between sweat and plasma. Assuming that skin temperature is not different from each condition, the concentration difference in exercising condition is larger than thermal exposure. The sodium concentration appears higher in the exercise condition. From these results, it may be expected that sweat pressure may allow determining body conditions like sweat concentration so on.

Figure 10:
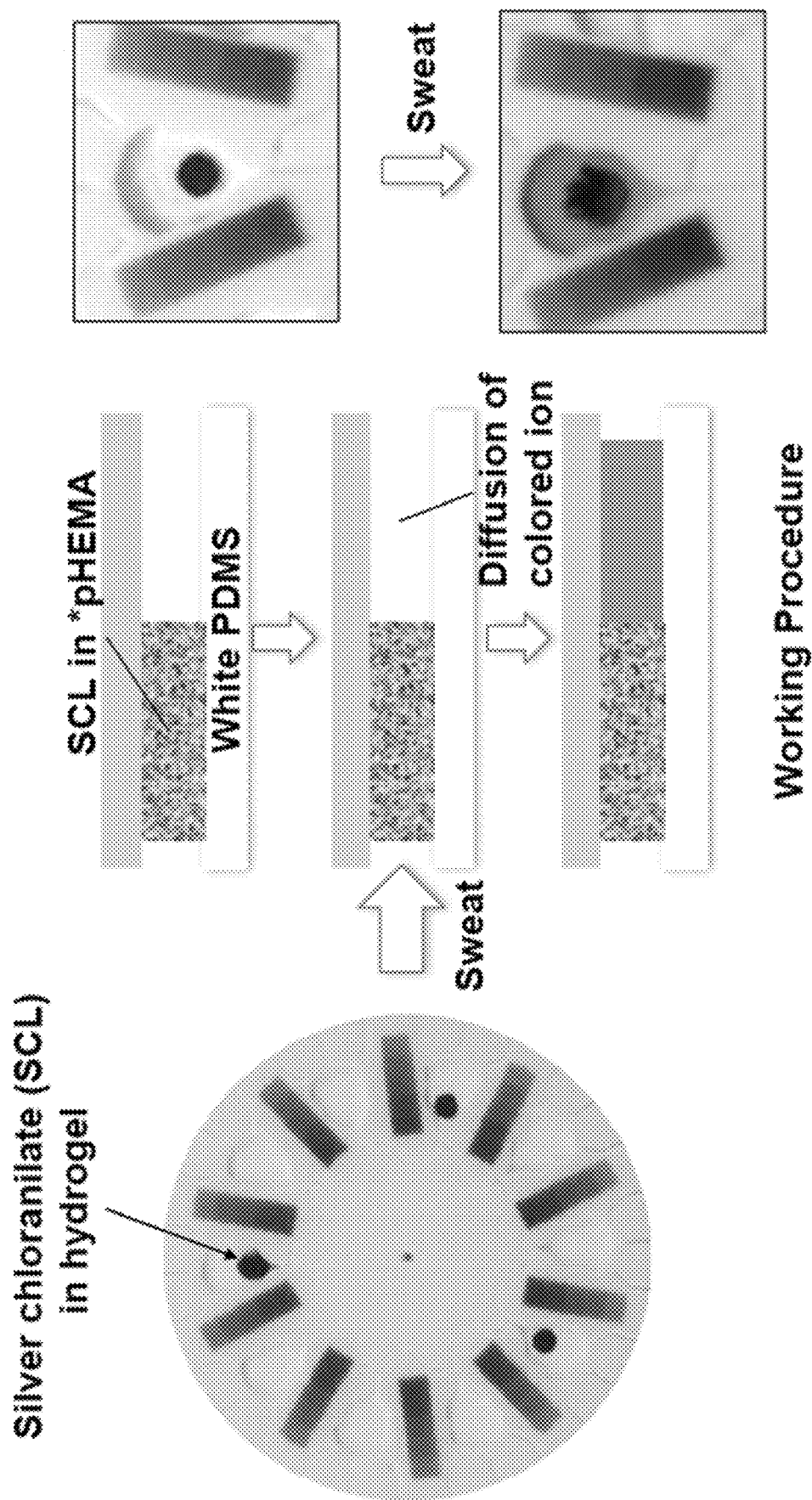
FIG. 10 shows colorimetric chloride concentration detection using silver chloranilate in a microfluidic system.
Figure 11:
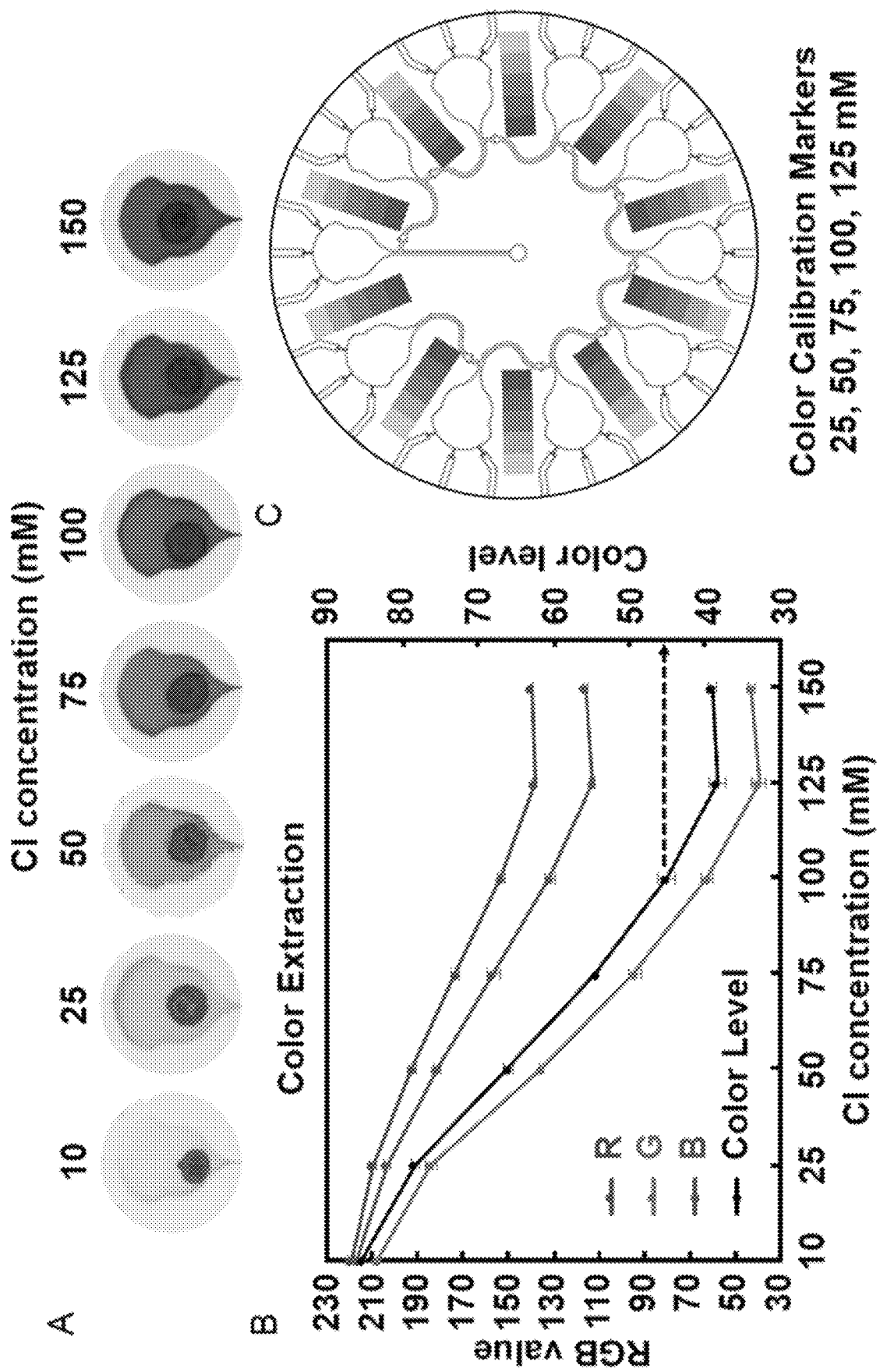
FIG. 11 shows: (a) color development in the chamber with silver chloranilate according to the chloride concentrations; (b) graph of the extracted color value from the chamber in (a); (c) schematic of color calibration marker.

Colorimetric detection of chloride using silver chloranilate and microfluidic device: For the in situ analysis of sweat, colorimetric sensors may be used. Colorimetric may be read by naked eye or camera in smartphone. For the detection of chloride, silver chloranilate (SCL) may be used (FIG. 10). SCL may be mixed with pHEMA (Polyhydroxyethylmethacrylate) as a carrier. When sweat comes into the chamber it reacts with SCL and generates a colored ion. By detecting the color density, the chloride concentration may be estimated.

Equation two represents the chemistry of SCL. The SCL is slightly soluble in water and reacts with chloride ions and hydrogen from water. The reaction generates silver chloride and acid chloranilate ion with purple color. With sufficient amount of SCL in the chamber, therefore, the color density is proportional to the chloride concentration.

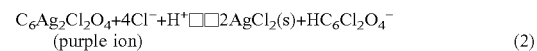
$$C_6Ag_2Cl_2O_4 + 4Cl^- + H^+ \rightleftharpoons 2AgCl_2(s) + HC_6Cl_2O_4^- \text{ (purple ion)} \quad (2)$$

According to the Cl concentration, the amount of colored ion is set which defines the color of the chamber. A predefined volume for consistent color development is advantageous.

Color Changes and Calibration Markers: The concentration range of Cl in sweat is from 10 to 100 mM. The microfluidic system is tested with different Cl concentration from 10 to over 100 mM (e.g., 150 mM) to determine limits. The color changed with Cl concentration from 10 to 125 mM continuously, which covers the chloride concentration range in sweat. A simplified concentration to color level is derived (e.g., FIG. 12). Using the color value, we made a color calibration marker and located it at each sides of the chamber.

Figure 12:
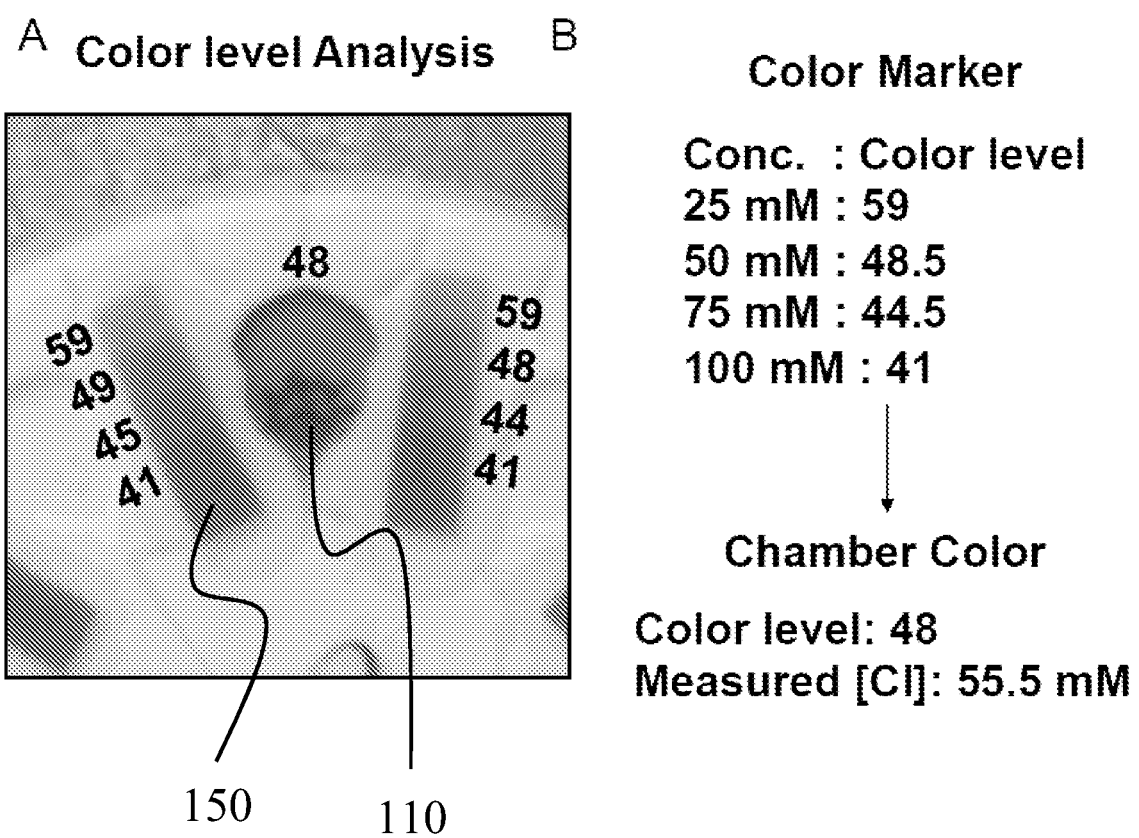
FIG. 12 shows detection of chloride concentration in the biofluid using the color marker (indicator) strip: (a) color level from the chambers and color calibration marker; (b) measuring the chloride concentration using color level.

Detection using Color Marker: This microfluidic system may be used in real world applications like gym and jogging conditions. By naked eye, the color level is compared to the calibration marker to see the Cl concentration roughly. By a smartphone app, the Cl concentration is determined more accurately. For example, after taking picture, the app analyzes color level using color meter in the app (FIG. 12). After extracting the color level in the calibration marker and chamber, they are compared the Cl concertation is determined. In FIG. 12, the concentration value is 55.5 mM.

Figure 13:
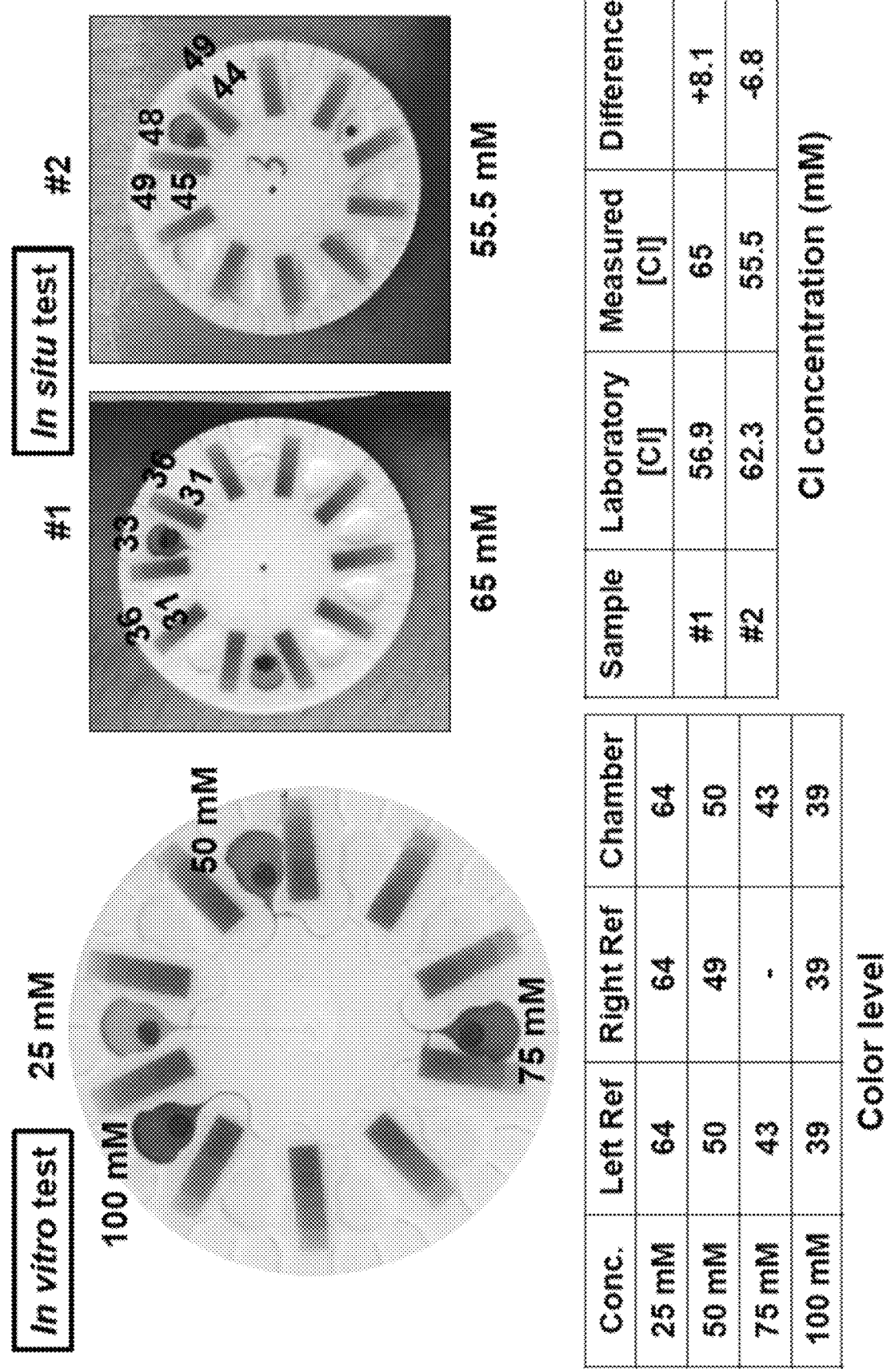
FIG. 13 shows images and tables corresponding to in vitro and in situ tests with a microfluidic system, illustrating the accuracy of chloride detection using silver chloranilate.

Accuracy of Cl Detection: To test accuracy of chloride concentration detection in vitro the chamber of the microfluidic system is filled with known a concentration and the color level in the chamber is analyzed and compared to calibration indicator strip (FIG. 13). In all concentration levels, the concentration values are well matched to the calibration marker. In the in vivo test, the concentration according to color in the chamber with collected sweat is compared to results using lab sweat analysis. In the first trial, the device measures a 65 mM chloride concentration, which is 8.1 mM higher than laboratory results. In the second test, the measured concentration is 6.8 mM lower than laboratory results.

Applications: The ability to collect sweat non-invasively, and longitudinally has significant implications in human health tracking in both normal and diseased states. Conventional technologies do not perform this task. For health tracking during physical activity, embodiments of the presently disclosed microfluidic systems and methods provide quantified feedback on sweat loss. This may serve as an early warning system of dehydration. Conventionally, the ability to assess volume loss depends on clinical signs (e.g. dry mucous membranes, delayed capillary refill) that are often lagging. Also, embodiments of the presently disclosed microfluidic systems and methods may be used to assess the sweat response of an individual in the setting of physical activity. Individuals with greater athletic ability are capable of dissipating sweat to maintain core body temperature with more efficiency than non-athletes. embodiments of the presently disclosed microfluidic systems and methods create novel metrics of athletic performance by quantifying sweat response to physical activity and local skin temperature.

Beyond athletics, sweat loss has important clinical implications as well. The assessment of sweat content is used for the diagnosis of cystic fibrosis (CF). CF is the most common fatal genetic disorder in Caucasians. embodiments of the presently disclosed microfluidic systems and methods provide an alternative advantageous diagnostic platform for this disease. Conventionally, the sweat analysis for CF requires expensive equipment, specialized technician expertise, and lacks repeatability (variations greater than 30% between hospitals). There are also rare genetic diseases (e.g. hypohidrotic ectodermal dysplasia, ichthyotic diseases) where the sweat glands are dysfunctional or impaired. These individuals are at great risk of fatal heat stroke. The ability to assess sweat rate and skin temperature may provide an early warning system for these vulnerable patients. The detection of biomarkers and electrolytes in sweat can be correlated to serum biomarkers and electrolytes. Embodiments of the presently disclosed microfluidic systems and methods enable a new platform that allows for continuous, non-invasive assessment of body homeostasis, including tracking sweat glucose to assess serum glucose for diabetics. For patients with significant needle aversion, venipuncture for basic labs can be very challenging. In pediatric patients, venipuncture can also be very traumatic. Embodiments of the presently disclosed microfluidic systems and methods sweat device are useful in collecting important clinical data without the need for venipuncture.

Series of separated chambers chemically decoupled from each other has capabilities to provide a reaction chambers for different biomarker detection and to analyze the biomarker in time-sequential method. Series of capillary bursting valves (CBVs) enables the device to collect the sweat in time sequence and to provide individual reaction chambers without cross contamination to other chambers (ref). Liquid flows to the route with less fluidic resistance, low bursting pressure of CBV. Young-Laplace equation provides the bursting pressure (BP) of CBV in a rectangular channel as described in Eq. (1) above.

$$BP = -2\sigma\left(\frac{\cos\theta_I^*}{w} + \frac{\cos\theta_A}{h}\right) \quad (1)$$

Figure 14:
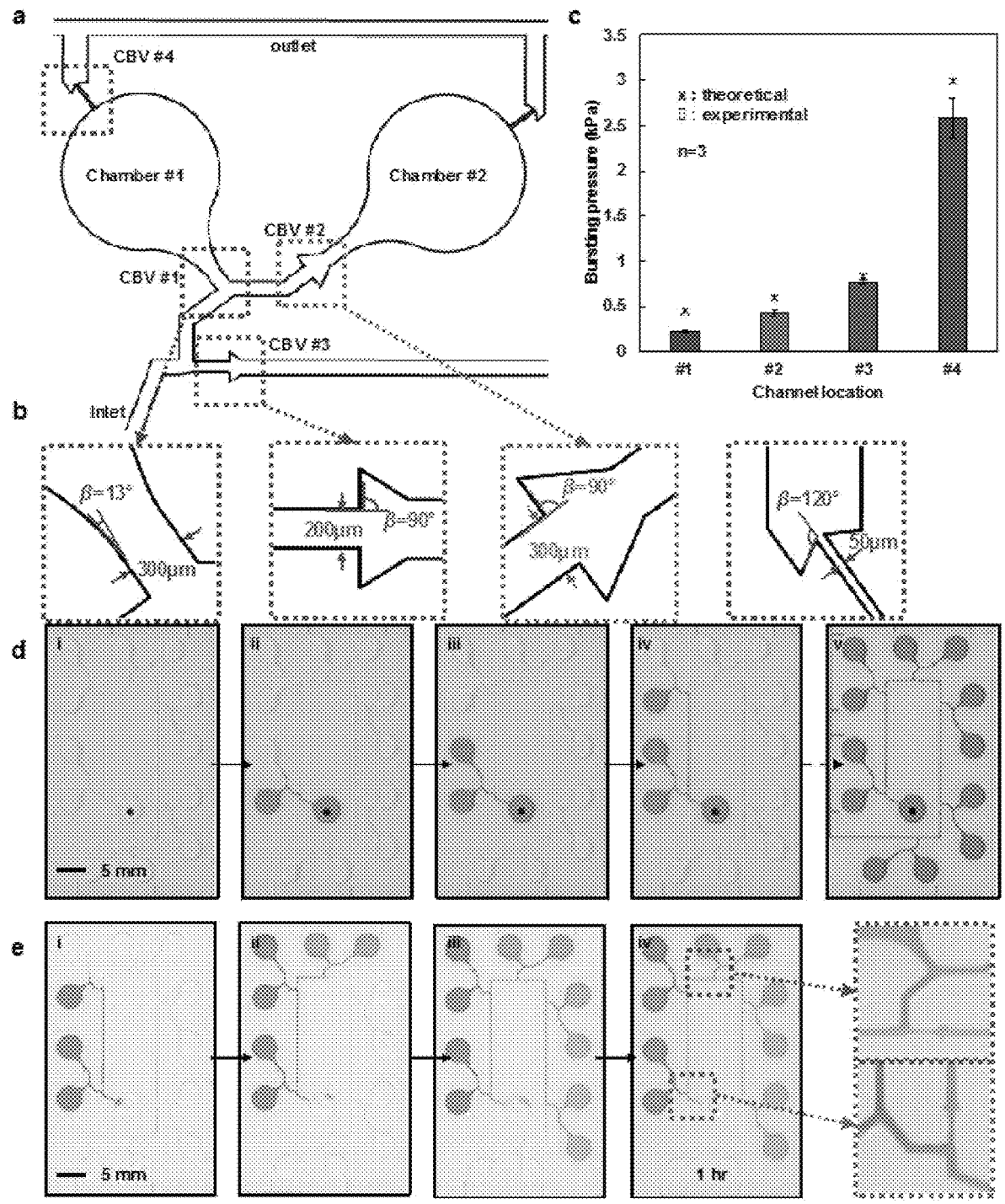
FIG. 14 shows: (a) Detailed schematic illustration of a unit cell in a device, including a collection chamber, sampling outlet, and four capillary bursting valves (CBV). (b) Sketch of capillary bursting valves with indicated channel width and diverging angle. (c) Experimental results (bars) and theoretical values (asterisk) of capillary bursting pressure of CBV #1, #2, #3 and #4 of device. (d) Optical images of the working principle of the capillary bursting valves for chrono-sampling. (i) Before entering collection chamber (ii) filling the collection chamber #1 (iii) flowing to chamber #2 (iv) flowing to next chamber (v) after filling all chambers. (e) Optical images of in vitro testing of chrono-sampling with different colored dyes in water (red, green, and blue) and enlarged images of the interface between different colored dye.

By locating CBVs with different bursting pressure, the microfluidic channel controls the direction of the liquid in the channel. Panel (a) of FIG. 14 shows a set of CBVs. From #1 to #4 and the bursting pressure increases with its number; CBV #1 and #2 has 300 μm wide channel with 13° and 90° of diverging outlet, respectively. CBV #3 and #4 has 200 μm and 50 μm wide channel with 90° and 120° of diverging outlet, respectively. Experimental results show the difference of bursting pressure from each CBVs. The values were smaller than theoretical value and it is mainly due to the round edge generation during fabrication process that leads diverging angles to be decreased than the design values. When sweat flows from inlet, it first reach to intersection composed of CBV #1, #2 and #3. Sweat first burst CBV #1 and fills the chamber #1. Then, CBV #4 with highest BP blocks the sweat flow and sweat burst chamber #2. After filling chamber #1 and #2, sweat burst CBV #3 and flows to the next chambers. panel (d) of FIG. 14 shows that the microfluidic device can sequentially collect liquid without undesired bursting of CBVs. The flow properties of the microchannels and geometry of the microfluidic channel prevent unwanted mixing. Specifically, for channel dimensions of hundreds of micrometers and flow rates from sweat up to 1.0 μl min' in the device, the laminar flow with low Reynolds numbers (<1) generated and mixing occurs only by molecular diffusion. The small intersection area between the chambers defined by width and height of inlet of the chamber is 0.18 mm² also minimize the diffusion effect. The example illustrates operation with water dyed using different colors and introduced in a time sequenced manner. Over relevant time scales (≈1 h) and temperatures (≈37° C.), diffusion occurs only within the connecting channel between water with different colors that does not affect to the reaction in the chamber (panel e(iv) of FIG. 14). The fourth chamber in this example is relatively dark due to mixing of the red dye in the bridge channel with blue dye.

Example 2: Mitigating Inadvertent Water Transport in Epidermal Microfluidic Sensors (U.S. Pat. App. 62/514,374 Atty Ref NU2017-071: 46-17P)

The accuracy of sweat capture and analysis from athletes in hot climates and/or for long durations may be challenged by the evaporation of sweat from the device during and after capturing the sweat. This may be caused by the use of polymer materials which are poor barriers to water vapor, and/or through vapor loss through the outlet(s), for example. Described herein are systems and methods for mitigating water vapor loss from epidermal microfluidic systems via polymers with high barrier properties and/or by augmenting the vapor pressure of the captured sweat via gelling agents.

Applications of the present systems and methods include: preventing water loss via evaporation from epidermal microfluidic sensors; and preventing water uptake into epidermal microfluidic sensors from the environment during aquatic exercise.

Advantages of the present systems and methods include: improving accuracy of epidermal microfluid sensors by reducing rate of evaporative water loss; and Reducing water uptake from the environment during aquatic exercise In certain embodiments, biofluid and/or vapor loss or uptake from epidermal microfluidic systems may be mitigated by having layers (e.g., the substrate and/or capping layer) at least partially formed of one or more thermoplastic elastomers (TPEs) with good water barrier properties and high-strain-to-failure. In certain embodiments, biofluid and/or vapor loss or uptake from epidermal microfluidic systems may be mitigated by having a thin, patterned, high-barrier capping lay on top of a PDMS-based substrate layer, for example, which includes a microfluidic network and sensor(s). In certain embodiments, biofluid and/or vapor loss or uptake from epidermal microfluidic systems may be mitigated by including one or more gelling agents in the microfluidic system to augment the vapor pressure of the collected sweat. Biofluid and/or vapor loss or uptake from epidermal microfluidic systems may also be mitigated by any combination of the above described features and methods.

FIG. 15 illustrates cross sections of certain embodiments of the microfluidic systems disclosed herein. The data plot shows fluid loss due to evaporation from the microfluidic systems as a function of time. The data shows that water may evaporate through PDMS and that a capping layer, including a PET capping layer for example, may reduce fluid loss.

Thin, Soft Microfluidic Devices for Sweat Capture and Analysis of Aquatic Athletes: The thin geometries and soft mechanics of these microfluidic systems allows for intimate and comfortable adhering to the skin for the purpose of collecting, manipulating, analyzing, and/or storing biofluid (e.g., sweat), captured from aquatic athletes. The microfluidic system may include two layers (e.g., substrate with the microfluidic features and a protective or capping layer) of a styrenic block copolymer (SBC) supported on an adhesive film (e.g., medical-grade acrylic) for bonding to the skin. The SBC may be styrene-ethylene-butadiene-styrene (SEBS), styrene-isoprene-styrene (SIS), or styrene-butadiene-styrene (SBS), for example. The styrenic block copolymer may be an oleogel styrenic block copolymer. The styrene composition may be between 10-50% of the polymer. The mechanical properties (e.g., modulus and elongation to failure) of the SBC may be augmented by the addition of an additive such as low molecular weight hydrocarbon (e.g., paraffin oil). For example, weight ratios of additive (e.g., paraffin oil) to the SBC may be from 1:1 to 3:1, for example. Furthermore, any of the layers may further include a tackifier, such as rosin gum, to improve the adhesion of the device layers to each other or to the adhesive. Example weight ratios of tackifier additive to SBC polymer with an additive may be 0.5:1 to 4:1, for example. The first layer (e.g., substrate) may define a network of microfluidic channels, reservoir chambers, an inlet, an outlet, and capillary burst valves, such as illustrated in FIG. 15. For example, the channels may be 400 μm in thickness, and channel widths and heights may be 200 and 300 respectively). The second layer may be a capping layer. For example, the capping layer may be in 200 μm thickness and may have a biofluid inlet aligned to the biofluid inlet of the first layer. The third layer may be an adhesive layer to establish adhesion to the skin and further define openings from which sweat can enter the microfluidic system. For example, the adhesive layer may be 50 μm in thickness and the openings in the adhesive layer may be 2 mm in diameter. The microfluidic system includes a biofluid inlet, which may be 1 mm in diameter, for example. The microfluidic system includes reservoir chambers connected a microfluidic outlet conduit network. The microfluidic outlet conduit network includes an outlet, which may be 0.5 mm in diameter, for example. The outlet is designed to allow release of air that would otherwise be trapped in the chamber and serve as a source of backpressure to frustrate the filling of sweat into the chamber. FIG. 15 illustrates cross sections of certain embodiments of the microfluidic systems disclosed herein. FIG. 15 further shows fluid loss from the depicted microfluidic systems as a function of time. The data shows that water may evaporate through PDMS and that a PET capping layer, for example, may reduce fluid loss.

Figure 16:
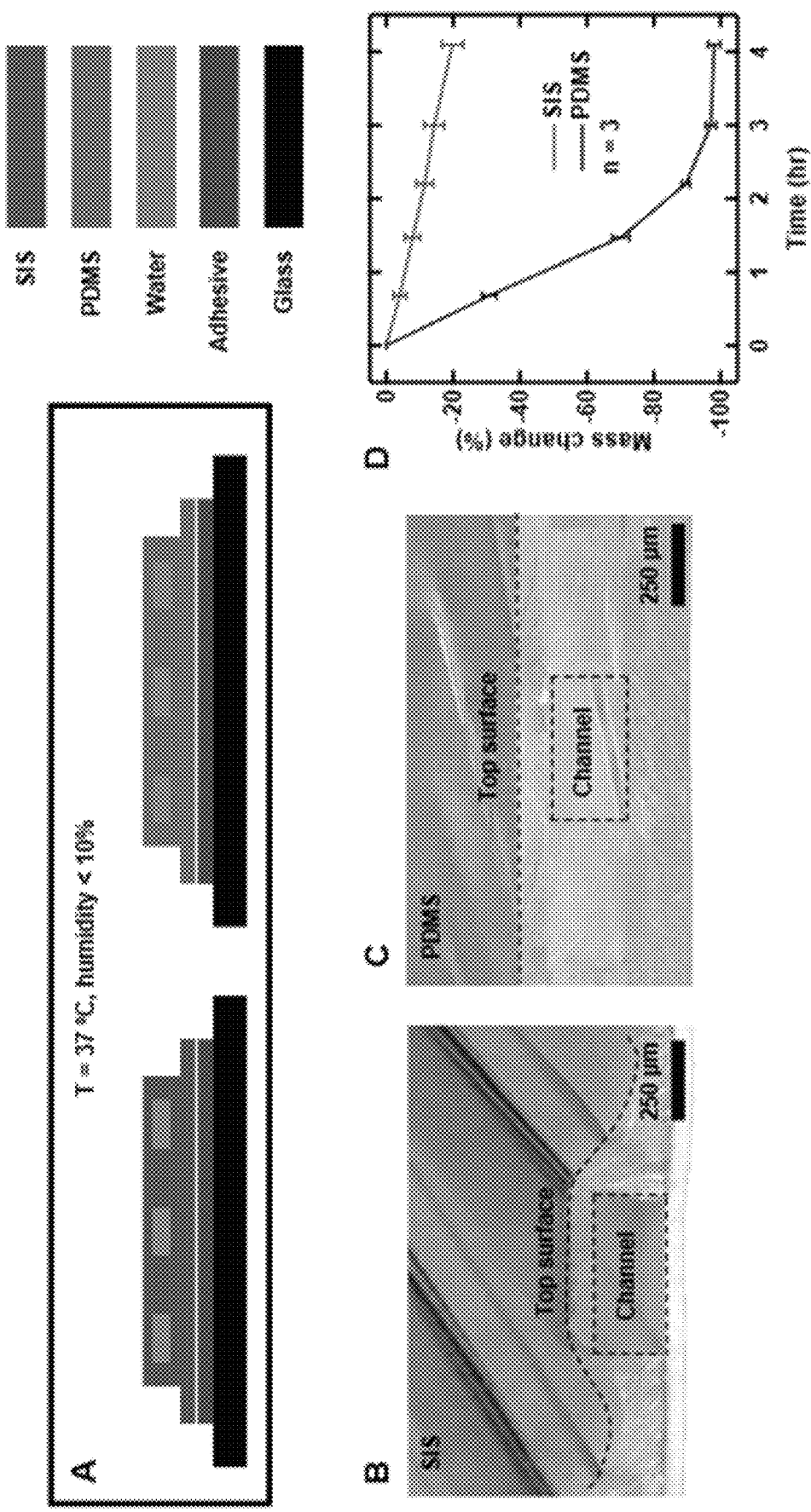
FIG. 16 shows comparison of evaporation rate of sweat after collection. (A) Experimental setup for measuring evaporative water loss from epifluidic devices. (B) Cross-sectional micrograph of an SIS device. (C) Cross-sectional micrograph of a PDMS device. (D) The mass change of PDMS and SIS epifluidic devices after filling with water and heating at 37° C. SIS devices are able to store sweat for 4 hours with less than 20% loss, while PDMS devices lost ~100% within 3 hrs.

Reliable sweat collection in aquatic settings or in arid climates requires constituent materials with excellent barrier properties to prevent contamination or to eliminate evaporative loss, respectively. Results of measurements of water transport through SIS membranes and water absorption into bulk SIS appear in FIG. 16D. Less than 80 mg of water vapor passes through a 125 μm thick, 1.8 cm2 SIS membrane over 12 days in a humid (>90%) environment (a permeability of 4.6×10-8 g-m/mm2/hr/Pa). SIS at 37° C. water absorbs less than 1.5% of its weight over the same period. Comparisons of evaporative loss of water from devices constructed in SIS and PDMS highlight the importance of barrier properties for collecting and storing sweat (FIG. 16). SIS devices with open outlets can store sweat at 37° C. for 4 hours with less than 20% loss while PDMS devices of comparable geometry lose ~100% within 3 hours.

Example 3: Mitigating Loss of Collected Sweat Due to Mechanical Motion in Epidermal Microfluidic Sensors (U.S. App. No. 62/514,455 Atty Ref NU2017-072: 47-17P)

The capture and analysis of sweat from athletes requires the storage of sweat to be resistant to a variety of motions including bending, stretching, twisting, and compression. Sweat that is stored and contained by capillary burst valves may be susceptible to premature bursting if environmental forces cause the pressure in the chamber to increase above the capillary burst pressure. Disclosed herein are systems and methods to mitigate the bursting of outlet valves by mechanical reinforcement of the chamber ceilings and/or gelling agents, according to certain embodiments.

Applications of the present systems and methods include preventing loss of sweat in epidermal microfluidic sensors due to motion, twisting, bending, or compression Advantages of the present systems and methods include improving robustness of epidermal microfluidic sensors against motion-induced sweat loss In certain embodiments, sweat loss from the microfluidic system due to mechanical forces may be mitigated by having a thin, patterned, high modulus capping layer on top of a PDMS or styrenic block copolymer (SBC) substrate layer having a microfluidic network. In certain embodiments, sweat loss from the microfluidic system due to mechanical forces may be mitigated by including one or more gelling agents in the microfluidic system to augment the viscosity of collected sweat. Sweat loss from the microfluidic system may also be mitigated with the combination of a thin, patterned, high modulus capping layer on top of a PDMS or styrenic block copolymer (SBC) substrate layer and gelling agents supported by the microfluidic network.

FIG. 17 illustrates cross sections of certain embodiments of the microfluidic systems disclosed herein. In particular, a viscosity modifier may be utilized to provide additional stability to the chamber and capillary burst valve (CBV). Examples of viscosity modifiers are provided and the photograph shows without viscosity modifier and attendant unwanted ejection (left photo) and with a viscosity modifier where unwanted ejection is avoided (right photo), each under a mechanical deformation.

Patterned rigid capping layer for strain localization: A thin, flexible polymer with high barrier properties may be laminated on top of sweat collection chambers. The capping layer may be selectively removed (e.g., etched) above non-essential areas (e.g., regions not corresponding to microchannels, reservoirs, capillary burst valves, inlets, outlets, and/or sensors) to localize strains to these non-essential regions and allow stretching and flexing of the microfluidic system. The capping layer may mechanically reinforce the sweat chamber ceiling, thereby reducing the effect of mechanical strains on the volume and pressure inside the chamber. Capping layer materials may include commercially available polyolefins (polyethylene, polypropylene and polyisobutylene), polyesters (polyethylene terephthalate and polyethylene naphthalate), fluorocarbons (polyvinylidene chloride and polytetrafluoroethylene), polyamides (nylon), and polyimides (poly-oxydiphenylene-pyromellitimide).

Gelling agents for increasing the viscosity of collected sweat: Gelling agents (also referred herein as a viscosity modifier) may include water-soluble cellulose derivatives (e.g., methyl cellulose or hydroxypropyl methylcellulose). Gelling agents may be added to any of features of the microfluidic system, such as the biofluid collecting reservoir chambers. The gelling agents may be selected according to their ability to absorb a large amount of water relative to their mass, while undergoing relatively small changes in their volume. During use, for example, sweat may enter reservoir chambers and mix with the gelling agent(s), as a result of which the viscosity of the sweat may increase without a large volumetric expansion. For example, at concentrations higher than 1:5 by weight (cellulose to biofluid) the captured biofluid may become a semi-solid gel. For example, the gelling agents may be depositing using air brushing. Exemplary gelling agents may also further include one or more of agar, sodium alginate or any of a number of water soluble polymers.

Viscosity modifier for stable CBVs: Increasing the viscosity of biofluid at collection chambers can selectively contain it and prevents inadvertent ejection from the chamber when pressed, twisted, or otherwise subjected to mechanical deformation. Various viscosity modifiers can be used, and by adding it to individual chambers and enables unimpeded operation of the surrounding network of channels and chambers.

Viscosity modifiers include Methyl cellulose, hydroxypropyl methylcellulose (HPMC), Agar, sodium alginate, or any number of water soluble polymers.

Example 4: "Skin-Like" Wearable Sensor for Capturing and Measuring Insensible Sweat Loss for Analysis (U.S. Pat. App. 62/514,546)

Systems for capturing and measuring insensible sweat loss (e.g. sweat loss not measurable by conventional methods such as absorbent pads) during resting offer the potential to enable analysis of temporal variations in water loss and biomarkers. Current sensors that rely on absorbent pads and microfluidics need a certain amount of sweat in a sequential manner for analysis, and are not easy to use for subjects who are in the situation where it is difficult to do exercise for sweating, e.g., infants, patients, etc. A thin and "skin-like" wearable wireless devise is described that bonds to the skin to allow for capturing and detecting insensible sweat in an interconnected set of micropumps and electronic systems. Embodiments of the device have two characteristics: one is that the device is able to measure insensible sweat loss with time as signals of capacitance changes by high sensitive electrodes and send the data via a wireless system with NFC chips, the other that the device is able to capture and collect the sweat pumped up from skin by two kinds of capillary forces for biomarker analysis. The systems also can be combined with a RF heater for the purpose of inducing sweat and capturing the sweat more efficiency.

Described herein are methods and system for measuring temporal changes in insensible sweat loss during resting by a high sensitivity electrode with water capturable absorbents. The described system can capturing and store a small amount of biofluid such as sweat, tear, blood, etc., for analysis. Further, the systems may induce sweat by a local heating system without specific drugs such as pilocarpine or acetylcholine.

Described is a method for measuring insensible sweat rates by using a high sensitivity electrode with water absorbents and systems therefor. Also described is a method for capturing a small amount of biofluid by using a microporous absorbent as a micropump and systems therefor. In some embodiments, the described systems and methods provide a heater to induce sweat without drugs and collecting the sweat for use in diagnosis.

The described systems and methods can capture and detect a small amount of insensible sweat using a water capturable absorbent and an electronic system. The technology consists of two specific characteristics: one is a high sensitivity electrode combined with water capturable absorbent which enable to detect a small amount of sweat loss and measure the sweat rate, the other is a micropump system formed from two kinds of capitally force which enable to capture insensible sweat from skin and store it. The device provides the information about water loss and biomarkers in insensible sweat inducing physiological or psychological stimulations, which is useful both for diagnosis and for basic science study in neuron science, sleeping study, etc.

A "Skin-like" Wearable Wireless Sensors for Capturing and Measuring Insensible Sweat Loss for Analysis is described herein. The soft mechanics, electronics, and hydrophilic microporous geometries of the devices enable them to reliably fit to the skin and to capture and detect the nanoliter volume of insensible sweat released from skin efficiency (panel (a) of FIG. 18) during resting. A representative device shown in panel (a) of FIG. 18 has a rectangular geometry (the height, width and length are 930 µm, 2 cm and 4 cm) and two detection areas: one consists of a electronic system for detecting and measuring the amount of insensible sweat loss with time, and the other consists of microporous polymers for capturing and collecting insensible sweat from skin to analyze biomarkers. The device can be attached to any part of body. The whole device involves four layers, i.e., bottom layer that is a polyester mesh having pores with diameter of 74 µm (the thickness of 90 µm; the width and length are 1 cm and 1.5 cm) to absorb sweat from skin, the second layer that is a medical-grade silicon adhesive film with thickness of 140 µm for supporting the bottom and next layers and bonding to the skin, the third layer that is a poly(dimethylsiloxane) (PDMS) with thickness of 400 µm to support electrodes and porous polymer in the two areas, respectively, and the top layer that is a polyethylene film with thickness of 300 µm to prevent from gas evaporations.

Figure 18:
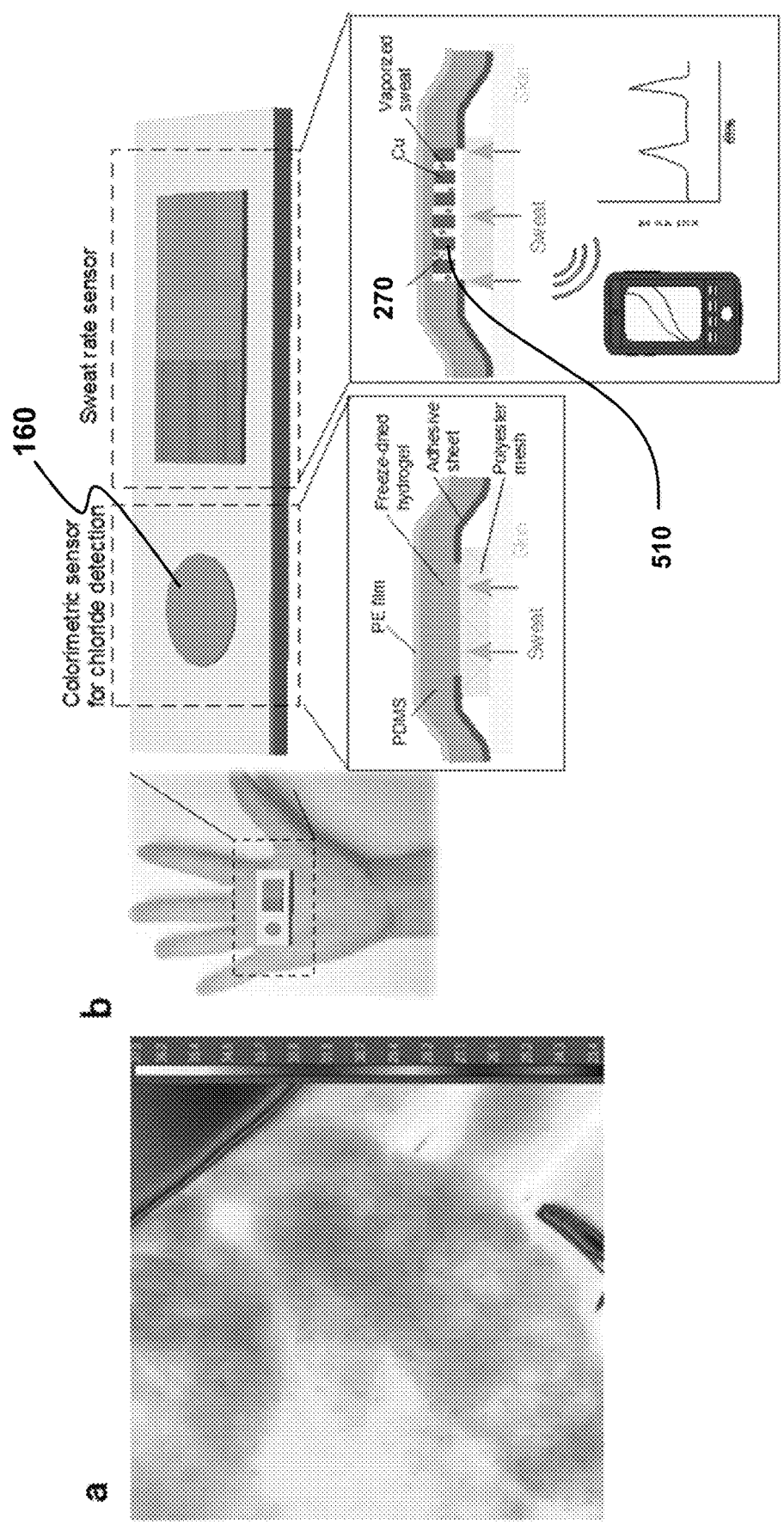
FIG. 18 shows the soft mechanics, electronics, and hydrophilic microporous geometries of the devices enable them to reliably fit to the skin and to capture and detect the nanoliter volume of insensible sweat released from skin efficiency (panel (a)) during resting. A representative device shown in panel (b) has a rectangular geometry (the height, width and length are 930 µm, 2 cm and 4 cm) and two detection areas: one comprises an electronic system for detecting and measuring the amount of insensible sweat loss with time, and the other comprises absorbents (e.g., microporous polymers) for capturing and collecting insensible sweat from skin to analyze biomarkers. The device can be attached to any part of body.

The structure of the area for measuring sweat rate is shown in the bottom right of panel (b) of FIG. 18. The amount of sweat loss can be estimated from the amount of evaporated sweat captured on the electrodes (the height, width and length are 80 µm, 70 µm and 1 cm). Insensible sweat evaporates immediately in a normal condition because the amount is very small. (panel (a) of FIG. 18). The first layer of a polyester mesh capture the insensible sweat came from skin by capillary force. The mild hydrophobic polyester can release the captured liquid easily. The vaporized sweat from the polyester is captured by the dried polyvinyl alcohol (PVA) gel installed between the electrodes, and induces capacitance changes in the electrode. By measuring the variation of the capacitance with time, the rate of the sweat evaporated from skin can be estimated. The dried PVA gel that has a hydrophilic microporous structure enables the electrodes to detect a small amount of vaporized insensible sweat and to prevent from the pressure in the area from increasing too much. The temporal variations in the signal of capacitance can be recorded on an application installed in a cell phone via wireless system with a NFC chip. From the analysis of the data, the amount of sweat loss with time for an appropriate time period such as sleeping time can be estimated.

The structure of the area for capturing and collecting insensible sweat to analyze chloride concentration in the sweat is shown in the bottom left of FIG. 18b. The first layer of the polymer mesh fixed on one side by medical-grade silicon/acrylic adhesive film is attached to skin and absorbs the small amount of insensible sweat directly by their capillary force in the same way to the area for measuring sweat rate. The other side of the polyester mesh is attached to a dried PVA hydrogel with diameter of 1 cm and thickness of 400 µm including a chloride assay reagent that is installed on the top layer of PDMS. The dried hydrogel is same material to that on the electrode in the other area and has a porous structure of nanometer to several micro miters. The narrower pore size and the hydrophilicity of the PVA enable it to get stronger capillary force compared with the polyester mesh. Because of the difference of the capillary force, the liquid moves from the polymer mesh to the dried PVA hydrogel like a tree trunk. The reagent of the chloride assay kit introduced in the PVA hydrogel react with the chloride in the sweat and its color changes to blue in dependence of the chloride concentration. From the amount of sweat loss measured from the other area and the intensity of the color, the concentration can be calculated.

Figure 19:
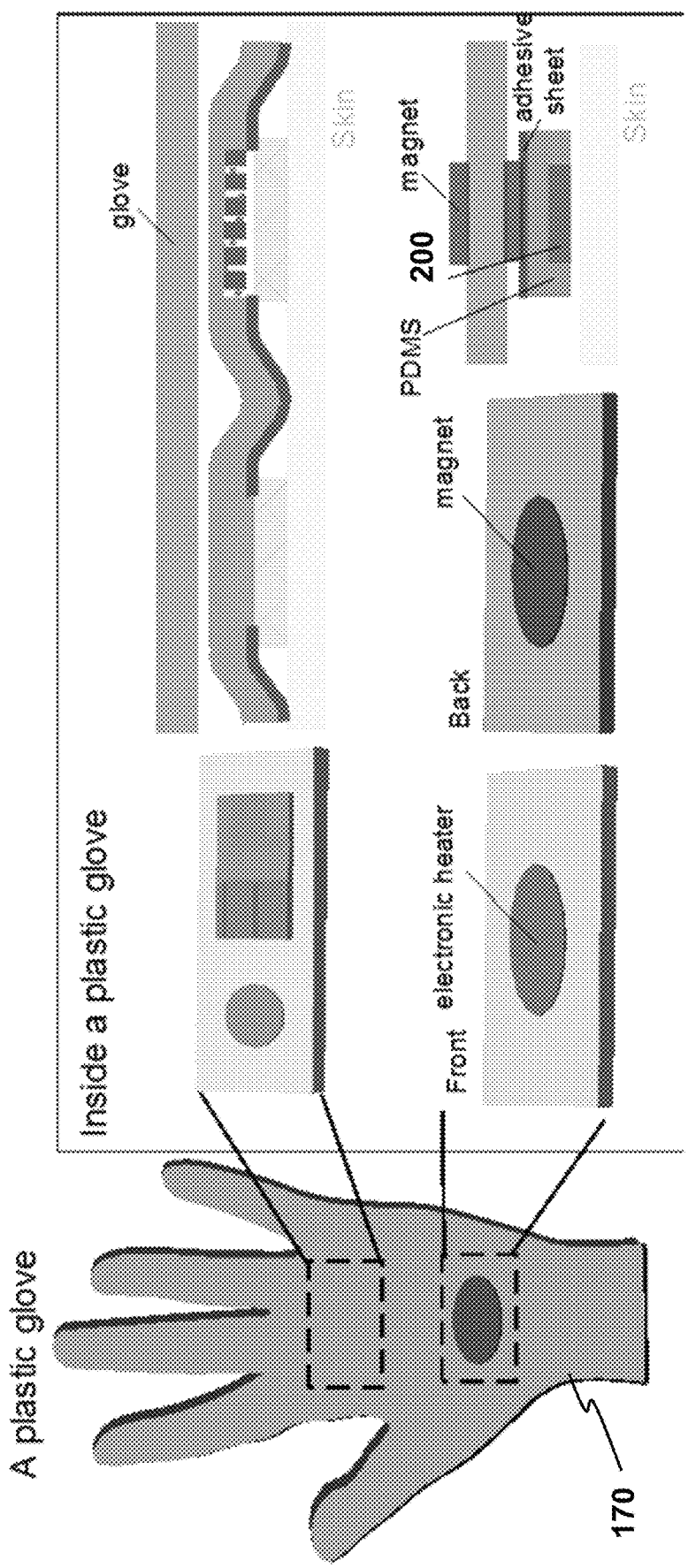
FIG. 19 shows a representative sweat inducing system with RF heaters for collecting sweat efficiency, with the system incorporated into a glove.

Sweat inducing system with RF heaters for collecting sweat efficiency. Local heating under high humidity can induce sweat efficiency without drugs. We propose a system combined a radio frequency (RF) heating system and a sweat sensor for collecting sweat in a short time for analysis of chloride, glucose, lactate acid, etc. A representative system is shown in FIG. 19. The RF heaters with magnet can be introduced inside a glove and can be moved to any parts using magnetic force from outside of the glove. When the skin is heated above 40° C., a heat-stimulated sweat begins to be induced. A RF heater is installed on one side of a PDMS film with thickness of 400 $\square$m that has a magnet on the other side. By placing two or three heaters inside of a disposable plastic glove, the hand can be heated under a high humidity condition. The heat-stimulated sweat induced by the heater can be captured by the device of insensible sweat for an analysis of biomarkers in the sweat.

Example 5: Device Fabrication

Fabrication of the microfluidic module: The fabrication process begins with sequential cleaning of a 4" silicon wafer with isopropyl alcohol, acetone, deionized water, and a final rinse with isopropyl alcohol. Next, spin coating a 15 µm thick film of photoresist (KMPR 1010; Microchem, MA, USA) following by baking at 110° C. for 5 min on a hot plate prepares the system for photolithographic patterning to define the geometry of the microfluidics. Exposing the wafer to UV light through a photomask mounted on the wafer, followed by baking at 110° C. for 3 min in a closed chamber, and then for 2 min in an open setup patterned the photoresist. Immersing the substrate in developer solution (AZ 917 MIF; Integrated Micro Materials, TX, USA) completed the process. Subsequently, deep reactive ion etching (STS Pegasus ICP-DRIE, SPTS Technologies Ltd.) created 600 µm deep micro patterned trenches in the silicon wafer. Finally, spin coating poly(methylmethacrylate) (PMMA; Microchem, MA, USA) on the pattered silicon mold and baking at 180° C. for 3 min primed the mold to facilitate release of polydimethylsiloxane (PDMS; Sylgard 184, Dow corning, MI, USA) cast and cured on top, as described next.

Dispersing 5 wt % white silicone (Reynolds Advanced Materials, IL, USA) into a transparent PDMS precursor (10:1, Sylgard 184) yielded a thick liquid cast onto the mold by spin coating at 200 rpm. Curing at 70° C. for 1 h yielded a 700 µm thick, soft, white microfluidic structure. A mechanical punch tool defined 1-mm diameter inlet holes for the colorimetric channels and 3-mm diameter inlet holes for the electrochemical chambers. Pouring PDMS (10:1) on a PMMA coated silicon wafer then spin casting at 400 rpm and curing at 70° C. for 1 h produced a uniform, 200 µm thick slab as a cap for the microfluidic platform. An additional layer of PDMS (60:1) spin cast at 1000 rpm and cured for another 1 h at 70° C. formed a thin, tacky coating. Separately, a commercial laser printer (Konica Minolta C454 PS color, Tokyo, Japan) printed color reference markers on a 25 µm thick polyester (PET) film (FLX000464; FLEXcon, MA, USA), and a CO2 laser (Universal Laser Systems, AZ, USA) defined sweat inlet holes in a skin adhesive membrane (PC2723U, ScapaHealthcare). Assembly of the microfluidic patch involved placing the colorimetric assays, electrochemical sensors, and neodymium magnets (D0105 Nickel; SuperMagnetMan, AL, USA) into their respective chambers and then laminating the sticky side of the capping layer onto the top of the microfluidic patch. Plasma treating a skin adhesive membrane, the color reference marker film and the microfluidic platform with a handheld corona generator yielded hydrophilic surfaces that allowed efficient bonding of the stack to complete the fabrication.

Development of colorimetric assays for chloride and pH: The colorimetric chloride assay solution consisted of 50 mg of silver chloranilate (MP Bioscience, CA, USA) dispersed in 200 µl of 2 wt % polyhydroxyethylmethacrylate (Sigma-Aldrich, MO, USA) methanolic suspension. Drop-casting 0.5 µl delivered this chloride assay cocktail in the chambers designated for chloride sensing. Suspending 4 mL of universal pH dye (Fisher Scientific, NH, USA), 274 mg of polyvinyl chloride (M.W. ~233,000; Sigma Aldrich, MO, USA), 635 µl of o-nitrophenyloctylether (Sigma Aldrich, MO, USA) and 508 µl of Aliquat (Sigma Aldrich, MO, USA) in 10 ml of tetrahydrofuran (Sigma Aldrich, MO, USA) yielded the pH assay solution. Dip-coating filter papers (Sigma Aldrich, MO, USA) in the pH cocktail for 10 s, and allowing them to dry at ambient conditions for 15 min formed the solid-state pH assay. Cutting the pH assay paper into circular pads using a metal punch (diameter, 2 mm) and placing them in each of the chambers designated for pH sensing completed the process.

Fabrication of biofuel cell-based electrochemical sensors for lactate and glucose: Electron beam evaporation (AJA International Inc., MA, USA) formed a thin film of chromium (thickness, 10 nm) as an adhesion layer, followed by a layer of gold (thickness, 100 nm) as a conductor on a 75-μm thick sheet of polyimide (Argon Inc., CA, USA). A UV laser (LPKF, Germany) patterned the gold coated polyimide sheet to define the circular current collector, serpentine interconnects, and contact pads. The first step in realizing a biofuel cell-based lactate sensor involved punching out circular pads (diameter, 2 mm) of CNT paper (Thin Film BA-01-145; NanoTechLabs, NC, USA). Coating with 2 μl of 0.1M tetrathiafulvalene (Sigma Aldrich, MO, USA) solution prepared in acetone/ethanol (1:9 v/v) and 4 μl of lactate oxidase (Toyobo Chemicals, Japan), and allowing them to dry, yielded enzyme functionalized CNT pads. The enzyme solution resulted from dispersing the enzyme (60 mg/ml) in 0.1M phosphate buffer containing 0.25 wt % glutaraldehyde (Sigma Aldrich, MO, USA). Subsequently, drop-casting and drying 2 μl of chitosan (CAS Number 9012-76-4; Sigma Aldrich, MO, USA) suspension prepared in 0.1M acetic acid onto each pad formed a chitosan-based membrane. Dipping the dried pads into the chitosan solution for 5 s and then allowing to dry resulted in an additional chitosan membrane. Finally, dipping the pads for 5 s in 3 wt % polyvinyl chloride (PVC) (CAS Number 9002-86-2; Sigma Aldrich, MO, USA) suspension in tetrahydrofuran, and thoroughly air drying them formed the outer layer of PVC membrane. Conductive silver glue then bonded the pads to the gold current collectors to complete the anode functionalization process. The cathode for the lactate sensor resulted from drop casting 15 μl of 10 mg/ml platinum black (Sigma Aldrich, MO, USA) suspension prepared in deionized water, followed by applying 1 μl of Nafion® 117 solution (Sigma Aldrich, MO, USA), onto the cathode designated gold current collector. Storing the sensors at 40 C for at least 1 week before use allowed the chitosan and PVC membranes to stabilize. Fabrication of biofuel-cell based glucose sensors involved steps similar to those discussed for the lactate sensor with some modifications. The process began with drop-casting 1 μl of 0.1M tetrathiafulvalene solution onto CNT pads. Separately, preparing a 40 mg/ml solution of glucose oxidase in 0.1M phosphate buffer containing 10 mg/ml bovine serum albumin (Sigma Aldrich, MO, USA) and a 1 wt % suspension of Nafion® in 0.1M phosphate buffer and then mixing of the two suspensions in equal volumes yielded the enzyme coating suspension. Application of 2 μl of the enzyme coating suspension functionalized the tetrathiafulvalene coated CNT pads. Conductive silver glue bonded the pads to the gold current collectors to complete the anode. The glucose sensor cathode resulted from preparing a 10 mg/ml suspension of 10% platinum on carbon (Sigma Aldrich, MO, USA) in a 2 wt % ethanolic suspension of Nafion® followed by casting 5 μl of the suspension on each current collector. Storing the sensors at 40° C. for at least 1 week before use allowed the Nafion® membrane to equilibrate. Both the lactate and glucose sensors were stable for at least 6 months when store at 40 C without any additional storing conditions. Prior to use exposure of glucose sensors to buffer solution resulted in stabilized signals for micromolar detection in sweat.

Fabrication of battery-free NFC-based electronics: A LPKF U4 UV laser patterned a commercial substrate (Du pont Pyralux AP8535R) to form a flexible printed circuit board (PCB) for the wireless, battery-free electronics. Pulsed mode electroplating (LPKFContac S4) filled the vias with copper to form connections between the top and bottom layers of the device. The electronics assembly consisted of soldering the microcontroller and NFC frontend combination (TI RF430FRL152H), zero crossover operational amplifier (Analog devices ADA4505-2) and various passive resistor and capacitor components in 0201 form-factor, using low temperature solder (Indium corp. In/Sn 90/10) paste. Finally, a 14 μm thick layer of parylene formed by chemical vapor deposition (SCS Labcoter® 2 Parylene Deposition System, Specialty Coating Systems, IN) serves as a waterproof encapsulation for the entire system of NFC electronics.

Working principle of biofuel-cell based electrochemical sensors: A typical biofuel cell based electrochemical sensor comprises of an enzyme functionalized anode and an oxygen reducing cathode. The enzyme selectively catalyzes the oxidation of the desired analyte (for e.g.: lactate or glucose) and thus offers selectivity to the biofuel cell based sensors. In addition to the enzyme, the anode also includes a redox mediator for efficiently shuttle electrons from the enzyme's active site to the current collector. The cathode is fabricated by coating catalysts for oxygen reduction reaction. Oxidases and dehydrogenase enzymes are typically used for selectively oxidizing the desired analyte. Commonly used redox species, such as, but not limited to, tetratiafulvalene, quionones, redox dyes act as electron shuttles. Current collectors include, gold, platinum, stainless steel, carbon. Performance of the sensors can be increased by incorporating nanomaterials such as but not limited to, carbon nanotubes, graphene, metal nanoparticles, metal oxide nanoparticles, etc. The oxygen reducing cathodes include functionalizing current collectors with noble catalysts (platinum black, platinum on carbon, ruthenium on carbon), or enzymes such as laccase, bilirubin oxidase that reduce dissolved oxygen to water. Both anode and cathode are further coated with polymeric membranes to obviate leaching of chemical reagents, as permselective layer to reduce interference from other chemicals and extend the detection range of the sensor.

When exposed to the sample (sweat), the analyte (e.g. but not limited to glucose, lactate) gets spontaneously oxidized at the anode while dissolved oxygen gets reduced at the cathode. These spontaneous reactions lead to a flow of current between the two electrodes whose magnitude is proportional to the concentration of analyte. By applying a fixed resistor between the anode and the cathode one can measure the output voltage (which is a function of concentration; $V=I*R$ and $I \alpha$ concentration) using NFC electronics.

Hybrid, battery-free, skin-mounted system for sweat sensing: The platform includes two components: a disposable soft, microfluidic network, and a re-usable, thin NFC electronics module. An exploded view illustration of the overall construction of each of these subsystems is in panel (A) of FIG. 20. A low-modulus (~1 MPa) silicone elastomer, patterned using soft lithographic techniques, defines a set of isolated chambers for colorimetric and electrochemical sensing, a ratcheted channel for quantifying sweat rate and total sweat loss, and a collection of interconnecting microchannels with passive, capillary bursting valves for routing sweat through the device. A patterned layer of skin-compatible adhesive enables robust attachment to the skin and it defines openings as interfaces between the skin and inlet ports in the bottom side of the microfluidic structure. The soft, flexible construction, as illustrated in panel (B) of FIG. 20, allows comfortable, water-tight, irritation-free mounting onto curved regions of the body.

Panel (C) of FIG. 20 shows the electronics module, where the NFC interface supports both wireless power delivery and data transmission to any NFC-enabled consumer device, such as a smart phone, tablet or watch. The design exploits a two-layered flexible circuit with minimal component count and a battery-free configuration for real-time data acquisition from lactate and glucose sensors in a biofuel cell layout located in the microfluidic structure. The biofuel cell design involves a voltage amplifier with defined sensor element load implemented with a small footprint operational amplifier and miniature passive components. The circuit conditions the signal for digitalization within the integrated NFC chip (TI RF430FRL152H). The analog electronics are robust, with minimal susceptibility to external noise caused by the NFC electronics and fluctuations in the supply voltage.

To enable re-use, the electronics mount onto disposable microfluidic systems with a releasable electro-mechanical interface. Specifically, a set of thin, small-scale neodymium magnets (diameter, 1 mm; height, 0.5 mm) affixed with conductive adhesives to contact pads on the backside of the electronic platform and another set embedded in recessed wells underneath contact pads to the electrochemical sensors in the microfluidic platform enable reversible, mechanically robust and self-aligning attachment with low resistance electrical coupling (panel (D) of FIG. 20). Panel (E) of FIG. 20 shows a photograph of the complete system. The user first adheres the microfluidic system to the skin, then magnetically mounts the electronics on top. An NFC enabled portable device or a long-range reader placed in proximity initiates wireless, real-time data acquisition from the lactate and glucose biofuel cell sensors. Visual readout or analysis of digital images allows colorimetric quantification of chloride, pH, and sweat rate/loss. Panel (F) of FIG. 20 shows a system attached to the forearm during sweating. In one example of use, the NFC functionality in a smartphone enables wireless data extraction and its camera permits digital colorimetric analysis, as illustrated in panel (G) of FIG. 20.

NFC electronics: panel (A) of FIG. 21 presents a simplified schematic illustration to highlight that amplification relies on a simple voltage follower design with a high frequency filter that eliminates fluctuations introduced by the electric field of the primary NFC antenna. This NFC electronics sub-system magnetically couples to electrochemical sensors embedded in a disposable microfluidic substrate. Panel (B) of FIG. 21 shows a completed device adhered to surfaces with small radii of curvature to demonstrate the mechanical robustness of this coupling scheme. FIG. 21 (panels (C)-(D)) presents the corresponding current (I) vs voltage (V) curves associated with the magnetic connection and the variation in phase response for the antenna in response to bending. These results highlight stable antenna performance metrics (i.e. Q-factor and resonance peak position) even during mechanical deformations and under cyclical attachment/detachment conditions. FIG. 21 (panels (E)-(F)) displays recorded I-V curves and impedance characterization at frequencies up to 1 MHz collected at regular intervals during cyclic testing.

Robust operation follows from electrical working principles that are tolerant to fluctuations in supply voltage that can occur during weak NFC coupling to the reader antenna. Because a non-regulated harvesting circuit scheme yields the highest possible coupling efficiency, the analog frontend must operate in a manner that is independent of voltage supply to allow for variances in magnetic resonant power transfer and, thus, stable operation in practical scenarios. This goal is accomplished by using a zero-crossover operational amplifier that amplifies the sensor signal regardless of supply voltage, without distortion.

Figure 25:
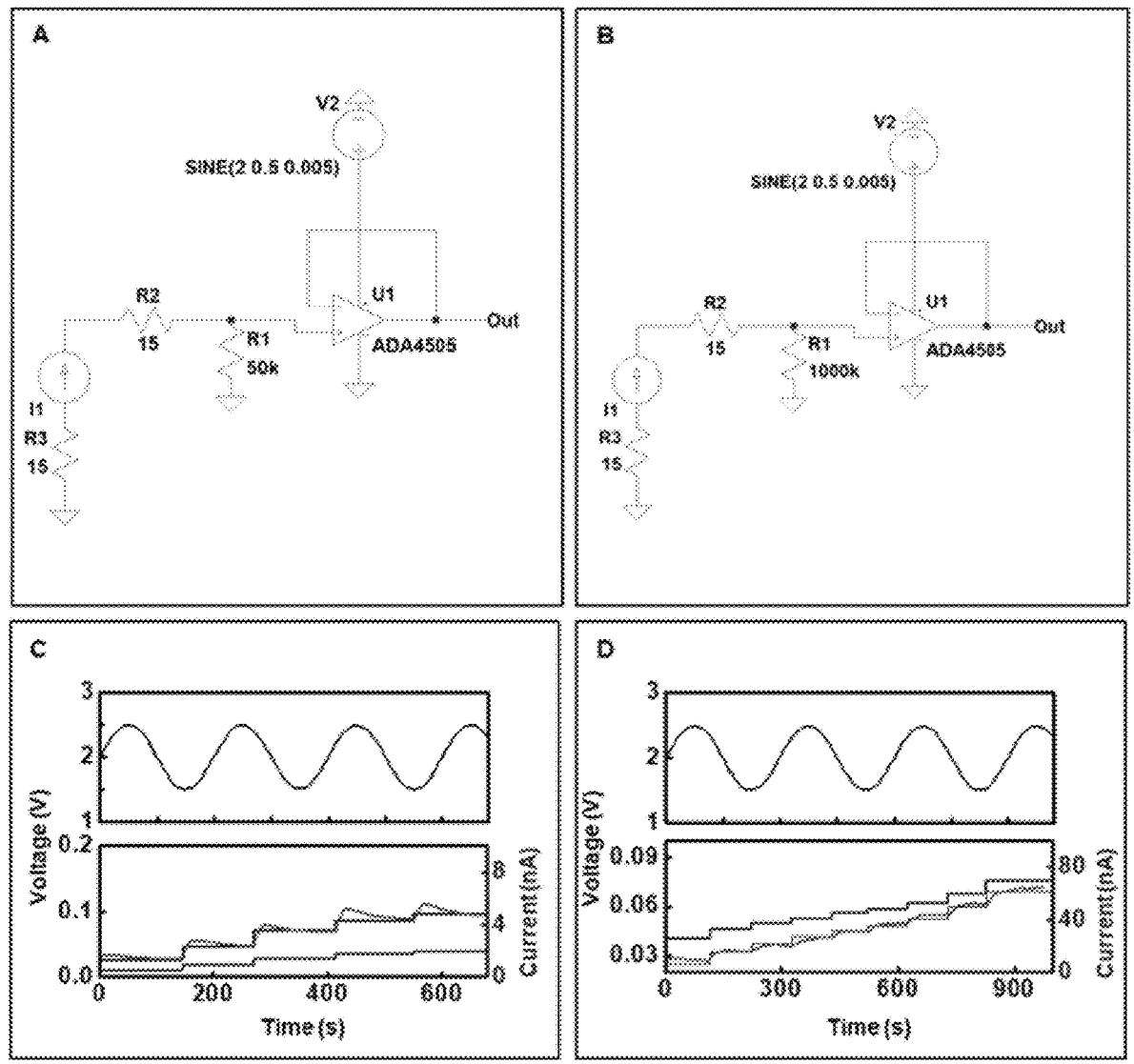
FIG. 25 shows (A and B) SPICE schematic of amplification scheme where R3 and R2 represent contact resistance of magnetic connection and R1 represents the respective load for (A) lactate and (B) glucose biofuel cell-based sensor. (C-D) Simulation results for amplified signal (black trace for voltage and blue trace for sensor current) vs. benchtop measurements (red trace) with oscillating supply voltage; demonstrating supply voltage insensitivity for (C) lactate and (D) glucose measurements with increasing concentrations.

Simulation Program with Integrated Circuit Emphasis (SPICE) software reveals the behavior of the biofuel cell-based lactate and glucose sensors signal conditioning when subject to varying supply voltage (FIG. 25). FIG. 25 (panels (C)-(D)) clearly confirms stable data acquisition over the entire range of supply voltages. FIG. 21 (panels (G)-(H)) show experimental validation through studies of the effect of distance and angle between the device and a hand-held reader with antenna size comparable to a smartphone (5×3 cm2) on sensor signal quality for the case of a constant reference sensor signal (100 mV) applied to the circuit. Panel (G) of FIG. 21 illustrates that the reader records stable signal from the device at a distance up to ~38 mm. Panel (H) of FIG. 21 shows that the reader is capable of recording uninterrupted, constant signals from the device at angles up to 600. These results demonstrate the broad range of conditions for which reliable data can be acquired, thus highlighting the robust, practical operational capabilities.

Biofuel cell-based electrochemical sensors for lactate and glucose: The biofuel cell design for the sensors is a critical feature of the systems. A scheme that illustrates different components of the lactate sensor is in panel (A) of FIG. 22, whereby the anode consists of circularly cut carbon nanotube (CNT) paper that provides a conductive, high surface area substrate to immobilize lactate oxidase (LOx) enzyme, for selectively catalyzing lactate oxidation, and the redox mediator tetrathiafulvalene, for shuttling electrons between the enzyme's active sites and the underlying CNT paper. A chitosan and polyvinyl chloride membrane coat the anode to minimize leaching of the mediator and enzyme, and to extend the linear detection range of the sensor. The cathode consists of a functionalized current collector of gold with an overlayer of platinum black, all coated with a Nafion® membrane. The platinum black acts as a catalyst for oxygen reduction while the Nafion® membrane prevents leaching of platinum black. The fluoride backbone of the Nafion® polymer facilitates adsorption of dissolved oxygen onto the cathode's surface, thereby improving the kinetic rate of oxygen reduction. An optical photograph of the complete lactate sensor is in panel (B) of FIG. 22.

Figure 22:
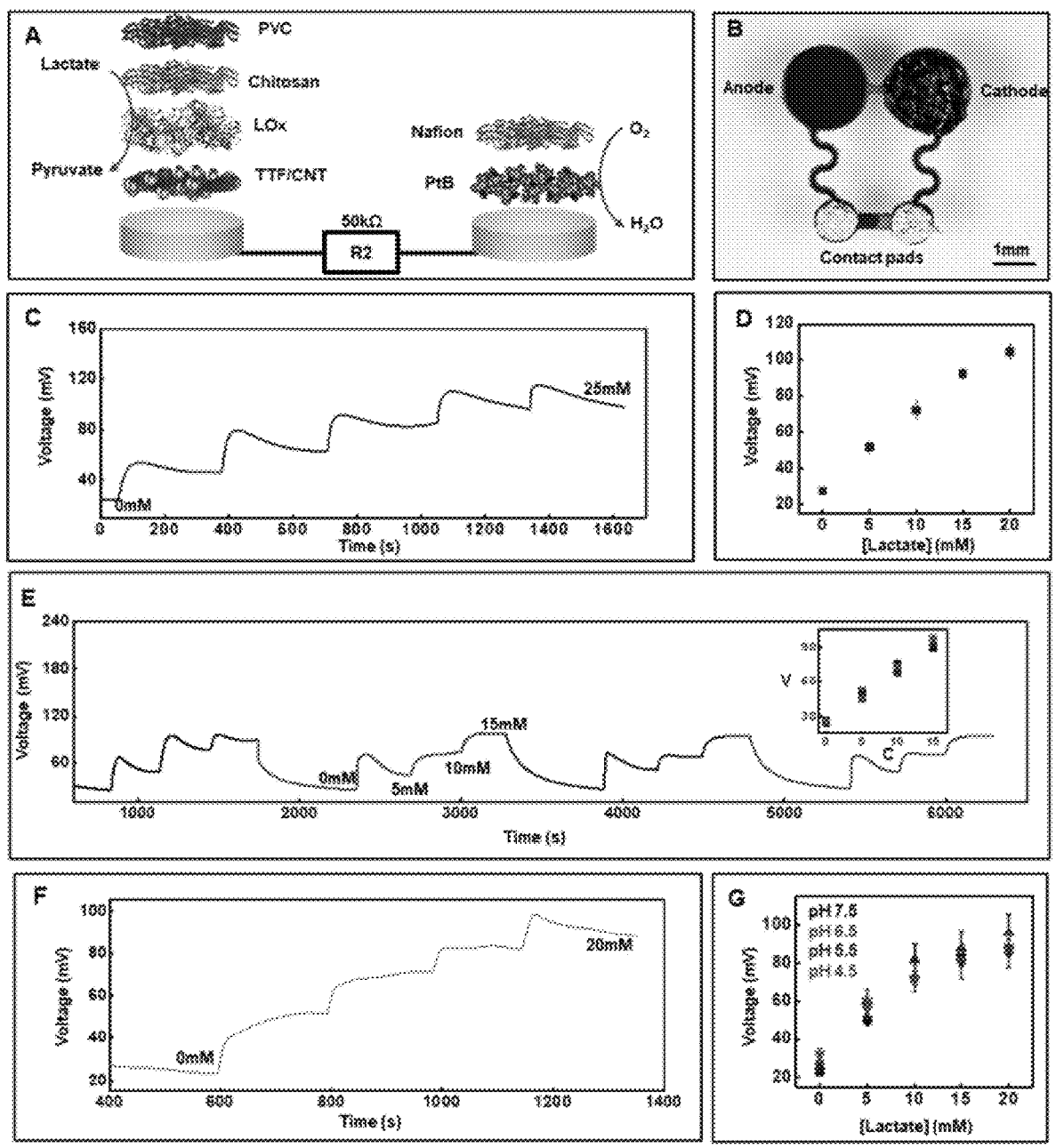
FIG. 22 shows lactate sensor characterization. (A) Exploded-view schematic visualizing layer makeup of the fuel cell-based lactate sensor. (B) Image of the actual lactate sensor. (C) Real-time sensor response to increasing lactate concentration in phosphate buffer (pH 7.0) at 25° C. and (D) the corresponding calibration (n=3). (E) Plot illustrating reversible sensor response for lactate sensor for four consecutive cycles of varying lactate concentration. (Inset: Calibration plot comparing the sensor signal plotted in (E) for the four cycles. V: voltage in millivolts; C: concentration in millimolar). (F) Real-time data acquired for increasing lactate concentration in artificial sweat under common physiological sweat conditions (temperature=30° C.; pH=5.5). (G) Calibration plot obtained for lactate sensors in artificial sweat at different pH (n=3).

The anodic and cathodic reactions that generate electrical currents in the lactate sensor are proportional to the concentration of lactate. A resistor connected across the sensor transforms the current into a voltage-based signal for detection and wireless transmission via the NFC electronics. The response of the sensor with increasing lactate concentration, evaluated in phosphate buffer solution at ambient conditions, appears in panel (C) of FIG. 22. Panel (D) of FIG. 22 shows the corresponding calibration plot, which indicates that the sensor signal stabilizes within 300 s and increases linearly with lactate concentration. This response is reversible (panel (E) of FIG. 22) as demonstrated in experiments that involve increasing the lactate concentration from 0 mM to 15 mM, reducing it to 0 mM, and then increasing it again in a step-wise fashion back to 15 mM for 4 consecutive cycles. The results highlight linear, reversible responses to time-varying concentrations of lactate concentrations with minimal hysteresis (panel (H) of FIG. 22) across a physiologically relevant range. Panel (F) of FIG. 22 displays response at 30° C. in artificial sweat at pH 5.5 while panel (G) of FIG. 22 shows calibration plot for increasing lactate concentration in artificial sweat with different pH at 30° C.

Figure 23:
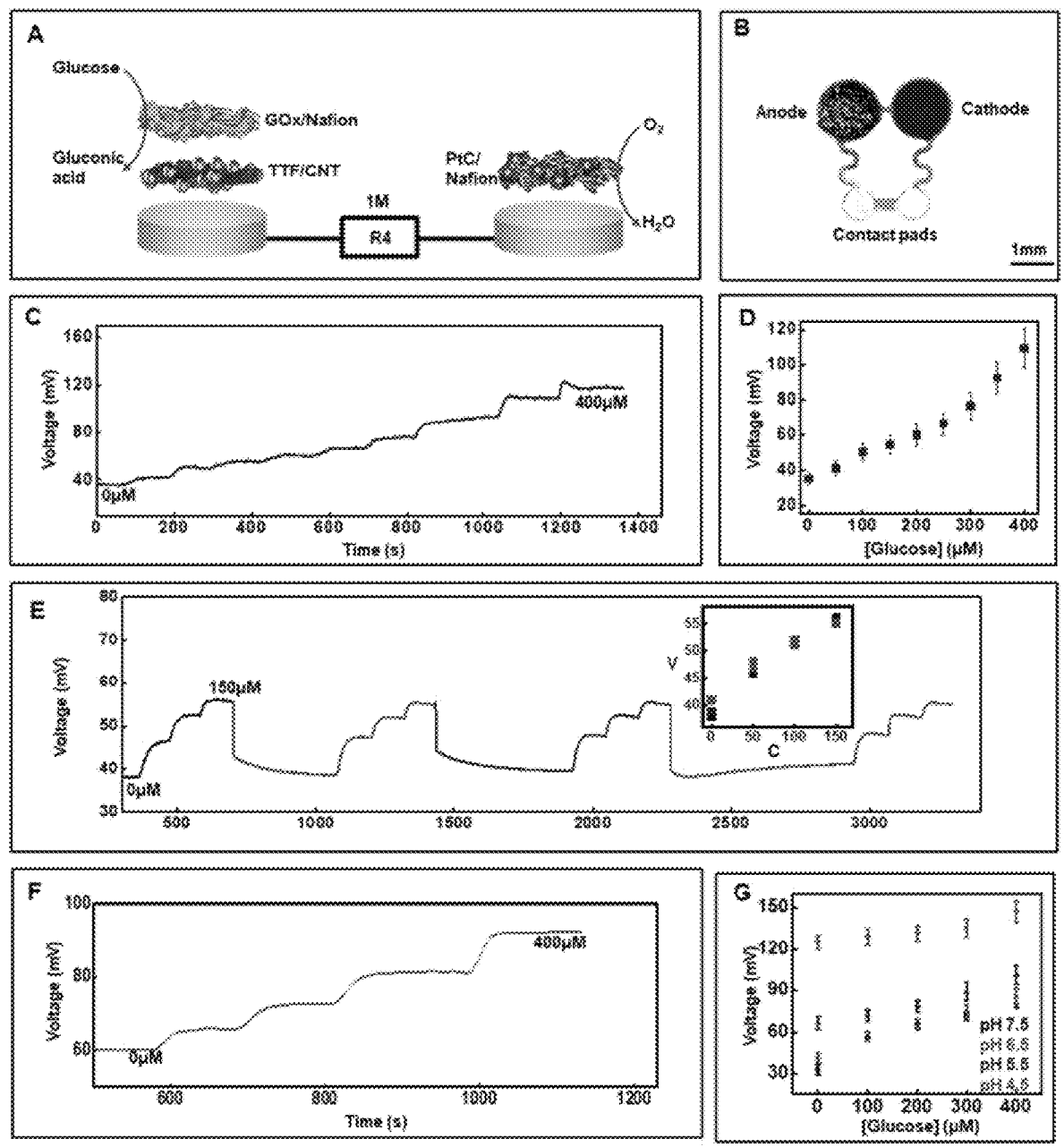
FIG. 23 shows glucose sensor characterization. (A) Exploded-view schematic visualizing layer makeup of the fuel cell-based glucose sensor. (B) Image of the actual glucose sensor. (C) Real-time sensor response to increasing glucose concentration in phosphate buffer (pH 7.0) at 25° C. and (D) the corresponding calibration. (n=3) (E) Plot illustrating reversible sensor response for glucose sensor for four consecutive cycles of varying glucose concentration. (Inset: Calibration plot comparing the sensor signal plotted in (E) for the four cycles. V: voltage in millivolts; C: concentration in micromolar). (F) Real-time data acquired for increasing glucose concentration in artificial sweat under common physiological sweat conditions (temperature=30° C.; pH=5.5). (G) Calibration plot obtained for glucose sensors in artificial sweat at different pH (n=3).

A similar approach, applied with a few modifications, yields sensors for glucose. Here, glucose oxidase enzyme is directly dispersed in the Nafion® to ensure rapid interaction of glucose with the enzyme and consequent capabilities in detection of micromolar concentrations. The cathode involves a gold-based current collector coated with a suspension of platinized carbon in Nafion® solution. panel (A) of FIG. 23 illustrates the different components of the sensor and panel (B) of FIG. 23 presents an image. Comprehensive studies conducted in a manner similar to those for the lactate sensor define the response. panel (C) of FIG. 23 summarizes real-time measurements as a function of increasing concentrations of glucose in buffer at ambient conditions, with a corresponding calibration plot (panel (D) of FIG. 23). panel (E) of FIG. 23 shows reversible nature of the sensor response. Panels (F)-(G) of FIG. 23 illustrate response of sensor in artificial sweat (pH 5.5, 30° C.) and effect of pH on sensor response respectively.

Figure 26:
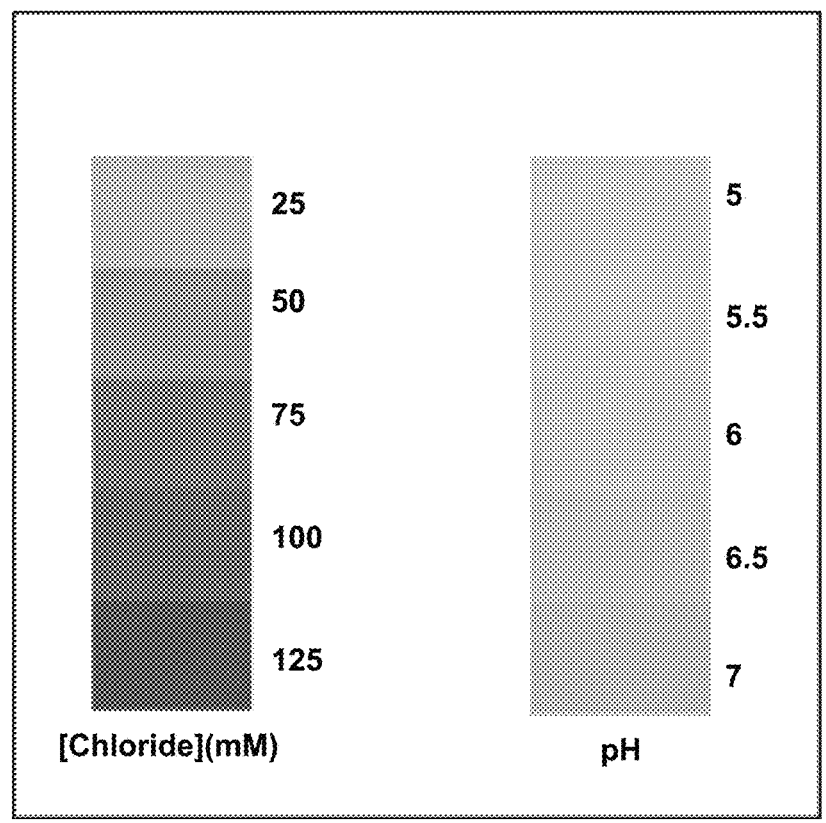
FIG. 26 shows color reference marker of a biofluid property that is chloride concentration (mM) and pH.

Colorimetric assays and microfluidics: The disposable microfluidic substrate houses the electrochemical sensors, various colorimetric assays and it supports valves, channels and reservoirs for handling small volumes of sweat delivered into the system by the action of the glands themselves. For chloride concentration, the colorimetric assay relies on silver chloranilate, a chemical that complexes with chloride ions to generate a species with a distinct purple color. Mixing silver chloranilate with pHEMA solution creates a gel-like suspension that immobilizes the insoluble silver byproduct in the assay well. The result prevents migration of silver particulates during flow of sweat in the microfluidic channel, thereby eliminating their effects on color extraction. The extent of change in color determines the concentration of chloride through a linear calibration curve, as shown in panel (A) of FIG. 24. This chemical reaction provides a more reliable, accurate colorimetric response compared to previously reported alternatives for analysis of chloride in sweat. Similarly, paper pads coated with a pH sensitive dye and a phase transfer catalyst serve as a colorimetric means for determining pH. The evolution of color as a function of pH over a physiologically relevant range is in panel (B) of FIG. 24. Calibration plots reveal the linear relationship between the R value (of the RGB code) at different pH levels. FIG. 26 shows simple color reference bars developed for each of these calibration plots to facilitate visual or digital color extraction and conversion to concentration.

Figure 24:
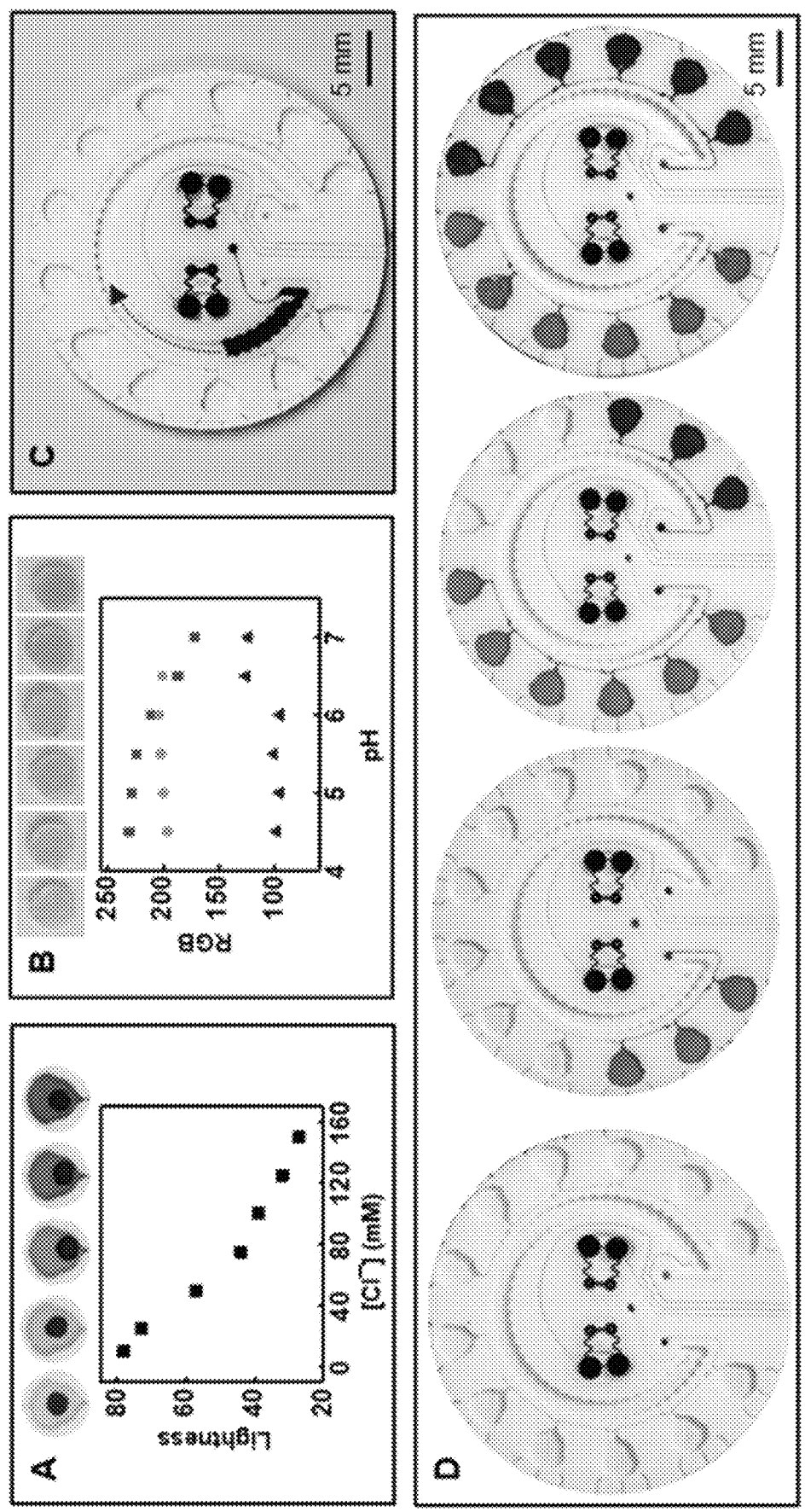
FIG. 24 shows colorimetric assay characterization. Calibration and corresponding color evolution for physiologically relevant levels of (A) chloride (n=3) and (B) pH (n=3). (C) Filling of sweat rate sensor. (D) Image illustrating chrono-sampling feature of the microfluidics system.
Figure 27:
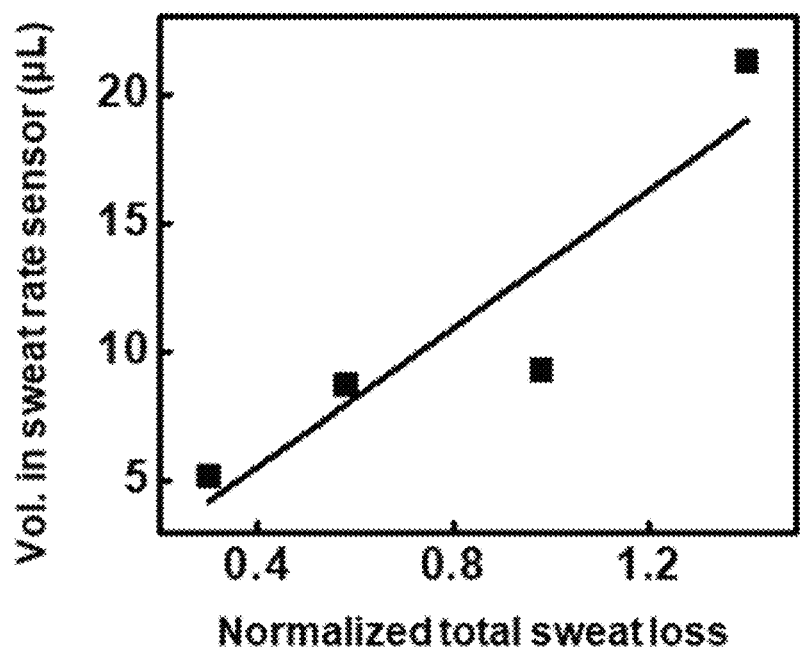
FIG. 27 shows relationship between normalized total sweat loss and volume captured in sweat rate sensor.

The part of the system designed to measure sweat rate/loss involves a simple, circular channel with a water-soluble dye located near the inlet (panel (C) of FIG. 24). The incoming sweat dissolves the dye as it flows past, thereby creating a visible, colored fluid with an easily identifiable filling front in the channel. The position of this front defines the local rate and loss of sweat from the corresponding location on the skin. FIG. 27 shows a linear correlation between data acquired from the sweat rate sensor to the normalized total, or full-body, sweat loss. In this particular design, the channel volume (~58 µl) and the dimensions of the inlet interface to the skin allow tracking of sweat loss for up to 6 hours based on an average sweat rate in the range of 12 to 120 ml/hr/cm$^2$.

Although these assays have an irreversible response, time dependent changes in sweat composition can be captured by using fluidic designs that enable time-sequential sampling (chrono-sampling) of sweat using passive valve constructs. The example in panel (A) of FIG. 28 uses collections of capillary bursting valves (CBVs) to enable sequential filling of a series of independent microreservoirs, each pre-impregnated with a colorimetric reagent. The left and right sides of the device provide chrono-sampling analysis of pH and chloride, respectively.

Since the electrochemical sensors for lactate and glucose are reversible, a single-chamber design with a single channel to divert sweat from this chamber to an outlet is sufficient. These two microfluidic structures flank either side of the patch. The sweat sensor channel resides in between the regions for electrochemical and colorimetric sensing. Panel (B) of FIG. 28 and panel (D) of FIG. 24 highlight the multimodal microfluidic substrate and chrono-sampling features of the system. Circular holes (diameter, 1 mm) serve as inlets in the base of the microfluidic platform for the sweat rate, chloride and pH sensors while ellipsoidal shaped holes (major axis, 5 mm; minor axis, 3 mm) act as inlets for glucose and lactate sensors. The skin adhesive layer has corresponding circular (diameter of 3 mm) and ellipsoidal (major axis, 6 mm; minor axis, 4 mm) openings.

TABLE 1

Comparison of data acquired from sensor patch and conventional techniques during human trials.

| Subject | Parameter | Hybrid Sensor Patch | Conventional technique |
|---|---|---|---|
| Subject #1 | Chloride | 62 ± 5 mM | 66 mM |
| | | 36 ± 5 mM | 43 mM |
| | pH | 6.3 ± 0.05 | 6 |
| | | 6.2 ± 0.03 | 5.5 |
| | Lactate | 10.4 ± 0.1 mM | 17.5 mM |
| | Glucose | 23.2 ± 2.4 µM | 53 µM |
| Subject #2 | Chloride | 34 ± 2 mM | 40 mM |
| | pH | 6.4 ± 0.1 | 6.5 |
| | Lactate | 19.3 ± 0.5 mM | 28 mM |
| | Glucose | 52. ± 14 µM | 100 µM |

Example 6: Resettable Epidermal Microfluidic Sweat Loss Sensor (U.S. Pat. App. 62/514,520 Atty Ref NU2017-073: 48-17P)

Current methods for measuring sweat volume loss from the skin rely on absorbent pads taped to the skin, but do not offer the ease of use in sweat capture needed for quantitative or real time tracking over multiple uses. Described herein is a thin, soft, "skin-like" microfluidic platform is introduced that bonds to the skin to allow for collection and storage of sweat in an interconnected set of microreservoirs. A visual indicator of sweat volume is formed by exploiting refractive index differences between air, sweat, and the device layers.

Provided herein is a resettable, real-time sweat loss monitoring microfluidic device. The device allows for resetting or draining of the reservoir chambers during use, allowing for multiple monitoring periods without requiring a new device. An optically based water indicator may be provided into the microfluidic flexible substrate, allowing for the detection or monitoring of biofluids without single use indicators such as water indicator tape or $CoCl_2$.

Two methods of indicating when sweat is present in a microfluidic chamber are provided, both of which exploit differences in refractive index. FIG. 29 illustrates a nano/micro patterned grating in a hydrophilic polymer which diffuses light when the chamber is empty, but transmits light when the chamber is full. A micropatterned grating in a hydrophilic surface scatters light when there is a refractive index mismatch and transmits light when the mismatch is negligible. When light is able to travel past the grating, the colored indicator is visible. n=refractive index.

FIG. 30 illustrates a similar concept, but utilizes a hydrophobic polymer surface and a nano/micro patterned grating to trap air bubbles which reflect light when the chamber is full. Patterned features in a hydrophobic surface trap air bubbles when filled with sweat and reflect incident light, changing the appearance of the colored indicator.

FIG. 31 illustrates a potential method of resetting the sensor to its initial state. Dual expunge ports reduce the likelihood of accidental sweat discharge, but when covered and pressed simultaneously empty the chamber and reset the device back to its initial state.

Figure 33:
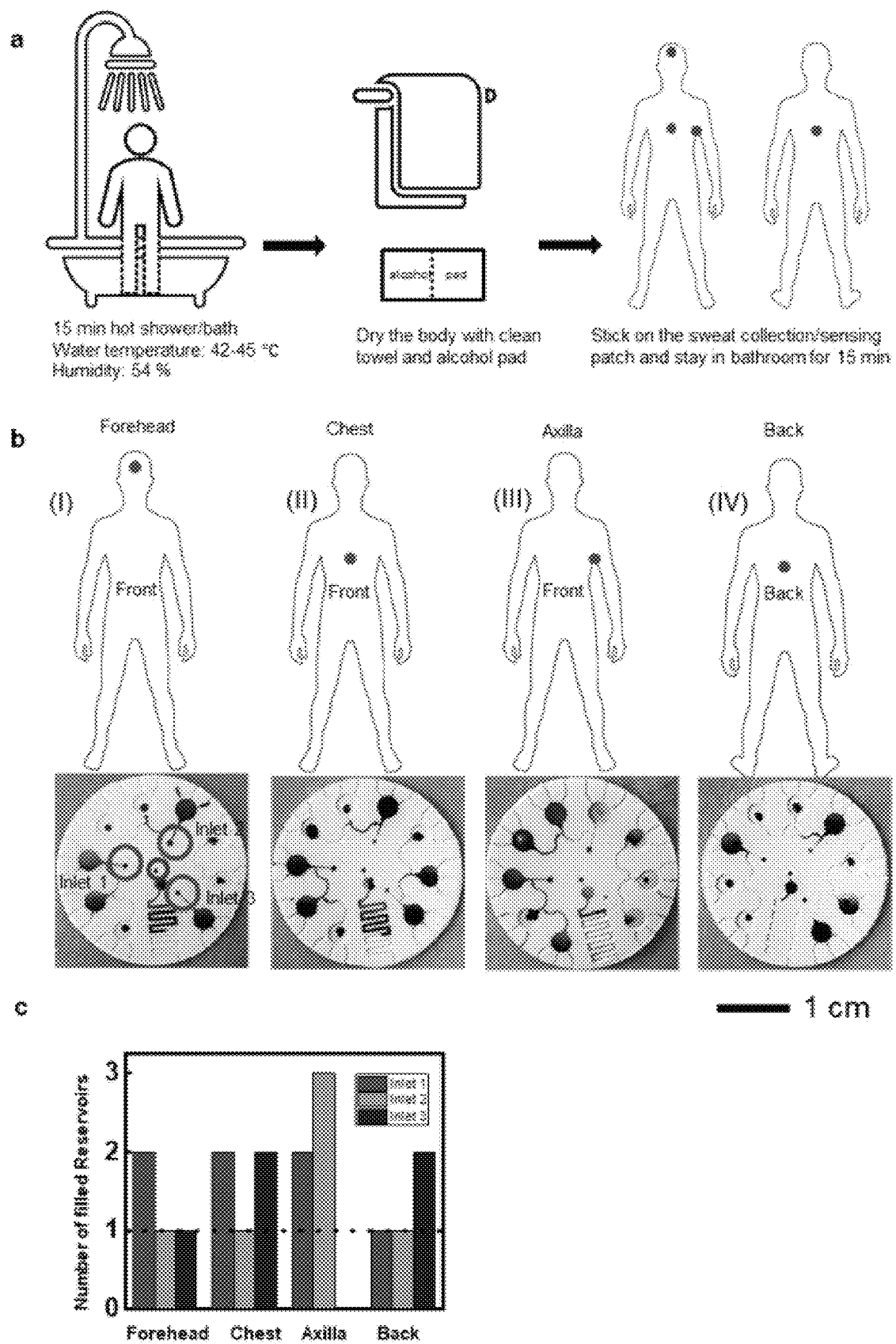
FIG. 33 shows sweat induction through hot shower/bath (e.g., extrinsic heater). (a) Instructions and procedures of how to induce and collect sweat through hot shower/bath. (b) (I-IV) Schematic illustration of the positions of the devices and a demonstration of sweat collection result in human study of one subject. Diameter of sweat harvesting area: red circle: 5 mm, blue circle: 3 mm. (c) Number of filled reservoirs from inlet 1-3 on forehead, chest, axilla, and back. Black dash line indicates the minimum volume/reservoir needed for colorimetric analysis.

Example 7: Microfluidic Systems for Epidermal Sampling, Sensing and Tissue Actuation Sweat induction through hot shower/bath: Sweat induction has been reported through daily (heavy) exercise, sauna, and iontophoresis. However, daily (heavy) exercise limits the application of epidermal sweat sensing for disease diagnostics and health monitoring for patients who often present multiple comorbidities. The high cost and inconvenience of sauna prevent its wide use for sweat stimulation. The iontophoresis process involves the delivery of stimulating agents to the desired sweat glands with the aid of electrical current. This process involves complex electronics for power delivery. In addition, the electrode corrosion and burning can cause discomfort in subjects. Here we report a patient-friendly, low-cost, and convenient method using hot-water shower/bath for sweat induction. A soft, epidermal microfluidic device that captures and routes sweat through a network of microchannels and reservoirs adheres and conforms to skin. The following procedures will be involved to extract sweat through hot-water shower/bath. First, take a hot shower/bath, which usually takes 15-30 minutes to induce sweat, with water temperature around 43° C. Dry the body with a clean towel. The application sites are prepped with a disposable alcohol prep wipe (Dyanrex) to remove skin oils and dirt (panel (A) of FIG. 33). Second, sweat patch is placed on up to five locations on the body including upper arm, chest, lower back, upper back, and forehead (panel (B) of FIG. 33). Third, stay in the shower room to keep sweating until one reservoir in each part is filled. It usually takes 15 to 30 minutes. Devices are left on for less than one hour. Finally, take photographs of each device using a cell phone camera. Photographs are used for data analysis. Epidermal microfluidic device is removed by gently pulling the adhesive and sensor off the subject. Skin surfaces underneath are cleaned immediately with an alcohol wipe, and devices are disposed of and replaced after each use. Panel (C) of FIG. 33 shows representative optical images of microfluidic device spotted with blue dye that mixes with sweat using hot-water shower/bath. Panel (D) of FIG. 33 shows the number of reservoirs filled with sweat from the inlets of 1-3 on forehead, chest, axilla, and back. This study suggests that hot-water shower/bath can induce large volume sweat for on-demand and in situ analysis. It opens the door for the application of sweating sampling and sensing in disease diagnostics and health monitoring.

Example 8: Thin, Soft, Skin-Mounted Microfluidic Networks for Detection and Analysis of Targets of Interest in Sweat Described herein is a thin, soft, "skin-like" microfluidic platform is introduced that bonds to the skin to allow for collection and storage of sweat in an interconnected set of microreservoirs for the quantitative analysis of different targets of interest. Quantitative analysis can either be performed on the device or after collection via elution of sweat for external lab analysis. This platform is suitable for an array of applications including disease diagnostics through quantitative analysis of sweat chloride concentration for cystic fibrosis screening, monitoring of kidney health by measuring urea content in sweat, clinical and personal alcohol screening to quantify alcohol consumption, drug detection/screening, and personal/clinical glucose monitoring both continuously and at periodic time intervals. Each use case harnesses the soft, flexible mechanics, integrated sensors, and microfluidic handling of sweat to achieve precise, accurate, and quantitative measurements suitable for both clinical and personal health monitoring.

The provided systems and methods are useful for collecting and recovering biofluid such as sweat, blood from the epidermis for disease diagnosis, for example, by analyzing biomarkers in the biofluid. Additionally, the systems and methods are useful in collecting and analyzing organic and inorganic chemicals in sweat for home monitoring and self-quantification of conditions (e.g. drug screening, alcohol content monitoring).

Provided is a single device for collecting sweat and analyzing biomarkers or other targets of interest. A self-adhesive is used to stick the device to the subject, so no additional skin-attachment assistance such as tourniquets or gauze. The device has a conformal, skin-compatible design for storage and final extraction of sweat. The device utilizes microfluidics to allow for analysis of small volumes of sweat. Further, the device may have a wireless connection to analytical components (smartphone, computer)

Described are systems and methods for collection and storage of a liquid in a microfluidic channel network for either in-situ or external, lab-based analysis. The device is in a soft, flexible configuration that enables conformal attachment to the epidermis promoting sweat collection while preventing loss. The device allows for the collection of either large or small volumes of sweat and performance on-board analysis thereby enabling custom-tailored, rapid disease diagnosis and/or screening.

The described device is suitable for screening a wide array of targets of interest including biomarker concentration, such as chloride, for cystic fibrosis screening, organic/inorganic compounds for monitoring alcohol or drug consumption (such as marijuana), monitoring dialysis efficacy for patients with kidney failure (urea content in sweat), continuous (or discontinuous) monitoring of glucose levels in sweat, and other clinically/health relevant markers for disease screening, monitoring, and diagnosis.

The thin construction and soft mechanics of this device enables conformal attachment to the skin for the purpose of collecting, storing, and analyzing sweat. Overall, the device geometry may be both circular and rectangular in form. Radial geometries enable sweat extraction via centrifugation after the device is removed from the skin. Rectangular and radial geometries enable sweat extraction via pipetting or via a purpose-built extraction tool.

Figure 34:
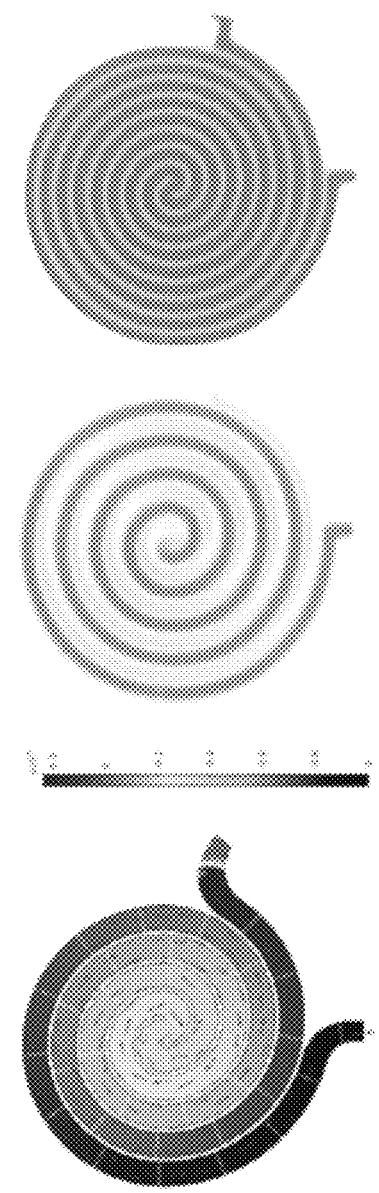
FIG. 34 illustrates microfluidic networks optimized to be filled and to store biofluids in discrete amounts without the trapping of air to fully extract the biofluid with approximately 100% efficiency.
Figure 35:
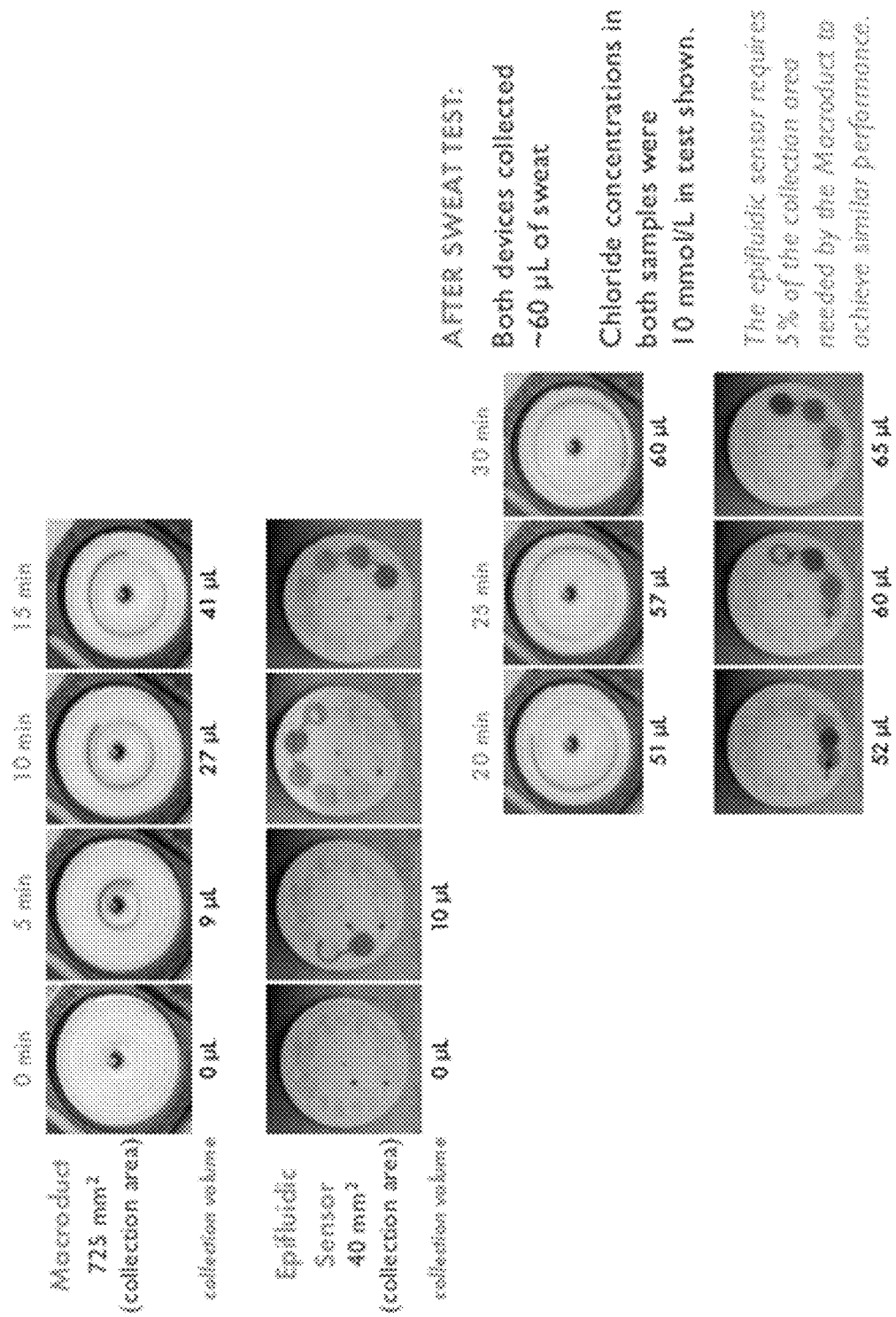
FIG. 35 illustrates the benefit of the design combining a pipe into a bowl shape for facile fluid filling or extraction without air entrapment while providing clear visual volume information.

Advantageously, devices may be optimized for biofluid extraction. FIG. 34 illustrates microfluidic networks optimized to be filled and to store biofluids in discrete amounts without the trapping of air so that you can fully extract the biofluid with approximately 100% efficiency. Clinically it is advantageous to have a discrete volume of fluid, but, in some embodiments, a continuous channel for sweat storage with a visual design that provides the simulation of a "reservoir" to the human eye is implemented. The design is similar to a pipe designed to look like a bowl. While a bowl provides more visually apparent volume to a viewer, it may also trap air during filling or trap fluid during extraction. In contrast, in a pipe fluid flows easily but doesn't provide as clear visual volume information. The design utilizes both benefits by combining a pipe into a bowl shape for facile fluid filling or extraction without air entrapment while providing clear visual volume information. The benefit of this design is illustrated in FIG. 35. The channels are designed so that they offer information about the current state of collection. Fluid changes direction based upon a particular filling condition (¼ full, ½ full, of a target volume) providing have real-time, visual information about the current state of collection. Thus, the overall image of the device dynamically conveys information (e.g. visually).

Devices are fabricated from layers of poly(dimethylsiloxane) (PDMS) or other soft polymer supported upon either medical-grade acrylic adhesive film or on a custom spin-on adhesive composite for bonding to the skin. Materials used in device fabrication can be tailored for specific applications such as attachment to newborns, collection of volatile compounds, or long term drug monitoring (such as providing evidence of tampering with device). An exemplary multi-layer device is provided in FIG. 36. Further, in some devices, the device is epifluidic (e.g. controls the expose skin surface area to the device). This allows the amount of sweat and the collection rate into the device to be modified or "tuned" by creating prescribed patterns in the adhesive or the skin/device interface layer. Patterning allows optimized collection with maximum adhesion (see FIG. 36).

By controlling the skin surface area and thus collection area of the device, the efficiency and performance of the device is increased as compared to other collection methods (FIGS. 35 and 36). The same volume of sweat is collected in the same time, but with much less area exposed. This is due to the soft mechanics of the device, including flexible, conformal, and air/water tight sealed against the skin devices.

Devices are designed to extract specific volumes of sweat in a specified timeframe with particular embodiments fabricated with different fluidic channel widths, heights, and layouts. For a representative device, the first layer defines the microfluidic channel network (total thickness 400 µm). The second layer has no molded features and serves as the capping layer (thickness 200 µm) to the first layer to form enclosed channels. Both layers are fabricated from PDMS. The third layer forms the adhesive bond to the skin. Fluid (sweat) is routed into the device from the skin by way of an inlet formed by removal of the PDMS capping layer/adhesive layer. The diameter of the inlet determines how many sweat pores are sampled by the device.

A sweat chloride test is the gold-standard diagnostic method used for screening cystic fibrosis whereby the quantitative analysis of the sweat chloride concentration is measured in microliter volumes of sweat captured from targeted collection sites on the skin by external laboratory methods. Current sweat test collection methods rely on either absorbent pads taped to the skin or a commercially available product; however, both methods are limited by ease of use, sample contamination, and poor sealing with the skin, especially when used for neonatal cystic fibrosis screening. A thin, soft, "skin-like" microfluidic platform that bonds to the skin to is advantageous as it allows for collection and storage of sweat in an interconnected set of microreservoirs. Quantitative analysis can either be performed on the device or after collection via elution of sweat for external lab analysis.

A sweat sample captured via a sweat test is analyzed in a laboratory where coulometry is used to determine the concentration of chloride. While the foundational operation of the epifluidic device is the collection of sweat in a sweat test, quantitative chloride analysis can also be performed through integrated electrical sensors or via colorimetric analysis. By integrating ion-selective electrodes for chloride into the microfluidic network, electrochemical analysis of the chloride concentration can be performed in real-time as the sweat enters the device during elution. Using near-field communications, this data transfer and sensing can be conducted wirelessly. Furthermore, through continuous monitoring of the concentration, sweat rate can be measured and validated against the minimum sweat rate necessary for a valid cystic fibrosis test. As a result of the device flexibility, colorimetric analysis can also be performed either separately or simultaneously with electrochemical analysis to determine chloride concentration using commercially available colorimetric chemical assays.

Devices for either acute or chronic drug screening are fabricated either for use in a clinical environment or as a temporary, at-home monitoring for analysis either by the wearer or by a clinician. Devices must be tamperproof if worn for home monitoring achieved via means such as destruction of sensitive components in the device itself (embedded art, fragile device construction in shear, broken indicator areas), staining of the skin with a colored dye, or electronic recording stored on the device so as to protect the integrity of the measurement. The same requirements are necessary for the clinic, but with a decreased need for long-term (~24 h) stability as tests are typically shorter (~10 min). Screening itself is achieved either via collection of sweat for external analysis, integrated electronic detection of key markers of drug/alcohol activity, via colorimetric analysis of key markers, or a combination thereof. Individual device barcoding will be required for drug screenings necessitated by legal requirements/chain of custody.

Devices for personal alcohol testing are fabricated in similar manner to other devices. Designed for personal use, these devices integrate graphics to provide clear, simple read-outs to accurately gauge alcohol consumption versus time. As aesthetics are important for use in a non-clinical setting the devices are designed to have as minimal a footprint as possible. Sensing is performed using either colorimetric or integrated electrode approaches. Key points of distinction are form factor, sampling volume, and chrono-sampling. Discrete monitoring is also possible via wireless sensing coupled with a smartphone.

Devices for glucose monitoring are fabricated in similar manner to other devices. Designed for both clinical and personal use, these devices integrate graphics to provide clear, simple read-outs to accurately gauge glucose over a specified time. Sensing is performed using either colorimetric or integrated electrode approaches depending upon measurement requirements. Key points of distinction are form factor, sampling volume, and chrono-sampling. Discrete monitoring is also possible via wireless sensing coupled with a smartphone.

Multiple stacked microfluidic network device layers provide multifunctionality to the epifluidic sweat collection and analysis platform. Benefits include increased sweat storage in same epidermal surface area, independent collection areas for on-device controls, inclusion of active components (valving, electronic sensing), multiple analytical channels (electronic, colorimetric, external lab), and increased collection rates via multiple inlets. Multiple microfluidic network layers can be interwoven with graphical constructs to provide additional functionality by interacting dynamically with printed images.

Integration of microlenses (e.g. cylindrical, hemi-spherical) into the microfluidic channel network can improve the accuracy of the colorimetric assay performance by either increasing the effect pathlength for light to pass through the device or by collecting more light scattered by the regions of interest (e.g. microfluidic channels). Additionally, integration of lenses into the device offer increased complexity for integration of art into the device such that the art can interact dynamically with the measurement in real-time.

To provide sensing capabilities, active components such as photodetectors, laser diodes, vertical cavity surface-emitting lasers (VCSEL), waveguides, optical resonance cavities can be integrated into the device. Additionally, device surfaces or composition can be modified to provide additional sensing capabilities through integration of plasmonic nanoparticles (e.g. gold nanorods) that respond to the presence of different analytes of interest. These components provide enhanced sensitivity to the described sensing requirements.

Molds for fabricating these devices can be produced using standard cleanroom processing techniques, via refined additive manufacturing processes, or via micromilling. A molding process is used to produce accurate (~50 um channel width) channels using 3D printing via selective laser sintering of high-temperature photocurable resin. Whereas other photocurable resins warp at the temperatures required to cure polymers such as PDMS, the combination of photocurable resin with 3D printing enables production of physically stable molds at the temperatures required for fabricating these devices. Mold production via micromilling aluminum also provides a method to rapid prototype molds with extremely fine resolution (~100 um channel width, >30 um depth).

A composite material comprised of soft-skin adhesive (e.g. Dow Corning) with uncured PDMS precursor is used to fabricate layers of soft polymer suitable for reversible bonding to virgin PDMS with a bond strength sufficient for a fluid-tight seal. Beneficially, neither heat nor oxygen plasma are required to form sealed, flexible, soft epifluidic devices. Furthermore, the reversible nature of the bond enables reusable device fixtures (e.g. electronics) with disposable fluidic networks. Formulations of different composite mixtures (30:1, 40:1, 50:1) provide different adhesive strength suitable for a variety of applications including bonding to electronic components and temporarily sealing channels for surface treatment/activation. Absence of surface plasma activation or heat treatment enables integration of sensitive assays (enzymes) or rapid prototyping while maintaining same surface chemistry.

We have demonstrated an analytical platform for the diagnosis of cystic fibrosis that exploits ultrasoft, conformal, "skin-like" microfluidic channels to collect sweat from eccrine sweat glands stimulated via pilocarpine iontophoresis. A representative device, shown in FIG. 37A, has an overall circular geometry with a diameter of 34 mm. The radial construction allows for both maximal sweat collection of a stimulated region (30 mm, diameter of Wescor Pilodisc) and attachment to multiple body locations (e.g. forearm, thigh) on multiple subjects (e.g. infants, adults).

The device, comprised of three layers of soft, medical-grade silicone elastomer (polydimethylsiloxane, PDMS, Dow Corning) exploits thin geometries and soft mechanics to enable intimate, conformal bonding to fragile newborn skin. This bond is a zero-pressure, fluid-tight interface between the device and the skin formed via a medical-grade, irritation-free, FDA-approved gentle skin (i.e. newborn safe) adhesive (3M silicone adhesive; thickness, 100 μm). Laser-patterned openings define the sweat harvesting regions through which sweat, driven by the sweat gland pressure (~3 kPa) passes into one of three independent chambers (panel (B) of FIG. 37), which each store up to 70 μL of sweat. Optimization of the adhesive pattern maximizes sweat collection (70 mm$^2$ exposed surface area per region corresponding to ~100 sweat glands) while maintaining conformal adhesive contact during a sweat test.

Figure 38:
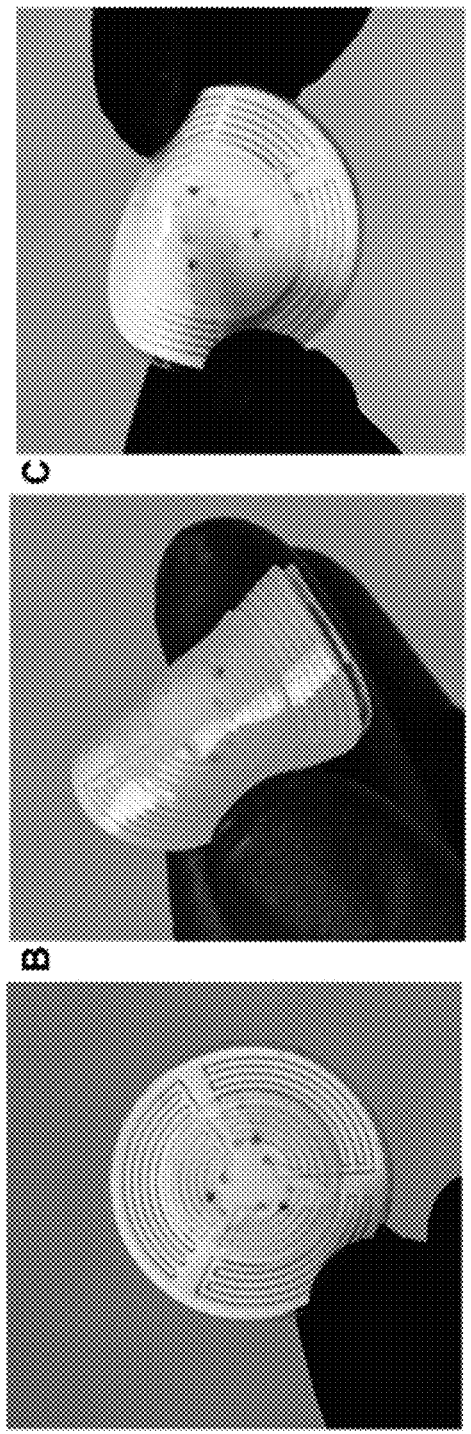
FIG. 38 shows optical image of the device, including undergoing bending and twisting, panels (A)-(C), respectively, also referred herein as being flexible.

The device comprises an embedded microfluidic network of embossed channels (500 μm width, 350 μm uniform depth) in a soft (~145 kPa) PDMS layer (thickness, 400 μm). A capping layer (thickness, 100 μm) serves to seal the first collection layer in which a single, continuous channel comprises a collection chamber with an inlet (open to skin) and an outlet to the second collection layer. This second layer contains embossed channels (500 μm width, 300 μm uniform depth) which form three secondary collection chambers connected to the first layer chambers by independent inlets. The middle capping layer also serves to seal the second layer microfluidic channel network. The first layer chambers each hold 50 μL of sweat while the second layer chambers each hold an additional 20 μL of sweat. Constructed in a tiered manner (first layer diameter, 34 mm; second layer diameter, 20 mm), the variable thickness of the device (edge thickness, 500 μm; center thickness, 900 μm), coupled with the soft material properties of the PDMS, improves device flexibility (FIG. 38). The thin, soft, compliant device construction provides a key differentiating factor between this device and the current FDA-approved technology (e.g. Macroduct® sweat collection system) as it enhances the conformal coupling to the skin, especially for neonates.

Figure 39:
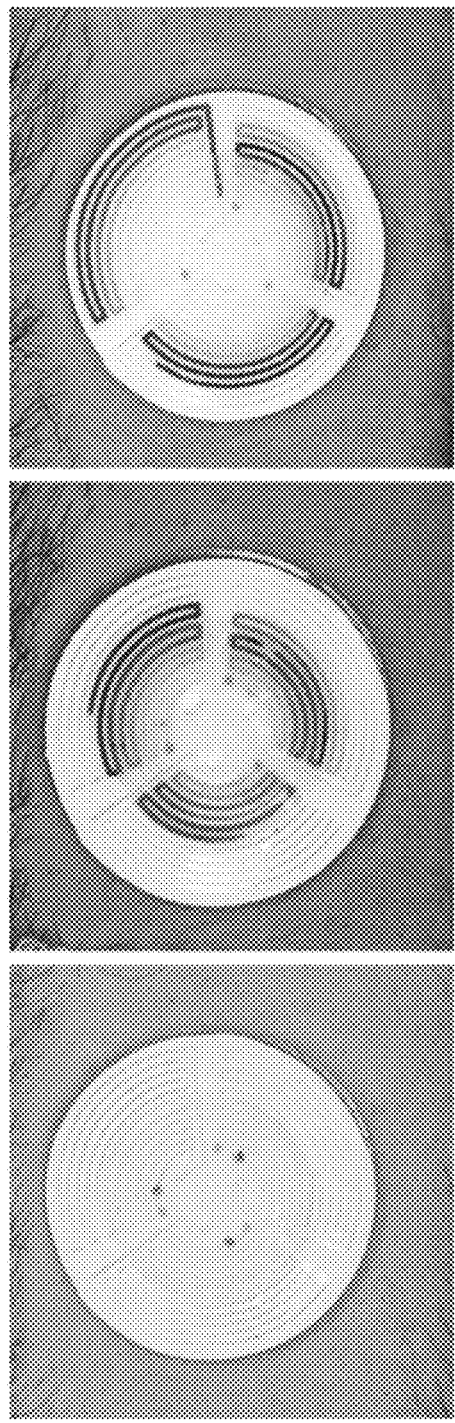
FIG. 39 shows optical image of the device filling with sweat (teal) over a 30 min collection period after pilocarpine iontophoresis.

Optimization of the microfluidic channel design enables maximized sweat collection after pilocarpine iontophoresis. FIG. 39 shows a sequence of optical images of the device immediately after sweat stimulation, 15 min into the collection, and at the conclusion of a sweat test (30 min). The channels on the first layer contain reservoirs of teal dye (FDA approved, verified chloride-free) to visualize the flow of sweat as soon as sweat enters the device. As the device samples from three independent regions within the stimulation area, slight variations may result due to the biological variation of sweat gland density. The use of medical-grade soft skin adhesive provides a robust, water-tight bond between the device and skin promoting the complete and rapid collection of sweat without the application of a tourniquet. This eliminates a significant risk to neonates, especially when the diameter of the arm is smaller than the size of a Macroduct® sweat collection system device. As the adhesive layer provides an optimal balance between bond strength and sweat collection (evaluated by the absence of leakage), rather than high-pressure contact, the collection device does not suffer from motion-induced collection failures.

Figure 40:
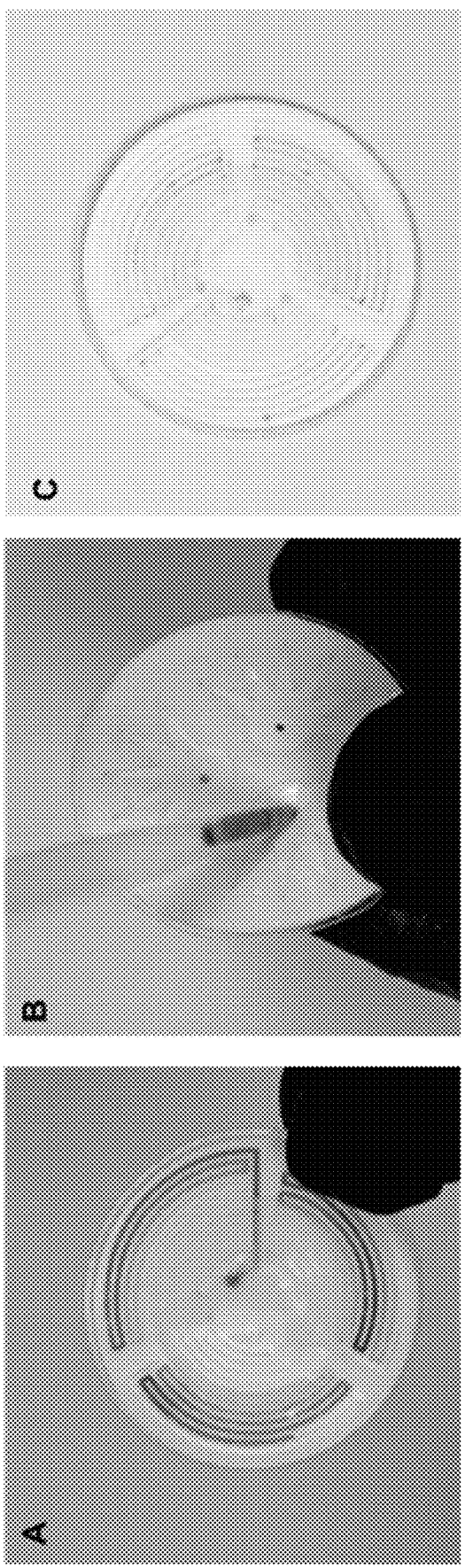
FIG. 40 shows optical image sequence showing extraction of sweat from a filled device (A). Once removed from the skin, a standard pipette provides sufficient negative pressure to extract sweat (B). Device geometry optimized to fully extract sweat (C).

An additional design consideration of the collection device is the efficacy of sweat extraction and ease-of-extraction. Not only must sweat be fully extracted from the device, but the extraction mechanics must promote ease of operation and eliminate potential sources of chloride contamination. The location of the collection inlets (i.e. opening to skin) in the central region of the device (FIG. 37) eliminates sweat leakage upon the removal of the device from the skin as the mechanics of removal (i.e. vertical lifting from the device edge) creates a temporary pumping action to transport sweat contained in the channel farther into the collection chamber as observed in positional difference between the optical image in FIG. 39 (30 min) and that of panel (A) of FIG. 40. The only additional equipment required to extract sweat from the collection device is a standard pipette (1 mL, generic). The device-layer inlet size (1.2 mm diameter) is smaller than the pipette opening (1.5±0.1 mm diameter, brand dependent) so that when the pipette contacts the elastomeric device a strong, temporary water-tight and gas-tight seal forms so that a negative pressure occurs in the microfluidic channel upon extraction with the pipette. This negative pressure is sufficient to fully extract sweat from each chamber, regardless of filled volume. The sweat extraction rate is linearly proportional to the amount of negative pressure applied (set volume on a variable pipetter) and rate of draw on the pipetter. The combination of extracted sweat from all three collection chambers defines the total collected sweat volume.

Example 9: Multilayer Channel Construction

Figure 41:
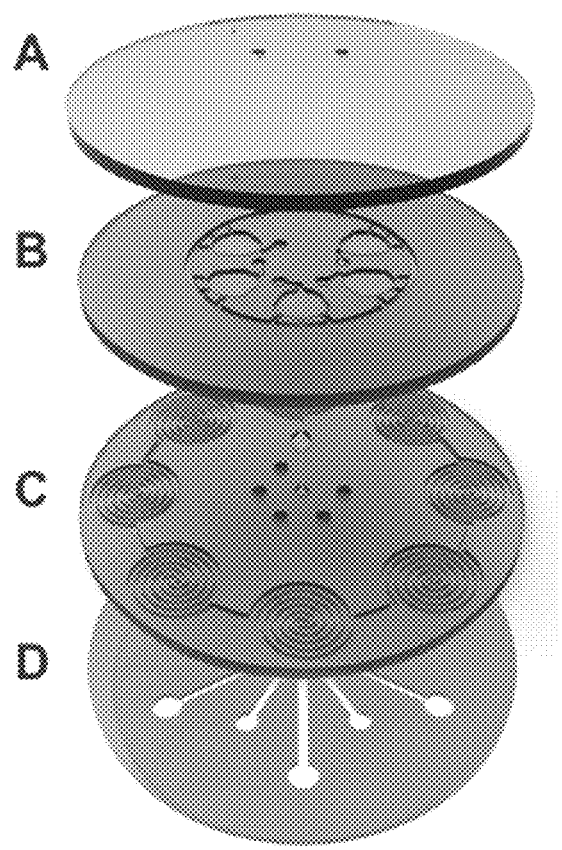
FIG. 41 shows schematic of a multilayer device in a stack configuration where (A) is a capping layer, (B) is a colorimetric analysis layer, (C) is a collection layer, (D) is a skin interface layer. (B) and (C) are independent of each other providing on-board analysis of sweat collected for external analysis.
Figure 42:
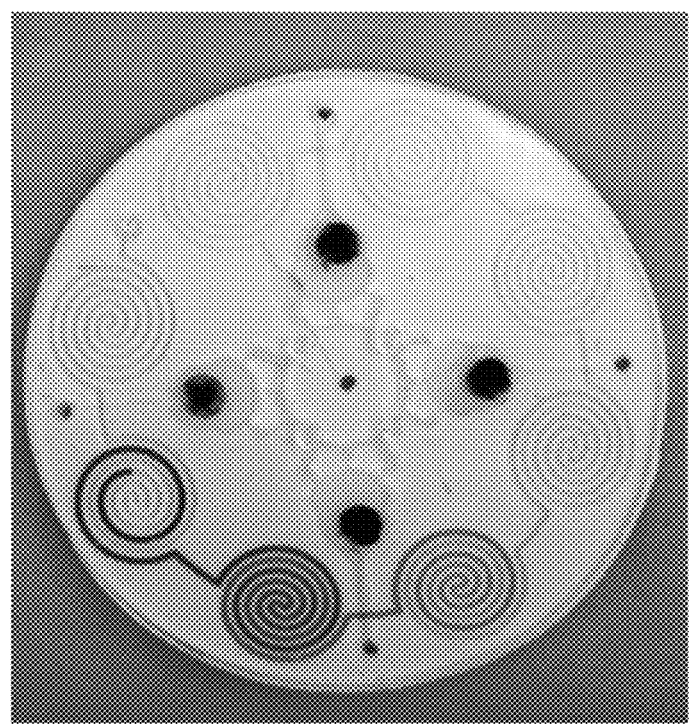
FIG. 42 shows representative device fabricated using a multistack construction.
Figure 43:
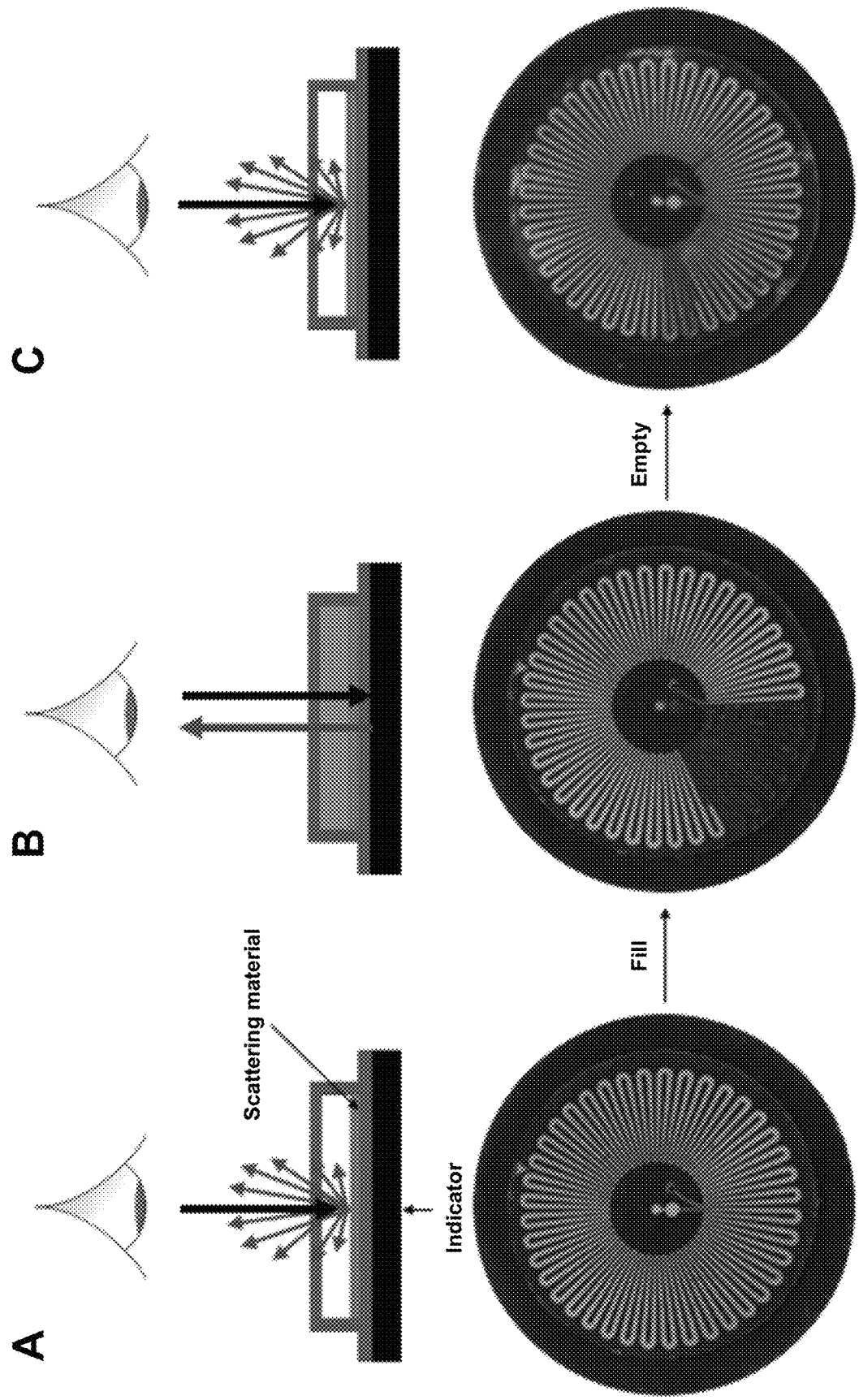
FIG. 43 shows resettable sweat indicator via light scattering. A) Scattering material patterned in the channel of a microfluidic device causes light scattering and presents a white color. B) Captured sweat enters the microchannel and reduces scattering and presents the color of the indicator (black). The scattering media has a comparable refractive index to sweat. C) Extracting sweat resets the device to the initial state.
Figure 44:
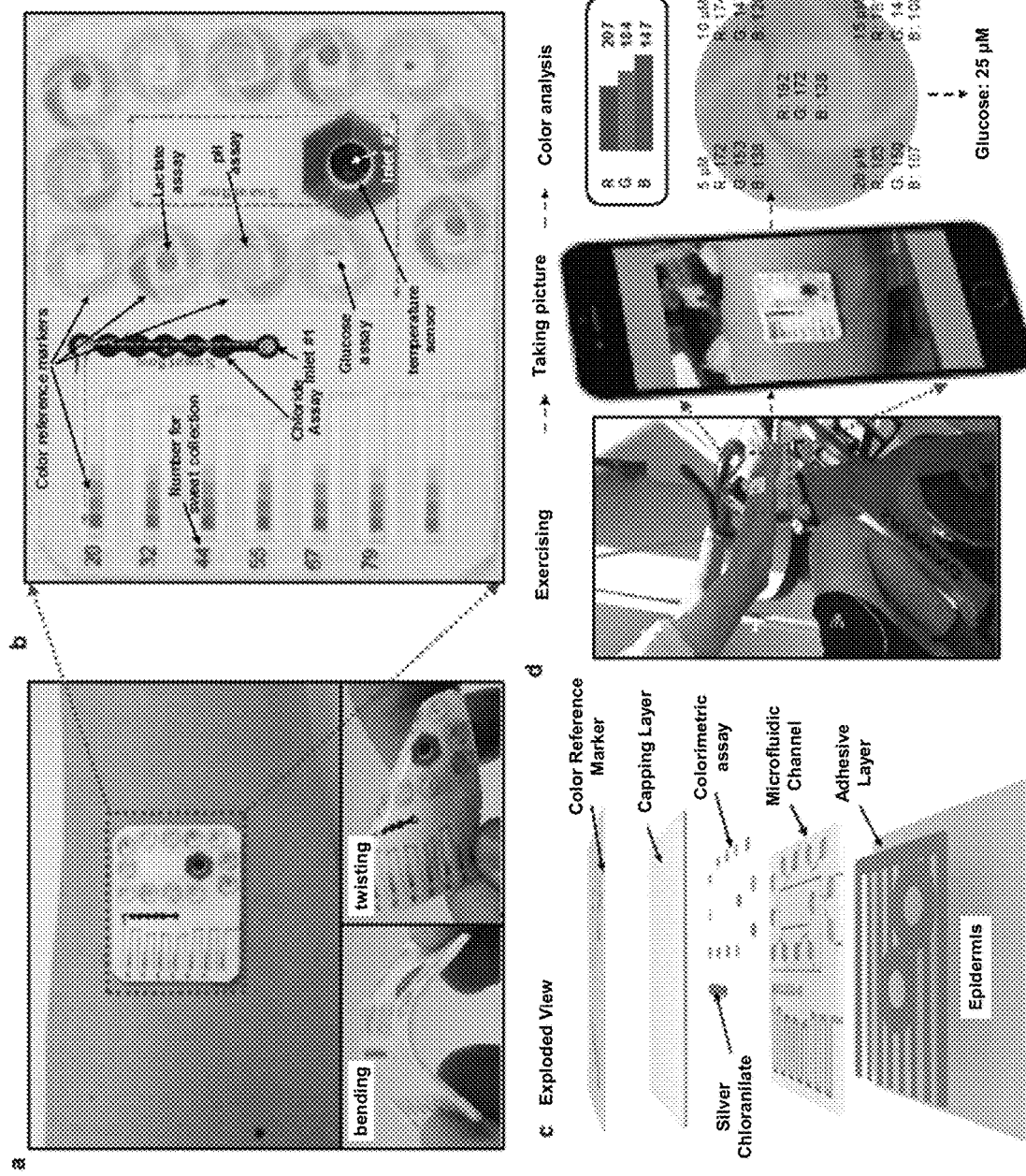
FIG. 44 shows: (a) Optical images of soft and flexible microfluidic devices for colorimetric analysis of sweat on the skin (top) and under mechanical diction of bending (bottom left) and twisting (bottom right). (b) Top view illustration of microfluidic channels filled with blue-dyed water. (c) Exploded view illustration of a device and its interface with skin. (d) Procedure of collecting sweat sample and color analysis of digital image of the device.

For certain applications, the device area must be restricted to certain regions of skin or must undergo aggressive bending to conform to a high radius of curvature (e.g. arm of an infant). For these cases, the device geometry can be structured to harness the device design in the vertical dimension. FIG. 41 is a render of a representative device stack that incorporates multiple levels to provide expanded functionality to a sweat device not possible in a planar geometry. Panel (A) of FIG. 41 is a capping layer providing fluidic access to the layer in panel (C) of FIG. 41 and an air-escape access to the layer in panel (B) of FIG. 41. Panel (B) of FIG. 41 is a layer for an integrated colorimetric assay that provides independent analysis of the fluid collected in the layer panel (C) of FIG. 41. Panel (C) of FIG. 41 is a collection channel network that collects fluid for external analysis (extracted via the layer in panel (A) of FIG. 41). The layer in panel (D) of FIG. 41 is the skin-interface layer that collects sweat from the skin and directs it to the independent channels in panels (B)-(C) of FIG. 41. FIG. 42 shows a representative device using a multistack layer construction.

Example 10: Resettable Epidermal Microfluidic Sweat Loss Sensor

The black indicator layer is formed by spin coating 10:1 PDMS containing 1.5 wt % black pigment and 1.5% white pigment on a flat PMMA coated wafer. The clear patterned layer is formed by spin coating 10:1 PDMS on a PMMA coated silicon wafer with bas-relief features. Both layers are cured at 100 C for 1 hr. The scattering material is a commercially available hydrochromic ink (LCR Hallcrest HI51000). The exact composition is unknown. The hydrochromic ink is dispersed in water (5:1 wt water:ink) deposited via air brushing onto the molded PDMS layer and dried at 100 C for 5 min. Scotch tape is used to remove the ink that is deposited outside the microchannel. Corona treatment of the molded and flat PDMS layers prepares the layers to be bonded. Lamination, light pressing, and heating at 70° C. for 24 hrs ensures a permanent bond between the layers and completes fabrication.

Example 11: Thin, Soft, Skin-Mounted Microfluidic Networks with Capillary Bursting Valves for Chrono-Sampling of Sweat and Measuring Pressure from Sweat Gland and Colorimetric Detection of Chloride Soft, multi-functional microfluidic device for colorimetric sweat analysis: A soft microfluidic device made from PDMS has flexibility and interfaces to the skin (panel (a) of FIG. 1). The device provides several functionalities that: 1) analyzes of concentration of chloride, glucose, pH and lactate in sweat, 2) temperature of sweat by colorimetric method, 3) calculates local sweat loss and instantaneous sweat rate via adhesive layer that provides a water-tight sealing between skin and the device that enables the device to collect sweat continuously (panel (b) of FIG. 1). Sweat gland under open region of skin under adhesive generates sweat flow about 2 kPa to 1) inlet #1 and fill the serpentine channel while developing color to detect chloride concentration in sweat and shows the local sweat loss, 2) inlet #2 and fills the collection chambers in clock-wise sequential manner through the guide of series of capillary bursting valves and develop color for detection temperature, glucose, pH and lactate of sweat. For colorimetric analysis, each chamber has thermochromic liquid crystal sensor or chemical assays that develop color according to the temperature or target biomarker in sweat and color reference markers placed around the chamber provide a standard color of target temperature or concentration for accurate color analysis that is not affected by light condition. The exploded view of the device shows the detailed compositions of one device (panel (c) of FIG. 1). The adhesive layer attaches the PDMS device on to the skin and the hole in the adhesive opens a route for the sweat from the region to enter to the microfluidic channels. White microfluidic PDMS channel layer formed by soft lithography has two channels: the left serpentine channel for measuring chloride concentration and sweat rate, the right sequential circular chambers for measuring glucose, pH and lactate concentration in sweat. The depth of the channel is 600 µm and its relatively thick depth provides sufficient color difference between concentration from the chamber for accurate detection of biomarker of sweat using colorimetric method. The chemical assay components are located in each chambers and channel for their purpose. A 200 µm thick clear 10:1 PDMS capping layer coated with stick PDMS from fully cured 50:1 PDMS generates the closed channel to the microfluidic layer. The sticky PDMS adhesion is preferred due to it does not require any heating process or oxygen plasma treatment that could affect to the stability of chemical assay in the chambers. On top the capping layer, a 25 µm thick thin PET film with reference color marker provide an accurate color analysis. FIG. 1d shows the process of 1) collecting sweat from exercising, 2) taking picture by smartphone camera, and 3) analyzing color from the chambers to calculate the sweat concentration. Comparing the color value from the reaction chamber with values from color reference marker estimates the sweat concentration in chamber.

Device Fabrication: Fabrication begins with making a silicon wafer mold. Patterning photo-resist of KMPR 1010 (Microchem, MA, USA) on 1 mm thick Si-wafer and deep reactive ion etching (STS Pegasus ICP-DRIE; SPTS Technologies, Newport, United Kingdom) generated a mold for microfluidic channel. Thin layer of poly(methylmethacrylate) (PMMA; Microchem, MA, USA) formed on the mold. Pouring 10:1 PDMS (Sylgard 184; Dow corning, MI, USA) mixed with white silicone dye (Reynolds Advanced Materials) at 10% wt on the mold and spin coating at 150 rpm with baking at 150° C. for 3 min yielded a 700 µm thick layer. All the chemical assays were located on the cured PDMS channel. Sequential process of pouring 10:1 and 50:1 PDMS and spin coating at 400 and 1000 rpm baking at 150° C. for 3 min yielded a 200 µm thick layer and 75 µm thick layer, respectively. 50:1 PDMS provided a sticky layer to bond between microfluidic channel layer and capping layer. 25 µm thick clear polyester film (THERMLfilm SELECT® 10852; FLEXcon, MA, USA) on the top of the device with color reference marker. 60 µm thick medical grade acrylate adhesive (1524; 3M, MN, USA) bonded to the bottom of the device through 30 sec of laboratory corona treater (Electro-Technic Products).

Figure 45:
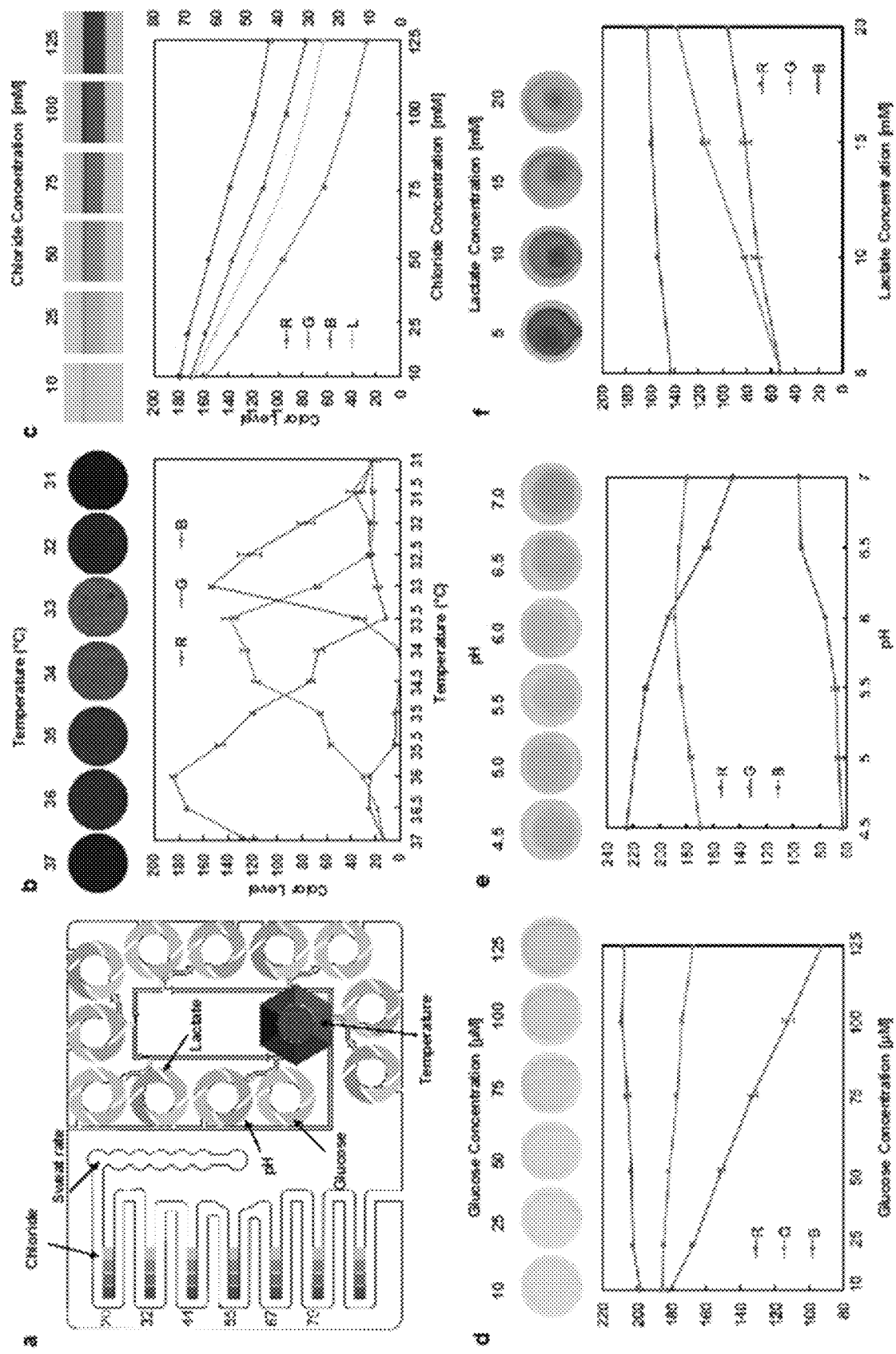
FIG. 45 shows: (a) Schematic illustration of device with color reference markers of chloride, glucose, pH and lactate, and number for indicating sweat collection volume. (b) Optical images color development of thermochromic liquid crystal temperature sensor according to temperature (top) and color level of each color (bottom). Optical images color development of assay chambers according to sample concentrations (top) and color level of each color (bottom) of (c) chloride, (d) glucose, (e) pH and (f) lactate.
Figure 46:
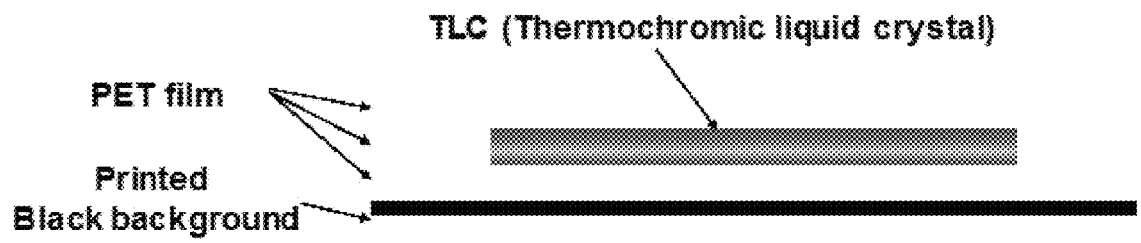
FIG. 46 shows the structure of temperature sensing film of thermochromic liquid crystal.
Figure 47:
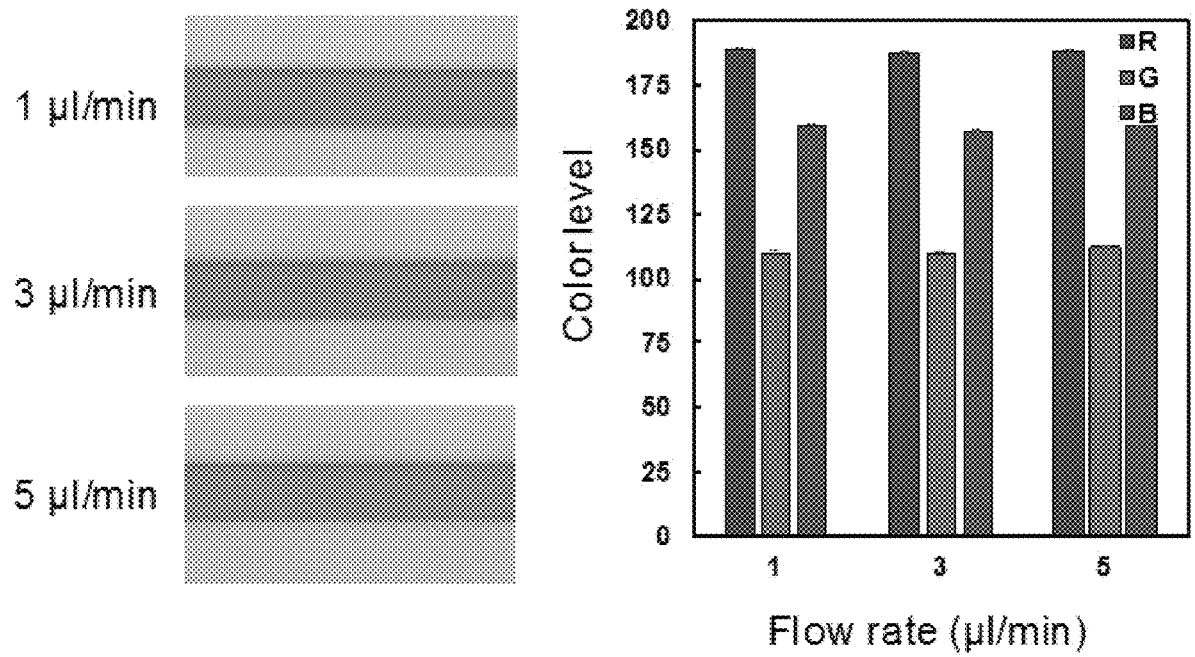
FIG. 47 shows color development at various flow rate.
Figure 48:
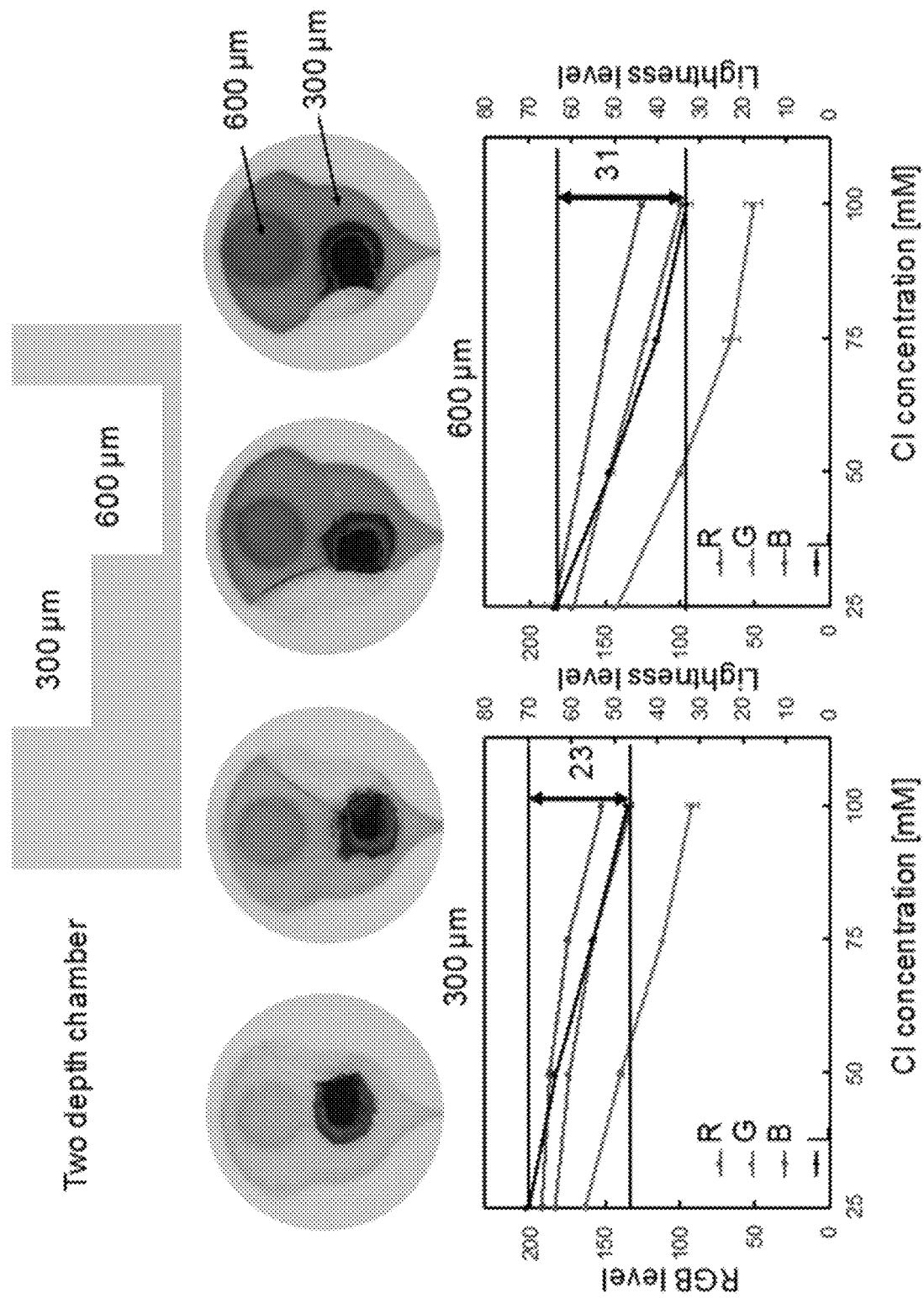
FIG. 48 shows color development at different channel depth.

Color development and reference marker: Colorimetric method for detection of biomarkers needs a color reference marker for accurate analysis of color regardless of light condition. Panel (a) of FIG. 45 shows the collection of color reference markers for analyzing temperature, chloride, glucose, pH and lactate from sweat. For the preparation of the color reference marker, in vitro test with standard solution produced reference color and digital imaging and image analysis provides color value of each assay. From the values, the color reference marker is generated and printed on the thin and clear film and attached to the top of the device. Mixture three kinds of thermochromic liquid crystals, 40 wt % cholesteryl oleyl carbonate (COC), 40 wt % cholesteryl nonanoate (CN), and 20 wt % cholesteryl 2, 4-dichlorobenzoate (CD) encapsulated by thin PET film with black background provides temperature sensor that has red-start at 32° C., green-start at 33° C. and blue-start at 34° C. enables to detect the temperature from 31° C. to 37° C. (FIGS. 45-46). Silver chloranilate immobilized in pHEMA produces purple colored ion from reaction with chloride ion sweat and the color level continuously decreases with chloride concentration that allow lightness (L) level to provide a representative number of the color of assay (panel (c) of FIG. 45). As the sweat continuously flow the chamber, the color development has a chance to be sensitive to flow rate. Sufficient reaction time from long reaction area provide uniform color development independent to flow rate from 1 to 5 µl min' (FIG. 47). Glucose in the sweat produces hydrogen peroxide ($H_2O_2$) from the enzymatic reaction with glucose oxidase and peroxidase reacts with glucose substrate dye using $H_2O_2$ results yellowish color that changes blue level in the chamber dominantly (panel (d) of FIG. 45). Universal pH dye provides a pH sensor and red level from the sensor that changes dominantly with pH of solution serve a comparing parameter of the color of assay (panel (e) of FIG. 45). Lactate assay follows the similar enzymatic reaction as glucose assay and produces red color at low concentration at 5 mM and yellow color from 15 mM. The green level changes dominantly and serves a representative color value from the assay (panel (f) of FIG. 45). For enhancement of the color difference between concentration that makes more accurate color detection, the channel depth makes a dominant effect because thicker chamber produces longer path length of light (FIG. 48). As the chamber thickness defines the total thickness of the device and volume of chamber, 600 um thick chamber provides soft mechanics of device and appropriate volume of sweat into the device as ~6 µl.

Colorimetric assay: 1) chloride: 8 µl of mixture of 50 mg of silver chloranilate (MP Biomedicals, CA, USA) and 200 µl of 2% pHEMA provides assay for chloride detection.

2) glucose: 1.0 µl of buffer, 0.5 µl of substrate, 0.5 µl of enzyme located in a chamber developed color for glucose detection. (Glucose Colorimetric Assay Kit II; Biovision, CA, USA)

3) pH: pH cocktail solution was realized by thoroughly vortexing 4 ml of universal pH dye (Fisher Scientific, NH, USA), 274 mg of polyvinyl chloride (M.W. ~233,000, Sigma-Aldrich, MO, USA), 635 µl of o-nitrophenyloctylether (Sigma-Aldrich, MO, USA) and 508 µl of aliquot in 10 ml of tetrahydrofuran (Sigma-Aldrich, MO, USA) till a homogenous suspension was obtained. Thereafter, a filter paper was dipped in the cocktail solution for 10 s and allowed to dry at ambient conditions for 15 min to realize the solid-state pH assay. Finally, a metal punch (diameter, 2 mm) was used to excise circular pads of the pH assay paper for incorporating in the wearable patch.

4) lactate: the lactate assay cocktail was prepared by thoroughly mixing 17% v/v dye, 17% v/v peroxidase from horseradish (HRP) (20 mg/ml; Sigma-Aldrich, MO, USA) and 66% v/v lactate oxidase (LOx) (60 mg/ml, activity of 101 U/mg; Toyobo Corp., Osaka, Japan) solution. The dye solution was earlier prepared by mixing 0.5 M 3,5-dichloro-2-hydroxy-benzenesulfonic acid (Sigma-Aldrich, MO, USA) with 0.25 M 4-aminoantipyrine in 1:1 v/v ratio, while the enzyme and dye solutions were prepared in 0.1 M sodium phosphate buffer (pH 7.0) and deionized water respectively. The lactate assay spot was prepared by first coating 2 µl of lactate assay cocktail in the designated chamber of the patch and letting it dry. A second coat of 1.5 µl of enzyme solution containing HRP (20 mg/ml) and LOx (60 mg/ml) in 1:2 v/v ratio was applied to the assay spot to extend the detection range up to the physiologically relevant lactate concentration and to enhance the color contrast. The assay spot was allowed to dry for at 1 hour at ambient room temperature before utilizing if for lactate detection.

Colorimetric Temperature Sensor:

A thermochromic liquid crustal is fully sterol-based ternary mixture containing 20 wt % cholesteryl oleyl carbonate (COC, Sigma-Aldrich, MO, USA), 40 wt % cholesteryl nonanoate (CN, Sigma-Aldrich, MO, USA), and 20 wt % cholesteryl 2, 4-dichlorobenzoate (CD, Pressure Chemical Company, PA, USA). The mixture was heated at 200 C with magnetic stirrer until forming a homogeneous mixture and was applied on the PET film with printing black for background and covered by another PET film. A CO2 laser (Universal Laser Systems, AZ, USA) defined the size of the TLC film as 2.5 mm in diameter.

Standard Color Development and Color Reference Marker Preparation:

Sodium chloride, D(+) Glucose and L(+) lactic acid (Sigma-Aldrich, MO, USA) generated standard solutions in DI water as its concentrations. pH buffer solution was made and pH meter (Mettler Toledo, Greifensee, Switzerland) measured it. A syringe pump (Harvard Apparatus, MA, USA) generated flow at 1 µl/min speed into the microfluidic device with chloride assay on the hot plate at 31° C. until the solution filled 20% of the channel. For glucose, lactate and pH test, pipetting flowed standard solution into the chambers. For full color development, the device with glucose and lactate assay filled by the solution stayed on the hot plate at 31° C. for 20 min and pH for 5 min. A digital SLR camera (EOS 6D; Canon, Tokyo, Japan) took the picture of the device. Photoshop (Adobe Systems, CA, USA) provided color extraction from the color in the chambers. A color laser printer (C454 PS; Konica Minolta, Tokyo, Japan) produced a reference maker on PET film at 1200 DPI resolution. The printed reference marker placed on the device again and smartphone camera (Iphone 5s; Apple, CA, USA) took picture of the chamber with reference marker. The color analysis compared the color level from the chamber and reference marker. Three spots from each chamber and reference marker provided the average color value. By adjusting brightness of the image, repetition of printing and comparing provided the optimum reference marker. For in vitro accuracy test, the color developed device with reference marker placed in laboratory with white light bulb and yellow light bulb and in outdoor.

Accuracy Test of Colorimetric Methods in Various Lighting Condition

Figure 49:
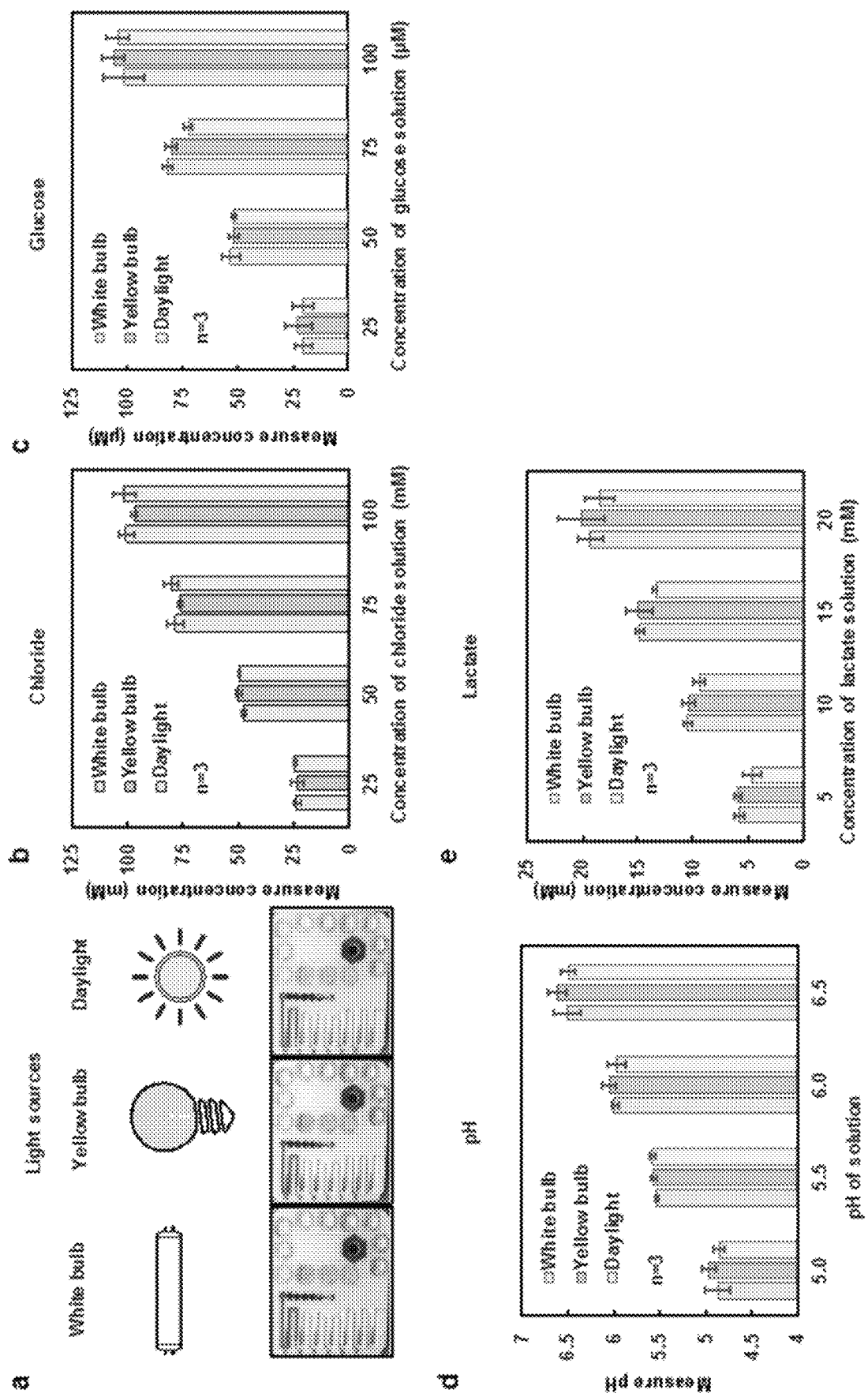
FIG. 49 shows: (a) Schematic illustration of in vitro accuracy test of color reference marker in various light sources of white light bulb, yellow light bulb, and daylight. Measured concentration using color reference marker in the device filled with standard solutions of (b) chloride, (c) glucose, (d) pH, and (e) lactate marker in various light sources.

The absolute color value from the image of assay chamber changes according to the lighting condition. The color reference marker attached to the device around the assay chamber represents color value of specific concentration and changes its color according to the lighting condition; this provide accurate color evaluation regardless of lighting condition. For validation of the functionality and accuracy of colorimetric method coupled with color reference marker, the devices supplied with known standard concentration produces images in white light bulb, yellow light bulb and daylight condition (FIG. 49a). Overall the accuracy of chloride, glucose, pH and lactate are about 5%, 10%, 2%, 10% of testing concentration, respectively (Table 2).

The type of lighting condition does not affect accuracy in general. In case of pH and lactate, daylight condition produces lower estimated concentration than expected concentration (Table 2).

TABLE 2

Accuracy of colorimetric method.

| concentrations (mM) | | | | | Concentrations (µM) | | | |
|---|---|---|---|---|---|---|---|---|
| Chloride | 25 | 50 | 75 | 100 | Glucose | 25 | 50 | 75 | 100 |
| White bulb | 23 | 48 | 78 | 101 | White bulb | 20 | 53 | 82 | 101 |
| S.D. | 2 | 1 | 4 | 3 | S.D. | 4 | 4 | 2 | 9 |
| Yellow bulb | 23 | 50 | 76 | 97 | Yellow bulb | 23 | 52 | 80 | 106 |
| S.D. | 3 | 1 | 1 | 1 | S.D. | 6 | 2 | 3 | 5 |
| Daylight | 25 | 50 | 80 | 102 | Daylight | 21 | 52 | 73 | 104 |
| S.D. | 1 | 0 | 3 | 5 | S.D. | 5 | 1 | 2 | 5 |

| pH | | | | | Concentration (mM) | | | |
|---|---|---|---|---|---|---|---|---|
| pH | 5.0 | 5.5 | 6.0 | 6.5 | Lactate | 5 | 10 | 15 | 20 |
| White bulb | 4.9 | 5.5 | 6.0 | 6.5 | White bulb | 5.7 | 10.4 | 14.8 | 19.3 |
| S.D. | 0.1 | 0.0 | 0.0 | 0.1 | S.D. | 0.4 | 0.4 | 0.3 | 1.1 |
| Yellow bulb | 5.0 | 5.6 | 6.1 | 6.6 | Yellow bulb | 5.9 | 10.3 | 14.9 | 20.1 |
| S.D. | 0.1 | 0.0 | 0.1 | 0.1 | S.D. | 0.3 | 0.5 | 1.2 | 2.2 |
| Daylight | 4.9 | 5.6 | 6.0 | 6.5 | Daylight | 4.6 | 9.4 | 13.4 | 18.4 |
| S.D. | 0.1 | 0.0 | 0.1 | 0.1 | S.D. | 0.8 | 0.5 | 0.2 | 1.4 |

Figure 50:
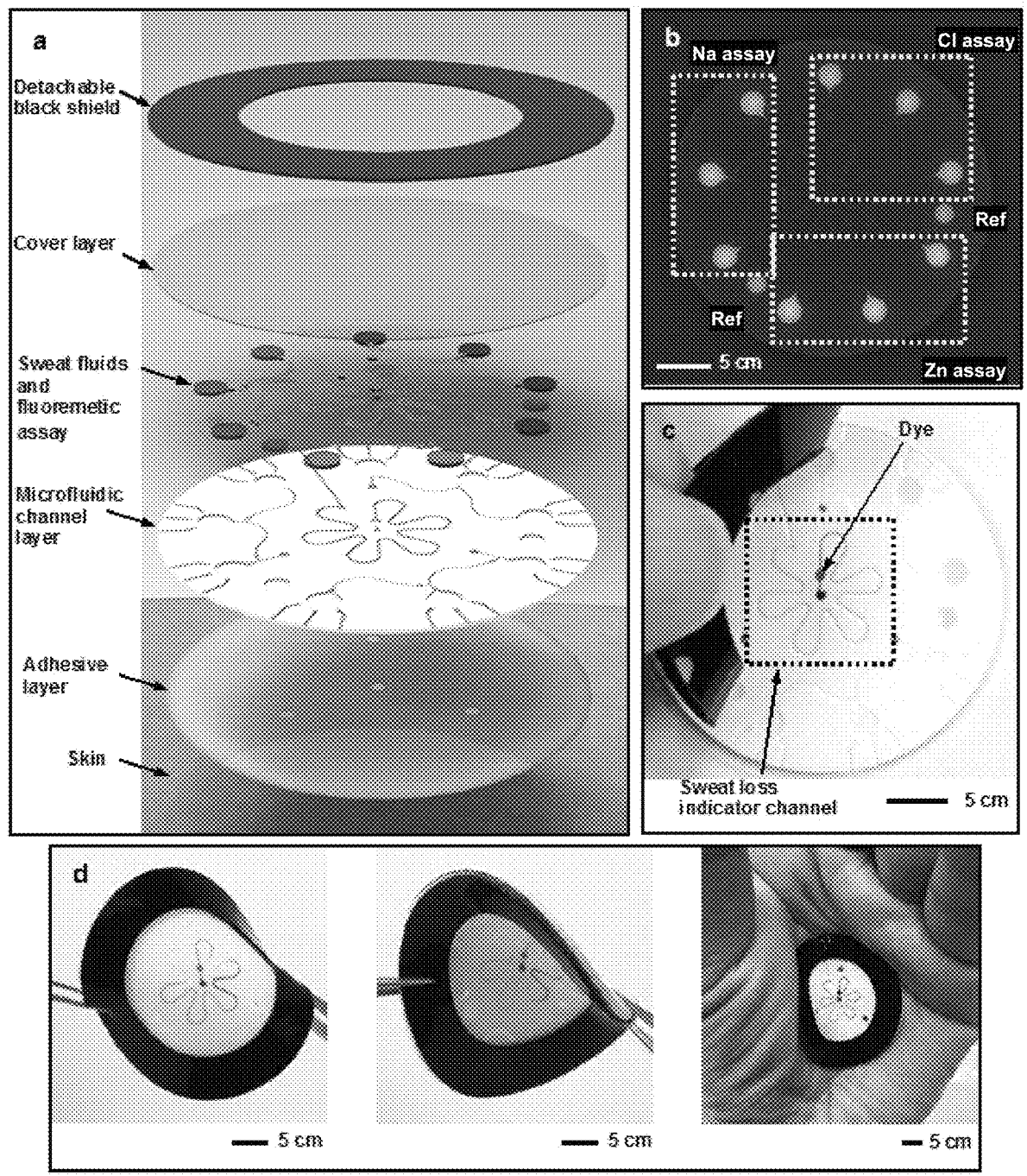
FIG. 50 shows schematic illustration and digital images of the microfluidic device for sweat chloride, sodium, and zinc sensing by fluorometric methods. a) Schematic illustrating the exploded view of the micro-fluidic device for fluorescence assays. b) Image illustrating fluorescence signals of chloride, sodium, and zinc probes on the device under the excitation light. Image illustrating c) the peeling of the detachable black shield from the microfluidic device and d) the mechanical flexibility under mechanical distortions: forward twisting (left) and backward twisting (center), and on the palm (right).
Figure 51:
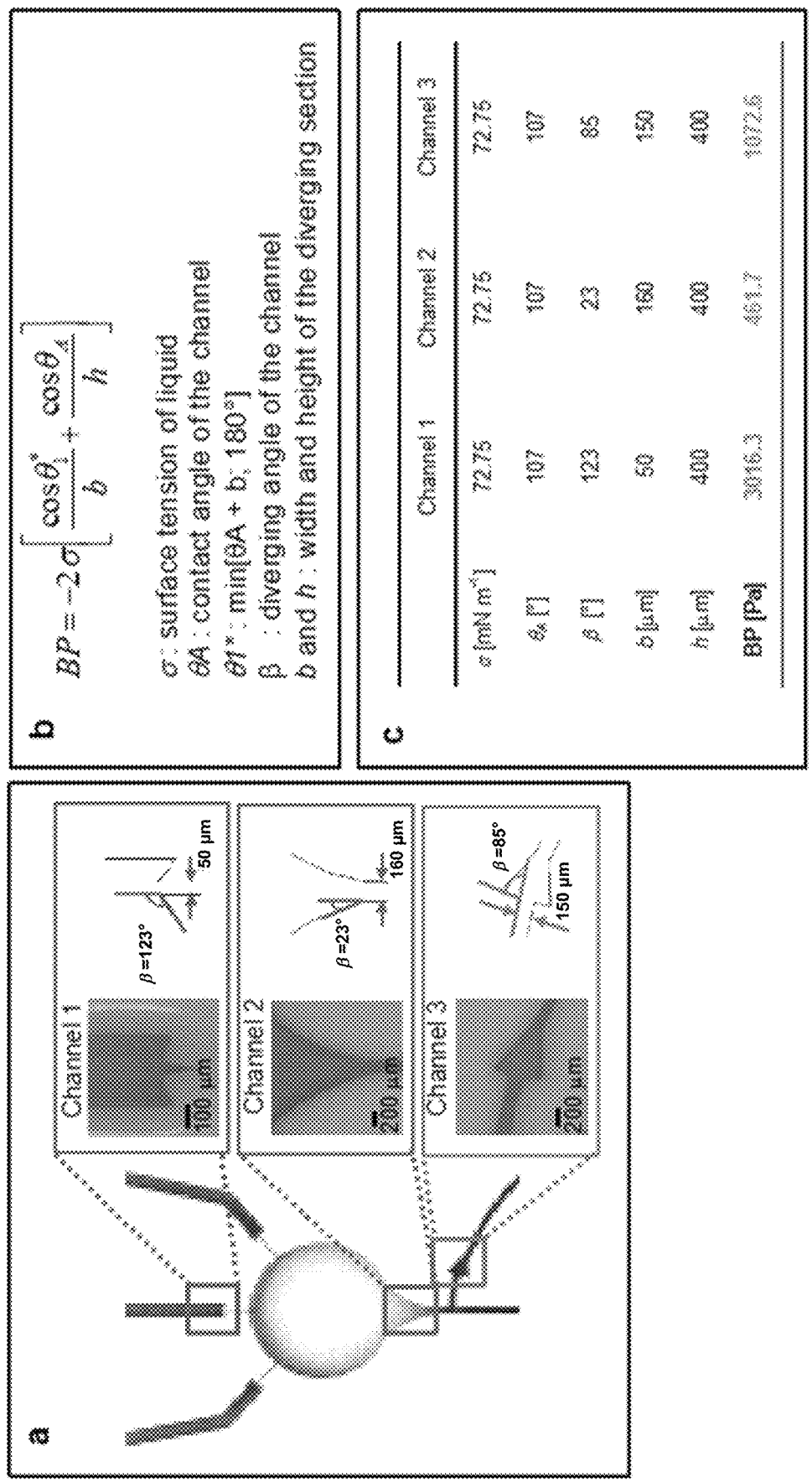
FIG. 51 shows description of the design of the microfluidic channel. (a) Detailed schematic illustration of a unit cell in a sweat device with a reservoir and three capillary bursting valves. (b) The Young-Laplace equation for calculating the bursting pressures (BP) of the valves. (c) Calculated BP of the three valves and the required parameters for the calculation.

Example 12: A "Skin-Like" Wearable Microfluidic Sensor for Fluorometric Sweat Analysis Layer structured microfluidic system for fluorometric assays: A fluorometric sweat-sensing system consisting of a wearable microfluidic device and a smartphone-based fluorescence-imaging device to analyze biomarkers in sweat in-situ with a simple procedure and high sensitivity. Microfluidic device composed of a multilayer stack of three subsystems: an adhesive membrane, a sealed microfluidic channel and reservoirs, and a detachable black light-shielding film provides a reaction chamber to analyze various biomarkers by fluorometric methods. The micro-patterns in the fluidic layer enable use of fluorometric assays and simple sweat loss monitoring. FIG. 50 shows the features of a microfluidic device for fluorometric sweat sensing. The diameter and total thickness of the device are 32 mm and ~2 mm, respectively. Three independent assays are designed along the inside of the round layer each with its own inlet hole with diameter of 0.3-1.5 mm and connected three micro-reservoirs, respectively. The channel widths and depths are 100-200 µm and ~400 µm, respectively, and the diameter of each reservoir is 2.64 mm. The micro-reservoirs are connected by the curved channels with capillary bursting valves (CBVs). The valves enable time-sequential sweat sampling with three intervals for each reservoir. FIG. 51 shows a set of CBVs in the chamber. CBV #1 has 50 µm wide channel with 123°, CBV #2 has 160 µm wide channel with 23°, CBV #3 has 150 µm wide channel with 85° of diverging outlet, respectively. Sweat first burst CBV #2 and fills the chamber #1. Then, CBV #3 with highest BP blocks the sweat flow. After filling chamber #1, sweat burst CBV #3 and flows to the next chambers. The assay reservoir having three assay chambers can store a total of 8.1 µL of sweat, with ~2 µL for each chamber. The two round reservoirs located between the assay systems were designed for a fluorescence reference system composed of ionic liquid and a fluorescence dye.

The doughnut-shaped black PDMS with 200 µm thickness placed on top of the device work as a light shield to prevent photobleaching of the fluorescence reagents while collecting sweat. The low elastic module (~145 kPa) and surface adhesion property of the PDMS allowed for detachable adhesion between the PDMS films without any treatment. The PDMS-PDMS adhesion could be detached easily by figures (panel (c) of FIG. 50). The flower-shaped channel designed in the center of the layer allows the device to indicate sweat loss for the fluorometric assays. The incoming sweat dissolves the water-soluble dye located near the inlet as it flows past, thereby creating a visible, colored fluid with an easily identifiable filling front in the channel. Since the channel volume (~8.1 µL) is designed to be almost equal to that of an assay system (~8.1 µL), the channel system can indicate the amount of sweat filling the fluorometric assay reservoirs, which are normally shielded by the black film. The low modulus and high elasticity (up to ~200%) of PDMS enabled soft and flexible devices, which are suitable as a skin wearable sensing system. Panel (d) of FIG. 50 shows deformation of a representative device by bending and twisting. The device exhibited excellent strength properties against various mechanical forces and distortions and can be applied to the skin on any part of the human body.

Device Fabrication: Soft lithographic techniques yielded the microfluidic silicon molds. Patterning photo-resist of KMPR 1010 (Microchem, MA, USA) on 1 mm thick Si-wafer and deep reactive ion etching (STS Pegasus ICP-DRIE; SPTS Technologies, Newport, United Kingdom) generated a mold for microfluidic channel. Thin layer of poly(methylmethacrylate) (PMMA; Microchem, MA, USA) formed on the mold. Pouring 10:1 PDMS (Sylgard 184; Dow corning, MI, USA) mixed with white silicone dye (Silc Pig; Smooth-on, Inc., PA, USA) at 10% wt on the mold and spin coating at 150 rpm with baking at 150° C. for 30 min yielded a 1 mm thick layer. All the chemical assays were located on the cured PDMS channel. Mechanical punches were used to cut out a round-shaped patch and to create inlet holes for collecting sweat. A transparent PDMS mixture in a ratio of 10:1 (rubber base:cure) casted on a PMMA coated flat wafer at 300 rpm and cured 150° C. for 30 min formed a uniform cover layer. Bonding the cover film to the white microfluidic channel film after placing fluorometric assays defined sealed microfluidic channels and assay chambers. A tiny amount of PDMS (10:1) was applied on the cover film before stacking on top of the channel layer, and then cured at 40° C. for 1 h. The process allowed efficient bonding of the stack without damage of the assay reagents. Casting a PDMS mixture containing a black silicone (Silc Pig; Smooth-on, Inc., PA, USA) in a ratio of 10:1:1 (rubber base:cure:black silicone) at 200 rpm and cured at 150° C. for 30 min yielded a uniformly black elastic film. The black cover film was placed on the top of the stack without any bonding agents to yield a detachable light shield. A CO2 laser (Universal Laser Systems, AZ, USA) cut a double-sided skin adhesive membrane (PC2723U; ScapaHealthcare, CT, USA) into a round shape with defined sweat inlet holes. The adhesive membrane with matching inlet holes was bonded to the bottom surface of the PDMS device on one side and to the skin on the other side. Plasma treating the micro microfluidic layer with a corona generator (Electro- Technic Products, IL, USA) created hydrophilic surfaces on the PDMS that allowed efficient bonding of the PDMS layer and the adhesive.

Figure 52:
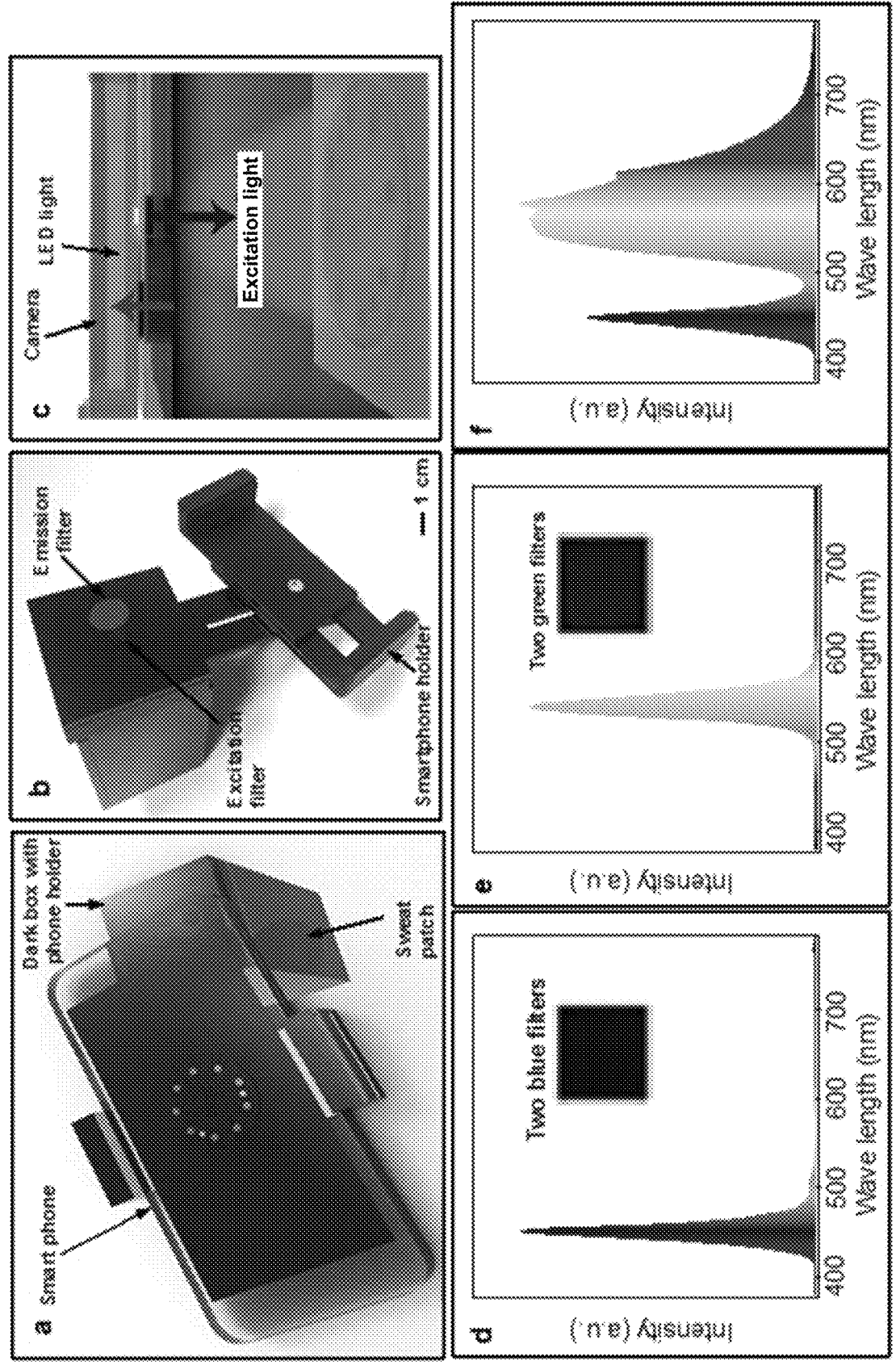
FIG. 52 shows description of the design of the smartphone based fluorometric imaging system. (a) Image illustrating the overall concept of fluorescence-imaging system with a smartphone-attached accessory. (b) Image of the photographed of smartphone attachment with the dark box and excitation/emission filters. (c) Image illustrating the fluorometric imaging system in the interfaces of smartphone and the filters. Spectra of smartphone LED light with excitation filters (two dark blue transparent filters) (d) and without filter (e) (f) Spectra of the smartphone LED light (400 nm-750 nm wavelength).

A smartphone-based fluorometric imaging system applicable for a sweat sensing device: A smartphone system yields fluorescence sweat sensing in-situ with microfluidic devices. FIG. 52(a) illustrates the features of a smartphone-based fluorescence imaging system consisting of a normal smartphone attached an accessory. The attachment involving a dark shield box with immobilized excitation and emission filters allows a normal smartphone to take fluorescence images using its camera function. The attachment includes two movable parts: one is for fixing the holder to the side of a smartphone, and the other is for adjusting the box position to make contact with the excitation and emission filters and the interfaced smartphone LED light and camera (panel (b) of FIG. 52). The filters allowed the LED light and camera to work as an excitation light and a detector for fluorescence signals (FIG. 52(c)). The blue transparent films that are generally used for display enabled transmittance of only blue light with narrow wavelength (451±35 nm) (panel (d) of FIG. 52) from the smartphone LED light (400 nm-750 nm wavelength, FIG. 52(f)). The transmitted blue light allows the fluorescent probes (excitation wavelength of 400 nm-530 nm) on the patch to be excited. To detect only the emitted fluorescence signal, a long-wave pass glass lens that can blocks light below 515 nm wavelengths was placed at the interface of the smartphone camera lens. Double green filters also provide green light with narrow wavelength (550±50 nm) from the smartphone LED light (panel (e) of FIG. 52). It means various excitation lights can be obtained from filtered smartphone LED light.

Figure 53:
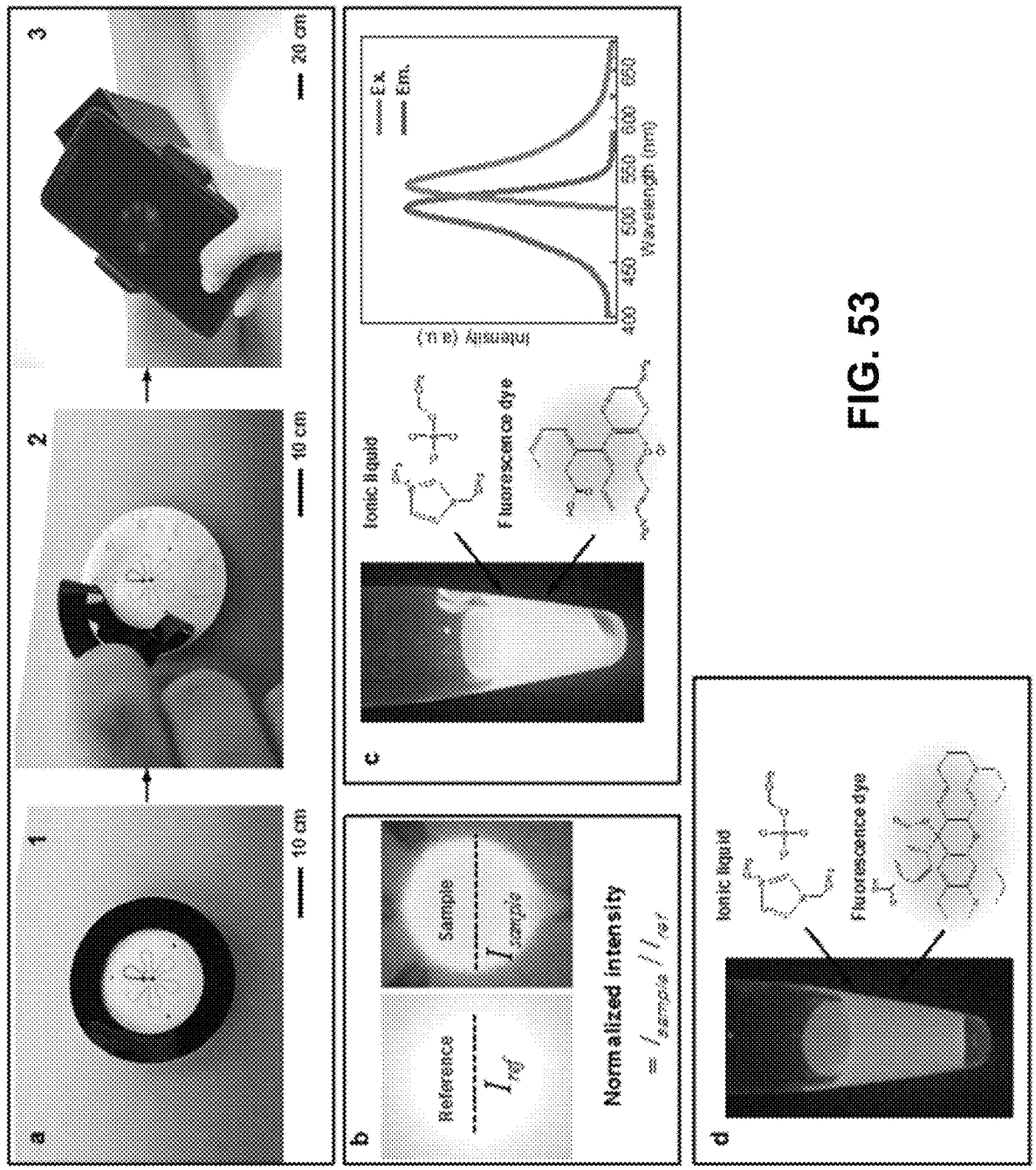
FIG. 53 shows: (a) Procedure of the fluorometric assay: 1. Collection of sweat using a sweat device 2. Peeling the black shield 3. Taking a photo of the device using a smartphone attached accessory. (b) Method of fluorescence calibration. Fluorescence reference material consisting of an ionic liquid and a green fluorescence dye (c) and red reference dye (d).

Panel (a) of FIG. 53 shows a procedure of fluorescence sweat sensing using the microfluidic device and the smartphone-based system. The skin-mounted microfluidic device introduced sweat from the co-glands to the flower-shaped channel and the three independent assay parts through the corresponding inlet holes (panel (a)-1 of FIG. 53). Completely filling the flower-shaped channel with the blue-colored sweat fluid indicates that the three assay reservoirs might be full. Then, the uppermost black film could be detached for taking a picture by the smartphone system (panel (a)-2 of FIG. 53). Taking a picture with flashlight using the smartphone with the attachment provided a fluorescence image of the signals on the device (panel (a)-3 of FIG. 53). PDMS that is transparent for wide range of wavelength and has a low refractive index (around 1.41) is applicable for fluorescence analysis.

The fluorescence signal intensity depends on the concentration of targets. To calibrate the fluorescence signals, the intensity analyzed by Image J software (NIH, USA) was divided by the reference intensity (panel (b) of FIG. 53). A stable fluorescence dye dissolved in ionic liquid was pre-placed as a reference in the device. The reference marker should have almost same excitation wavelength to those of probes. Nonvolatile ionic liquid enabled placement of the reference dye in vapors permeate PDMS stably. Various fluorescence colored references are prepared by using ionic liquid and dyes.

Figure 54:
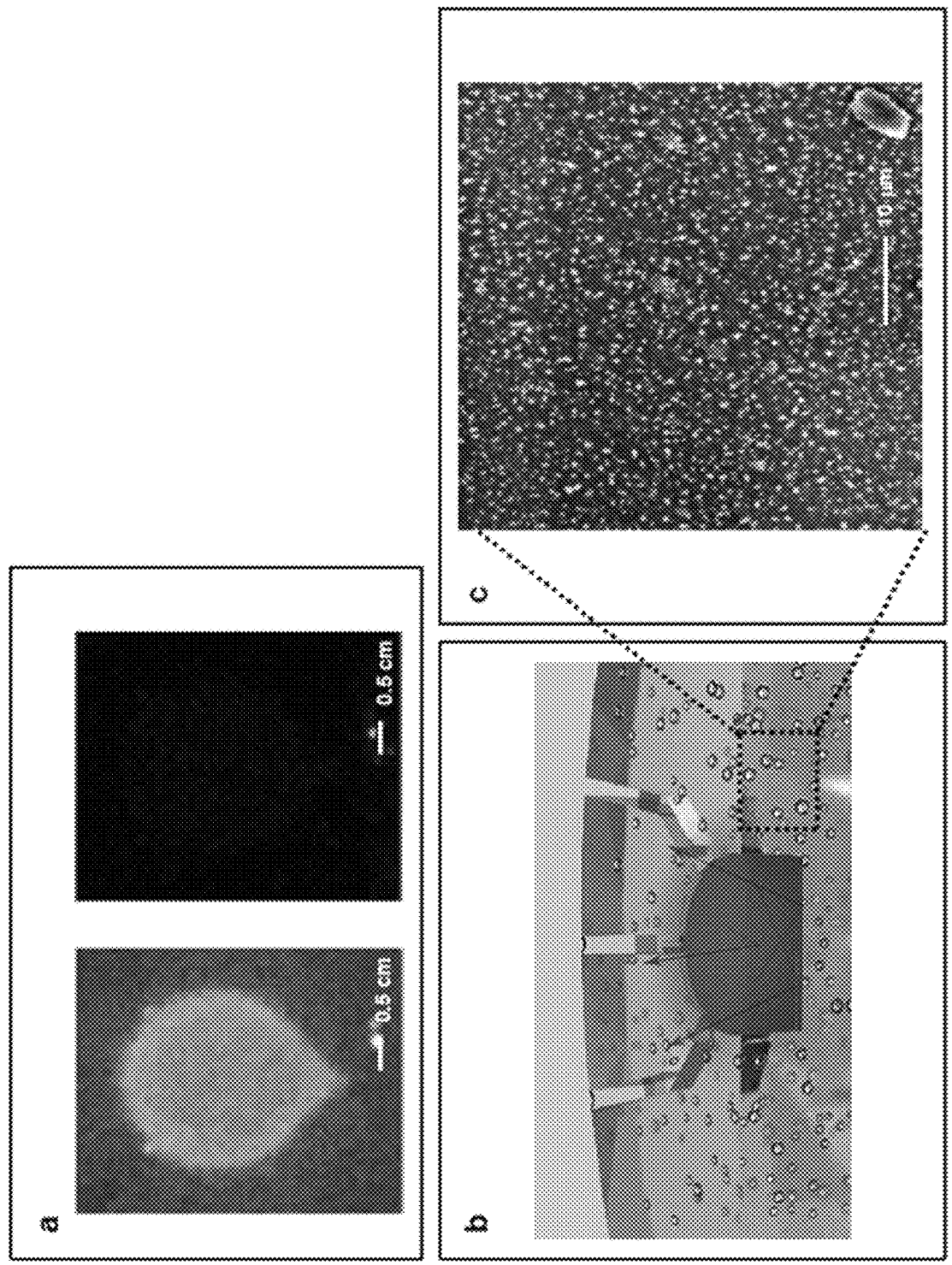
FIG. 54 shows effect of white PDMS on fluorescence intensity. (a) Difference of the fluorescence image between white and transparent PDMS devices. (b) Schematic illustrating the reflection of fluorescence by the titanium oxide particles included in the white PDMS. (c) SEM image of a white PDMS.

In addition, a white sweat device played an important role for enhancement of the fluorescence signals due to reflection of emitting fluorescence by titanium oxide particles of white pigments on the curvature of the micro reservoir (FIG. 54).

Device Fabrication: Assembly of black acrylic pieces (McMaster-Carr, IL, USA), excitation (Scotchcal™ graphic film, 3632-87; 3M, MN, USA) emission filters (colored-glass alternative filter, 5CGA-515, Newport Co., CA, USA), and a commercial smartphone holder (Lotus Tech, Wembley, UK) part using glue yielded a smartphone-based fluorometric-imaging device. The CO2 laser cut an acrylic black board with 3.18 mm into eight pieces. Gluing the four black plates together formed a square shaped box. Placing square plates with two holes for excitation and emission filters on the top of the box defined the light-shielding box. The excitation and emission filters were fixed to the holes of the plate. The box was attached to the smartphone holder by a long rectangular acrylic piece with a screw. For alignment of the sweat patch, a square plate having a hole with a size equivalent to that of the patch was placed on the bottom of the box. Putting pieces of black paper on the surface of the plates inside the box to prevent light reflection completed the assembly process. All the results of the fluorescence images were taken by using a smartphone, iPhone 6 Plus (Apple Inc., CA, USA).

Reference marker: Dissolving 0.4 mg of rhodamine 110 chloride (Sigma-Aldrich, MO, USA) in 2 mL of 1-ethyl-3-methylilimidazolium ethyl sulfate ionic liquid (Sigma-Aldrich, MO, USA) formed the green reference solution. Drop casting 0.5 μL of the ionic liquid dye onto the chambers designed for the reference fluorometric dye completed the process. Dissolving 0.4 mg of rhodamine Red-X (Thermo Fisher, USA) in 2 mL of 1-ethyl-3-methylilimidazolium ethyl sulfate ionic liquid formed the red reference solution.

Figure 55:
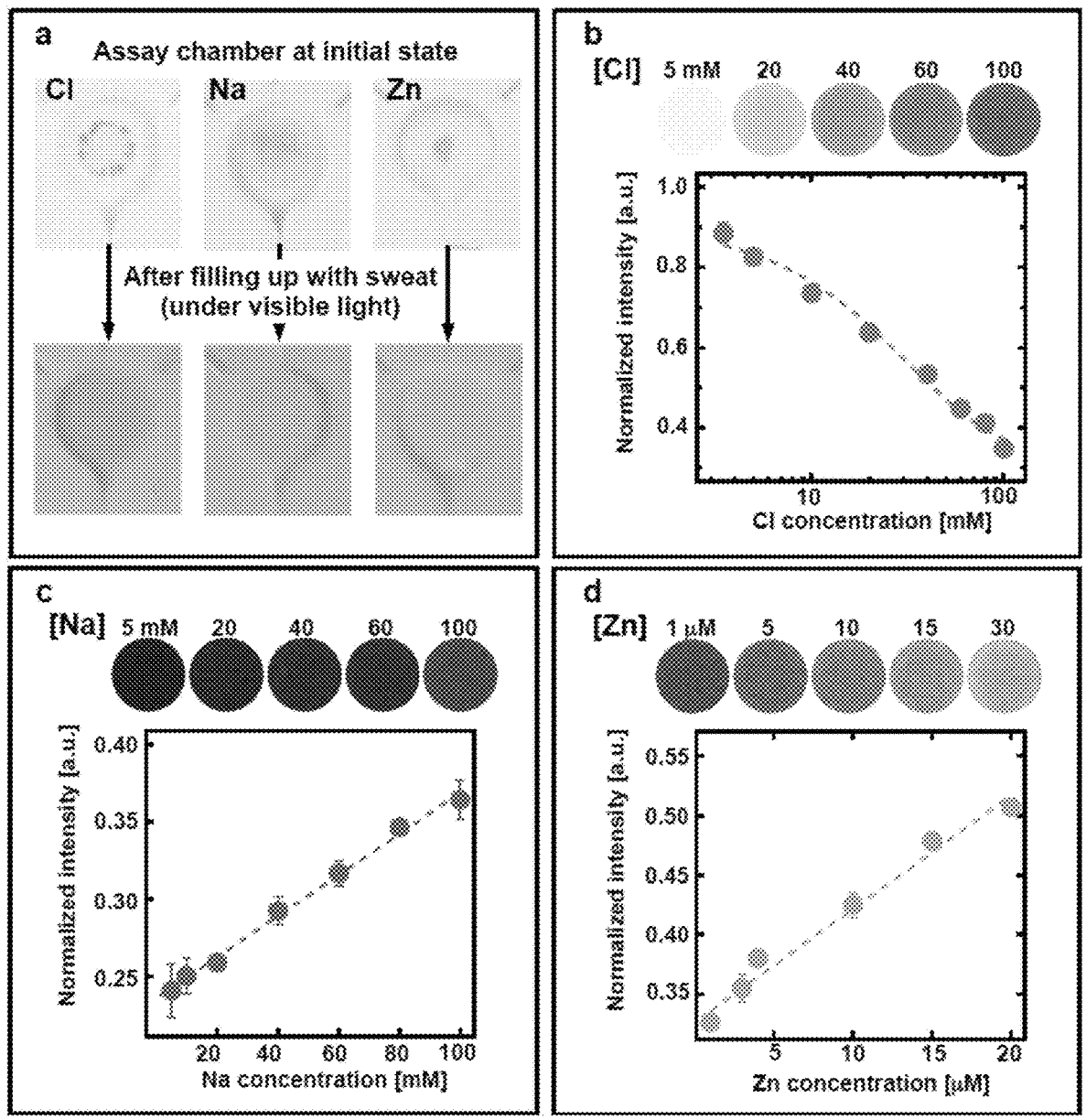
FIG. 55 shows fluorescence images of chloride, zinc, and sodium assays and its light intensity dependence on the concentration. (a) Image illustrating the micro reservoirs for the assays before (upper) and after (lower) filled up with sweat under visible light. Changes of the fluorescence and its normalized intensity at various concentrations of (b) chloride, (c) sodium, and (d) zinc.
Figure 56:
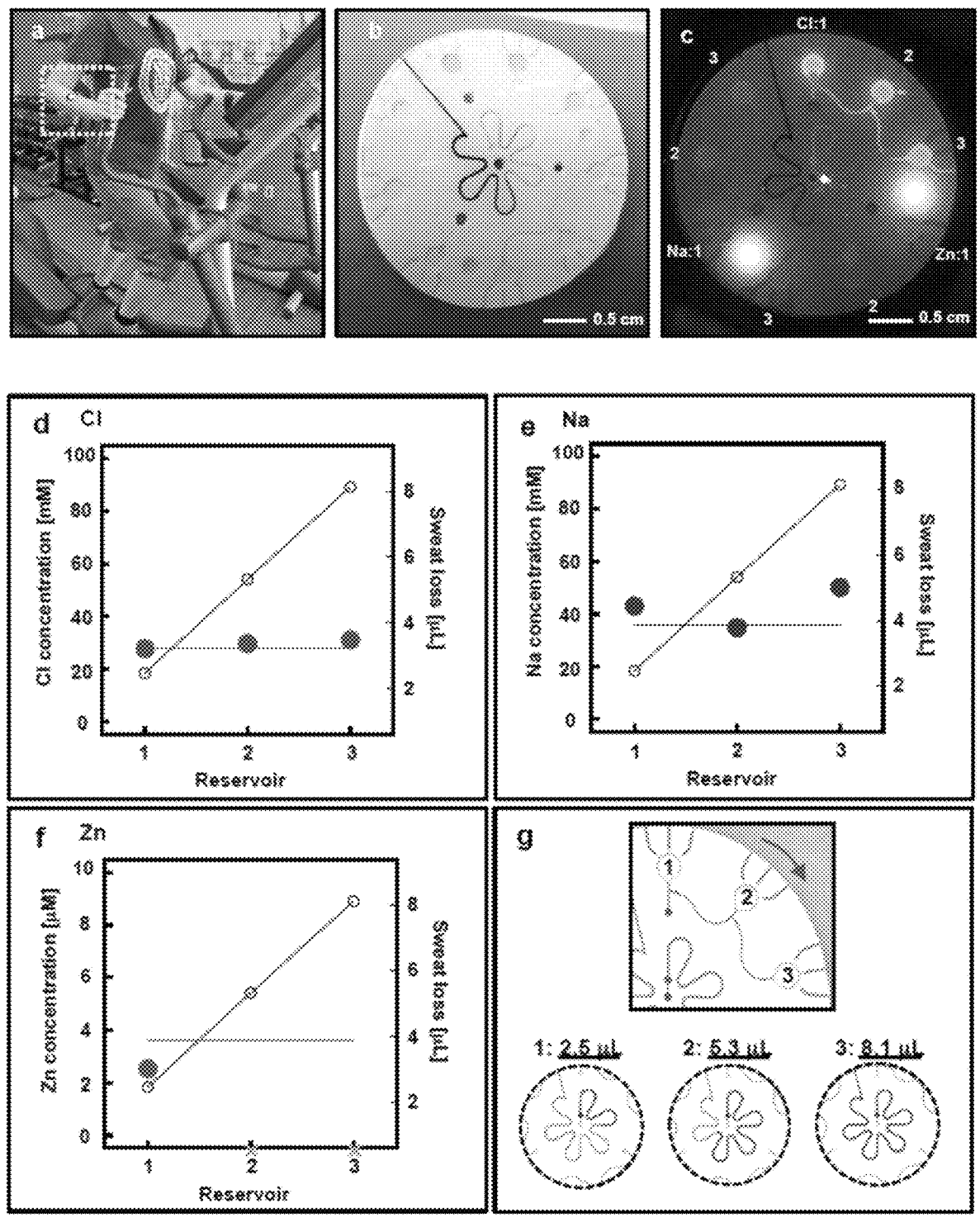
FIG. 56 shows: (a) Photograph of a subject wearing a micro-fluidic patch during sweat testing. Images of the sweat patch without the black shield after sweat collection under (b) visible light and (c) the blue light emitted by a smartphone. (d) Calculated concentrations of sweat (d) chloride (green closed circles), (e) sodium (blue closed circles), and (f) zinc (pink closed circles) with the estimated sweat loss (black dotted lines). solid green, blue and pink lines indicate the concentrations measured by ion chromatography for chloride, ICP-MS for zinc, and atomic absorption spectrometry for sodium in the sweat. (g) Changes of estimated sweat loss with being filled up the micro reservoirs and center microchannel structures.
Figure 57:
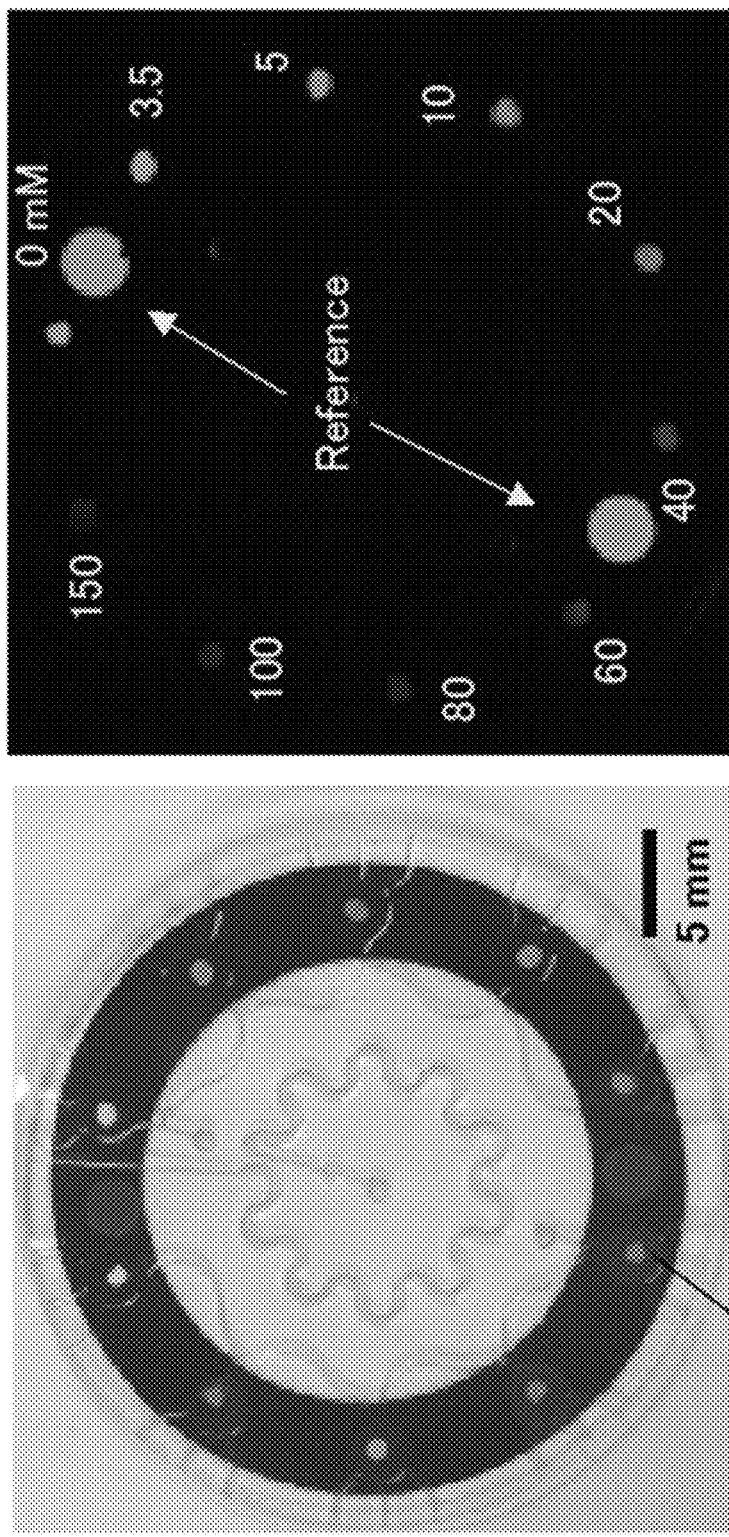
FIG. 57 shows fluorometric chloride assay using 0.3 µL of artificial sweat containing 0-150 mM chloride.

Fluorometric development: Dropping assay solution onto respective chambers of a microfluidic layer, and then drying at 35° C. for 1 h in a light shielded environment yields a solid-state fluorometric assay for various biomarkers. Panel (a) of FIG. 55 shows the assay chambers for chloride, sodium, and zinc before and after filling sweat under visible light. The fluorescence probes installed in each reservoir are easily dissolved by incoming sweat and reacted with their targets, chloride, sodium, and zinc selectivity. Panels (b)-(d) of FIG. 55 show the variation of the fluorescence images of chloride, zinc, and sodium probes reacted with artificial sweat at pH 6 containing various concentration of the targets under the excitation light of the smartphone. The graphs below the images show the dependence of the normalized intensity on the concentrations of the targets. The standard curves worked for calculating the concentration of the targets on a human trial. The calculated values were comparable with the values measured by the traditional methods, ion chromatography for chloride, ICP-MS for zinc, and atomic absorption for sodium (FIG. 56). The fluorometric assay works even in use of an extremely small amount of sweat. FIG. 57 shows the result of fluorometric chloride assay using 0.3 μL artificial sweat containing with 0-150 mM chloride. Lucigenin was placed in a microfluidic device using supporting papers.

Fluorometric assays: The chloride fluorometric assay solution consists of 2 mg lucigenin (Sigma-Aldrich, MO, USA) dispersed in 1 mL of MilliQ water. The zinc fluorometric assay solution was prepared by adding 25 μL of zinc detector (Zinc Quantification Kit (Fluorometric), Abcam Inc., MA, USA) into 5 mL of the zinc assay buffer. Dissolving 1 mg of the sodium detector (CoroNa™ Green; Molecular Probes, OR, USA) in 100 mL of dimethyl sulfoxide (Sigma-Aldrich, MO, USA) yielded a concentrated solution. Dispersing 2.3 μL of the concentrated solution into 1 mL of MilliQ water yielded the sodium fluorometric assay solution at the concentration of 40 μM. Dropping 2 μL volume of each assay solution onto the respective chambers of the microfluidic layer, and then drying at 35° C. for 1 h in a light shielded environment yielded the solid-state chloride, zinc, and sodium assays, respectively.

Figure 58:
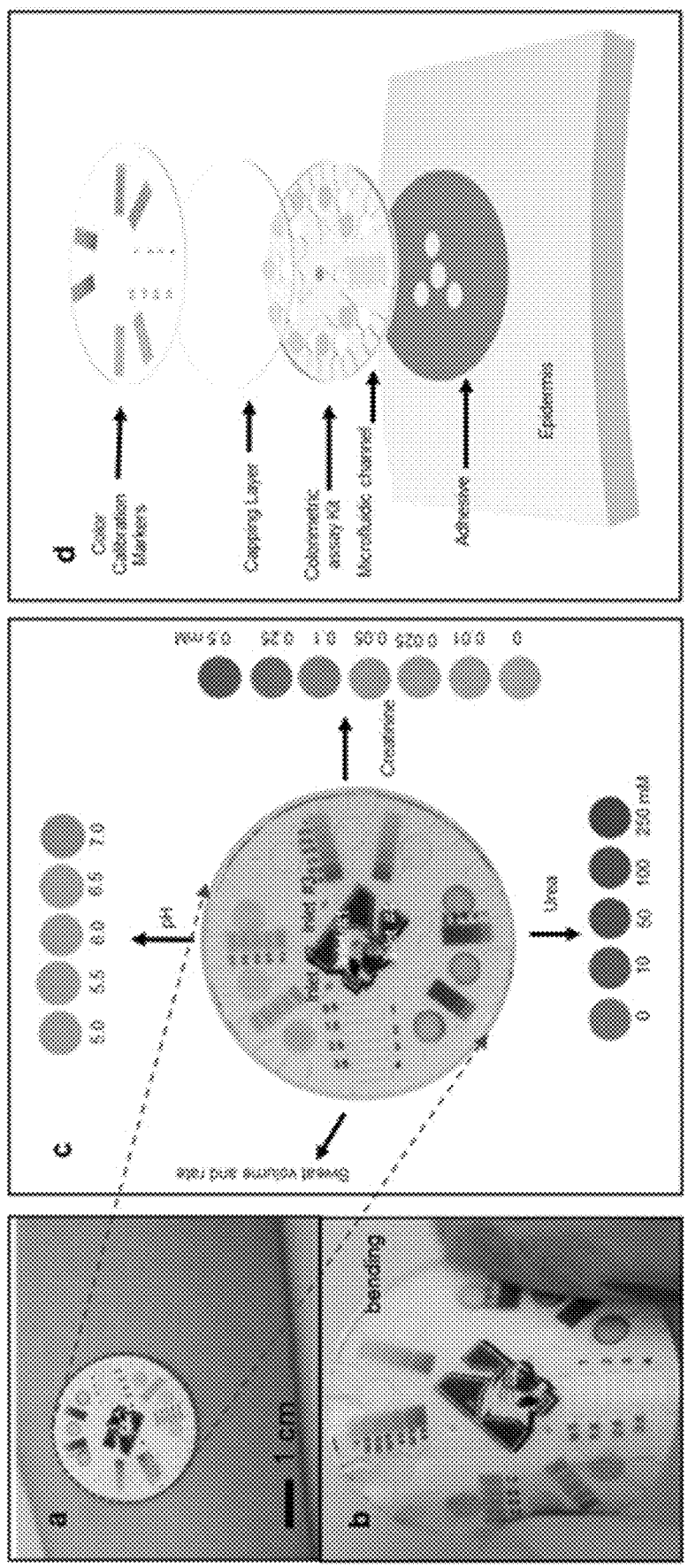
FIG. 58 shows: (a)-(b) Optical images of soft and flexible microfluidic devices for colorimetric analysis of sweat on the skin (a) and under mechanical diction of bending (b). (c) Top view illustration of microfluidic device with colorimetric assays and reference marker. d) Exploded view illustration of a device and its interface with skin.

Example 13: Soft, Multi-Functional Microfluidic Device for Colorimetric Analysis of Sweat Creatinine and Urea A soft microfluidic device made from PDMS has flexibility and interfaces to the skin (FIGS. 58a and b). The device provides several functionalities that: 1) analyzes the concentration of creatinine, urea, and pH in sweat, 2) calculates instantaneous sweat rate and local sweat loss via adhesive layer that provides a water-tight sealing between skin and the device that enables the device to collect sweat continuously (panel (c) of FIG. 58). Sweat gland under open region of skin under adhesive generates sweat flow about 2 kPa to 1) inlet #1 fills the serpentine channel then shows sweat rate and the local sweat loss, 2) inlet #2, 3 and 4 fills the collection chambers in clockwise sequential manner through the guide of series of capillary bursting valves and develop color for the detection of pH, creatinine, and urea in sweat. For colorimetric analysis, each chamber has a chemical assay paper that develop color according to target biomarker in sweat and color reference markers placed next the chamber to provide a standard color of target biomarker concentration for accurate color analysis that is not affected by light condition. The exploded view of the device shows the detailed compositions of one device (panel (d) of FIG. 58). The adhesive layer attaches the PDMS device on to the skin and the hole in the adhesive opens a route for the sweat from the region to enter to the microfluidic channels. White microfluidic PDMS channel layer formed by soft lithography has four channels: the bottom serpentine channel for measuring sweat rate and local sweat loss, other circular chambers for measuring pH, creatinine, and urea concentration in sweat. The chemical assay components are placed in each chambers and channel for their purpose. A 200 µm thick clear 10:1 PDMS capping layer, treated with oxygen plasma to make it sticky, was placed onto microfluidic PDMS channel, to generate the closed channel. On top the capping layer, a 25 µm thick thin PET film with reference color marker provide an accurate color analysis.

Device Fabrication: Fabrication begins with making a silicon wafer mold. Patterning photo-resist of KMPR 1010 (Microchem, MA, USA) on 1 mm thick Si-wafer and deep reactive ion etching (STS Pegasus ICP-DRIE; SPTS Technologies, Newport, United Kingdom) generated a mold for microfluidic channels and reservoirs. Thin layer of poly (methylmethacrylate) (PMMA; Microchem, MA, USA) formed on the mold as an anti-adhesion layer. Pouring 10:1 PDMS (Sylgard 184; Dow corning, MI, USA) mixed with white silicone dye (Reynolds Advanced Material, 5% wt) on the mold and spin coating at 200 rpm with baking at 70° C. for 45 min. Capping layer was spin coated with 10:1 PDMS at 200 rpm and baked at 70° C. for 45 min. Both microfluidic channel layer and capping layer were treated with laboratory corona treater (Electro-Technic Products) for better adhesion right before loading assays. All the chemical assays were located on the cured PDMS channel. 25 µm thick clear polyester film (THERMLfilm SELECT® 10852; FLEXcon, MA, USA) on the top of the device with color reference marker. 60 µm thick medical grade acrylate adhesive (1524; 3M, MN, USA) bonded to the bottom of the device with 30 sec of corona treatment.

Figure 59:
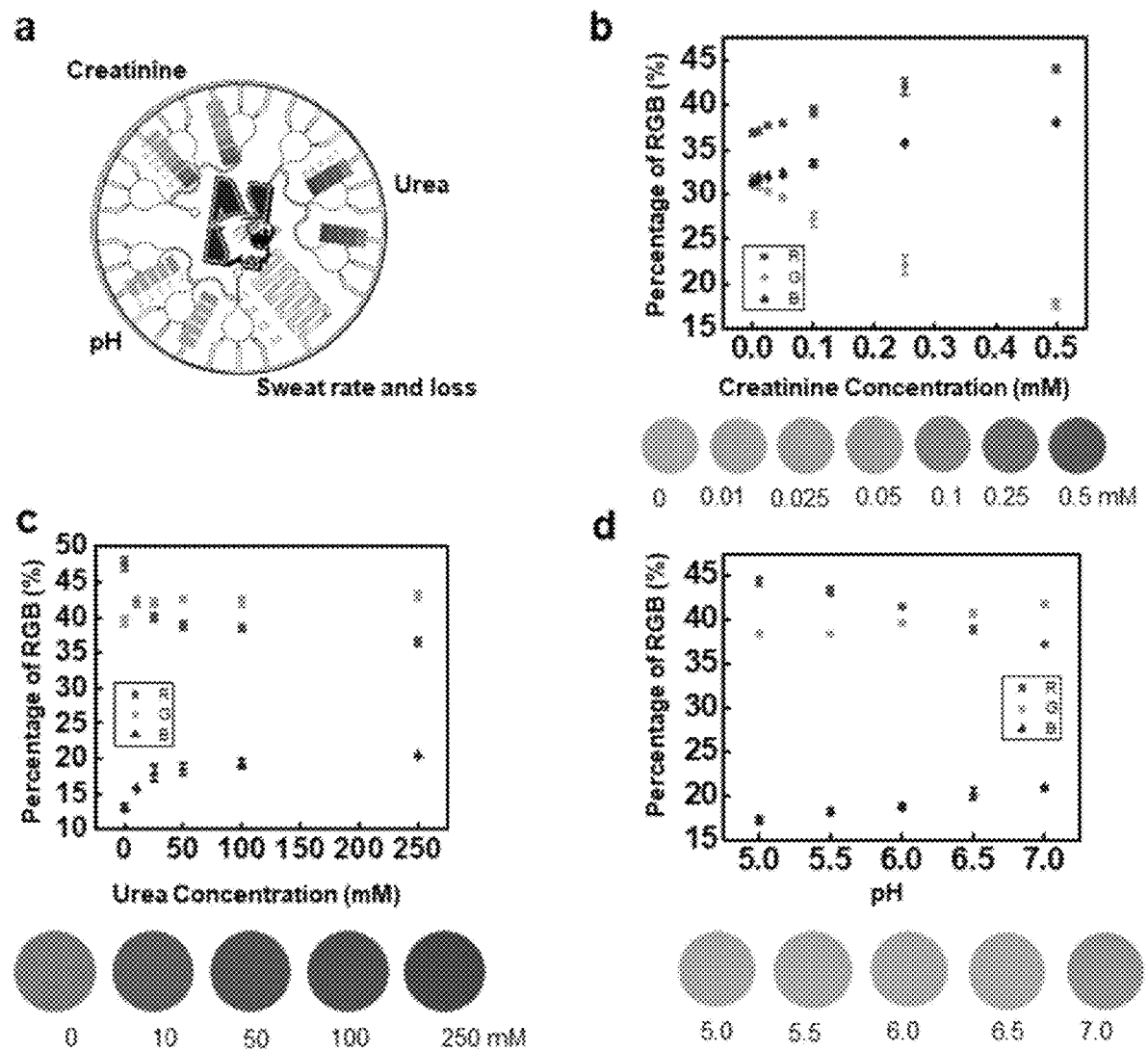
FIG. 59 shows: (a) Schematic illustration of device with color reference markers of pH, creatinine and urea, and number for indicating sweat collection volume. (b)-(d) Color level of each concentration (top) and optical images color development of assay chambers according to sample concentrations (top) of b) creatinine, c) urea, and d) pH.

Color development and reference marker: Colorimetric method for detection of biomarkers needs a color reference marker for accurate analysis of color regardless of light condition. Panel (a) of FIG. 59 shows the collection of color reference markers for analyzing pH, creatinine, and urea from sweat. For the preparation of the color reference marker, in vitro test with standard solution produced reference color and digital imaging and image analysis provides color value of each assay. From the values, the color reference marker is generated and printed on the thin and clear film and attached to the top of the device. Creatinine in the sweat produces hydrogen peroxide ($H_2O_2$) from the enzymatic reaction with creatininase, creatinase, sarcosine oxidase, and peroxidase and reacts with probe using $H_2O_2$ results red color that changes green level in the chamber dominantly (panel (b) of FIG. 59). Urease immobilized in pH paper decomposes urea in sweat into ammonia, changing the color of pH paper from yellow to green, where the red level changes dominantly with urea concentration (panel (c) of FIG. 59). Universal pH dye provides a pH sensor and red level from the sensor that changes dominantly with pH of solution serve a comparing parameter of the color of assay (panel (d) of FIG. 59).

Colorimetric assay: 1) urea: 0.01 mg/ml urease solution was prepared with urease (urease from *Canavalia ensiformis*, Jack bean, type III; Sigma-Aldrich, MO, USA) in deionized water. Urea assay paper was prepared by immobilizing 2 µl of urease solution onto a pH paper (diameter, 3 mm, Hydrion Strips B 1-11, Micro Essential Laboratory, NY, USA) and drying under vacuum in a desiccator for 15 min.

2) creatinine: the creatinine assay solution was generated by fully mixing 24 µl of buffer, 8 µl of each enzyme solution, creatininase, creatinase, and enzyme mix, and 2 µl of probe. Creatinine assay paper was prepared by spotting 2 µl of cocktail solution onto a filter paper (diameter, 3 mm) and drying under vacuum in a desiccator for 15 min (Creatinine Assay Kit; Sigma-Aldrich, MO, USA). A metal punch (diameter, 3 mm) was used to create circular pH papers for urea and filter papers for creatinine.

3) pH: pH cocktail solution was realized by thoroughly vortexing 4 ml of universal pH dye (Fisher Scientific, NH, USA), 274 mg of polyvinyl chloride (M.W. ~233,000, Sigma-Aldrich, MO, USA), 635 µl of o-nitrophenyloctylether (Sigma-Aldrich, MO, USA) and 508 µl of aliquot in 10 ml of tetrahydrofuran (Sigma-Aldrich, MO, USA) till a homogenous suspension was obtained. Thereafter, a filter paper was dipped in the cocktail solution for 10 s and allowed to dry at ambient conditions for 15 min to realize the solid-state pH assay. Finally, a metal punch (diameter, 3 mm) was used to excise circular pads of the pH assay paper for incorporating in the wearable patch.

Standard color development and color reference marker preparation: Creatinine solution was prepared by dissolving creatinine from creatinine assay kit (Sigma-Aldrich, MO, USA) in DI water. Urea (Sigma-Aldrich, MO, USA) generated standard solutions in DI water as its concentrations. pH buffer solution was made by 1×PBS buffer (pH 7.4, Sigma-Aldrich, MO, USA) and hydrochloric acid (37%, Sigma-Aldrich, MO, USA), and pH meter (Mettler Toledo, Greifensee, Switzerland) measured it. For creatinine, urea and pH test, pipetting 2 µl of standard solution into the chambers. For full color development, the device with creatinine and urea assay filled by the solution stayed in the oven at 37° C. for 15 min and pH for 5 min. A digital SLR camera (EOS 6D; Canon, Tokyo, Japan) took the picture of the device. Photoshop (Adobe Systems, CA, USA) provided color extraction from the color in the chambers. A color laser printer (C454 PS; Konica Minolta, Tokyo, Japan) produced a reference maker on PET film at 1200 DPI resolution. The printed the reference marker placed on the device again and smartphone camera (Iphone 5s; Apple, CA, USA) took picture of the chamber with reference marker. The color analysis compared the color level from the chamber and reference marker. Three spots from each chamber and reference marker provided the average color value. By adjusting brightness of the image, repetition of printing and comparing provided the optimum reference marker.

Method to improve accuracy of colorimetric assay analysis: Accuracy of colorimetric assays suffer in response to effects such as subtle color changes between different states (e.g. difference between 5 mM and 10 mM chloride levels), non-uniform lighting conditions, channel height, or variations in printed calibration marks (e.g. resolution, ink concentration, color print space). Whereas sampling colors in a device-independent color space, such as CIE L*a*b* color space, provides a facile method for color comparison, many colorimetric assays (such as chloride) contain a "white point measurement" indicating the absence of an analyte (i.e. 0 mM chloride). The utilization of white in a colorimetric assay is problematic when attempting to distinguish between subtle variations in color and thus analyte concentration as white is defined as L*=100, a*=0, b*=0. Luminance, L*, is most prone to variations in illumination, which propagates uncertainty into colorimetric assay analysis at low concentrations. For clinical applications, maximizing accuracy at low concentrations, which for chloride is <45 mM, is necessary to establish the assay as comparable to a diagnostic gold standard (e.g. chloride value <=1 mM standard deviation).

A flatbed scanner (Canon CanoScan LiDE 220) is used to eliminate variations in lighting. Illumination uniformity can be determined via a pixel-by-pixel variation analysis of each channel (RGB) of a full-bed scan. Typical variation was found to be <0.8% across the entire bed with <0.1% variation across a 30 mm×60 mm region (size of a test sweat device).

Figure 60:
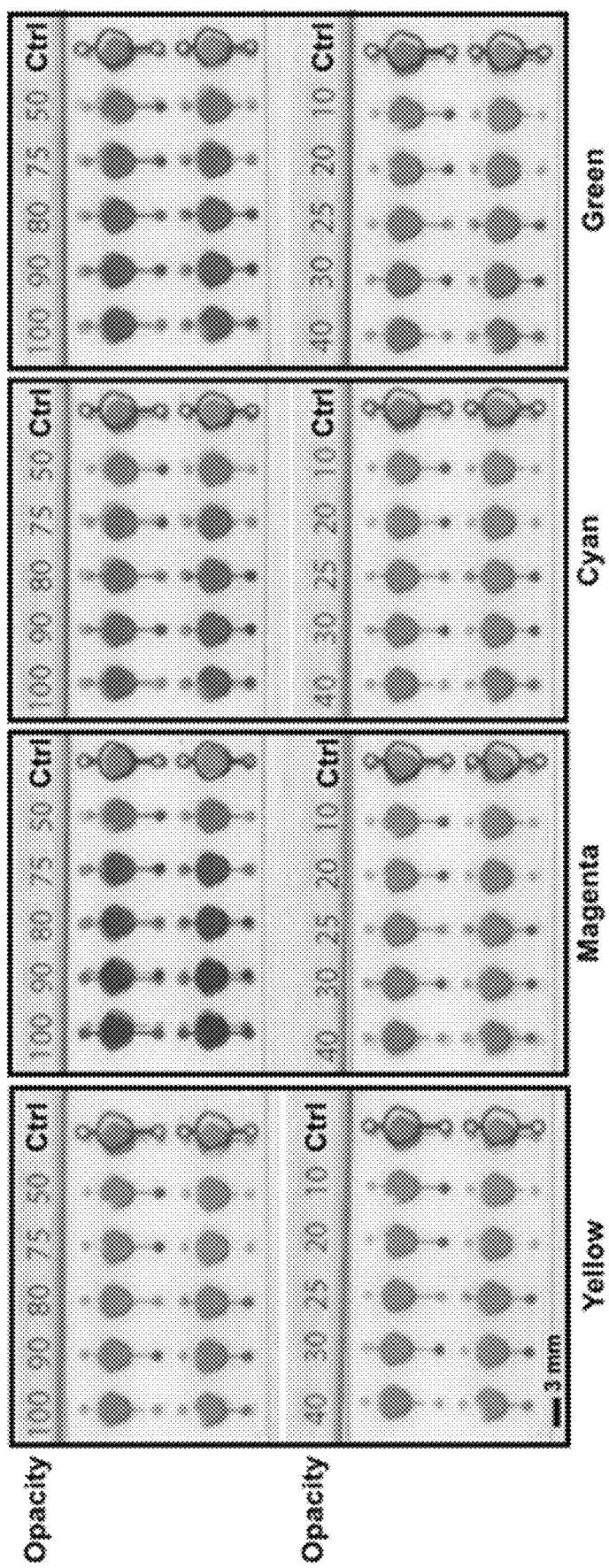
FIG. 60 shows sample analysis wells with overprinting colors (Yellow, Magenta, Cyan, Green) at different opacities (100, 90, 80, 75, 50, 40, 30, 25, 20, 10) and two control points per pattern. Control points have no printing, but contain printed overlay material (PET) to eliminate path length variations. Duplication of each row eliminates channel height variation. Colorimetric assay is silver chloranilate for a 75 mM concentration test solution.

One strategy to improve colorimetric assay accuracy is to eliminate the white point in an assay by overprinting the measurement region with a contrasting color. By overprinting, the relevant detection range of the assay is elongated to increase the range of distinguishable color measurements. A demonstration of this strategy appears in FIG. 60.

Figure 61:
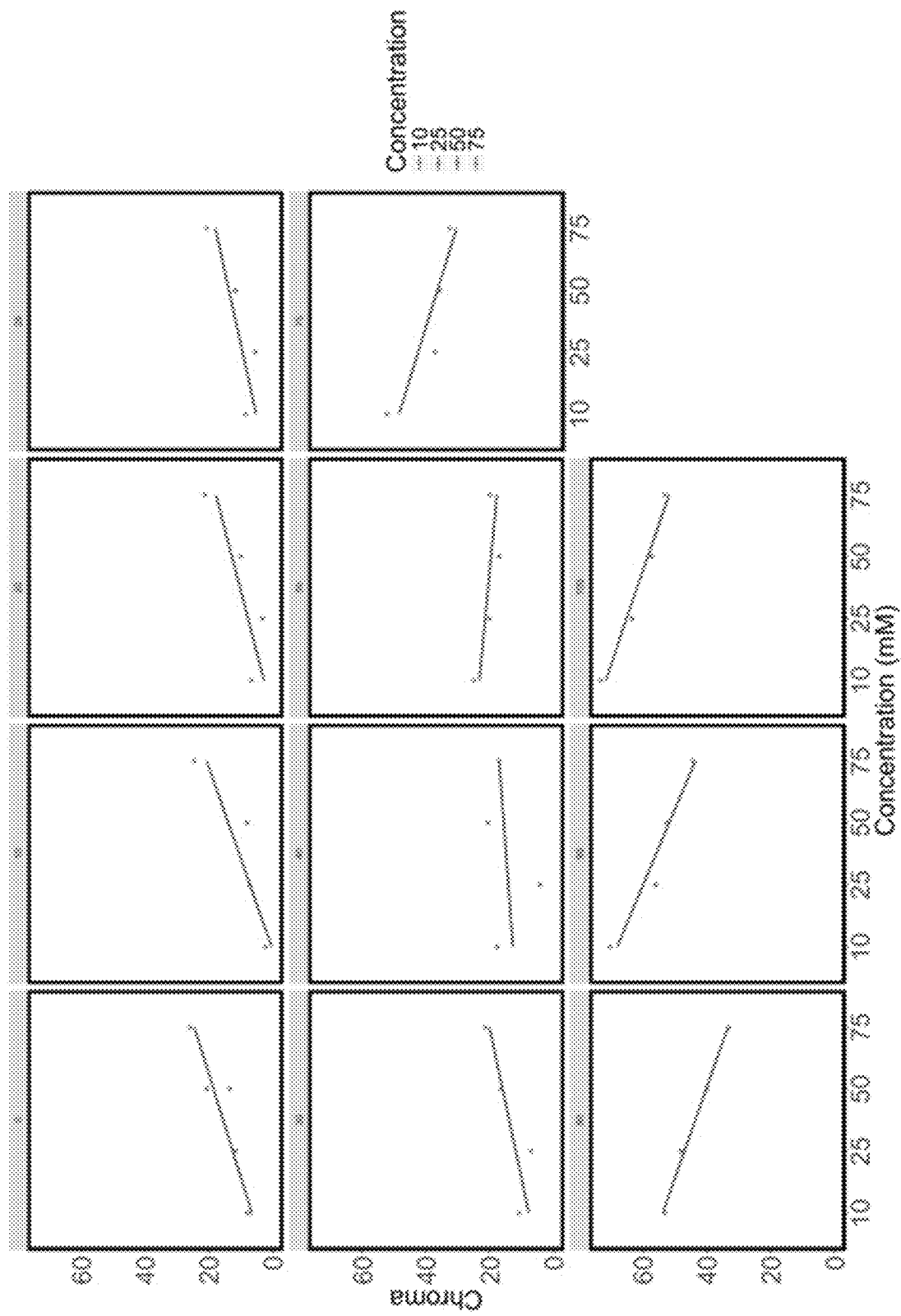
FIG. 61 shows facet plot of the color Green of measured chroma values versus concentration (known). The facets represent the different opacities. The overprints were made via laser printer.

Although several methods exist to relate measured differences in color in CIE L*a*b* space to assay concentration, accuracy is maximized while minimizing external factors (such as luminance variation) by using the established value for chroma (C) which is related to the a* and b* coordinates via the relationship $C=(a^{*2}+b^{*2})^{(1/2)}$. Using chroma, independent of L*, to map measured color to known analyte concentration establishes a calibration curve to measure unknown solutions. Identifying the optimal color for a particular colorimetric assay is rapidly ascertained via a facet plot of the different variables so as to identify the parameters that provide a linear fit with the best fit and the largest gradient (i.e. slope) as compared to the control points. An example of the facet plot appears in FIG. 61 for the Green color shown in FIG. 60.

A comparison of color overlays generated via an inkjet printer and a laser printer show minimal influence on the performance of a selected color.

After the identification of an optimized color and opacity for a given assay, comparison of the calibration curve to an "unknown" calibration sample provides a simple means for evaluating accuracy. For silver chloranilate assay for chloride samples in a diagnostically relevant range (10 mM to 75 mM), the best-fit regression equation has been determined to be a power-law fit. The $R^2$ values for control is 0.995 and for the green-color overlay 0.999 for the values provided in Table 3. Evaluating the calibration curve at the measured chroma values for 30 mM (not part of fit calculations), the control yields a concentration measurement of 25.7 mM, within the expected range of a colorimetric assay. However, when measured with a color overlay, the fit yields a concentration of 30.41 mM. The calibration solution, when measured using a chloridometer (clinical gold standard, Wescor Chlorochek), is 30.5 mM (N=3, resolution is ±1 mM).

TABLE 3

Measured chroma values for a control (no overlay) and green overlay for silver chloranilate chloride assay at given chloride concentrations. 30 mM represents the calibration solution that is used to check the goodness of fit and compare performance accuracy.

| Concentration (mM) | Chroma | |
| --- | --- | --- |
| | Control | Green Overlay |
| 10 | 7.07 | 53.15 |
| 25 | 11.66 | 48.09 |
| 50 | 20.62 | 40.02 |
| 75 | 25.81 | 33.12 |
| Calibration: 30 | 12.81 | 46.20 |

Example 14: Integrating Structural Features for Rapid Volume Readout

Figure 62:
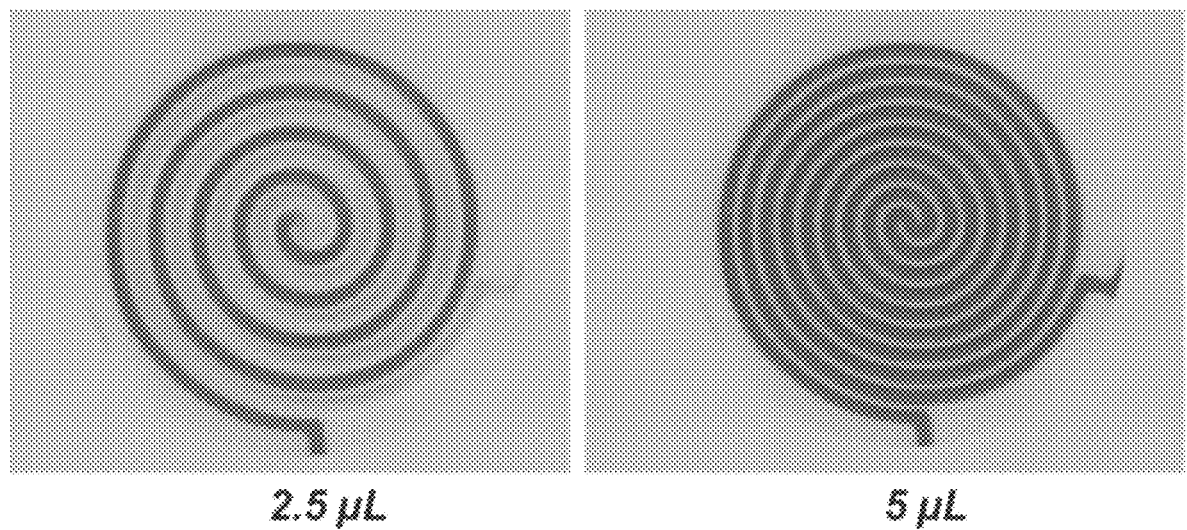
FIG. 62 shows microfluidic channels forming a "reservoir" that spatially holds 5 µL of fluid. When halfway full, the direction of fill changes thereby indicating both visually and via motion the current volume of collected fluid with respect to the total volume.
Figure 63:
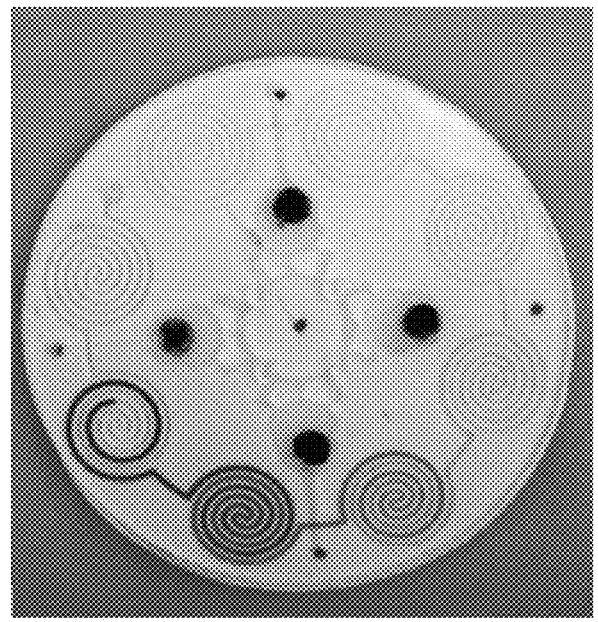
FIG. 63 shows a representative device showing a network of channel "reservoirs" that hold a larger volume of collected sweat with a "digital" indication of the total volume of collected sweat.

The planar microfluidic channels can be designed so that the method of filling provides information about the performance of the device. One example is the use of filling behavior in a spiral to indicate the fill percentage of a channel "reservoir" of a known volume. As shown in FIG. 62, a channel "reservoir" holds a total volume of 5 μL. The feature fills continuously but when half full (2.5 μL) the direction of filling switches. Using both motion and geometry, a person wearing the device can quickly monitor the collected sweat volume. As the sweat fills the device continuously, approximate percentages (such as ⅔ and ¾) are also easily assessed. When combined into a series of reservoirs, larger volumes of sweat can be quickly measured during a collection period as shown in FIG. 63.

Example 15: Device Performance (U.S. App. No. 62/514,515 Atty Ref NU2017-067 45-17P)

To test device performance in a laboratory setting, we conducted a study on a small (n=3) number of adult volunteers substituting our device for the Macroduct® sweat collection system. The study assessed the collection performance over a 9-day period with a variable hydration state (FIG. 64A), a contra-lateral study of the device efficacy vs. Macroduct device (FIG. 64B), and comparison of chloride values of collected sweat evaluated using the ChloroChek (FIG. 64C). For all cases no QNS instances occurred. Over the 9-day volume study, the collection device demonstrated reproducible collection performance.

Figure 64:
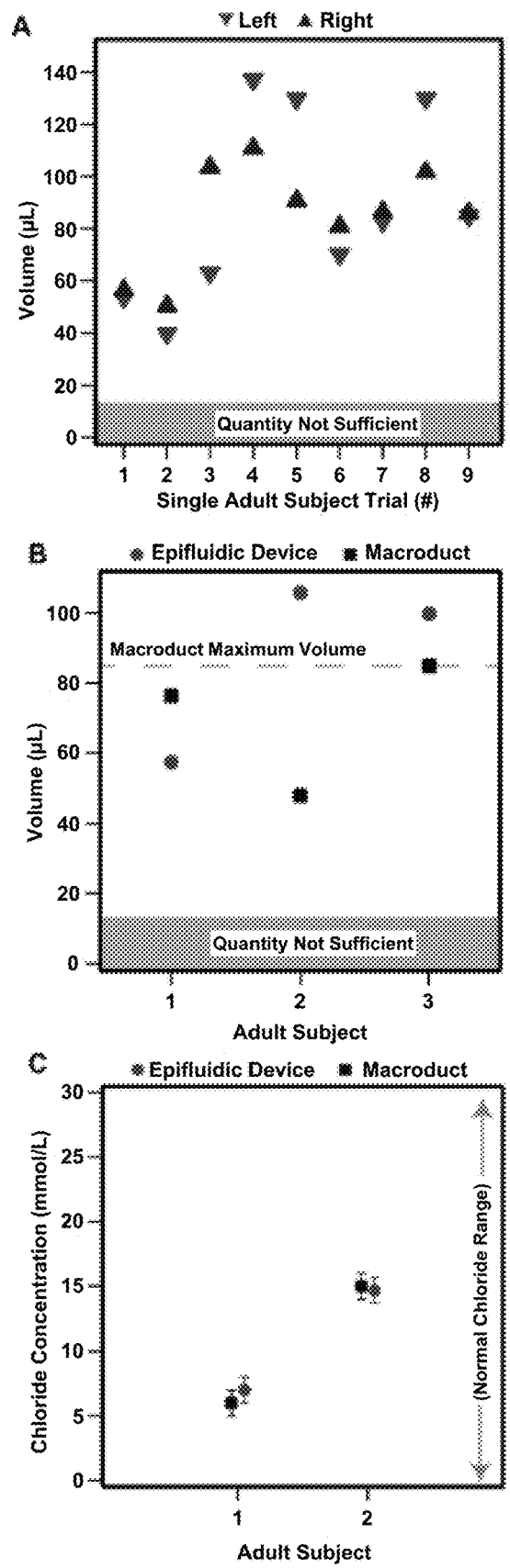
FIG. 64 shows: (A) Sweat collection volume for one adult volunteer over 9 days for both the left and right arms. (B) Comparison of epifluidic device and MACRODUCT® sweat collection volumes for three adult volunteers. (C) Chloride concentration for collected sweat for two adult volunteers.

Our novel epifluidic device collected at least 40 μL of sweat regardless of hydration state during the 30 min collection timeframe and for the majority of the study days sweat collected was in excess of 80 μL. Arm-to-arm variation was within expected ranges for iontophoretic stimulation (<35%). As shown in FIG. 64, an initial contra-lateral study between the Macroduct and the collection device on three adult volunteers (same day) demonstrated performance equivalence. Variation observed for Subjects 1 and 3 is within the expected aforementioned range; however, the device collection volume for Subject 2 indicates the potential for enhanced collection performance. This possibility will be investigated as part Specific Aim #1 of this proposed study.

Initial validation of the novel epifluidic collection device performance required verification of chloride level similarity between sweat obtained via the Macroduct® pilocarpine stimulation and collection device. Panel (C) of FIG. 64 shows the chloridometer (ChloroChek) measurements (N=5 runs) of each sweat sample from a single iontophoresis stimulation session (separate arms). The absence of variation between the measured values for the two subjects indicates that both the teal dye is chloride-free and no difference exists between the sweat collected via either method (beyond standard biological variation).

Advanced Functionality: The ability to integrate additional functionality beyond sweat collection offers a key advantage for epidermal microfluidic devices over the existing sweat collection methods. Reconfiguration of the epifluidic sweat collection device to include a colorimetric assay for the quantitative analysis of sweat chloride levels offers the possibility of significantly decreasing the time-to-answer at the point-of-care for CF diagnostics or offering a facile method for an initial chloride level screen. Panel (A) of FIG. 65 showcases this device variation which features an integrated colorimetric assay for chloride and an independent sweat collection chamber (70 µL volume). The colorimetric assay uses an excess of silver chloranilate for the quantitative analysis of chloride levels in sweat. The intensity of the violet color (panel (B) of FIG. 65) increases with increasing sweat chloride levels. Imaging the assay reservoirs with a smartphone camera provides a simple method for rapidly quantifying the reservoir color by comparing the measured color with a calibrated color reference (not shown).

Figure 66:
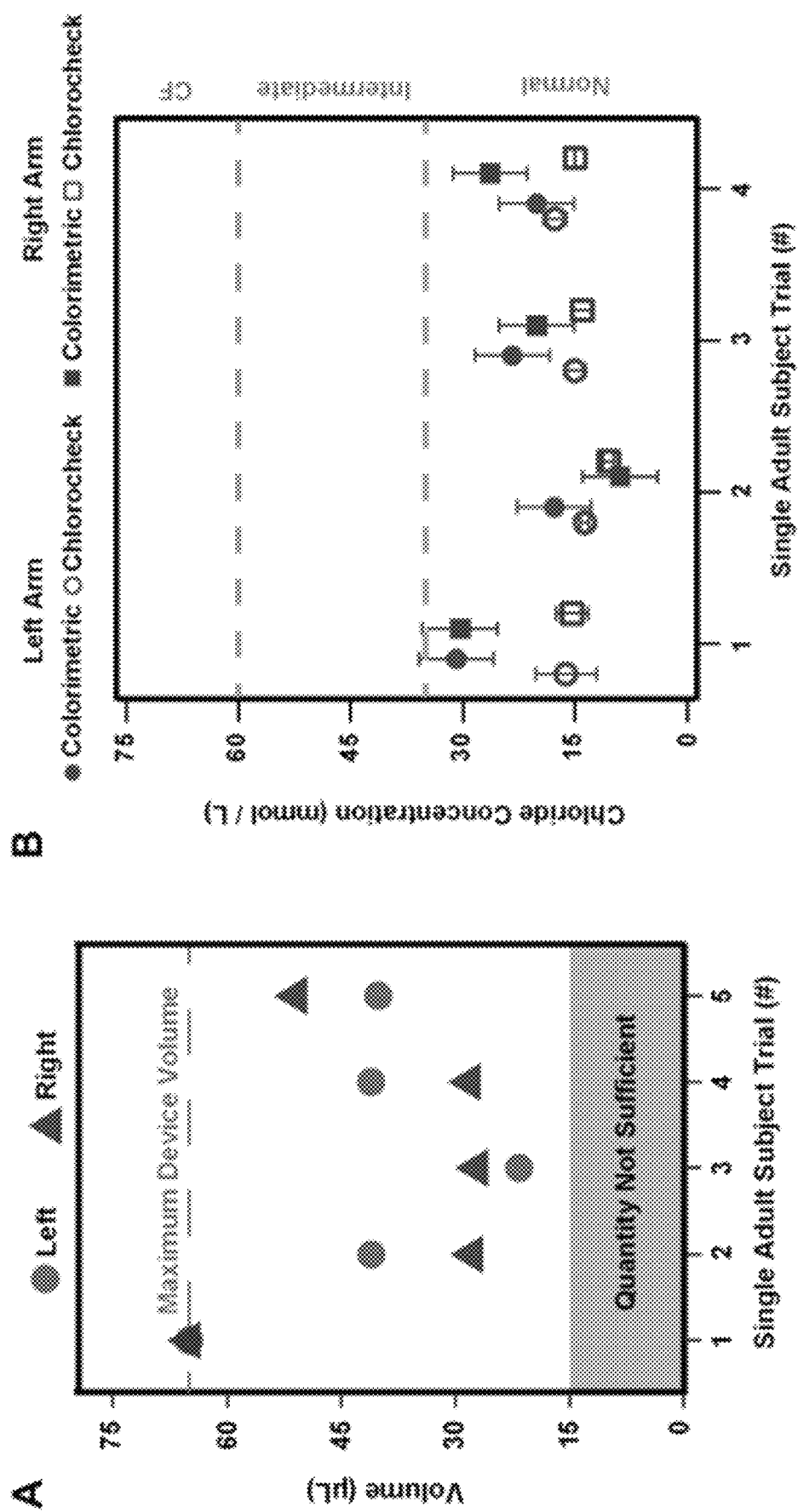
FIG. 66 shows: (A) Volume of collected sweat over a 5-day trial for a single adult volunteer using a collection device with integrated analysis. (b) Comparison of colorimetric assay performance to CHLOROCHEK® measurements over a 4-day trial for a single adult volunteer.

A small, one-person study of the sweat collection reproducibility of the device variation revealed lower volumes of collected sweat; however, no instants of QNS were recorded. This decrease in collection volume reflects the elimination of two additional collection points to provide independent colorimetric analysis of sweat chloride levels (panel (A) of FIG. 66). Panel (B) of FIG. 66 shows assay performance against the ChloroChek benchmark over a 4-day trial. Although the colorimetric assay results indicate an elevated level of chloride, as compared to the measurements from a chloridometer, the assay correctly indicates the absence of CF in the adult volunteer. As a screening method, this integration with an effective collection device offers a promising opportunity for on-board chloride screening.

Figure 67:
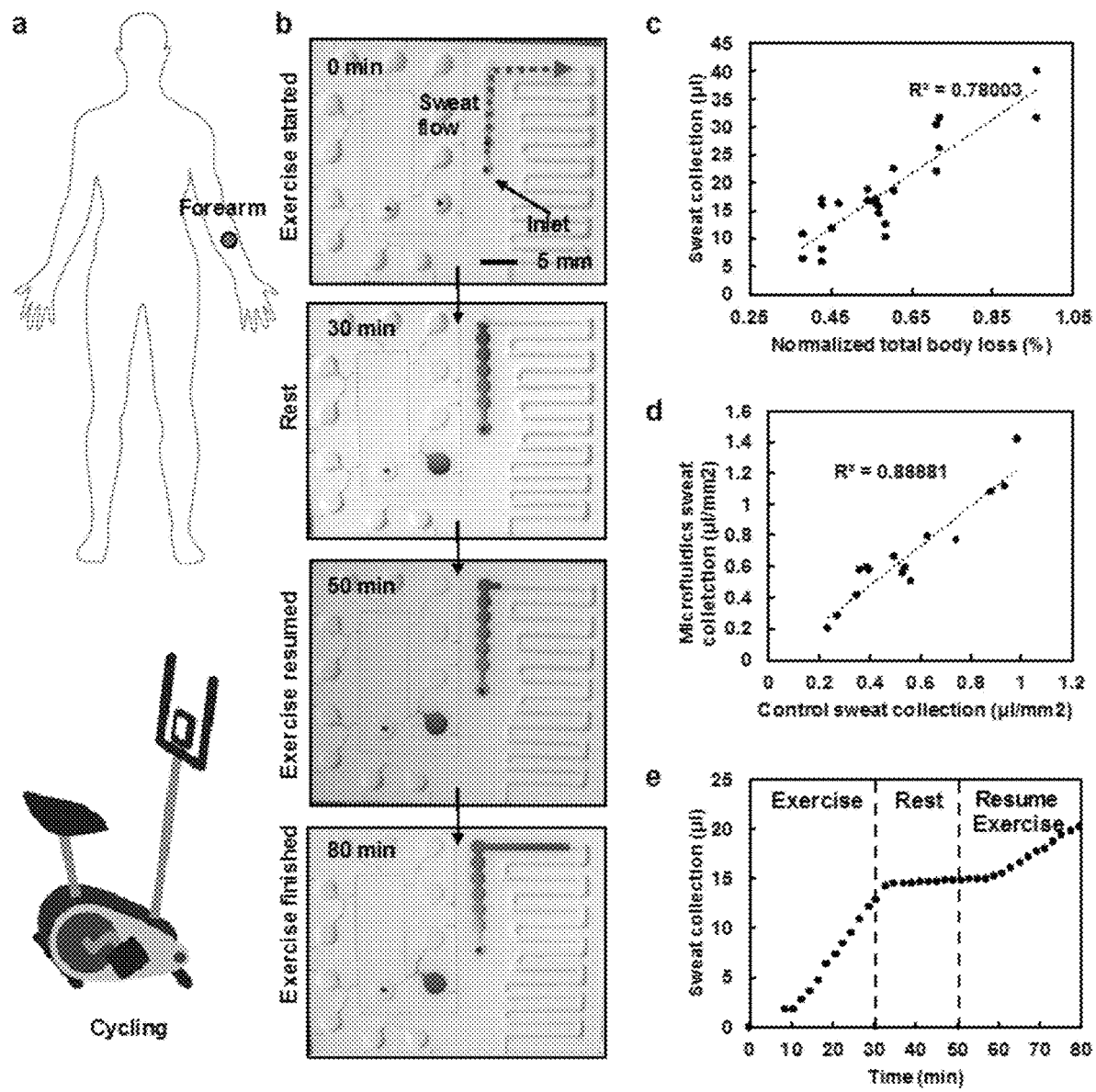
FIG. 67 shows: (a) Schematic illustration of mounting position of sweat collection device on the body at forearm and type of exercise. (b) Optical image of microfluidic device spotted with blue dye that mixes with sweat. The extent of blue dye in the channel during sweat provides a measure of total sweat volume at any given instant in time.

Measurements of sweat loss and instantaneous sweat loss: The serpentine microfluidic channel has capability to measure sweat rate over a local region (anterior forearm) during cycling, and to correlate this measure with the total body sweat loss (panel (a) of FIG. 67). The simple microfluidic device with colored dye in the channel shows the filling of the sweat from the skin (panel (b) of FIG. 67). The comparison of the sweat collection from the microfluidic device with total body loss which measured by weighing body weight before and after exercise without water consumption shows good correlation (panel (c) of FIG. 67), indicating that microfluidic devices could be used to estimate total body loss in ambulatory environments. The amount of sweat captured with the microfluidic device and the control method using fabric based skin patch (Tegaderm® absorbent pad) also shows good correlation (panel (d) of FIG. 67). Furthermore, microfluidic devices enable measurement of instantaneous sweat rates during exercise routines. Panel (e) of FIG. 67 shows instantaneous sweat rates at three different intervals in time. During the first session of exercise (labeled 'exercise'), there is constant sweat rate followed by a decrease in sweat rate approaching zero sweating when the subject is at rest (labeled 'rest'). The instantaneous sweat rate returns to initial levels once the subject re-initiates physical exertion (labeled 'resumed exercise').

Control sweat collection and Total body loss measurement: Subjects performed exercise on standing bicycle for 20-90 min with no fluid intake or restroom use during exercise. Tegaderm® with pad (3582; 3M, MN, USA) provided a control method to measure sweat generation at defined region. After collecting the sweat from the skin, the sweat weight was calculated by subtracting the initial mass of the Tegaderm®. Weighing by digital scale (Adam Equipment, CT, USA) with 2 g accuracy before and after exercise in nude provided the data for calculating total body loss.

Field testing involves healthy, non-diabetic, human subject volunteers (three males) instrumented with devices on the upper wrist. The physical exercise involves cycling on a stationary bike with increasing resistance. Real-time data acquisition during each trial occurs either through a compact, short-range reader, or an extended, long-range reader were positioned in the vicinity of the device. The long-range reader offers significant spatial latitude to the user during data collection. Panel (A) of FIG. 68A displays an image of a subject on a stationary bike wearing the patch, with an extended antenna (60×30 cm2) in the background. Panel (B) of FIG. 68 summarizes the effective communication distance between the device and antenna (shown in panel (A) of FIG. 68), presented here is the largest distance that enables successful operation. The data shows a maximum operating distance of about 18 cm with this configuration.

Panels (C)-(E) of FIG. 68 show a device after cycling, along with a summary of data acquired from the lactate and glucose sensors. Similarly, panels (F)-(H) of FIG. 68 presents images of the device for another subject, illustrating lactate and glucose sensor measurements. For both subjects, the respective electrochemical sensors produce voltage signals that yield corresponding concentrations based on calibration plots obtained at −300 C (usual sweat temperature). Analyte concentrations reported in these studies are consistent with previously published studies 21, 38. Image analysis of panels (C) and (F) of FIG. 68 reveal that the concentration of chloride is 34±2 mM (subject #1; chamber #1) and 62±5 mM (subject #2; chamber #1) and 36±5 mM (subject #2; chamber #2); the pH is 6.4±0.1 (subject #1; chamber #1) and 6.3±0.1 (subject #2; chamber #1) and the sweat rate is ~0.52 µl/min (subject #1) and −0.88 µl/min (subject #2). Separate analyses using conventional techniques such as commercial bench-top chloridometry, pH analysis and high-resolution nuclear magnetic resonance (NMR) spectroscopy provide points of comparison. Panel (I) of FIG. 68 illustrates capabilities in monitoring of glucose and lactate levels in sweat over multiple days for subject #1. See FIG. 69 for data from an additional two subjects (subject #2 and #3). Separate measurements capture blood lactate and glucose levels over the same time period, as points of comparison. In these studies, the subjects wear sensors on the upper wrist for two consecutive days. On each day, the subject performs a cycling exercise on a stationary bike once in the morning in a fasting state, 20 min after consuming a sweetened drink containing 150 g of sugar and then again in the evening. Blood tests with commercial blood lactate (Lactate Plus®, Nova Biomedical, MA) and blood glucose (Accu-Check® Nano meter, Roche Diabetes Care, Inc.) meters capture the concentrations of these analytes before and after each cycling event. Photos of the device at different stages of the study, as shown in panel (I) of FIG. 68 and FIG. 69, indicate robust adhesion to the skin throughout the study. Analysis of the data reveals that the blood levels after each session follow trends that are similar to those of data measured on sweat using the skin-interfaced devices. These findings are generally in agreement with those of previous studies that compare lactate and glucose levels in blood to those measured in sweat using conventional collection and ex-situ analysis techniques 44, 70. Further support for the long-term stability of the sensors follows from comparisons of signals produced by a pair of devices after the two-day trial with an unused pair (FIG. 70). The data show that the performance of the glucose sensor remains unchanged while the response of the lactate sensor decreases by only ~20% even after these rigorous two-day trials. These results represent the first examples of long-term use of skin-interfaced sweat sensors. The outcomes suggest potential for non-invasive tracking of blood glucose and lactate levels.

Example 16: Battery Free NFC Based Soft Microfluidics to Readout Sweat Excretion Rate Using the system packaged, human tests were conducted. Panel (b) of FIG. 71 shows the device can be mounted on various location of the subject body. The human tests were conducted to show the difference of sweat rate in the thermal environment (panel (b) of FIG. 71) and exercise environment (panel (c) of FIG. 71). Also in the exercise test, two locations on the bodies were compared. Subject #1 and #2 were tested and both showed the chloride and sweat rate were higher at running condition. The correlation of sweat rate and chloride concentration was also allowed as reported by Smith et al. in 2011 and Taylor et al. in 2013. Also other four subjects (panels (f)-(i) of FIG. 71) were tested to see the difference of sweat rate for forehead and forearm. Forehead is known to be a location which has most dense sweat gland, and generally shows high sweat excretion rate and pressure. The four subjects show similar results and sweat excretion trend.

For human test, four healthy volunteers were involved in the on-body test with jogging and operating stationary bike in door with 00% humidity and 25° C. temperature condition. The devices were placed on fore head, chest, lower back, and fore arm. Before mounting the device, the skin was cleaned with 70% methyl alcohol. In the process of human test, there was no drinking water for hydration.

A second set of studies focus on exploring temporal variations in sweat glucose and lactate as compared to those of blood due to consumption of food and engagement in physical exercise. Here, the subjects wear the patch for one day and perform a cycling exercise (15-20 min) on a stationary bike in the morning in a fasting state, 30 min and 90 min after consuming breakfast and then again 30 min before lunch and 30 min and 90 min after lunch. Blood tests are performed using protocols similar to those for the first set of studies. FIG. 72 shows data acquired for subject #1 and #2 during these long-term sweat monitoring. Analysis reveals that the blood levels after each session follow trends that are similar to those of data measured on sweat using the skin-interfaced devices. The sweat glucose values lag behind those acquired from blood tests by ~30-60 min, while a much smaller time lag exists between blood lactate and sweat lactate. Such time lags is attributed to complex biological pathways through which the blood constituents reach other biofluids.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A microfluidic system for measuring a characteristic of a biofluid, comprising:
   a flexible substrate;
   a collection layer embedded in or supported by the flexible substrate, wherein the collection layer is configured to promote transport of the biofluid from a skin surface;
   at least one reservoir chamber embossed in the collection layer, the at least one reservoir chamber having:
     an absorbent provided to receive at least a portion of the biofluid from the collection layer; and
     a sensor for measuring the characteristic of the biofluid received by the absorbent; wherein the absorbent provides a force for transporting the biofluid that is greater than a capillary force of the collection layer for transporting the biofluid; and
   a protective layer embedded in or supported by the flexible substrate, wherein the protective layer is configured to prevent the biofluid from escaping from the at least one reservoir chamber.

2. The microfluidic system of claim 1, wherein the characteristic of the biofluid is amount of sweat loss or presence or absence of a biomarker from the skin surface.

3. The microfluidic system of claim 1, wherein the sensor is an electronic sensor, wherein the electronic sensor comprises one or more high sensitivity electrodes configured to measure a change in an electrical parameter caused by the biofluid received by the absorbent, wherein the electrical parameter is capacitance.

4. The microfluidic system of claim 1, wherein the sensor comprises one or more colorimetric assay reagents.

5. The microfluidic system of claim 1, further comprising a wireless communication device for transmitting wireless information corresponding to the characteristic of the biofluid from the skin surface.

6. The microfluidic system of claim 1, wherein said flexible substrate comprises a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, chitosan, and any combination thereof.

7. The microfluidic system of claim 1, further comprising an adhesive layer configured to mount the microfluidic system to the skin surface, wherein the adhesive layer reversibly adheres the microfluidic system to the skin surface.

8. The microfluidic system or claim 7, wherein the adhesive layer comprises medical grade acrylic or medical grade silicon.

9. The microfluidic system of claim 1, wherein said protective layer is polyethylene.

10. The microfluidic system of claim 1, wherein the collection layer has an average thickness selected from a range of 50 μm to 1 mm.

11. The microfluidic system of claim 1, wherein the collection layer is a mesh.

12. The microfluidic system of claim 1, wherein the collection layer has a plurality of pores having an average diameter selected from a range of 10 μm to 250 μm.

13. The microfluidic system of claim 1, wherein the collection layer is polyester.

14. The microfluidic system of claim 1 that is incorporated into a glove.

15. The microfluidic system of claim 1, wherein a property of the biofluid is visually observable.

16. The microfluidic system of claim 1, wherein a signal corresponding to a property of the biofluid is transmitted from said microfluidic system to an external receiving device.

17. The microfluidic system of claim 1, wherein a property of the biofluid is one or more of a sweat volume, a sweat rate, or a sweat loss.

18. The microfluidic system of claim 1, wherein a property of the biofluid is pH.

19. The microfluidic system of claim 1, wherein a property of the biofluid comprises the presence of, amount or concentration of an analyte in said biofluid or component thereof.

20. The microfluidic system of claim 19, wherein said analyte is an electrolyte, a metabolite, or a biomarker in said biofluid or component thereof.

21. The microfluidic system of claim 1, wherein a leading edge of the biofluid in a sensor microfluidic channel or reservoir is sensed as a function of time.

22. The microfluidic system of claim 21, wherein the leading edge is sensed visually or measured using a photodetector.

23. The microfluidic system of claim 1, wherein the flexible substrate is a functional substrate.

24. The microfluidic system of claim 1, further comprising an electronic sensor operably connected to a microfluidic network, wherein an amount of the biofluid is proportional to an electrical resistivity or electrical conductivity parameter measured by the electronic sensor.

25. The microfluidic system of claim 1, comprising a disposable portion comprising a microfluidic network and a reusable portion corresponding to an electronic device, wherein the disposable portion and the reusable portion are connected to each other by one or more selectively releasable coupling elements.

26. The microfluidic system of claim 25, wherein the selectively releasable coupling elements comprise a magnet.

27. The microfluidic system of claim 1, comprising a plurality of distinct component layers arranged in a stacked configuration.

28. A microfluidic system for measuring a characteristic of a biofluid, comprising:
- a flexible substrate;
- a collection layer embedded in or supported by the flexible substrate, wherein the collection layer is configured to promote transport of the biofluid from a skin surface;
- at least one reservoir chamber embedded in or supported by the flexible substrate and fluidically connected to the collection layer, the at least one reservoir chamber having:
  - an absorbent provided to receive at least a portion of the biofluid from the collection layer; and
  - a sensor for measuring the characteristic of the biofluid received by the absorbent; wherein the absorbent provides a force for transporting the biofluid that is greater than a capillary force of the collection layer for transporting the biofluid;
- a disposable portion comprising a microfluidic network and a reusable portion corresponding to an electronic device, wherein the disposable portion and the reusable portion are connected to each other by one or more selectively releasable coupling elements, wherein the selectively releasable coupling elements comprise a magnet; and
- a protective layer embedded in or supported by the flexible substrate, wherein the protective layer is configured to prevent the biofluid from escaping from the at least one reservoir chamber.

* * * * *